(12) United States Patent
Michalakis et al.

(10) Patent No.: US 12,246,072 B2
(45) Date of Patent: Mar. 11, 2025

(54) GENE THERAPY FOR THE TREATMENT OF CNGB1-LINKED RETINITIS PIGMENTOSA

(71) Applicants: Stylianos Michalakis, Munich (DE); Martin Biel

(72) Inventors: Stylianos Michalakis, Munich (DE); Martin Biel, Munich (DE)

(73) Assignees: Stylianos Michalakis, Munich (DE); Martin Biel, Munich (DE)

( * ) Notice: Subject to any disclaimer, the term of this patent is extended or adjusted under 35 U.S.C. 154(b) by 307 days.

(21) Appl. No.: 16/495,826

(22) PCT Filed: Mar. 21, 2018

(86) PCT No.: PCT/IB2018/051905
§ 371 (c)(1),
(2) Date: Sep. 19, 2019

(87) PCT Pub. No.: WO2018/172961
PCT Pub. Date: Sep. 27, 2018

(65) Prior Publication Data
US 2020/0030458 A1    Jan. 30, 2020

Related U.S. Application Data

(60) Provisional application No. 62/474,409, filed on Mar. 21, 2017.

(51) Int. Cl.
*A61K 48/00* (2006.01)
*A61P 27/02* (2006.01)
(Continued)

(52) U.S. Cl.
CPC .......... *A61K 48/0058* (2013.01); *A61P 27/02* (2018.01); *C07K 14/705* (2013.01); *C12N 15/86* (2013.01); *A01K 2267/0306* (2013.01)

(58) Field of Classification Search
CPC .... A61K 48/00; A61K 48/0058; C12N 15/86; C12N 15/8645; A61P 27/02
See application file for complete search history.

(56) References Cited

U.S. PATENT DOCUMENTS

2010/0190841 A1* 7/2010 Farrar ................ A61K 48/0066
514/44 R
2018/0353620 A1* 12/2018 Michalakis ........ A61K 48/0075

FOREIGN PATENT DOCUMENTS

WO    2015020522    2/2015

OTHER PUBLICATIONS

Rehemtulla et al, PNAS 93: 191-195, 1996.*
(Continued)

*Primary Examiner* — Kevin K Hill
(74) *Attorney, Agent, or Firm* — McDonnell Boehnen Hulbert & Berghoff, LLP

(57) ABSTRACT

The present invention relates to a polynucleotide comprising a promoter comprising a human photoreceptor-specific promoter element, a core promoter and at least one transgene. Further, the invention provides a plasmid comprising the polynucleotide, a viral vector comprising the polynucleotide and a pharmaceutical composition comprising the polynucleotide. The invention also relates to the plasmid, the viral vector or the pharmaceutical composition for use as a medicament, in particular for use in the therapy of diseases of the retina.

4 Claims, 14 Drawing Sheets
Specification includes a Sequence Listing.

(51) Int. Cl.
*C07K 14/705* (2006.01)
*C12N 15/86* (2006.01)

(56) References Cited

OTHER PUBLICATIONS

May et al, Clinical & Experimental Opthalmology 31(5): 445-450, 2003.*
Pestell et al, Cell Growth & Differentiation, 1996.*
Pavlou et al, Novel AAV capsids for intravitreal gene therapy of photoreceptor disorders, EMBO Molecular Medicine 13: e13392, 19 pages, 2021.*
Devchand Paul et al: "Construction of a 9, 10,31 recombinant adeno-associated virus (rAAV) vector expressing murine interleukin-12 (IL-12)", Cancer Gene Therapy, vol. 7, No. 2, Feb. 1, 2000 (Feb. 1, 2000) pp. 308-315, XPQ55482058.
S. Koch et al: "Gene therapy restores vision and delays degeneration in the CNGB1−/− mouse model of retinitis pigmentosa", Human Molecular Genetics, vol. 21, No. 20, Oct. 15, 2012 (Oct. 15, 2012), pp. 4486-4496, XP055250888, gb ISSN : 0964-6906, DOI : 10. 1093/hmg/dds290 abstract p. 2, right-hand column, paragraph 1.
May Leigh A et al: "In vitro comparison studies of truncated rhodopsin promoter fragments from various species in human cell lines", Clinical and Experimental Ophthalmology, Blackwell Science, AU, vol. 31, No. 5,Oct. 1, 2003 (Oct. 1, 2003), pp. 445-450, XP002477126, ISSN: 1442-6404, DOI :10. 1046/.1442-9071. 2003 .00694.X p. 449, left-hand column, paragraph 3; figure 3.
Batni, S. et al., Characterization of the Xenopus Rhodopsin Gene, The Journal of Biological Chemistry, 1996, 271(6), p. 3179-3186.

* cited by examiner

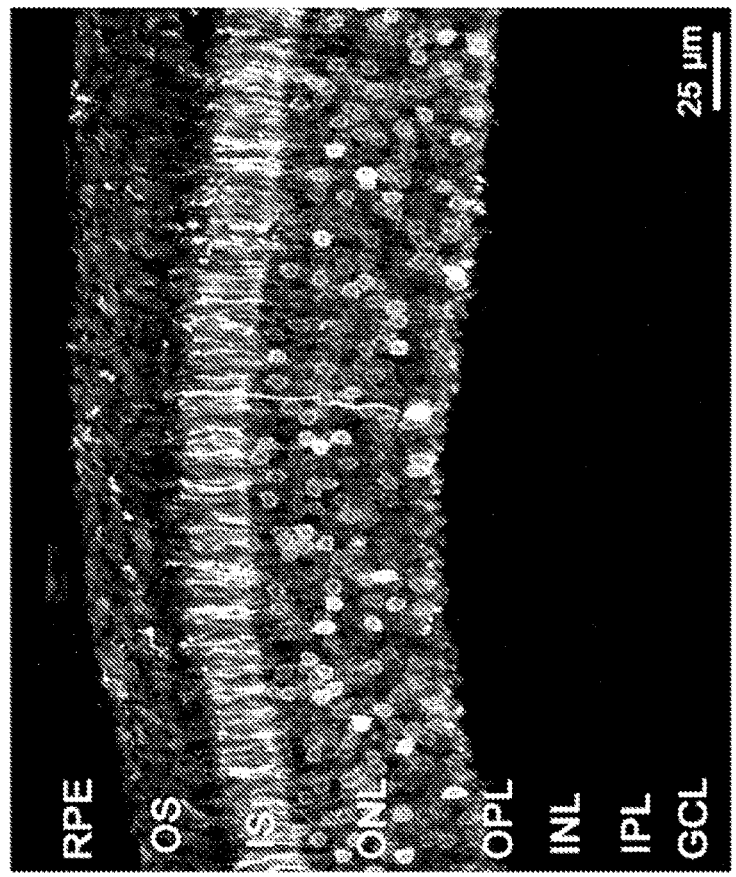
Fig. 3A
Fig. 3B

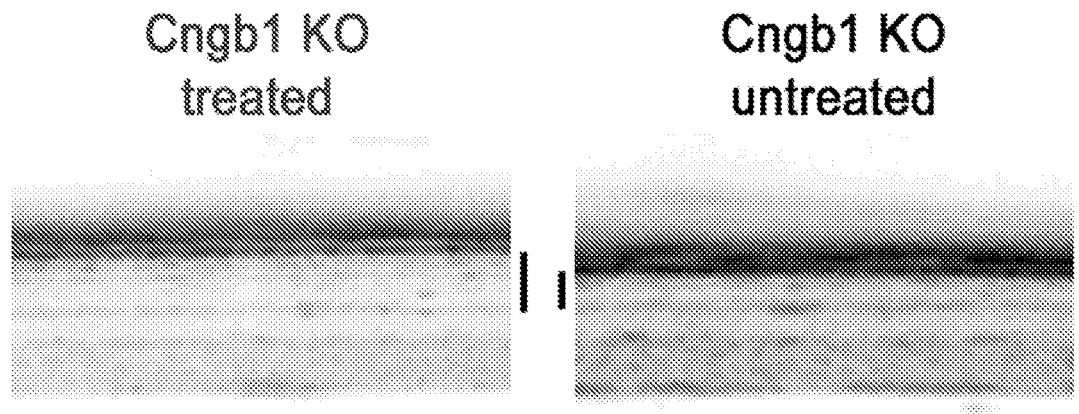
Fig. 5A  Fig. 5B
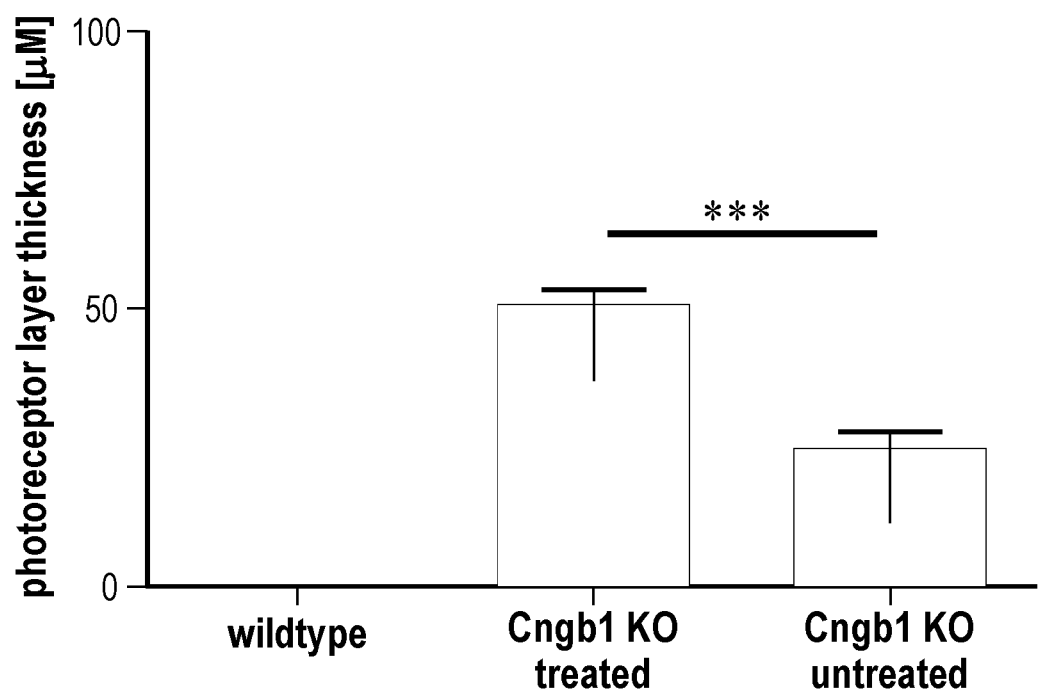
Fig. 5C

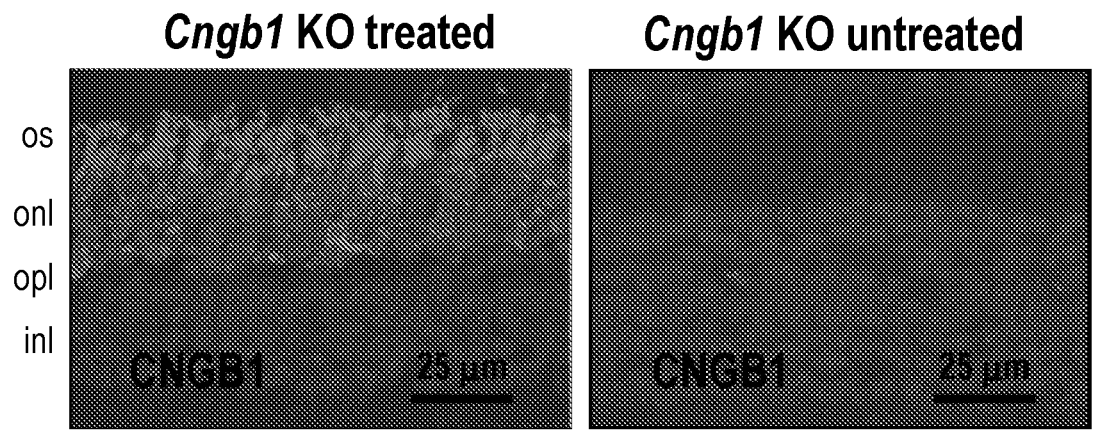
Fig. 9A  Fig. 9B
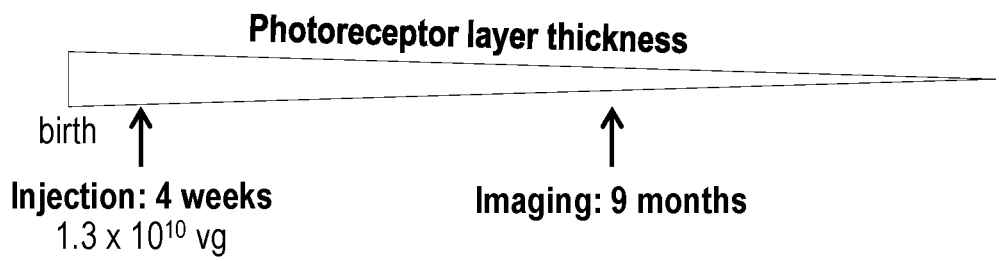
Fig. 10A
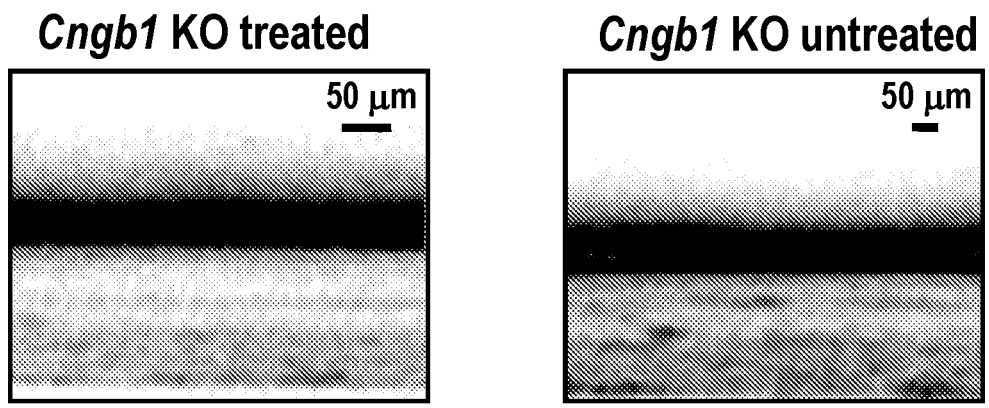
Fig. 10B  Fig. 10C

GENE THERAPY FOR THE TREATMENT OF CNGB1-LINKED RETINITIS PIGMENTOSA

CROSS-REFERENCE TO RELATED APPLICATIONS

This application is a US National Phase filing of PCT/IB2018/051905, filed on Mar. 21, 2018, which claims the benefits of U.S. Provisional application No. 62/474,409, filed on Mar. 21, 2017. The disclosure therein is expressly incorporated entirely by reference.

BACKGROUND OF THE INVENTION

Retinitis pigmentosa (RP) is a term that is used to refer to a genetically diverse group of inherited degenerative diseases of the retina affecting the photoreceptors. The genetic mutation concerns genes that are either exclusively or primarily expressed in rod photoreceptors. Accordingly, the disease is characterized by a primary impairment or loss of rod function and structure. Deterioration of rods is followed by a secondary degeneration of the cones. Onset and time course of retinal degeneration varies from early-onset and fast progressing forms to late-onset and slow progressing forms, respectively. The most common symptoms of RP are night blindness, progressive constriction of the visual field, and abnormal accumulation of pigmentation in the retina. Clinical features include characteristically shaped pigmentary deposits and a progressive attenuation of retinal vessels. In many cases RP finally leads to legal blindness. The overall prevalence of RP is estimated to 1:4,000. RP is genetically very heterogeneous and the number of identified RP genes approximates 50 (Daiger S P, et al. (1998) Investigative Ophthalmology and Visual Science (Supplement) 39:S295). Many disease genes encode proteins required for light detection and processing (e.g. rhodopsin) or for maintenance of rod cellular morphology (e.g. peripherin-2). 10-25% of RP cases show an autosomal dominant pattern of inheritance (adRP), 6-18% are X-linked (xRP) and 20-30% are autosomal recessively inherited (arRP). Another 40-50% are sporadic arRP and is genetically the most diverse RP subgroup and none of the known disease genes has a relative frequency of more than 15%. The most prevalent arRP genes are EYS (5-12%), USH2A (5-15%), CRB1 (approx. 5%), and PDE6B (4-10%). However, most likely due to founder effects these values vary between different subpopulations and across regions.

CNGB1 encodes the beta subunit of the rod cyclic nucleotide-gated (CNG) channel (RP45 locus). Mutations in the RP45 locus causing so-called CNGB1-linked RP or RP type 45, respectively, are found in 2-4% of arRP cases (Hartong D T, et al. (2006) Lancet 368 (9549):1795-1809). Therefore, the estimated number of patients with CNGB1-linked arRP is approximately 900 in Germany and 5,000 in the EU. Vision impairment is considered one of the most important non-mortal handicaps with high clinical and socioeconomic importance. RP Patients suffer from severe loss of quality of life throughout an extensive period of their lifetime. Unfortunately, no curative or symptomatic treatments of RP exist. Clinical experts and health organizations list RP as one of the top candidates for gene therapy. Previously, it could be demonstrated that gene supplementation therapy restores vision and delays degeneration in the CNGB1 (−/−) mouse model of retinitis pigmentosa (Koch S, et al. (2012) Hum Mol. Genet. 21(20):4486-96) by using recombinant AAV2/8 vector comprising the mouse Cngb1 gene under the control of the mouse rhodopsin (Rho) promoter: AAV2/8(Y733F)-Rho-Cngb1. The vector was injected into the eye of mice with a genetic deletion in exon 26 of the gene encoding Cngb1 (Cngb1 KO). The injection enhanced survival of photoreceptors and improved retinal function. However, several issues render this approach less promising for the treatment of humans suffering from retinal degenerations due to CNGB1-linked RP:
(a) the rAAV cis vector genome size (5.0 kb) was above the size of the wildtype AAV genome (<4.7 kb);
(b) a murine rhodopsin (Rho) gene promoter was used; and
(c) a murine Cngb1 gene sequence was used.

Petersen-Jones et al. (2016) Invest. Ophthalmol. 57: 1842, describe an rAAV2/5 vector comprising the coding sequence of the canine Cngb1 gene (cCngb1) under control of a human rhodopsin kinase 1 (hGRK1) promoter: AAV5-hGRK1-cCngb 1. The vector was injected into the eye of dogs with a mutation in exon 26 of the Cngb1 gene. The injection improved retinal function. However, the following issues render this approach less promising for the treatment of humans suffering from retinal degenerations due to CNGB1-linked RP:
(a) the hGRK1 promoter used in this approach drives expression in rods, but also off-target expression in cone photoreceptors. This off-target expression could have a negative impact on retinal function and morphology; and
(b) a canine Cngb1 gene sequence was used.

Thus, there is a need in the art to identify transgenic elements that have a small size without negatively affecting or losing their activity in the in vivo situation.

SUMMARY OF THE INVENTION

The present invention is based on the surprising discovery that a short part of the human rod promoter transfers rod photoreceptor-specific expression to transgenes operably linked to this promoter element in vivo. When the promoter element defined herein was used in an in vivo setting, stable expression of a transgene was observed. The expression level was suitable to improve the visual capabilities of the test animals infected with an adeno-associated virus vector comprising the transgene. This surprising finding provides inter alia the following advantages over the prior art: (i) reduction of the size of the construct that is introduced into a cell, (ii) an increase of the packaging efficiency of the transgene into viral vectors, (iii) a decrease of the chance that recombination events occur in vivo, (iv) an increase the efficiency of introduction of the transgene into the target cells, in particular into the nucleus of the target cell; (v) a suitable expression level in a human patient to treat rod associated diseases, (vi) preservation and/or improvement of retinal function and (vii) preservation and/or improvement of vision.

In a first aspect the invention relates to a polynucleotide comprising in this order:
a) a promoter comprising a human rod photoreceptor-specific promoter element (hRPSPE) comprising, consisting essentially of or consisting of the nucleic acid sequence according to SEQ ID NO: 1 or variants thereof and a core promoter (CP); and
b) a transgene (TG) operably linked to the promoter of a); wherein the variant of SEQ ID NO: 1 comprises one or more nucleic acid substitutions outside nucleotide positions 6 to 13, 32 to 40, 70 to 83, and 87 to 94 of SEQ ID NO: 1 and wherein the length of the promoter is in particular 350 bases or less.

In certain exemplary embodiments, the 5' end of the hRPSPE is at a nucleic acid position from 1 to 160 and the 3' end at a nucleic acid position from 290 to 310 of SEQ ID NO: 2 or variants thereof.

In certain exemplary embodiments, the CP comprises a TATA-box and/or an initiator (Inr).

In certain exemplary embodiments, the 5' end of the promoter is at a nucleic acid position from 1 to 160 and the 3' end at a nucleic acid position from 340 to 350 of SEQ ID NO: 2 or variants thereof.

In certain exemplary embodiments, the transgene comprises a nucleic acid encoding a protein that maintains or improves the physiological function of rods.

In certain exemplary embodiments, the transgene: (i) comprises a nucleic acid encoding the human rod cyclic nucleotide-gated channel beta subunit (hCNGB1), ABCA4, AIPL1, BEST1, CACNA1F, CLN3, CLRN1, CNGA1, CEP290, CRB1, CRB2, CRX, GPR98, GUCA1A, GUCA1B, MYO7A, NRL, PDE6A, PDE6B, PRPH2, PROM1, RHO, ROM1, RP1, RP2, RPE65, RPGR, SAG, USH1C, USH1G, USH2A or functional fragments or variants thereof; a nucleic acid encoding a miRNA or shRNA targeting a mRNA encoding a dominant negative mutant thereof; and/or a nucleic acid encoding an antibody or antibody binding fragment that specifically binds to a dominant negative mutant thereof; or (ii) comprises a nucleic acid encoding a protein that inhibits proliferation of rod cells, preferably a toxin; a prodrug converting enzyme, e.g. thymidine kinase; cell cycle inhibitors, e.g. retinoblastoma protein (pRB), p53, p21CIP1, p27KIP1 and p57KIP2; comprises a mRNA encoding a dominant negative mutant of the cell cycle inhibitor thereof; and/or comprises a nucleic acid encoding a dominant negative mutant of a cell cycle inhibitor thereof.

In certain exemplary embodiments, the hCNGB1 comprises an amino acid sequence according to SEQ ID NOs: 3, 40, or 41, or variants thereof.

In certain exemplary embodiments, the polynucleotide comprises one or more further nucleotide sequence elements selected from the group consisting of: (i) a polyadenylation signal (PAS); and/or (ii) one or two inverted terminal repeat (ITR) sequences; and/or (iii) viral nucleotide sequences necessary to form an infectious viral vector, preferably an adenovirus, a retrovirus, a lentivirus, a vaccinia/poxvirus, or a herpesvirus vector, in particular herpes simplex virus (HSV) vector.

In certain exemplary embodiments, the polyadenylation signal comprises, essentially consists or consists of a Simian-Virus 40 PAS.

In certain exemplary embodiments, the polyadenylation signal comprises, essentially consists or consists of a nucleic acid according to SEQ ID NO: 4 or functional variants thereof.

In certain exemplary embodiments, the ITR sequence is an adeno-associated virus (AAV) ITR.

In certain exemplary embodiments, the AAV is AVV serotype 2, 5, 8 or 9.

In certain exemplary embodiments, the promoter and the transgene are flanked at their 5' with a L-ITR and at their 3' end with a R-ITR.

In certain exemplary embodiments, the L-ITR comprises, essentially consists or consists of a sequence according to SEQ ID NO: 5 or variants thereof and/or the R-ITR comprises, essentially consists or consists of a sequence according to SEQ ID NO: 6 or variants thereof.

In certain exemplary embodiments, the total length of the polynucleotide is 5200 bases or less, preferably 5100 bases or less, more preferably 5000 bases or less.

In a second aspect the invention further relates to a plasmid comprising the polynucleotide of the first aspect.

In certain exemplary embodiments, the plasmid comprises a nucleic acid sequence according to SEQ ID NOs: 7, 42-44, or variants thereof.

A third aspect of the invention relates to a viral vector comprising the polynucleotide of the first aspect of the invention.

In certain exemplary embodiments, the virus is selected from the group consisting of AAV2, AAV5, AAV8, AVV9 or variants thereof.

A fourth aspect of the invention relates to the polynucleotide according to the first aspect of the invention, the plasmid of the second aspect of the invention and/or the viral vector according to the third aspect of the invention for use as a medicament.

A fifth aspect of the invention relates to a pharmaceutical composition comprising the polynucleotide according to the first aspect of the invention, the plasmid of the second aspect of the invention and/or the viral vector according to the third aspect of the invention, and a pharmaceutically acceptable carrier.

A sixth aspect of the invention relates to the polynucleotide according to the first aspect of the invention, the plasmid according to the second aspect of the invention and/or the viral vector according to the third aspect of the invention for use in the therapy of a disease of the retina, in particular retinal degeneration.

In certain exemplary embodiments, the route of administration is selected from intraocular, intrabulbar, intravitreal or subretinal.

In certain exemplary embodiments, the retinal degeneration is associated with a genetic mutation, substitution, and/or deletion.

In certain exemplary embodiments, the retinal degeneration is selected from the group consisting of night blindness, blindness, retinal degeneration, retinal dystrophy and retinitis pigmentosa.

In certain exemplary embodiments, the retinitis pigmentosa is CNGB1-linked retinitis pigmentosa or retinitis pigmentosa type 45 (RP45).

A seventh aspect of the invention relates to a polynucleotide comprising in this order:
  a) a human rhodopsin promoter comprising the nucleic acid sequence according to SEQ ID NO: 9 or variants thereof; and
  b) at least one transgene (TG) operably linked to the promoter of a).

In certain exemplary embodiments, the transgene comprises a nucleic acid encoding a protein that maintains or improves a physiological function of rods.

In certain exemplary embodiments, the transgene: (i) comprises a nucleic acid encoding the human rod cyclic nucleotide-gated channel beta subunit (hCNGB1), ABCA4, AIPL1, BEST1, CACNA1F, CLN3, CLRN1, CNGA1, CEP290, CRB1, CRB2, CRX, GPR98, GUCA1A, GUCA1B, MYO7A, NRL, PDE6A, PDE6B, PRPH2, PROM1, RHO, ROM1, RP1, RP2, RPE65, RPGR, SAG, USH1C, USH1G, USH2A or functional fragments or variants thereof; a nucleic acid encoding a miRNA or shRNA targeting a mRNA encoding a dominant negative mutant thereof; and/or a nucleic acid encoding an antibody or antibody binding fragment that specifically binds to a dominant negative mutant thereof; or (ii) comprises a nucleic acid encoding a protein that inhibits proliferation of rod cells, preferably a toxin; a prodrug converting enzyme, e.g. thymidine kinase; cell cycle inhibitors, e.g. retinoblastoma protein (pRB), p53, p21CIP1, p27KIP1 and p57KIP2; comprises a mRNA encoding a dominant negative mutant of the cell cycle inhibitor thereof; and/or comprises a nucleic acid encoding a dominant negative mutant of a cell cycle inhibitor thereof.

In certain exemplary embodiments, the polynucleotide comprises one or more further nucleotide sequence elements selected from the group consisting of:
(i) a polyadenylation signal (PAS);
(ii) one or two inverted terminal repeat (ITR) sequences; and
(iii) viral nucleotide sequences necessary to form an infectious viral vector, preferably an adenovirus, a retrovirus, a lentivirus, a vaccinia/poxvirus, or a herpesvirus vector, in particular herpes simplex virus (HSV) vector.

In certain exemplary embodiments, the polyadenylation signal comprises a Simian-Virus 40 PAS.

In certain exemplary embodiments, the ITR sequence is an adeno-associated virus (AAV) ITR.

In certain exemplary embodiments, the AAV is AVV serotype 2, 5, 8 or 9.

An eighth aspect of the invention relates to a viral vector comprising the polynucleotide according to the seventh aspect of the invention.

In certain exemplary embodiments, the virus is selected from the group consisting of AAV2, AAV5, AAV8, AVV9 or variants thereof.

A ninth aspect of the invention relates to a method for treating retinal degeneration in a subject in need thereof, comprising administering to the subject a therapeutically effective amount of a polynucleotide according to the seventh aspect of the invention, or the viral vector according to the eighth aspect of the invention.

In certain exemplary embodiments, the polynucleotide or viral vector comprises the nucleic acid sequence set forth in SEQ ID NO: 43.

A tenth aspect of the invention relates to a method for treating retinitis pigmentosa in a subject in need thereof, comprising administering to the subject a therapeutically effective amount of a polynucleotide according to the seventh aspect of the invention, or the viral vector according to the eighth aspect of the invention.

In certain exemplary embodiments, the polynucleotide or viral vector comprises the nucleic acid sequence set forth in SEQ ID NO: 43.

An eleventh aspect of the invention relates to a method for treating retinal degeneration in a subject in need thereof, wherein the retinal degeneration is characterized by a defect or absence of CNGB1 in the retinal cells of the subject, the method comprising administering to the subject a therapeutically effective amount of a viral vector comprising the nucleic acid sequence set forth in SEQ ID NO: 43.

In certain exemplary embodiments, the retinal degeneration is CNGB1-linked retinitis pigmentosa or retinitis pigmentosa type 45 (RP45).

A twelfth aspect of the invention relates to a method for treating CNGB1-linked retinitis pigmentosa or retinitis pigmentosa type 45 (RP45) in a subject in need thereof, comprising subretinal administration to the subject a therapeutically effective amount of a viral vector comprising the nucleic acid sequence set forth in SEQ ID NO: 43.

A thirteenth aspect of the invention relates to a polynucleotide comprising in this order:

a) a promoter comprising a human rod photoreceptor-specific promoter element (hRPSPE) comprising the nucleic acid sequence according to SEQ ID NO: 1 or variants thereof and a core promoter (CP); and
b) a transgene encoding the human rod cyclic nucleotide-gated channel beta subunit (hCNGB1) operably linked to the promoter of a),
wherein the variant of SEQ ID NO: 1 comprises one or more nucleic acid substitutions outside nucleotide positions 6 to 13, 32 to 40, 70 to 83, and 87 to 94 of SEQ ID NO: 1.

A fourteenth aspect of the invention relates to a pharmaceutical composition comprising a polynucleotide comprising in this order:
a) a promoter comprising a human rod photoreceptor-specific promoter element (hRPSPE) comprising the nucleic acid sequence according to SEQ ID NO: 1 or variants thereof and a core promoter (CP); and
b) a transgene encoding the human rod cyclic nucleotide-gated channel beta subunit (hCNGB1) operably linked to the promoter of a);
wherein the variant of SEQ ID NO: 1 comprises one or more nucleic acid substitutions outside nucleotide positions 6 to 13, 32 to 40, 70 to 83, and 87 to 94 of SEQ ID NO: 1, and
a pharmaceutically acceptable carrier.

A fifteenth aspect of the invention relates to a pharmaceutical composition comprising a viral vector comprising the nucleic acid sequence set forth in SEQ ID NO: 43 and a pharmaceutically acceptable carrier.

LIST OF FIGURES

In the following, the content of the figures comprised in this specification is described. In this context please also refer to the detailed description of the invention above and/or below.

FIGS. 3A-3B depict representative confocal images showing native eGFP fluorescence in wild type mice treated with a version of the vector expressing eGFP instead of hCNGB1. These representative confocal images show native eGFP fluorescence in retinal cross-sections from 8-week-old wildtype mice treated subretinally at 4 weeks with rAAV.hRHO194.eGFP vector. Intense and rod-specific eGFP signal was observed in treated animals (FIG. 3A), but was absent in non-injected controls (FIG. 3B).

Figure 4A:
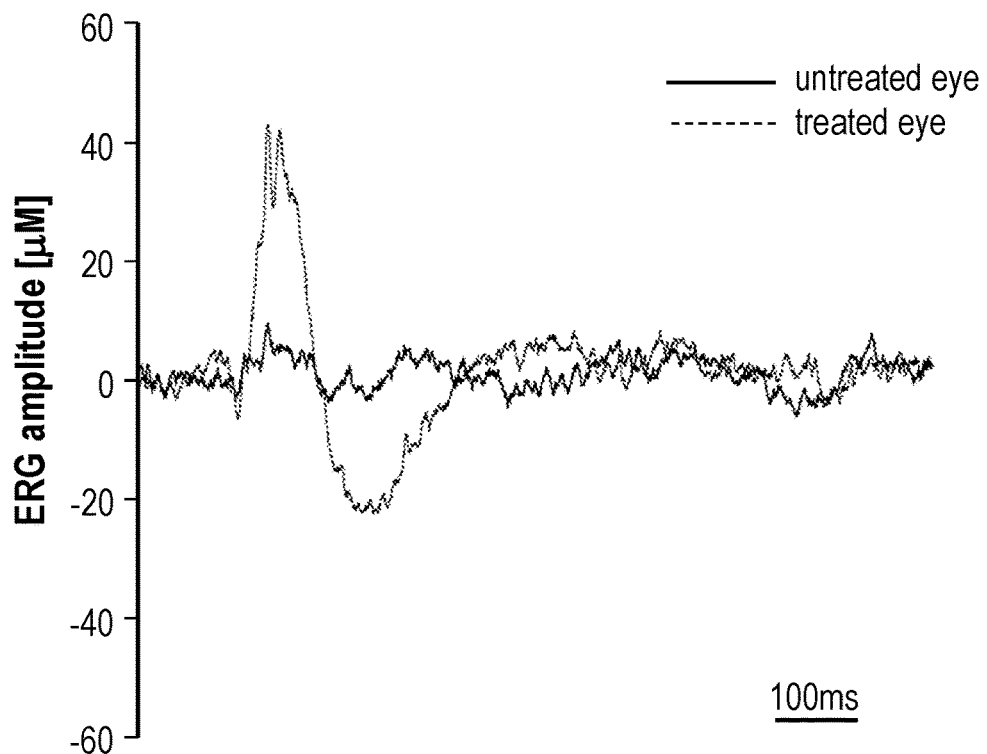
Figure 4B:
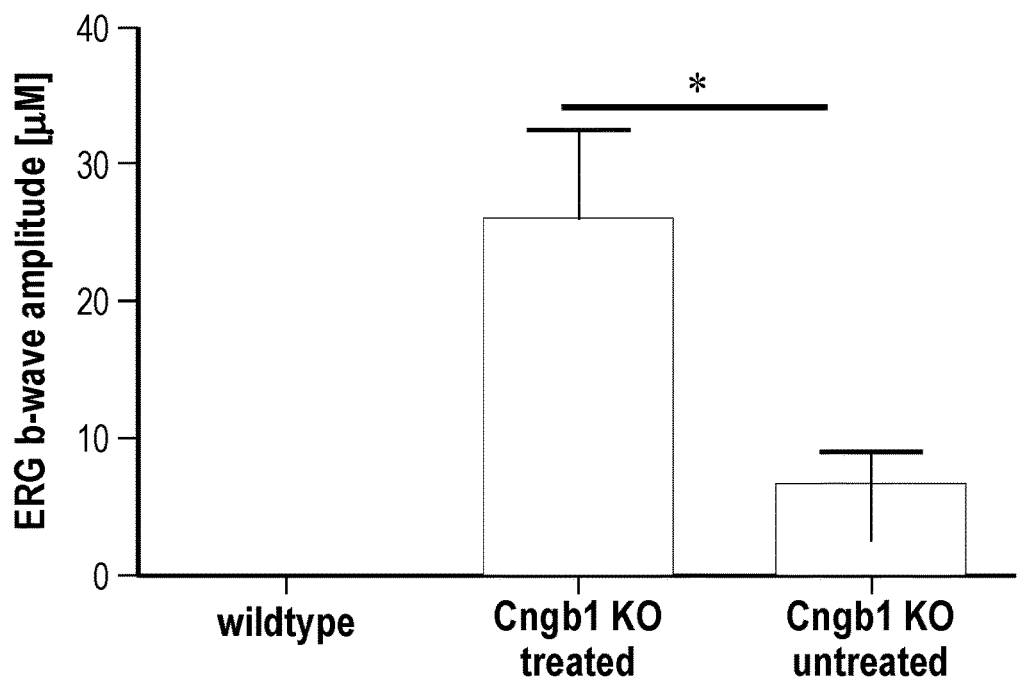

FIGS. 4A-4B show representative ERG measurements from CNGB1 (−/−) mice treated with the vector according to the invention; Electroretinography (ERG) measurement data from CNGB1 (−/−) mice treated in one eye with the vector according to the invention. (FIG. 4A) Representative ERG traces obtained upon 4.4 cd/m2 single flash stimulation. The hatched trace is from the treated eye and the black trace from the untreated eye of a CNGB1 (−/−) mouse at 4 months after treatment. (FIG. 4B) Summary graph showing the ERG b-wave amplitudes measured under the same conditions from wild type mice (grey), treated CNGB1 (−/−) mice (dark grey) and untreated CNGB1 (−/−) mice (black). *p<0.05, Student's t-test, N=4.

FIGS. 5A-5C show optical coherence tomography (OCT) measurements of photoreceptor layer thickness from CNGB1 (−/−) mice treated in one eye with the vector according to the invention. (FIGS. 5A-5B) Representative OCT scans from treated (FIG. 5A) and untreated eye (FIG. 5B). The thickness of the photoreceptor layer is marked with a vertical black bar. Quantification of photoreceptor layer thickness using OCT (FIG. 5C). ***p<0.001, 1 way ANOVA, N=9.

Figure 6B:
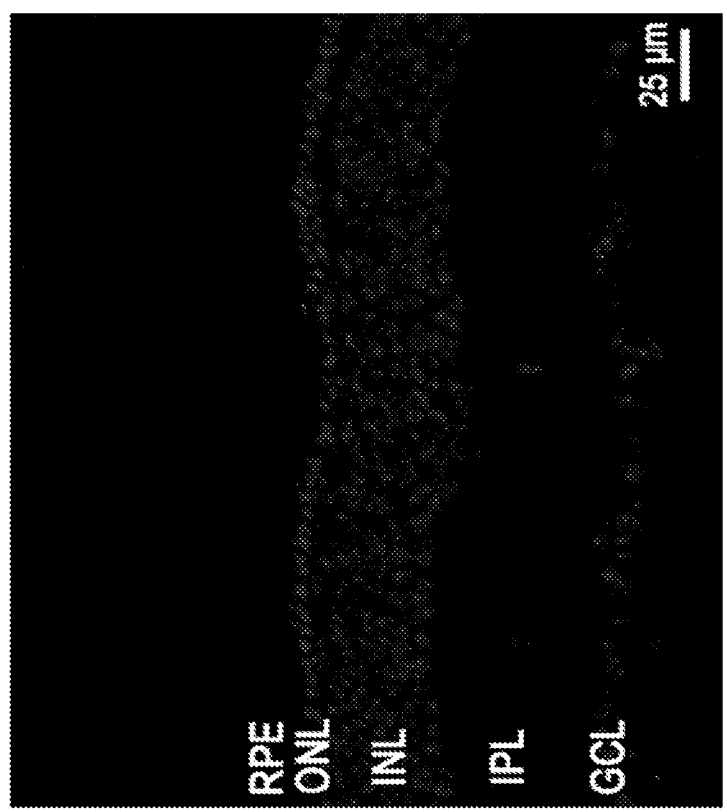
Figure 6A:

FIGS. 6A-6B depict representative confocal images from immunohistological stainings of hCNGB1 in CNGB1 (–/–) mice treated with the vector according to the invention (FIG. 6A) or untreated (FIG. 6B).

Figure 7:

FIG. 7 depicts a schematic showing the general vector design according to the invention.

Figure 8A:
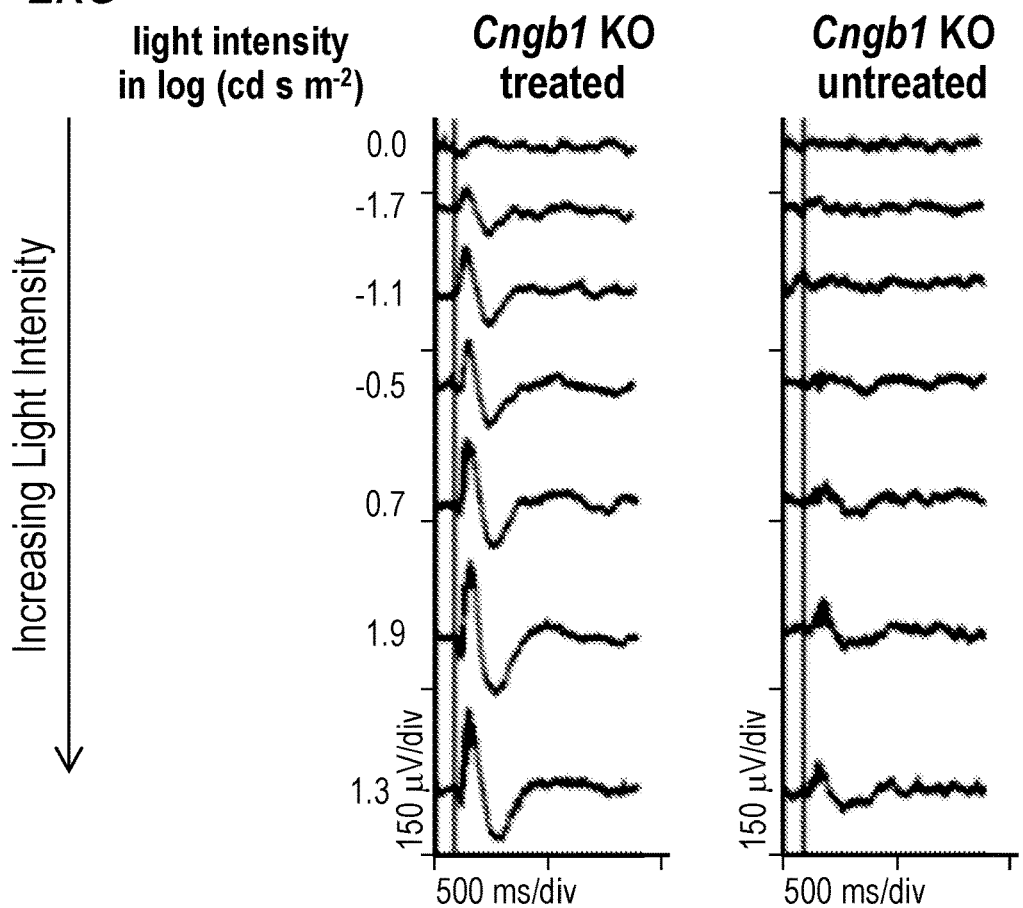
Figure 8B:
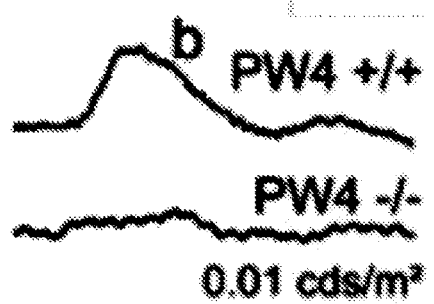

FIGS. 8A-8B show representative ERG measurements from CNGB1 (–/–) mice treated with the vector according to the invention (FIG. 8A). Representative ERG measurements in wild-type and CNGB1 (–/–) mice before treatment (FIG. 8B).

FIGS. 9A-9B depict representative confocal images from immunohistological stainings of hCNGB1 in CNGB1 (–/–) mice treated with the vector according to the invention (FIG. 9A), and untreated mice (FIG. 9B).

FIGS. 10A-10C depict OCT analysis revealing a significant delay in retinal degeneration. General injection schedule of the vector according to the invention (FIG. 10A). OCT images collected at 9 months in CNGB1 (–/–) mice treated with the vector according to the invention (FIG. 10B), and untreated mice (FIG. 10C).

Figure 11A:
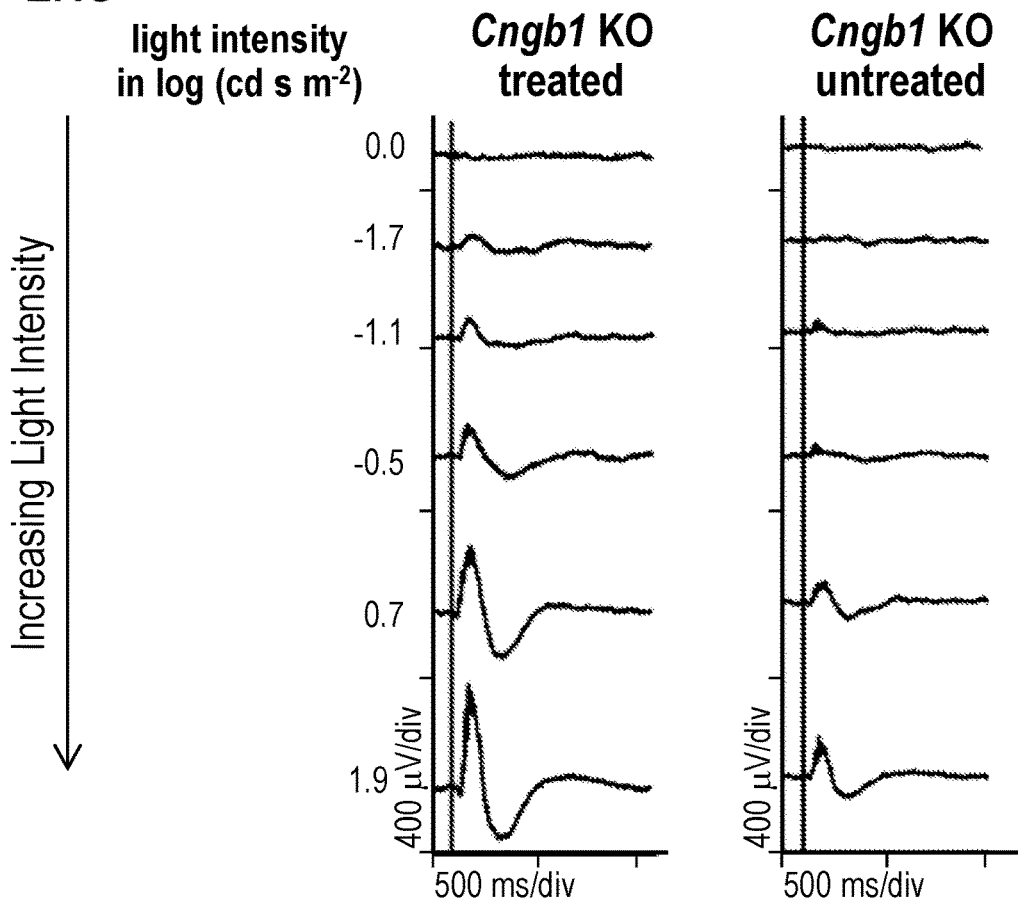
Figure 11B:
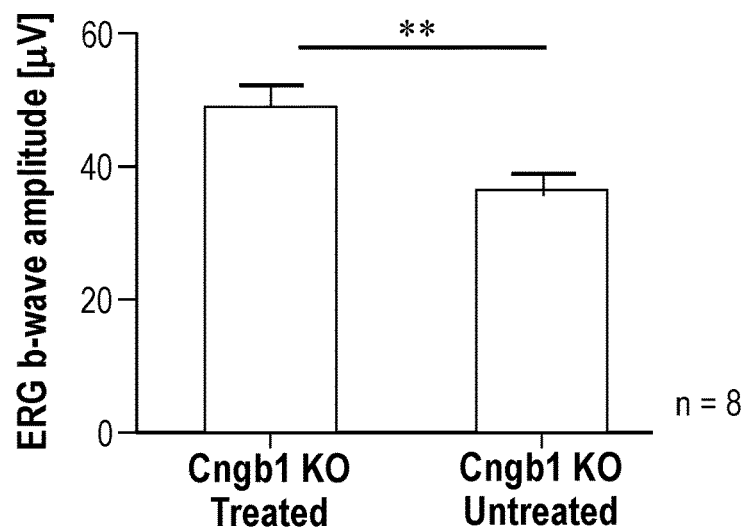
Figure 11C:
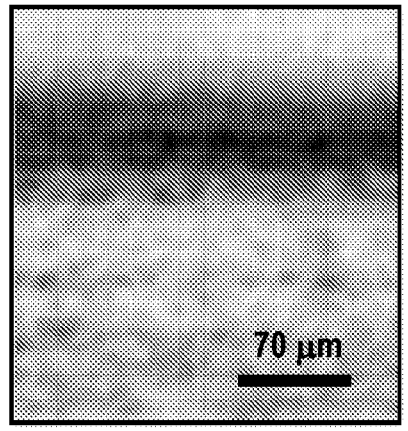
Figure 11D:
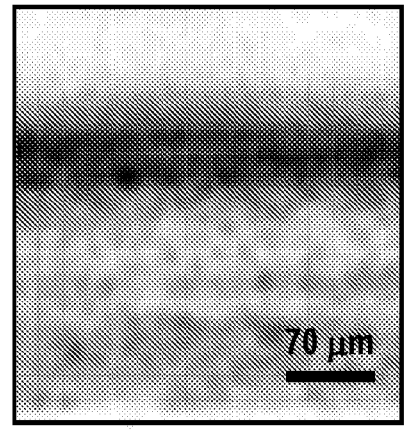
Figure 11E:
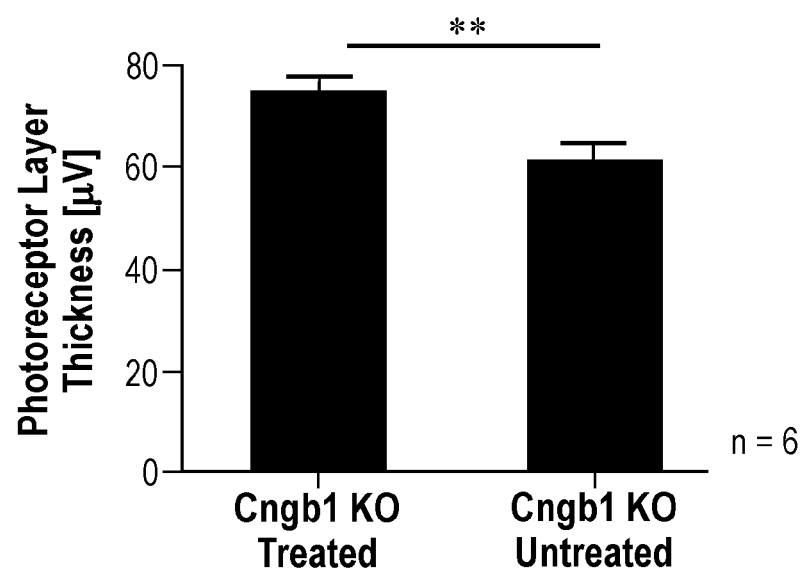

FIGS. 11A-11E depict restoration of rod function by two months in CNGB1 (–/–) mice treated with the vector according to the invention. Representative ERG B-wave measurements in CNGB1 (–/–) mice treated with the vector according to the invention, and untreated mice (FIG. 11A) Summary graph showing the ERG b-wave amplitudes measured in response to a light stimulus of –0.5 log (cd s/m2) in CNGB1 (–/–) mice treated with the vector according to the invention, and untreated mice (FIG. 11B). OCT measurements of photoreceptor layer thickness from CNGB1 (–/–) mice treated with the vector according to the invention (FIG. 11C), and untreated mice (FIG. 11D). Quantification of photoreceptor layer thickness using OCT (FIG. 11E). N=6.

Figure 12A:
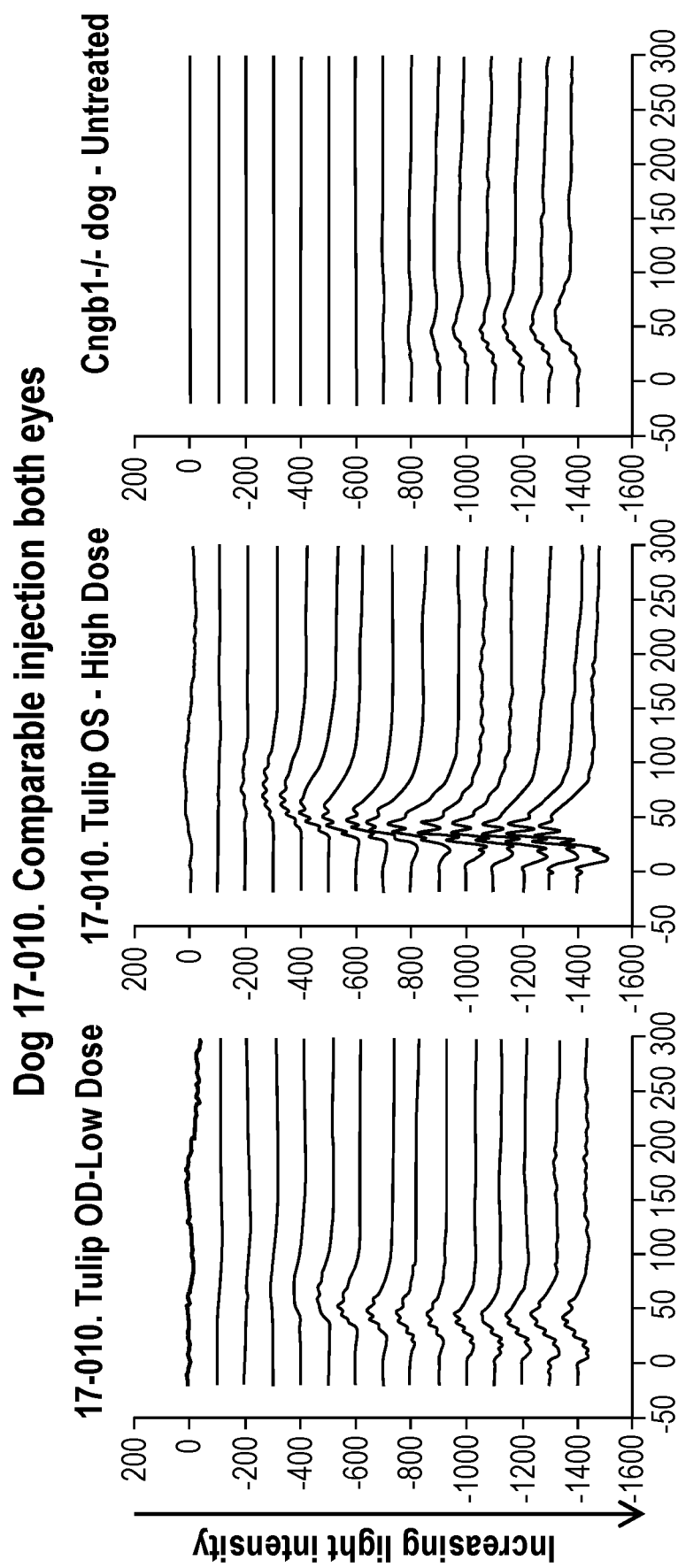
Figure 12B:
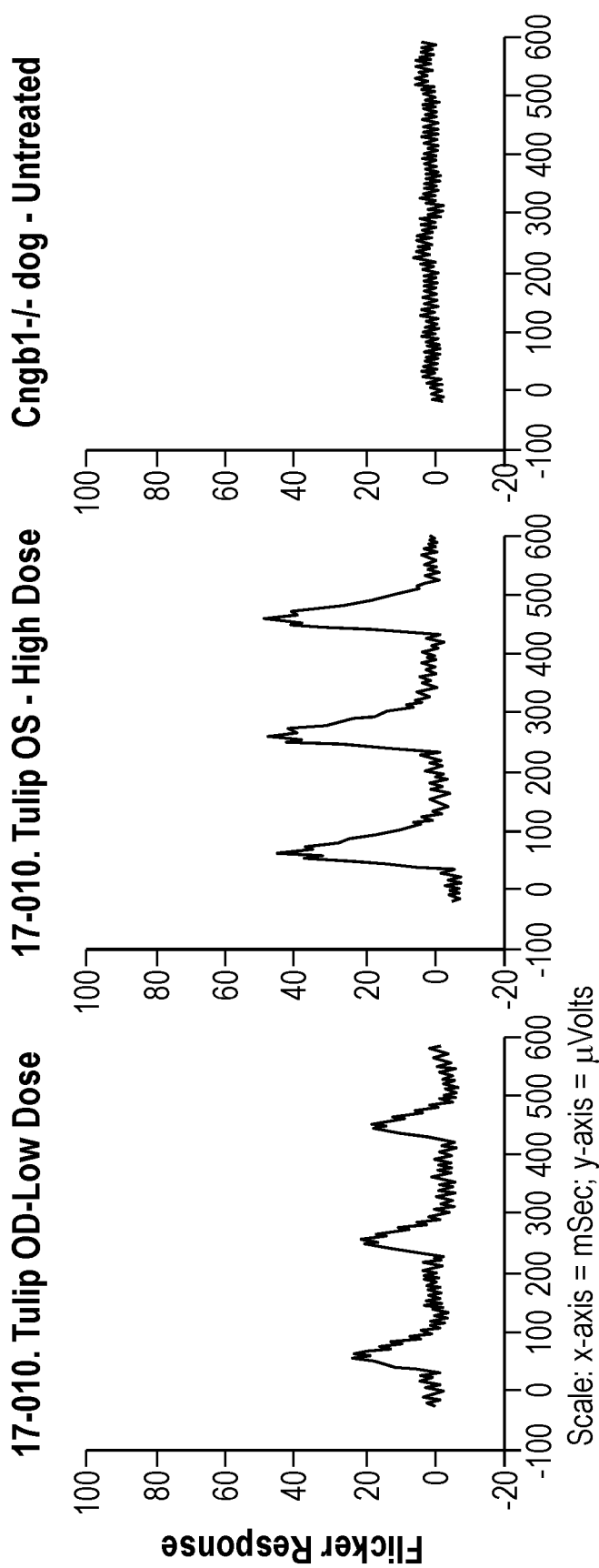

FIGS. 12A-12B depict obvious ERG rescue observed in eyes of CNGB1 (–/–) dogs treated with the vector according to the invention, and untreated dogs, using a rod-specific stimulus (FIG. 12A), and a flicker response (FIG. 12B).

Figure 13A:
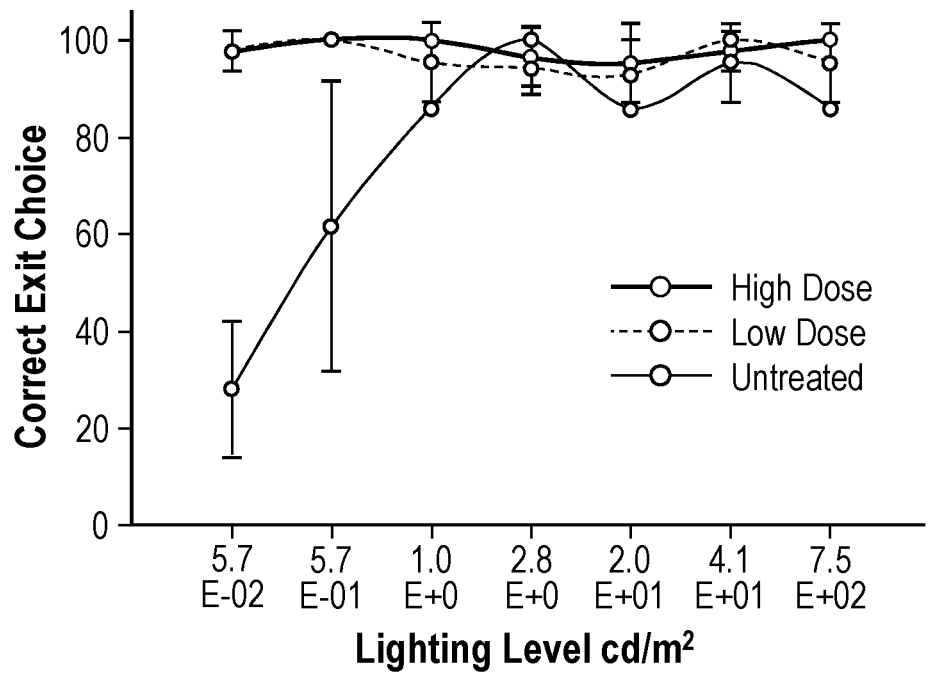
Figure 13B:
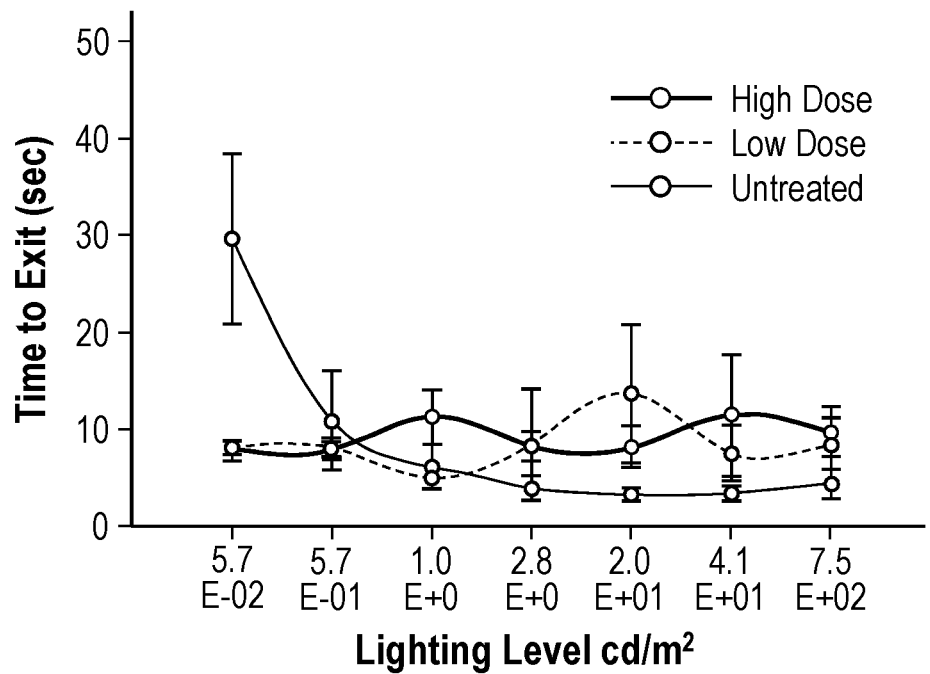

FIGS. 13A-13B depict vision testing data showing that CNGB1 (–/–) dogs treated with the vector according to the invention have rod-mediated vision and improved vision testing performance. Restored rod vision indicated by improved performance in correct exit choice (FIG. 13A), and time to exit (FIG. 13B).

Figure 14A:
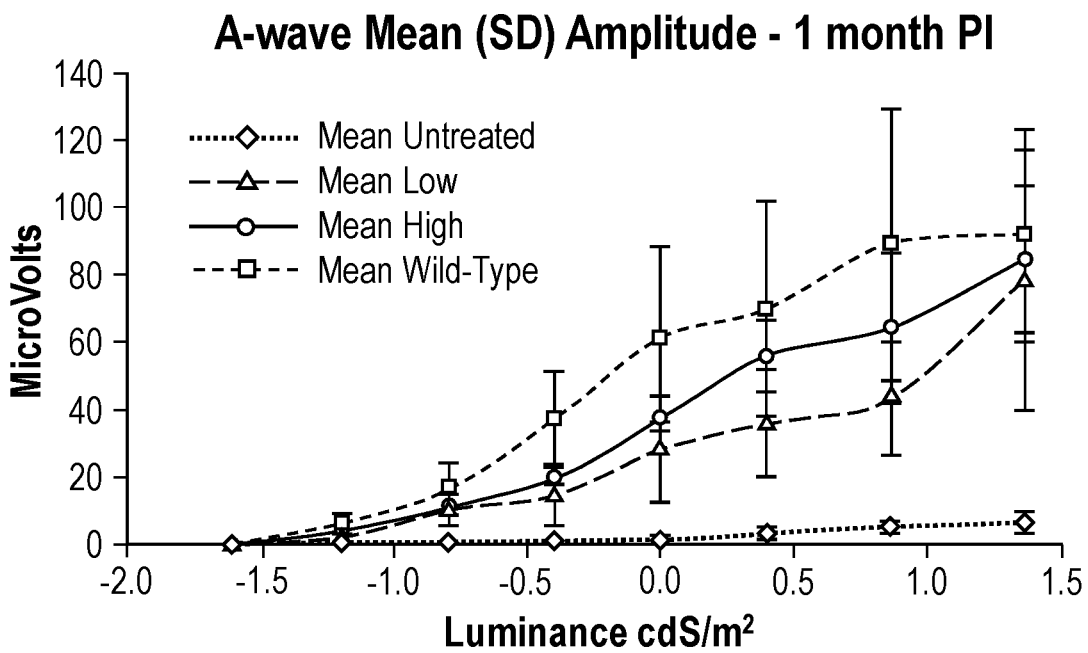
Figure 14B:
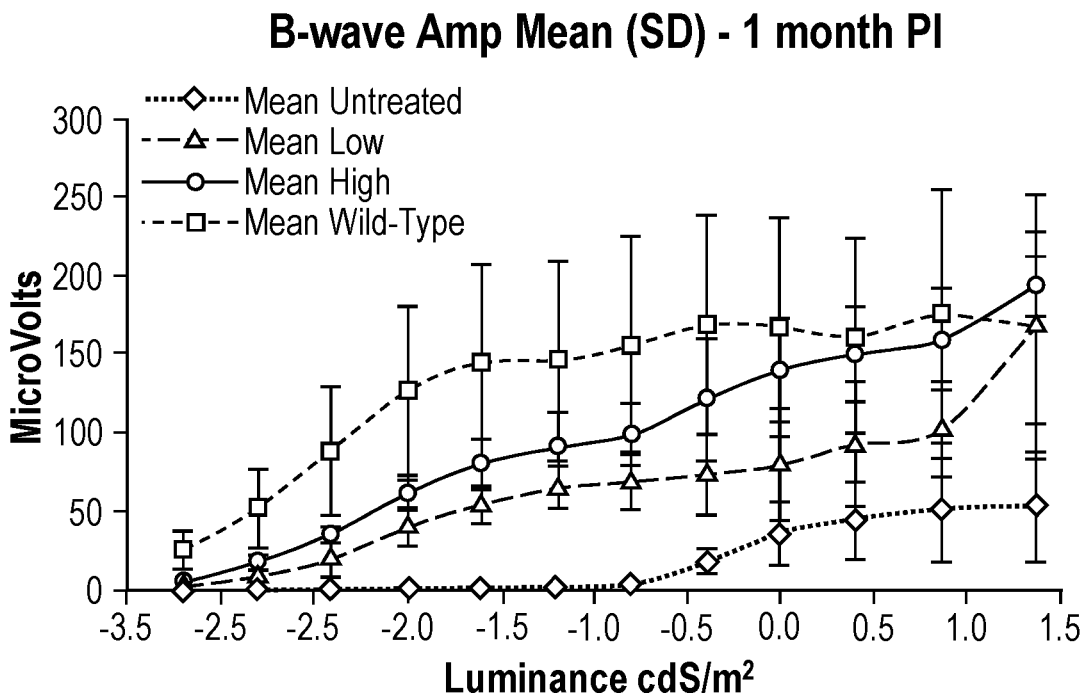

FIG. 14 depict ERG measurements showing improvement in A- and B-wave amplitude in CNGB1 (–/–) dogs treated with the vector according to the invention. A-wave amplitude indicated-improvement in response threshold in treated eyes was found to be greater than 1.5 log units (FIG. 14A). B-wave amplitude-indicated improvement in response threshold in treated eyes was found to be greater than 2 log units (FIG. 14B).

LIST OF SEQUENCES

SEQ ID NO: 1 Sequence of a 99 nucleotides long fragment of the human rhodopsin promoter comprising the core tissue specific elements;

SEQ ID NO: 2 Sequence of a 350 nucleotides long fragment of the human rhodopsin promoter comprising the tissue specific elements and the transcriptional start site;
SEQ ID NO: 3 Sequence of the human CNGB1 protein;
SEQ ID NO: 4 Sequence of a polyadenylation signal SV40;
SEQ ID NO: 5 Sequence of the left inverted terminal repeat (L-ITR);
SEQ ID NO: 6 Sequence of the right inverted terminal repeat (R-ITR);
SEQ ID NO: 7 Sequence of vector construct: pGL2.0-hRho194-hCNGB1a-SV40;
SEQ ID NO: 8 Sequence of the human CNGB1 gene;
SEQ ID NO: 9 Sequence of a fragment of the human rhodopsin promoter 194 bp;
SEQ ID NO: 10 Sequence of the human Abca4 protein;
SEQ ID NO: 11 Sequence of the human AIPL1 protein;
SEQ ID NO: 12 Sequence of the human BEST1 protein;
SEQ ID NO: 13 Sequence of the human CACNA1F protein;
SEQ ID NO: 14 Sequence of the human CLN3 protein;
SEQ ID NO: 15 Sequence of the human CLRN1 protein;
SEQ ID NO: 16 Sequence of the human CNGA1 protein;
SEQ ID NO: 17 Sequence of the human CEP290 protein;
SEQ ID NO: 18 Sequence of the human CRB1 protein;
SEQ ID NO: 19 Sequence of the human CRB2 protein;
SEQ ID NO: 20 Sequence of the human CRX protein;
SEQ ID NO: 21 Sequence of the human GPR98 protein;
SEQ ID NO: 22 Sequence of the human GUCA1A protein;
SEQ ID NO: 23 Sequence of the human GUCA1B protein;
SEQ ID NO: 24 Sequence of the human MYO7A protein;
SEQ ID NO: 25 Sequence of the human NRL protein;
SEQ ID NO: 26 Sequence of the human PDE6A protein;
SEQ ID NO: 27 Sequence of the human PDE6B protein;
SEQ ID NO: 28 Sequence of the human PRPH2 protein;
SEQ ID NO: 29 Sequence of the human PROM1 protein;
SEQ ID NO: 30 Sequence of the human RHO protein;
SEQ ID NO: 31 Sequence of the human ROM1 protein;
SEQ ID NO: 32 Sequence of the human RP1 protein;
SEQ ID NO: 33 Sequence of the human RP2 protein;
SEQ ID NO: 34 Sequence of the human RPGR protein;
SEQ ID NO: 35 Sequence of the human SAG protein;
SEQ ID NO: 36 Sequence of the human USH1C protein;
SEQ ID NO: 37 Sequence of the human USH1G protein;
SEQ ID NO: 38 Sequence of the human USH2A protein;
SEQ ID NO: 39 Sequence of the human NR2E3 protein;
SEQ ID NO: 40 Sequence of the human CNGB1 protein (next generation sequencing; NGS);
SEQ ID NO: 41 Sequence of the human CNGB1 protein (GenBank NG_016351);
SEQ ID NO: 42 Sequence of 5'ITR-hRHO promoter-CNGB1a-SV40polyA-3'ITR;
SEQ ID NO: 43 Sequence of 5'ITR-hRHO promoter-CNGB1a-SV40polyA-3'ITR (NGS);
SEQ ID NO: 44 Sequence of 5'ITR-hRHO promoter-CNGB1a-SV40polyA-3'ITR (GenBank); and
SEQ ID NO: 45 Sequence of the human RPE65 protein.

DETAILED DESCRIPTION OF THE INVENTION

Before the present invention is described in detail below, it is to be understood that this invention is not limited to the particular methodology, protocols and reagents described herein as these may vary. It is also to be understood that the terminology used herein is for the purpose of describing particular embodiments only, and is not intended to limit the scope of the present invention which will be limited only by the appended claims. Unless defined otherwise, all technical and scientific terms used herein have the same meanings as commonly understood by one of ordinary skill in the art.

Several documents are cited throughout the text of this specification. Each of the documents cited herein (including all patents, patent applications, scientific publications, manufacturer's specifications, instructions etc.), whether supra or infra, is hereby incorporated by reference in its entirety. Nothing herein is to be construed as an admission that the invention is not entitled to antedate such disclosure by virtue of prior invention. Some of the documents cited herein are characterized as being "incorporated by reference". In the event of a conflict between the definitions or teachings of such incorporated references and definitions or teachings recited in the present specification, the text of the present specification takes precedence.

In the following, the elements of the present invention will be described. These elements are listed with specific embodiments, however, it should be understood that they may be combined in any manner and in any number to create additional embodiments. The variously described examples and preferred embodiments should not be construed to limit the present invention to only the explicitly described embodiments. This description should be understood to support and encompass embodiments which combine the explicitly described embodiments with any number of the disclosed and/or preferred elements. Furthermore, any permutations and combinations of all described elements in this application should be considered disclosed by the description of the present application unless the context indicates otherwise.

Definitions practice the present invention, unless otherwise indicated, conventional methods of chemistry, biochemistry, and recombinant DNA techniques are employed which are explained in the literature in the field (cf., e.g., *Molecular Cloning: A Laboratory Manual*, $2^{nd}$ Edition, J. Sambrook et al. eds., Cold Spring Harbor Laboratory Press, Cold Spring Harbor 1989).

In the following, some definitions of terms frequently used in this specification are provided. These terms will, in each instance of its use, in the remainder of the specification have the respectively defined meaning and preferred meanings.

As used in this specification and the appended claims, the singular forms "a", "an", and "the" include plural referents, unless the content clearly dictates otherwise.

The term "nucleic acid" as used in this specification comprises polymeric or oligomeric macromolecules, or large biological molecules, essential for all known forms of life. Nucleic acids, which include DNA (deoxyribonucleic acid) and RNA (ribonucleic acid), are made from monomers known as nucleotides. Most naturally occurring DNA molecules consist of two complementary biopolymer strands coiled around each other to form a double helix. The DNA strand is also known as polynucleotides consisting of nucleotides. Each nucleotide is composed of a nitrogen-containing nucleobase as well as a monosaccharide sugar called deoxyribose or ribose and a phosphate group. Naturally occurring nucleobases comprise guanine (G), adenine (A), thymine (T), uracil (U) or cytosine (C). The nucleotides are joined to one another in a chain by covalent bonds between the sugar of one nucleotide and the phosphate of the next, resulting in an alternating sugar-phosphate backbone. If the sugar is deoxyribose, the polymer is DNA. If the sugar is ribose, the polymer is RNA. Typically, a polynucleotide is formed through phosphodiester bonds between the individual nucleotide monomers. In the context of the present invention the term "nucleic acid" includes but is not limited to ribonucleic acid (RNA), deoxyribonucleic acid (DNA), and mixtures thereof such as e.g. RNA-DNA hybrids (within one strand), as well as cDNA, genomic DNA, recombinant DNA, cRNA and mRNA. A nucleic acid may consist of an entire gene, or a portion thereof, the nucleic acid may also be a miRNA, siRNA, piRNA or shRNA. miRNAs are short ribonucleic acid (RNA) molecules, which are on average 22 nucleotides long but may be longer and which are found in all eukaryotic cells, i.e. in plants, animals, and some viruses, which functions in transcriptional and post-transcriptional regulation of gene expression. miRNAs are post-transcriptional regulators that bind to complementary sequences on target messenger RNA transcripts (mRNAs), usually resulting in translational repression and gene silencing. Small interfering RNAs (siRNAs), sometimes known as short interfering RNA or silencing RNA, are short ribonucleic acid (RNA molecules), between 20-25 nucleotides in length. They are involved in the RNA interference (RNAi) pathway, where they interfere with the expression of specific genes. A short hairpin RNA (shRNA) also referred to as small hairpin RNA is an artificial RNA molecule with a tight hairpin turn that can be used to silence target gene expression via RNA interference (RNAi). Expression of shRNA in cells is typically accomplished by delivery of plasmids or through viral vectors.

The term "polynucleotide" when used in the context of the present invention, refers to a nucleic acid not restricted to a specific number of nucleotides in length.

The term "human rod photoreceptor" used in the context of the present invention refers to a special type of cells, i.e. photoreceptor cells. The retina of the human eye contains two type of photoreceptor: rods and cones. On average, there are approximately 90 million rod cells in the human retina. Rods are more sensitive than cones. However, they are not sensitive to color. They are responsible for dark-adapted, or scotopic, vision. Rods are usually found concentrated at the outer edges of the retina and are used in peripheral vision. Thus, the peripheral vision is more light-sensitive, enabling one to see dimmer objects in your peripheral vision. Rod cells are more sensitive than cone cells and are almost entirely responsible for night vision. Rods employ a sensitive photopigment called rhodopsin. Photoreceptors are highly specialized, light-sensitive neurons and designed for capturing light quanta triggering a change in the cell's membrane potential. Rod photoreceptors enable dim light vision, whereas cone photoreceptors mediate color vision and high visual acuity under brighter light conditions. Only one type of rod photoreceptor, carrying the rhodopsin visual pigment, is present in the vertebrate retina, including in mouse and human. When in its 'ready to be activated' state, each opsin molecule is covalently bound to a light-sensitive chromophore, 11-cis retinal. Upon photon capture, the chromophore isomerizes to all-trans retinal, causing a conformational change in rhodopsin and activation to meta-rhodopsin II. This initiates the process of phototransduction, a cascade of biochemical events that culminate in closure of ionic channels in the cell membrane hyperpolarization of the photoreceptor and transmission of the signal(s) to second-order neurons in the inner retina via modulation of neurotransmitter release at the synaptic terminals. The integrity and function of photoreceptors are absolutely crucial for vision, and mutations that affect photoreceptor function or survival disrupt the phototransduction process, leading to vision loss.

The term "promoter" in the context of the present invention refers to a nucleotide sequence that comprises both elements required for transcription control including binding sites for transcriptional activator and repressor proteins and elements that initiate transcription. The binding sites for transcriptional activator and/or repressor proteins are typically located directly upstream or at the 5' end of the transcription initiation site comprised within the core promoter. Thus, RNA polymerase and the necessary transcription factors bind to the promoter sequence and initiate transcription. Promoter sequences define the direction of transcription and indicate which DNA strand will be transcribed; this strand is known as the sense strand. The promoter of the present invention transfers rod-photoreceptor specificity on a transgene that is positioned downstream, i.e. at the 3' end of the promoter.

The term "core promoter" (CP) is used herein in its ordinary sense to refer to a nucleotide region including a DNA regulatory sequence, wherein the regulatory sequence is derived from a gene which is capable of binding RNA polymerase and initiating transcription of a downstream (3'-direction) coding sequence. Thus, the core promoter is the minimal portion of the promoter required to properly initiate gene transcription and contains a binding site for RNA polymerase (RNA polymerase I, RNA polymerase II, or RNA polymerase III). The RNA polymerase binding site of the CP is approximately 25 to 35 bases upstream (5') from the transcriptional TSS. The core promoter may comprise a so-called TATA box (also called the Goldberg-Hogness box) which is a DNA sequence (cis-regulatory element) often found in the promoter region of genes in archaea and eukaryotes. The TATA box has the core DNA sequence 5'-TATAAA-3' or variants thereof, which is usually followed by three or more adenine bases. The TATA box is usually located 25-35 base pairs upstream of the transcription start site. The core promoter may also be TATA box-less. Genes lacking a TATA box use an initiator element or downstream core promoter instead. The core promoter may also comprise an initiator (Inr). An Inr consists of an initiator motif and is similar in function to the TATA box. The Inr element facilitates binding to transcription factor II D (TFIID).

The term "human rod photoreceptor specific promoter element" (hRPSPE) as used in the context of the present invention means a promoter element which mediates transcription of the downstream transgene only in rod cells, in particular in human rod cells. Use of the tissue-specific promoter allows a protein or a functional RNA to be expressed tissue-specifically in retina cells of the human eye. The hRPSPE only comprises parts or fragments of the naturally occurring human rod photoreceptor promoter sequence.

The term "gene" or "coding sequence" or a sequence which "encodes" a particular protein or peptide is used in the context of the invention to refer to a nucleic acid molecule that is transcribed (in the case of DNA) and translated (in the case of mRNA) into a polypeptide in vitro or in vivo when placed under the control of appropriate regulatory sequences. The boundaries of the gene are determined by a start codon at the 5' (i.e., amino) terminus and a translation stop codon at the 3' (i.e., carboxy) terminus. The term gene includes, but is not limited to prokaryotic or eukaryotic mRNA, cDNA, genomic DNA sequences from prokaryotic or eukaryotic DNA, and even synthetic DNA sequences. A transcription termination sequence will usually be located 3' to the gene sequence.

The term "transgene" is used in the context of the present invention to refer to a gene that is removed from its natural context and placed under the expression control of a heterologous promoter. An example of a transgene of the present invention is the "rod cyclic nucleotide-gated channel beta" (CNGB1) gene which encodes the rod cyclic nucleotide-gated channel beta subunit. In further embodiments transgenes may comprise the human proteins: ATP Binding Casette Subfamily A Member 4 (ABCA4), Aryl Hydrocarbon Receptor Interacting Protein Like 1 (AIPL1), Bestrophin 1 (BEST1), Calcium Voltage-Gated Channel Subunit Alpha 1 F (CACNA1F), Ceroid-Lipofuscinosis Neuronal 3 (CLN3), Clarin 1 (CLRN1), Cyclic Nucleotide Gated Channel Alpha 1 (CNGA1), Centrosomal Protein 290 (CEP290), Crumbs 1 (CRB1), Crumbs 2 (CRB2), Cone-Rod Homeobox (CRX), G-Protein Coupled Receptor 98 (GPR98), Guanylate Cyclase Activator 1A (GUCA1A), Guanylate Cyclase Activator 1B (GUCA1B), Myosin VIIA (MYO7A), Nuclear Receptor Subfamily 2 Group E Member 3 (NR2E3), Neural Retina Leucine Zipper (NRL), Phosphodiesterase 6A (PDE6A), Phosphodiesterase 6B (PDE6B), Peripherin 2 (PRPH2), Prominin 1 (PROM1), Rhodopsin (RHO), Retinal Outer Segment Membrane Protein 1 (ROM1), Retinitis Pigmentosa 1 Protein (RP1), Retinitis Pigmentosa 2 Protein (RP2), Retinal Pigment Epithelium Specific Protein 65 (RPE65), Retinitis Pigmentosa GTPase Regulator (RPGR), S-Antigen Visual Arrestin (SAG), Usher Syndrome Type-1C Protein (USH1C), Usher Syndrome Type-1G Protein (USH1G), Usher Syndrome Type-2A Protein (USH2A) or functional fragments or variants thereof. The amino acid sequences of particular embodiments of above proteins are indicated in SEQ ID NO: 10 to 41, and 45. Functional fragments are those fragments that maintain the function of the respective protein in normal function of the rod photoreceptor. Similarly, variants also maintain the function of the respective protein in the rod photoreceptor. Proteins with long amino acid sequences, for example human CACNA1F, CEP290, GPR98, MYO7A, RP1 and USH2A protein, which are too long to be encoded by a transgene deliverable by the respectively chosen vector system, in particular AAV vector. To fit the size limitation of AAV vectors "split vector" technologies using the development of an intein-mediated split system for gene therapy can be used. By the use of split-inteins the packaging limit of the AAV can be bypassed. Therefore, each half transgene of interest can be fused to the corresponding split-intein moiety and, only upon co-expression, the intein-mediated trans-splicing occurs and the full transgenic protein is reconstituted. Thus, it would be possible to construct two vectors encoding fragments of the transgenic protein that would upon co-transduction assemble in the target cell into the full-length functional protein.

The term "CNGB1" as used in the context of the present application refers to either the gene or the protein encoded by the CNGB1 gene, i.e. the rod photoreceptor cGMP-gated cation channel which helps regulate ion flow into the rod photoreceptor outer segment in response to light-induced alteration of the levels of intracellular cGMP. This channel consists of two subunits, alpha and beta, with the protein encoded by this gene representing the beta subunit. Diseases associated with CNGB1 and defects in this gene include Retinitis Pigmentosa 45 and CNGB1-related Retinitis Pigmentosa. The CNGB1 subunit of cyclic nucleotide-gated channels plays an important role in both visual and olfactory signal transduction. When associated with CNGA1, it is involved in the regulation of ion flow into the rod photoreceptor outer segment (ROS), in response to light-induced alteration of the levels of intracellular cGMP.

The term "proliferation" as used herein refers to an increase in the number of cells as a result of cell growth and cell division which may lead to either increased or decreased cell proliferation. Extensive cell proliferation occurs with hyperproliferative disorders, wherein the cell division of the cells is increased in relation to normal tissue. Such disorders are characterized by an abnormal proliferation (production) i.e. overproduction of cells. Hyperproliferative disorders comprise tumor diseases. Tumor diseases may comprise benign or malignant tumors wherein malignant tumor diseases are referred to as cancer. The term hyperproliferative disorder comprises cancers as well as pre-cancerous disorders. In particular embodiments the hyperproliferative disorders are hyperproliferative disorders of rod cells, in particular retinoblastoma.

The term "amino acid" generally refers to any monomer unit that comprises a substituted or unsubstituted amino group, a substituted or unsubstituted carboxy group, and one or more side chains or groups, or analogs of any of these groups. As used herein, the term "amino acid" includes the following twenty natural or genetically encoded alpha-amino acids: alanine (Ala or A), arginine (Arg or R), asparagine (Asn or N), aspartic acid (Asp or D), cysteine (Cys or C), glutamine (Gln or Q), glutamic acid (Glu or E), glycine (Gly or G), histidine (His or H), isoleucine (Ile or I), leucine (Leu or L), lysine (Lys or K), methionine (Met or M), phenylalanine (Phe or F), proline (Pro or P), serine (Ser or S), threonine (Thr or T), tryptophan (Trp or W), tyrosine (Tyr or Y), and valine (Val or V). In cases where "X" residues are undefined, these should be defined as "any amino acid." The structures of these twenty natural amino acids are shown in, e.g., Stryer et al., Biochemistry, 5th ed., Freeman and Company (2002). Additional amino acids, such as selenocysteine and pyrrolysine, can also be genetically coded for (Stadtman (1996) "Selenocysteine," Annu Rev Biochem. 65:83-100 and Ibba et al. (2002) "Genetic code: introducing pyrrolysine," Curr Biol. 12(13):R464-R466). Amino acids can be linked by peptide bonds to form peptides or polypeptides.

In the context of the present invention, the term "peptide" refers to a short polymer of amino acids linked by peptide bonds. It has the same chemical (peptide) bonds as proteins, but is commonly shorter in length. The shortest peptide is a dipeptide, consisting of two amino acids joined by a single peptide bond. There can also be a tripeptide, tetrapeptide, pentapeptide, etc. Typically, a peptide has a length of up to 8, 10, 12, 15, 18 or 20 amino acids. A peptide has an amino end and a carboxyl end, unless it is a cyclic peptide.

In the context of the present invention, the term "polypeptide" refers to a single linear chain of amino acids bonded together by peptide bonds and typically comprises at least about 21 amino acids. A polypeptide can be one chain of a protein that is composed of more than one chain or it can be the protein itself if the protein is composed of one chain.

The term "fragment" used herein refers to naturally occurring fragments (e.g. splice variants) as well as artificially constructed fragments, in particular to those obtained by gene-technological means. Typically, a fragment has a deletion of up to 1, 2, 3, 4, 5, 6, 7, 8, 9, 10, 15, 20, 25, 30, 35, 40, 45, 50, 55, 60, 65, 70, 75, 80, 85, 90, 95, 100, 110, 120, 130, 140, 150, 160, 170, 180, 190, 200, 210, 220, 230, 240, 250, 260, 270, 280, 290, or 300 amino acids at its N-terminus and/or at its C-terminus and/or internally as compared to the parent polypeptide, preferably at its N-terminus, at its N- and C-terminus, or at its C-terminus.

As used herein, the term "variant" is to be understood as a polypeptide or polynucleotide which differs in comparison to the polypeptide or polynucleotide from which it is derived by one or more changes in its length or sequence. The polypeptide or polynucleotide from which a polypeptide or polynucleotide variant is derived is also known as the parent polypeptide or polynucleotide. The term "variant" comprises "fragments" or "derivatives" of the parent molecule. Typically, "fragments" are smaller in length or size than the parent molecule, whilst "derivatives" exhibit one or more differences in their sequence in comparison to the parent molecule. Also encompassed are modified molecules such as but not limited to post-translationally modified proteins (e.g. glycosylated, biotinylated, phosphorylated, ubiquitinated, palmitoylated, or proteolytically cleaved proteins) and modified nucleic acids such as methylated DNA. Also mixtures of different molecules such as but not limited to RNA-DNA hybrids, are encompassed by the term "variant". Typically, a variant is constructed artificially, preferably by gene-technological means, whilst the parent protein or polynucleotide is a wild-type protein or polynucleotide, or a consensus sequence thereof. However, also naturally occurring variants are to be understood to be encompassed by the term "variant" as used herein. Further, the variants usable in the present invention may also be derived from homologs, orthologs, or paralogs of the parent molecule or from artificially constructed variant, provided that the variant exhibits at least one biological activity of the parent molecule, i.e. is functionally active.

In particular, the term "peptide variant", or "polypeptide variant" is to be understood as a peptide, polypeptide, or protein which differs in comparison to the peptide, polypeptide, or protein from which it is derived by one or more changes in the amino acid sequence. The peptide, polypeptide, or protein, from which a peptide, polypeptide, or protein variant is derived, is also known as the parent peptide, polypeptide, or protein. Further, the variants usable in the present invention may also be derived from homologs, orthologs, or paralogs of the parent peptide, polypeptide, or protein or from artificially constructed variant, provided that the variant exhibits at least one biological activity of the parent peptide, polypeptide, or protein. The changes in the amino acid sequence may be amino acid exchanges, insertions, deletions, N-terminal truncations, or C-terminal truncations, or any combination of these changes, which may occur at one or several sites. A peptide, polypeptide, or protein variant may exhibit a total number of up to 200 (up to 1, 2, 3, 4, 5, 6, 7, 8, 9, 10, 15, 20, 25, 30, 35, 40, 45, 50, 55, 60, 65, 70, 75, 80, 85, 90, 95, 100, 110, 120, 130, 140, 150, 160, 170, 180, 190, or 200) changes in the amino acid sequence (i.e. exchanges, insertions, deletions, N-terminal truncations, and/or C-terminal truncations). The amino acid exchanges may be conservative and/or non-conservative. Alternatively or additionally, a "variant" as used herein, can be characterized by a certain degree of sequence identity to the parent peptide, polypeptide, or protein from which it is derived. More precisely, a peptide, polypeptide, or protein variant in the context of the present invention exhibits at least 80% sequence identity to its parent peptide, polypeptide, or protein. The sequence identity of peptide, polypeptide, or protein variants is over a continuous stretch of 20, 30, 40, 45, 50, 60, 70, 80, 90, 100 or more amino acids.

The "percentage of sequences identity" is determined by comparing two optimally aligned sequences over a comparison window, wherein the portion of the sequence in the comparison window can comprise additions or deletions (i.e. gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison and multiplying the result by 100 to yield the percentage of sequence identity.

The term "identical" in the context of two or more nucleic acids or polypeptide sequences, refers to two or more sequences or subsequences that are the same, i.e. comprise the same sequence of nucleotides or amino acids. Sequences are "substantially identical" to each other if they have a specified percentage of nucleotides or amino acid residues that are the same (e.g., at least 70%, at least 75%, at least 80, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% identity over the aligned region), when compared and aligned for maximum correspondence over a comparison window, or designated region as measured using one of the following sequence comparison algorithms or by manual alignment and visual inspection. These definitions also refer to the complement of a test sequence. Accordingly, the term "at least 80% sequence identity" is used throughout the specification with regard to polypeptide and polynucleotide sequence comparisons. This expression preferably refers to a sequence identity of at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% to the respective reference polypeptide or to the respective reference polynucleotide.

The term "sequence comparison" refers to the process wherein one sequence acts as a reference sequence, to which test sequences are compared. When using a sequence comparison algorithm, test and reference sequences are entered into a computer, if necessary subsequence coordinates are designated, and sequence algorithm program parameters are designated. Default program parameters are commonly used, or alternative parameters can be designated. The sequence comparison algorithm then calculates the percent sequence identities or similarities for the test sequences relative to the reference sequence, based on the program parameters. In case where two sequences are compared and the reference sequence is not specified in comparison to which the sequence identity percentage is to be calculated, the sequence identity is to be calculated with reference to the longer of the two sequences to be compared, if not specifically indicated otherwise. If the reference sequence is indicated, the sequence identity is determined on the basis of the full length of the reference sequence indicated by SEQ ID, if not specifically indicated otherwise.

"Operably linked" as used in the context of the present invention refers to an arrangement of elements, wherein the components so described are configured so as to perform their usual function. A nucleic acid is "operably linked" when it is placed into a functional relationship with another nucleic acid sequence. For example, a promoter is operably linked to one or more transgenes, if it affects the transcription of the one or more transgenes. Further, control elements operably linked to a coding sequence are capable of effecting the expression of the coding sequence. The control elements need not be contiguous with the coding sequence, so long as they function to direct the expression thereof. Thus, for example, intervening untranslated yet transcribed sequences can be present between a promoter sequence and the coding sequence and the promoter sequence can still be considered "operably linked" to the coding sequence.

The term "polyadenylation signal" (PAS) as used herein refers to a sequence involved in the process of mature messenger RNA (mRNA) production for translation. It, therefore, forms part of the larger process of gene expression. The process of polyadenylation begins as the transcription of a gene terminates. The 3'-most segment of the newly made pre-mRNA is first cleaved off by a set of proteins; these proteins then synthesize the poly(A) tail at the RNA's 3' end. In some genes these proteins add a poly(A) tail at one of several possible sites. Therefore, polyadenylation can produce more than one transcript from a single gene (alternative polyadenylation), similar to alternative splicing. The poly(A) tail is important for the nuclear export, translation, and stability of mRNA. The tail is shortened over time, and, when it is short enough, the mRNA is enzymatically degraded. However, in a few cell types, mRNAs with short poly(A) tails are stored for later activation by re-polyadenylation in the cytosol. The PAS of the present invention may comprise a nucleic acid encoding a short Simian-Virus 40 (SV40) poly adenylation signal (SV 40 PAS). This modification of the polynucleotide has the advantage that expression of the gene of interest, for example the hCNGB1 in photoreceptor cells is significantly enhanced. The long-term expression that is achieved by the inclusion of SV40 PAS qualifies the polynucleotide for its use as an active gene therapy agent. In particular, the PAS can comprise the nucleic acid sequence according to SEQ ID NO: 4.

As used in this specification the term "vector", also referred to as an expression construct, is usually a virus designed for protein expression in cells. The term "vector" refers to a protein or a polynucleotide or a mixture thereof which is capable of being introduced or of introducing proteins and/or nucleic acids comprised therein into a cell. Examples of vectors include but are not limited to plasmids, cosmids, phages, viruses or artificial chromosomes. In particular, a vector is used to transport the promoter and transgene of the invention into a suitable host cell. Vectors may contain "replicon" polynucleotide sequences that facilitate the autonomous replication of the vector in a host cell. Foreign DNA is defined as heterologous DNA, which is DNA not naturally found in the host cell, which, for example, replicates the vector molecule, encodes a selectable or screenable marker, or encodes a transgene. Once in the host cell, the vector can replicate independently of or coincidental with the host chromosomal DNA, and several copies of the vector and its inserted DNA can be generated. In addition, the vector can also contain the necessary elements that permit transcription of the inserted DNA into an mRNA molecule or otherwise cause replication of the inserted DNA into multiple copies of RNA. Vectors may further encompass "expression control sequences" that regulate the expression of the gene of interest. Typically, expression control sequences are polypeptides or polynucleotides such as but not limited to promoters, enhancers, silencers, insulators, or repressors. In a vector comprising more than one polynucleotide encoding for one or more gene products of interest, the expression may be controlled together or separately by one or more expression control sequences. More specifically, each polynucleotide comprised on the vector may be control by a separate expression control sequence or all polynucleotides comprised on the vector may be controlled by a single expression control sequence. Polynucleotides comprised on a single vector controlled by a single expression control sequence may form an open reading frame. Some expression vectors additionally contain sequence elements adjacent to the inserted DNA that increase the half-life of the expressed mRNA and/or allow translation of the mRNA into a protein molecule. Many molecules of mRNA and polypeptide encoded by the inserted DNA can thus be rapidly synthesized.

The term "AAV vector" as used in the context of the present invention refers to a complete virus particle, i.e., including a linear, single-stranded AAV nucleic acid genome associated with an AAV capsid protein coat. In this regard, single-stranded AAV nucleic acid molecules of either complementary sense (i.e., "sense" or "antisense" strands) can be packaged into any one AAV virion; both strands are equally infectious. The AAV vector of the present invention may also be an infectious and replication-defective virus composed of an AAV protein shell, encapsidating a heterologous DNA molecule of interest (e.g., hCNGB1) which may be flanked on both sides by an AAV ITR. An exemplary AAV 5' ITR has the nucleic acid sequence according to SEQ ID NO: 5 and an exemplary AAV 3' ITR has the nucleic acid sequence of the complement of SEQ ID NO: 6. An AAV vector of the present invention may be produced in a suitable host cell which has had an AAV vector, AAV helper functions and accessory functions introduced therein. In this manner, the host cell is rendered capable of encoding AAV polypeptides that are required for packaging the AAV genome (i.e., containing a recombinant nucleotide sequence of interest) into recombinant virion particles for subsequent gene delivery.

Various naturally occurring serotypes of adeno-associated virus (AAV), including 12 human serotypes (AAV1, AAV2, AAV3, AAV4, AAV5, AAV6, AAV7, AAV8, AAV9, AAV10, AAV11, and AAV12) and several serotypes from nonhuman primates have been identified. The different AAV serotypes also differ in their genome sequence, e.g. in the sequence of the inverted terminal repeats (ITRs) or the sequence encoding the capsid. The term "AAV genome" as used in the context of the present invention refers to any nucleic acid sequence derived from an adeno-associated virus serotype, including, without limitation, AAV-1, AAV-2, AAV-3, AAV-4, AAV-5, AAV-9, AAV-7, etc. AAV genome can have one or more of the AAV wild-type genes deleted in whole or in part, preferably the Rep and/or Cap genes, but retain functional flanking inverted terminal repeat ("ITR") sequences. Functional ITR sequences are generally necessary for the rescue, replication and packaging of the AAV genome. Thus, an AAV genome is defined herein to include at least those sequences required in cis for replication and packaging (e.g., functional ITRs) of the virus. The ITRs need not be the wild-type nucleotide sequences, and may be altered (e.g., by the insertion, deletion or substitution of nucleotides) so long as the sequences provide for functional rescue, replication and packaging. The ITRs may comprise sequences according to SEQ ID NO: 5 and/or SEQ ID NO: 6.

"Antibodies" as used in the context of the present invention are glycoproteins belonging to the immunoglobulin superfamily; the terms antibody and immunoglobulin are often used interchangeably. An antibody refers to a protein molecule produced by plasma cells and is used by the immune system to identify and neutralize foreign objects such as bacteria and viruses. The antibody recognizes a unique part of the foreign target, its antigen.

The term "antibody binding fragment" as used herein, refers to one or more fragments of an antibody that retain the ability to specifically bind to an antigen. Examples of binding fragments encompassed within the term "antibody binding fragment" include a fragment antigen binding (Fab) fragment, a Fab' fragment, a F(ab')$_2$ fragment, a heavy chain antibody, a single-domain antibody (sdAb), a single-chain fragment variable (scFv), a fragment variable (Fv), a V$_H$ domain, a V$_L$, domain, a single domain antibody, a nanobody, an IgNAR (immunoglobulin new antigen receptor), a di-scFv, a bispecific T-cell engager (BITEs), a dual affinity re-targeting (DART) molecule, a triple body, a diabody, a single-chain diabody, an alternative scaffold protein, and a fusion protein thereof.

The term "pharmaceutical composition" as used in the present application include the formulation of the active compound or ingredient, i.e. the polynucleotide, the plasmid and/or the vector of the present invention and refers to a substance and/or a combination of substances being used for the identification, prevention, maintenance or treatment of a tissue status or disease. The pharmaceutical composition is formulated to be suitable for administration to a patient in order to prevent and/or treat disease and/or maintain the physiological state. Further a pharmaceutical composition refers to the combination of an active agent with a carrier, inert or active, making the composition suitable for therapeutic use. Pharmaceutical compositions can be formulated for oral, parenteral, topical, inhalative, rectal, sublingual, transdermal, subcutaneous or vaginal application routes according to their chemical and physical properties. Pharmaceutical compositions comprise solid, semisolid, liquid, transdermal therapeutic systems (TTS). Solid compositions are selected from the group consisting of tablets, coated tablets, powder, granulate, pellets, capsules, effervescent tablets or transdermal therapeutic systems. Also comprised are liquid compositions, selected from the group consisting of solutions, syrups, infusions, extracts, solutions for intravenous application, solutions for infusion or solutions of the carrier systems of the present invention. Semisolid compositions that can be used in the context of the invention comprise emulsion, suspension, creams, lotions, gels, globules, buccal tablets and suppositories.

"Pharmaceutically acceptable" means approved by a regulatory agency of the Federal or a state government or listed in the U.S. Pharmacopeia or other generally recognized pharmacopeia for use in animals, and more particularly in humans.

A "carrier" as referred to within this specification comprises a composition capable of delivering a reagent to a desired compartment, e.g. a certain cell type, of the human body and is useful for providing and controlling release of drugs after being administered by the chosen administration route and scheme.

As used in herein the route of administration describes the uptake of a xenobiotic in the human body and is classified by the location at which the xenobiotic is applied. The pharmaceutical composition comprising the polynucleotide and/or the viral vector, in particular in the method of treatment, is selected from intraocular, intrabulbar, intravitreal or subretinal The term "disease" refers to an abnormal condition, especially an abnormal medical condition such as an illness or injury, wherein a cell, a tissue, an organ, or an individual is not able to efficiently fulfil its function anymore. Typically, but not necessarily, a disease is associated with specific symptoms or signs indicating the presence of such disease. The presence of such symptoms or signs may thus, be indicative for a cell, a tissue, an organ, or an individual suffering from a disease. An alteration of these symptoms or signs may be indicative for the progression of such a disease. A progression of a disease is typically characterised by an increase or decrease of such symptoms or signs which may indicate a "worsening" or "bettering" of the disease. The "worsening" of a disease is characterised by a decreasing ability of a cell, tissue, organ or individual/patient to fulfil its function efficiently, whereas the "bettering" of a disease is typically characterised by an increase in the ability of a cell, tissue, an organ or an individual/patient to fulfil its function efficiently. A cell, a tissue, an organ or an individual being "susceptible" to a disease is in a healthy state but especially vulnerable to the emergence of a disease, e.g. due to genetic predisposition, lacking vaccination, poorly developed or immature immunity, poor nutritional status, or the like.

A "disease of the retina" in the context of the present invention refers but is not limited to any kind of retinal degeneration. Retinal dystrophies, belonging to the group of retinal degenerations, are a broad group of genetic retinal disorders of varying severity and with differing inheritance patterns. A retinal dystrophy belongs to the group of pigmentary retinopathies. Retinitis Pigmentosa is the most common retinal dystrophy and is characterized by retinal pigment deposits visible on fundus examination and primary loss of rod photoreceptor cells followed by secondary loss of cone photoreceptors. Patients typically have night vision blindness and loss of midperipheral visual field. As the condition of the disease progresses, patients suffering the disease lose their far peripheral visual field and eventually central vision as well. The retinal degeneration may be associated with a genetic mutation, substitution, and/or deletion. The retinal degeneration is selected from the group consisting of night blindness, blindness, retinal degeneration, retinal dystrophy and Retinitis Pigmentosa. The Retinitis Pigmentosa can be CNGB1-linked Retinitis Pigmentosa or Retinitis Pigmentosa type 45 (RP45).

Other examples of retinal disorders include, without limitation, RPE65-mediated retinal disorders, macular degeneration (e.g., age-related macular degeneration), inherited juvenile macular degeneration (e.g., Stargardt disease), Rod-cone dystrophy, Cone-rod dystrophy, Oguchi disease, Malattia Leventinese, and others.

As used herein, "CNGB1-linked Retinitis Pigmentosa" refers to a class of diseases involving progressive degeneration of the retina, typically starting in the mid-periphery and advancing toward the macula and fovea (Ferrani et al. (2011) Curr. Genomics 12(4):238). Typical phenotypic symptoms include night blindness followed by decreasing visual fields, leading to tunnel vision and eventually legal blindness or, in many cases, complete blindness. On the cellular level, this correlates with a predominantly affected rod photoreceptor system. In later stages, the disease may further affect the cone photoreceptor eventually causing complete blindness. The diseased photoreceptors undergo apoptosis, which is reflected in reduced outer nuclear layer thickness within the retina, as well as in lesions and/or retinal pigment deposits in the fundus. Patients may lose a significant portion of their photoreceptors before experiencing loss of visual acuity. Clinical phenotypical hallmarks include, but are not limited to: (i) an abnormal fundus with bone-spicule deposits and attenuated retinal vessels; (ii) abnormal, diminished or absent a- and b-waves in the electroretinogram (ERG); and (iii) reduced visual field. Symptoms typically start in the early teenage years and severe visual impairment occurs by ages 40 to 50 years.

An example of a genetic variation that is known to be pathogenic for Retinitis Pigmentosa is a homozygous splice site mutation at the donor site of exon 32 of the CNGB1 gene (3444+1G-A) that results in a frameshift and truncation of the last 28 amino acids. Another example of a genetic variation that is known to be pathogenic for Retinitis Pigmentosa is a homozygous 2978G-T transversion in exon 30 of the CNGB1 gene that is predicted to result in a Glycine to Valine substitution at position 993 of the protein (G993V). Glycine 993 of CNGB1 is a conserved residue. Another example of a genetic variation that is known to be pathogenic for Retinitis Pigmentosa is a homozygous c.1589C-G transversion in the CNGB1 gene, resulting in a proline to arginine substitution at position 530 of the CNGB1 protein (P530R). Another known genetic variation that is pathogenic for Retinitis Pigmentosa includes a c.2128C-T change in the CNGB1 gene, resulting in a Glutamine to Termination substitution at position 710 of the CNGB1 protein (Q710Stop). Other genetic variations that are pathogenic for Retinitis Pigmentosa can be found in the Online Mendelian Inheritance in Man (OMIM) database, and the ClinVar database maintained by the National Center for Biotechnology Information, incorporated herein by reference in their entirety for all purposes.

CNGB1-linked Retinitis Pigmentosa can be identified with methods known in the art to detect one or more phenotypic signs described herein, and/or one or more genetic variations in the CNGB1 gene. Any genetic variation that results in a change in a conserved residue of CNGB1 may be pathogenic for Retinitis Pigmentosa.

As used herein, "treat," "treating," "treatment," or "therapy" of a disease or disorder means accomplishing one or more of the following: (a) reducing the severity of the disorder; (b) limiting or preventing development of symptoms characteristic of the disorder(s) being treated; (c) inhibiting worsening of symptoms characteristic of the disorder(s) being treated; (d) limiting or preventing recurrence of the disorder(s) in an individual that has previously had the disorder(s); and (e) limiting or preventing recurrence of symptoms in individuals that were previously symptomatic for the disorder(s).

Embodiments

In the following different aspects of the invention are defined in more detail. Each aspect so defined may be combined with any other aspect or aspects unless clearly indicated to the contrary. In particular, any feature indicated as being preferred or advantageous may be combined with any other feature or features indicated as being preferred or advantageous.

In gene therapeutic and/or gene corrective therapy approaches in which nucleic acids are introduced into cells, e.g., to augment expression, replace a defective gene, and/or inhibit expression of a defective gene, it is generally desirable that all transgenic elements are small. Nevertheless, it is often difficult to identify transgenic elements that can be reduced in size without negatively effecting or losing their activity in the in vivo situation. Generally, in vitro experiments are not suitable to indicate the in vivo behaviour of the elements making the determination of possible size reductions difficult and unpredictable. In the work leading to the present invention, it was surprisingly shown that a short part of the human rod promoter, i.e. an element smaller than 200 bases, could transfer rod-photoreceptor specific expression on transgenes operably linked to this promoter element in vivo. When the promoter element defined herein was used in an in vivo setting, stable integration and expression of a transgene was observed. The expression level was suitable to improve the visual capabilities of the test animals transfected with an adeno-associated virus vector comprising the transgene.

This surprising finding provides inter alia the following advantages over the art: (i) reduction of the size of the construct that is introduced into a cell, (ii) an increase of the packaging efficiency of the transgene into viral vectors, (iii) a decrease of the chance that recombination events occur in vivo, (iv) increase the efficiency of introduction of the transgene into the target cells, in particular into the nucleus of the target cell; (v) a suitable expression level in a human patient to treat rod associated diseases, (vi) preservation and/or improvement of retinal function in vivo and/or (vii) preservation and/or improvement of vision in vivo.

In a first aspect the present invention relates to a polynucleotide comprising in this order:
a) promoter comprising a human rod photoreceptor-specific promoter element (hRPSPE) comprising, consisting essentially of or consisting of the nucleic acid sequence according to SEQ ID NO: 1 or variants thereof and a core promoter (CP); and
b) at least one transgene (TG) operably linked to the promoter of a);
wherein the variant of SEQ ID NO: 1 comprises one or more nucleic acid substitutions outside nucleotide positions 6 to 13, 32 to 40, 70 to 83, and 87 to 94 of SEQ ID NO: 1 and wherein the length of the promoter is in particular 350 bases or less. The promoter that provides one or more of above advantages may also be longer than 350 bases, e.g. 600 bp or less, 500 bp or less, or 400 bp or less. In particular embodiments the promoter has a length of 300 bases or less, in other embodiments it has a length of 300 bases or less, in other embodiments it has a length of 250 bases or less, in other embodiments it has a length of 200 bases or less, in other embodiments it has a length of 194 bases or less.

In an attempt to minimize the overall length of heterologous bases introduced into a patient, the polynucleotide comprises no other human rod promoter and/or gene nucleotide sequence other than expressly defined in a) above.

The indicated nucleotides are to be preserved in variants of SEQ ID NO: 1 since the present inventors believe that these nucleotide sequences are instrumental in conferring rod photoreceptor-specific expression to the hRPSPE. Outside the putative transcription factor binding sequences (TFBs) 1 or more nucleotides can be mutated or inserted. If nucleotides are inserted, the insertion of 1 to 70 nucleotides is an advantageous number with multiples of seven being particularly advantageous since this number maintains the relative rotational positions of the TFBs. It is, however advantageous, if the distance between the TFBs is not altered to avoid rotational displacement of the transcription factors binding to the promoter element. Thus, within the 99 bp long sequence according to SEQ ID NO: 1 it is permissible to mutate one or more nucleotides at positions 1 to 5, 14 to 31, 41 to 69, 84 to 86 and 95 to 99. Thus, maximally 50 nucleotides may be mutated within SEQ ID NO: 1. Accordingly, particular variants comprise between 1 to 50 mutations, i.e. 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50. Other particular variants comprise between 5 to 40, between 10 to 30 or between 20 to 25 mutations. The promoter comprising a variant of the hRPSPE shows a rod photoreceptor-specific expression level as a promoter comprising the hRPSPE comprising the nucleic acid sequence according to SEQ ID NO: 1, preferably a promoter consisting of nucleotides 155 to 350 or 155 to 348 of SEQ ID NO: 2. It is advantageous, if the variant shows at least 10% of the expression level of a promoter consisting of nucleotides 155 to 350 or 155 to 348 of SEQ ID NO: 2. Other advantageous expression levels are at least 20%, at least 30%, at least 40%, at least 50%, at least 60%, at least 70%, at least 80%, at least 90% or at least 100%. Different expression levels may be advantageous depending on the respective therapeutic approach, in particular lower expression levels than those obtained with a promoter consisting of nucleotides 155 to 350 of SEQ ID NO: 2 may be advantageous, if a higher expression level of the transgene overcompensates the deficiency or leads to deleterious effect.

It is also envisioned that the polynucleotide of the invention comprises two or more transgenes operably linked to the promoter of a). In such a situation separate expression of the two or more transgenes can be obtained by inserting a nucleotide sequence allowing separate translation of the two transgenes, e.g. encoding an Internal Ribosomal Entry Site (IRES), between the two transgenes.

In an embodiment of the first aspect of the invention the 5' end of the hRPSPE comprised in the promoter of a) is at a nucleic acid position from 1 to 160 and the 3' end at a nucleic acid position from 290 to 310 of SEQ ID NO: 2 or variants thereof. In a particular embodiment the 5' end of the hRPSPE is at one of the following nucleic acid positions: 1, 10, 20, 30, 40, 50, 60, 70, 80, 90, 100, 110, 120, 130, 140, 145, 150, 151, 152, 153, 154, 155, 156, 157, 158, 159 or 160 of SEQ ID NO: 2. In a particular embodiment the 3' end of the hRPSPE is at one of the following nucleic acid positions: 290, 291, 292, 293, 294, 295, 296, 297, 298, 299, 300, 301, 302, 303, 304, 305, 306, 307, 308, 309, or 310 of SEQ ID NO: 2. Thus, according to particular embodiments the hRPSPE comprised in the promoter of a) spans nucleic acid positions 1 to 310, 10 to 309, 20 to 308, 30 to 307, 40 to 306, 50 to 305, 60 to 304, 70 to 303, 80 to 302, 90 to 301, 100 to 300, 110 to 299, 120 to 298, 130 to 297, 140 to 296, 150 to 295, 151 to 294, 152 to 293, 153 to 292, 154 to 291 or 155 to 290 of SEQ ID NO: 2. The term "variants of hRPSPE" has the meaning outlined above. Thus, variants of the fragments indicated in this paragraph have the respectively indicated 5' and 3' end and may additionally comprise mutations outside the sequences indicated above with reference to SEQ ID NO: 1.

In an embodiment of the first aspect of the invention the CP comprises a TATA-box and/or an initiator (Inr). In a particular embodiment the TATA-box and Inr of the human rho promoter. In a particular embodiment the 5'end of the CP comprised in the promoter of a) is at nucleotide position 300, 301, 302, 303, 304, 305, 306, 307, 308, 309, 310, 311, 312, 313, 314 of SEQ ID NO: 2 and the 3' end is at nucleic acid position from 330, 331, 332, 333, 334, 335, 336, 337, 338, 339, 340, 342, 343, 344, 345, 346, 347, 348, 349 or 350 of SEQ ID NO: 2. Thus, according to particular embodiments the CP comprised in the promoter of a) spans nucleic acid positions 300 to 350, 301 to 350, 302 to 350, 303 to 350, 304 to 349, 305 to 349, 306 to 349, 307 to 349, 308 to 348, 309 to 348, 310 to 348, 311 to 348, 312 to 348, 313 to 348, or 314 to 348 of SEQ ID NO: 2. In an embodiment of the first aspect of the invention the 5' end of the promoter is at a nucleic acid position from 1 to 160 and the 3' end at a nucleic acid position from 340 to 350 of SEQ ID NO: 2 or variants thereof. In a particular embodiment the 5' end of the promoter is at one of the following nucleic acid positions: 1, 10, 20, 30, 40, 50, 60, 70, 80, 90, 100, 110, 120, 130, 140, 145, 150, 151, 152, 153, 154, 155, 156, 157, 158, 159 or 160. In a particular embodiment the 3' end of the promoter is at one of the following nucleic acid positions: 330, 331, 332, 333, 334, 335, 336, 337, 338, 339, 340, 342, 343, 344, 345, 346, 347, 348, 349 or 350 of SEQ ID NO: 2. Thus, according to particular embodiments the promoter of a) spans nucleic acid positions 1 to 350, 10 to 350, 20 to 350, 30 to 350, 40 to 350, 50 to 350, 60 to 350, 70 to 350, 80 to 350, 90 to 349, 100 to 349, 110 to 349, 120 to 349, 130 to 349, 140 to 348, 150 to 348, 151 to 348, 152 to 348, 153 to 348, 154 to 348 or 155 to 348 of SEQ ID NO: 2. In a particular embodiment the promoter comprises, essentially consists or consists of SEQ ID NO: 9.

In an embodiment of the first aspect of the invention the transgene comprises, essentially consists or consists of a nucleic acid encoding a protein that maintains or improves the physiological function of rod cells and/or inhibits proliferation of rod cells. Typically, such genes are naturally expressed in healthy rod cells. The skilled person is aware of a large number of genes expressed in rod cells that are involved in the physiological function of rod cells. This function comprises inter alia, the detection of photons and the generation of nerve pulses in response to the detection of one or more photons.

In an embodiment of the first aspect of the invention the transgene:
  (i) comprises a nucleic acid encoding the human rod cyclic nucleotide-gated channel beta subunit (hCNGB1), ABCA4, AIPL1, BEST1, CACNA1F, CLN3, CLRN1, CNGA1, CEP290, CRB1, CRB2, CRX, GPR98, GUCA1A, GUCA1B, MYO7A, NRL, PDE6A, PDE6B, PRPH2, PROM1, RHO, ROM1, RP1, RP2, RPE65, RPGR, SAG, USH1C, USH1G, USH2A or functional fragments or variants thereof; a nucleic acid encoding a miRNA or shRNA targeting a mRNA encoding a dominant negative mutant thereof; and/or a nucleic acid encoding an antibody or antibody binding fragment that specifically binds to a dominant negative mutant thereof; or
  (ii) comprises a nucleic acid encoding a protein that inhibits proliferation of rod cells, preferably a toxin; a prodrug converting enzyme, e.g. thymidine kinase; cell cycle inhibitors, e.g. retinoblastoma protein (pRB), p53, p21CIP1, p27KIP1 and p57KIP2; comprises a mRNA encoding a dominant negative mutant of the cell cycle inhibitor thereof; and/or comprises a nucleic acid encoding a dominant negative mutant of a cell cycle inhibitor thereof.

Some diseases of rod cells are characterized by recessive mutations in one or more of the genes that maintain or improve the function of rod cells or that prevent hyperproliferation, in particular genes encoding the proteins indicated in (i) or (ii). In such cases it is often sufficient in order to cure or at least to ameliorate the disease, if a transgene encoding the functional protein is introduced into the rod cell, in particular using a vector. If the disease is however, caused by a dominant negative mutation the provision of a transgene encoding the functional protein or functional fragment thereof, is often not sufficient to cure or ameliorate the disease. In such cases it is preferred that the expression or function of the dominant negative mutant protein is reduced in the cell, i.e. is knocked-down. Such knock-down may be affected by expressing a transgene encoding an inhibitory RNA that specifically reduces expression of the dominant negative mutant protein or by one or more transgenes encoding an antibody of fragment thereof that specifically binds to and inactivates the dominant negative mutant protein and does not significantly bind to the corresponding functional protein. The skilled person is well aware how to design such inhibitory RNA specific to the mRNA encoding the respective dominant negative mutant protein. Similarly, the skilled person knows how to generate antibodies that specifically bind only to the dominant negative mutant protein and not to the wild-type protein. In its natural form antibodies comprise two different protein chains. Thus, if both protein chains of an antibody are expressed to knockdown a protein, then one transgene may comprise nucleotides encoding the light chain linked through an Internal Ribosomal Entry Site (IRES) to another transgene encoding the heavy chain. In this way both antibody chains can be expressed from a single mRNA. It is apparent to the skilled person that the order of light and heavy chain can be reversed without affecting expression of the antibody within the rod cell. Alternatively, a single chain antibody may be encoded by the transgene.

In a particular embodiment the diseases to be treated are characterized by dominant negative mutations in one or more of the genes that maintain or improve the function of rod cells or that promote hyperproliferation, in particular in one or more of AIPL1, BEST1, NR2E3, NRL, PRPH2, RHO, ROM1, and/or RP1. In this case it is preferred that expression and/or function of the proteins encoded by the dominant negative mutant gene is knocked down and that a transgene encoding the functional protein or a functional fragment thereof. If size limitations of the respective vector allows, it is preferred that the polynucleotide comprises both a transgene encoding the functional protein or a functional fragment thereof and a transgene encoding an inhibitory RNA or an inhibitory antibody or fragment thereof. If both transgenes encode proteins they can be under the control of the same promoter and use, e.g. an IRES sequence between the two transgenes or if one transgene encodes a protein and the other an inhibitory RNA each transgene may be operably linked to a separate promoter according to i) of the first aspect of the invention.

The term "functional fragments" refers to N- and/or C-terminal deletions of the respective protein that does not lead to a loss of the rod cell specific function of the respective proteins. The term "variants thereof" refers to proteins that have at least 70% sequence identity to the respectively indicated human wild-type protein, in particular the proteins according to SEQ ID NO: 3, 10 to 41, and 45. In a particular embodiment the variant has at least 70% sequence identity, particularly 75% sequence identity, more particularly 80% sequence identity, more particularly 85% sequence identity, more particularly 90% sequence identity, and more particularly 95% sequence identity to SEQ ID NO: 3. In a particular embodiment the variant has at least 70% sequence identity, particularly 75% sequence identity, more particularly 80% sequence identity, more particularly 85% sequence identity, more particularly 90% sequence identity, and more particularly 95% sequence identity to SEQ ID NO: 10. In a particular embodiment the variant has at least 70% sequence identity, particularly 75% sequence identity, more particularly 80% sequence identity, more particularly 85% sequence identity, more particularly 90% sequence identity, and more particularly 95% sequence identity to SEQ ID NO: 11. In a particular embodiment the variant has at least 70% sequence identity, particularly 75% sequence identity, more particularly 80% sequence identity, more particularly 85% sequence identity, more particularly 90% sequence identity, and more particularly 95% sequence identity to SEQ ID NO: 12. In a particular embodiment the variant has at least 70% sequence identity, particularly 75% sequence identity, more particularly 80% sequence identity, more particularly 85% sequence identity, more particularly 90% sequence identity, and more particularly 95% sequence identity to SEQ ID NO:

13. In a particular embodiment the variant has at least 70% sequence identity, particularly 75% sequence identity, more particularly 80% sequence identity, more particularly 85% sequence identity, more particularly 90% sequence identity, and more particularly 95% sequence identity to SEQ ID NO: 14. In a particular embodiment the variant has at least 70% sequence identity, particularly 75% sequence identity, more particularly 80% sequence identity, more particularly 85% sequence identity, more particularly 90% sequence identity, and more particularly 95% sequence identity to SEQ ID NO: 15. In a particular embodiment the variant has at least 70% sequence identity, particularly 75% sequence identity, more particularly 80% sequence identity, more particularly 85% sequence identity, more particularly 90% sequence identity, and more particularly 95% sequence identity to SEQ ID NO: 16. In a particular embodiment the variant has at least 70% sequence identity, particularly 75% sequence identity, more particularly 80% sequence identity, more particularly 85% sequence identity, more particularly 90% sequence identity, and more particularly 95% sequence identity to SEQ ID NO: 17. In a particular embodiment the variant has at least 70% sequence identity, particularly 75% sequence identity, more particularly 80% sequence identity, more particularly 85% sequence identity, more particularly 90% sequence identity, and more particularly 95% sequence identity to SEQ ID NO: 18. In a particular embodiment the variant has at least 70% sequence identity, particularly 75% sequence identity, more particularly 80% sequence identity, more particularly 85% sequence identity, more particularly 90% sequence identity, and more particularly 95% sequence identity to SEQ ID NO: 19. In a particular embodiment the variant has at least 70% sequence identity, particularly 75% sequence identity, more particularly 80% sequence identity, more particularly 85% sequence identity, more particularly 90% sequence identity, and more particularly 95% sequence identity to SEQ ID NO: 20. In a particular embodiment the variant has at least 70% sequence identity, particularly 75% sequence identity, more particularly 80% sequence identity, more particularly 85% sequence identity, more particularly 90% sequence identity, and more particularly 95% sequence identity to SEQ ID NO: 21. In a particular embodiment the variant has at least 70% sequence identity, particularly 75% sequence identity, more particularly 80% sequence identity, more particularly 85% sequence identity, more particularly 90% sequence identity, and more particularly 95% sequence identity to SEQ ID NO: 22. In a particular embodiment the variant has at least 70% sequence identity, particularly 75% sequence identity, more particularly 80% sequence identity, more particularly 85% sequence identity, more particularly 90% sequence identity, and more particularly 95% sequence identity to SEQ ID NO: 23. In a particular embodiment the variant has at least 70% sequence identity, particularly 75% sequence identity, more particularly 80% sequence identity, more particularly 85% sequence identity, more particularly 90% sequence identity, and more particularly 95% sequence identity to SEQ ID NO: 24. In a particular embodiment the variant has at least 70% sequence identity, particularly 75% sequence identity, more particularly 80% sequence identity, more particularly 85% sequence identity, more particularly 90% sequence identity, and more particularly 95% sequence identity to SEQ ID NO: 25. In a particular embodiment the variant has at least 70% sequence identity, particularly 75% sequence identity, more particularly 80% sequence identity, more particularly 85% sequence identity, more particularly 90% sequence identity, and more particularly 95% sequence identity to SEQ ID NO: 26. In a particular embodiment the variant has at least 70% sequence identity, particularly 75% sequence identity, more particularly 80% sequence identity, more particularly 85% sequence identity, more particularly 90% sequence identity, and more particularly 95% sequence identity to SEQ ID NO: 27. In a particular embodiment the variant has at least 70% sequence identity, particularly 75% sequence identity, more particularly 80% sequence identity, more particularly 85% sequence identity, more particularly 90% sequence identity, and more particularly 95% sequence identity to SEQ ID NO: 28. In a particular embodiment the variant has at least 70% sequence identity, particularly 75% sequence identity, more particularly 80% sequence identity, more particularly 85% sequence identity, more particularly 90% sequence identity, and more particularly 95% sequence identity to SEQ ID NO: 29. In a particular embodiment the variant has at least 70% sequence identity, particularly 75% sequence identity, more particularly 80% sequence identity, more particularly 85% sequence identity, more particularly 90% sequence identity, and more particularly 95% sequence identity to SEQ ID NO: 30. In a particular embodiment the variant has at least 70% sequence identity, particularly 75% sequence identity, more particularly 80% sequence identity, more particularly 85% sequence identity, more particularly 90% sequence identity, and more particularly 95% sequence identity to SEQ ID NO: 31. In a particular embodiment the variant has at least 70% sequence identity, particularly 75% sequence identity, more particularly 80% sequence identity, more particularly 85% sequence identity, more particularly 90% sequence identity, and more particularly 95% sequence identity to SEQ ID NO: 32. In a particular embodiment the variant has at least 70% sequence identity, particularly 75% sequence identity, more particularly 80% sequence identity, more particularly 85% sequence identity, more particularly 90% sequence identity, and more particularly 95% sequence identity to SEQ ID NO: 33. In a particular embodiment the variant has at least 70% sequence identity, particularly 75% sequence identity, more particularly 80% sequence identity, more particularly 85% sequence identity, more particularly 90% sequence identity, and more particularly 95% sequence identity to SEQ ID NO: 34. In a particular embodiment the variant has at least 70% sequence identity, particularly 75% sequence identity, more particularly 80% sequence identity, more particularly 85% sequence identity, more particularly 90% sequence identity, and more particularly 95% sequence identity to SEQ ID NO: 35. In a particular embodiment the variant has at least 70% sequence identity, particularly 75% sequence identity, more particularly 80% sequence identity, more particularly 85% sequence identity, more particularly 90% sequence identity, and more particularly 95% sequence identity to SEQ ID NO: 36. In a particular embodiment the variant has at least 70% sequence identity, particularly 75% sequence identity, more particularly 80% sequence identity, more particularly 85% sequence identity, more particularly 90% sequence identity, and more particularly 95% sequence identity to SEQ ID NO: 37. In a particular embodiment the variant has at least 70% sequence identity, particularly 75% sequence identity, more particularly 80% sequence identity, more particularly 85% sequence identity, more particularly 90% sequence identity, and more particularly 95% sequence identity to SEQ ID NO: 38. In a particular embodiment the variant has at least 70% sequence identity, particularly 75% sequence identity, more particularly 80% sequence identity, more particularly 85% sequence identity, more particularly 90% sequence identity, and more particularly 95% sequence identity to SEQ ID NO: 39. In a particular embodiment the variant has at least 70% sequence identity, particularly 75% sequence identity, more particularly 80% sequence identity, more particularly 85% sequence identity, more particularly 90% sequence identity, and more particularly 95% sequence identity to SEQ ID NO: 40. In a particular embodiment the variant has at least 70% sequence identity, particularly 75% sequence identity, more particularly 80% sequence identity, more particularly 85% sequence identity, more particularly 90% sequence identity, and more particularly 95% sequence identity to SEQ ID NO: 41. In a particular embodiment the variant has at least 70% sequence identity, particularly 75% sequence identity, more particularly 80% sequence identity, more particularly 85% sequence identity, more particularly 90% sequence identity, and more particularly 95% sequence identity to SEQ ID NO: 45.

Functional fragments of the above indicated proteins are those fragments that maintain the function of the respective protein in normally functioning rod photoreceptor, in particular in detecting photons and/or transmitting the information on the detection of photons. Similarly, variants also maintain the function of the respective protein in normally functioning rod photoreceptors.

In an embodiment of the first aspect of the invention the hCNGB1 encoded by the transgene comprises an amino acid sequence according to SEQ ID NO: 3 or variants thereof. In an embodiment of the first aspect of the invention the hCNGB1 encoded by the transgene comprises an amino acid sequence according to SEQ ID NO: 40 or variants thereof. In an embodiment of the first aspect of the invention the hCNGB1 encoded by the transgene comprises an amino acid sequence according to SEQ ID NO: 41 or variants thereof.

In an embodiment of the first aspect of the invention the polynucleotide comprises one or more further nucleotide sequence elements selected from the group consisting of:
 (i) a polyadenylation signal (pA); and/or
 (ii) one or two inverted terminal repeat (ITR) sequences; and/or
 (iii) viral nucleotide sequences necessary to form an infectious viral vector, preferably an adeno-associated virus, an adenovirus, a retrovirus, a lentivirus, a vaccinia/poxvirus, or a herpesvirus vector, in particular herpes simplex virus (HSV) vector.

Viral nucleotide sequences that are essential to forming an infectious viral vector of the respective type are well known in the art. Any of these elements may be comprised in the polynucleotide of the first aspect of the invention.

In an embodiment of the first aspect of the invention the polyadenylation signal comprises, essentially consists or consists of a Simian-Virus 40 PAS.

In an embodiment of the first aspect of the invention the polyadenylation signal comprises, essentially consists or consists of a nucleic acid according to SEQ ID NO: 4 or functional variants thereof.

In an embodiment of the first aspect of the invention the ITR sequence is an adeno-associated virus (AAV) ITR.

In an embodiment of the first aspect of the invention the AAV ITR is of an AVV serotype 2, 5, 8 or 9.

In an embodiment of the first aspect of the invention the promoter and the transgene are flanked at their 5' with a L-ITR and at their 3' end with a R-ITR. In one particular embodiment the elements are arranged in 5' to 3' direction in the following order: L-ITR-promoter-transgene-R-ITR, L-ITR-transgene-promoter-R-ITR, R-ITR-promoter-transgene-L-ITR, or R-ITR-transgene-promoter-L-ITR. In another particular embodiment the elements are arranged in 5' to 3' direction in the following order: L-ITR-promoter-transgene-PAS-R-ITR, L-ITR-PAS-transgene-promoter-R-ITR, R-ITR-promoter-transgene-PAS-L-ITR, or R-ITR-PAS-transgene-promoter-L-ITR.

In an embodiment of the first aspect of the invention the L-ITR comprises, essentially consists or consists of a sequence according to SEQ ID NO: 5 or variants thereof and/or the R-ITR comprises, essentially consists or consists of a sequence according to SEQ ID NO: 6 or variants thereof.

Depending on the viral vector used the length of the nucleic acid that can be efficiently packaged in the viral vector greatly varies. Some vectors like adenoviral vectors can accommodate large nucleic acid inserts while others, like adeno-virus associated vectors efficiently package polynucleotides that have a length of 4700 bases or less. Irrespective of the nucleic acid packaging ability of a vector it is generally desirable to minimize the length of any heterologous nucleic acid introduced into a patient, in particular if the heterologous nucleic acid is stably introduced into the genome. Accordingly, in an embodiment of the first aspect of the invention the total length of the polynucleotide is 5200 bases or less, in particular 5100 bases or less, in particular 5000 bases or less, in particular 4900 bases or less, in particular 4800 bases or less, and more particular 4700 bases or less.

In a particular embodiment of the first aspect of the invention the polynucleotide comprises, essentially consists in 5' to 3' direction of the following nucleic acids elements: L-ITR-promoter-transgene-SV40 PAS-R-ITR, L-ITR-SV40 PAS-transgene-promoter-R-ITR, R-ITR-promoter-transgene-SV40 PAS-L-ITR, or R-ITR-SV40 PAS-transgene-promoter-L-ITR, wherein the transgene comprises, essentially comprises or consists of a nucleotide sequence encoding the hCNGB1 protein of SEQ ID NO: 3, the PAS comprises, essentially comprises or consists of the nucleotide sequence of SEQ ID NO: 4, the L-ITR comprises, essentially comprises or consists of the nucleotide sequence SEQ ID NO: 5, the R-ITR comprises, essentially comprises or consists of the nucleotide sequence SEQ ID NO: 6, and the promoter comprises, essentially comprises or consists of the nucleotide sequence that spans nucleotides 155 to 348 of SEQ ID NO: 2. Also in this embodiment the total length of the polynucleotide is 5200 bases or less, in particular 5100 bases or less, in particular 5000 bases or less, in particular 4900 bases or less, in particular 4800 bases or less, and more particular 4700 bases or less.

A second aspect of the invention relates to a plasmid comprising the polynucleotide of the first aspect of the invention. A plasmid is a circular DNA that can be replicated in bacteria.

In an embodiment of the second aspect of the invention the plasmid comprises, essentially consists or consists of a nucleic acid sequence according to SEQ ID NO: 7 or variants thereof. In an embodiment of the second aspect of the invention the plasmid comprises, essentially consists or consists of a nucleic acid sequence according to SEQ ID NO: 42 or variants thereof. In an embodiment of the second aspect of the invention the plasmid comprises, essentially consists or consists of a nucleic acid sequence according to SEQ ID NO: 43 or variants thereof. In an embodiment of the second aspect of the invention the plasmid comprises, essentially consists or consists of a nucleic acid sequence according to SEQ ID NO: 44 or variants thereof.

A third aspect of the invention relates to a viral vector comprising the polynucleotide of the first aspect of the invention. In a particular embodiment the viral vector is an AAV, an adenovirus, a retrovirus, a lentivirus, a vaccinia/poxvirus, or a herpesvirus vector, in particular herpes simplex virus (HSV) vector. In a particular embodiment the viral vector is an AAV.

In an embodiment of the third aspect of the invention the virus is selected from the group consisting of AAV2, AAV5, AAV8, AVV9 or variants thereof.

A fourth aspect of the invention relates to the polynucleotide according to the first aspect of the invention, the plasmid of the second aspect of the invention and/or the viral vector according to the third aspect of the invention for use as a medicament.

A fifth aspect of the invention relates to a pharmaceutical composition comprising the polynucleotide according to the first aspect of the invention, the plasmid of the second aspect of the invention and/or the viral vector according to the third aspect of the invention, and a pharmaceutically acceptable carrier.

A sixth aspect of the invention relates to the polynucleotide according to the first aspect of the invention, the plasmid of the second aspect of the invention and/or the viral vector according to the third aspect of the invention for use in the therapy of a disease of the retina.

Advantageously the polynucleotide according to the first aspect of the invention, the plasmid of the second aspect of the invention and/or the viral vector according to the third aspect of the invention can be used in diseases that are associated with a loss of or aberrant rod receptor function, in particular retinal degeneration or hyperproliferation of rod cells, in particular retinoblastoma. While tissue specific expression of the transgene is obtained through the promoter of the polynucleotide of the first aspect of the invention and, thus systemic administration of the therapeutic polynucleotide, plasmid or viral vector can be systemic without and will still be limited to rod receptors it is more efficient, if the therapeutic polynucleotide, plasmid or viral vector of the invention is directly administered to the eye of the patient. Accordingly, particular routes of administration are selected from intraocular, intrabulbar, intravitreal or subretinal administration.

In an embodiment of the sixth aspect of the invention the retinal degeneration is associated with a genetic mutation, substitution, and/or deletion.

In an embodiment of the sixth aspect of the invention the retinal degeneration is associated with a genetic mutation, substitution, and/or deletion.

In an embodiment of the sixth aspect of the invention the degeneration is selected from the group consisting of night blindness, blindness, retinal degeneration, retinal dystrophy and retinitis pigmentosa.

In an embodiment of the sixth aspect of the invention the retinitis pigmentosa is CNGB1-linked retinitis pigmentosa or retinitis pigmentosa type 45 (RP45).

A seventh aspect of the invention relates to a polynucleotide comprising in this order:
  a) a human rhodopsin promoter comprising the nucleic acid sequence according to SEQ ID NO: 9 or variants thereof; and
  b) at least one transgene (TG) operably linked to the promoter of a).

In an embodiment of the seventh aspect of the invention, the transgene comprises a nucleic acid encoding a protein that maintains or improves a physiological function of rods.

In an embodiment of the seventh aspect of the invention the transgene:
  (i) comprises a nucleic acid encoding the human rod cyclic nucleotide-gated channel beta subunit (hCNGB1), ABCA4, AIPL1, BEST1, CACNA1F, CLN3, CLRN1, CNGA1, CEP290, CRB1, CRB2, CRX, GPR98, GUCA1A, GUCA1B, MYO7A, NRL, PDE6A, PDE6B, PRPH2, PROM1, RHO, ROM1, RP1, RP2, RPE65, RPGR, SAG, USH1C, USH1G, USH2A or functional fragments or variants thereof; a nucleic acid encoding a miRNA or shRNA targeting a mRNA encoding a dominant negative mutant thereof; and/or a nucleic acid encoding an antibody or antibody binding fragment that specifically binds to a dominant negative mutant thereof; or
  (ii) comprises a nucleic acid encoding a protein that inhibits proliferation of rod cells, preferably a toxin; a prodrug converting enzyme, e.g. thymidine kinase; cell cycle inhibitors, e.g. retinoblastoma protein (pRB), p53, p21CIP1, p27KIP1 and p57KIP2; comprises a mRNA encoding a dominant negative mutant of the cell cycle inhibitor thereof; and/or comprises a nucleic acid encoding a dominant negative mutant of a cell cycle inhibitor thereof.

In an embodiment of the seventh aspect of the invention, the polynucleotide further comprises one or more nucleotide sequence elements selected from the group consisting of:
  (i) a polyadenylation signal (PAS);
  (ii) one or two inverted terminal repeat (ITR) sequences; and
  (iii) viral nucleotide sequences necessary to form an infectious viral vector, preferably an adenovirus, a retrovirus, a lentivirus, a vaccinia/poxvirus, or a herpesvirus vector, in particular herpes simplex virus (HSV) vector.

In an embodiment of the seventh aspect of the invention, the polyadenylation signal comprises a Simian-Virus 40 PAS.

In an embodiment of the seventh aspect of the invention, the ITR sequence is an adeno-associated virus (AAV) ITR.

In an embodiment of the seventh aspect of the invention, the AAV is AVV serotype 2, 5, 8 or 9.

An eighth aspect of the invention relates to a viral vector comprising the polynucleotide of the seventh aspect of the invention.

In an embodiment of the eighth aspect of the invention, the virus is selected from the group consisting of AAV2, AAV5, AAV8, AVV9 or variants thereof.

The polynucleotides of the invention comprising a human rod photoreceptor-specific promoter element (hRPSPE) or variants thereof and a core promoter (CP) operably linked to a transgene (e.g., CNGB1), or polynucleotides comprising a human rhodopsin promoter operably linked to a transgene (e.g., CNGB1) can be used in gene therapeutic and/or gene corrective therapies. In such therapies, the polynucleotides are introduced into cells to augment expression, replace a defective gene, and/or inhibit expression of a defective gene.

Accordingly, a ninth aspect of the invention relates to a method for treating retinal degeneration in a subject in need thereof, comprising administering to the subject a therapeutically effective amount of a polynucleotide according to a seventh aspect of the invention, or the viral vector according to an eighth aspect of the invention.

In an embodiment of the ninth aspect of the invention, the polynucleotide or viral vector comprises the nucleic acid sequence set forth in SEQ ID NO: 43.

A tenth aspect of the invention relates to a method for treating retinitis pigmentosa in a subject in need thereof, comprising administering to the subject a therapeutically effective amount of a polynucleotide according to a seventh aspect of the invention, or the viral vector according to an eighth aspect of the invention.

In an embodiment of the tenth aspect of the invention, the polynucleotide or viral vector comprises the nucleic acid sequence set forth in SEQ ID NO: 43.

An eleventh aspect of the invention relates to a method for treating retinal degeneration in a subject in need thereof, wherein the retinal degeneration is characterized by a defect or absence of CNGB1 in the retinal cells of the subject, the method comprising administering to the subject a therapeutically effective amount of a viral vector comprising the nucleic acid sequence set forth in SEQ ID NO: 43.

In an embodiment of the eleventh aspect of the invention, the retinal degeneration is CNGB1-linked retinitis pigmentosa or retinitis pigmentosa type 45 (RP45).

A twelfth aspect of the invention relates to a method for treating CNGB1-linked retinitis pigmentosa or retinitis pigmentosa type 45 (RP45) in a subject in need thereof, comprising subretinal administration to the subject a therapeutically effective amount of a viral vector comprising the nucleic acid sequence set forth in SEQ ID NO: 43.

A thirteenth aspect of the invention relates to a polynucleotide comprising in this order:
a) a promoter comprising a human rod photoreceptor-specific promoter element (hRPSPE) comprising the nucleic acid sequence according to SEQ ID NO: 1 or variants thereof and a core promoter (CP); and
b) a transgene encoding the human rod cyclic nucleotide-gated channel beta subunit (hCNGB1) operably linked to the promoter of a),
wherein the variant of SEQ ID NO: 1 comprises one or more nucleic acid substitutions outside nucleotide positions 6 to 13, 32 to 40, 70 to 83, and 87 to 94 of SEQ ID NO: 1.

A fourteenth aspect of the invention relates to a pharmaceutical composition comprising a polynucleotide comprising in this order:
a) a promoter comprising a human rod photoreceptor-specific promoter element (hRPSPE) comprising the nucleic acid sequence according to SEQ ID NO: 1 or variants thereof and a core promoter (CP); and
b) a transgene encoding the human rod cyclic nucleotide-gated channel beta subunit (hCNGB1) operably linked to the promoter of a);
wherein the variant of SEQ ID NO: 1 comprises one or more nucleic acid substitutions outside nucleotide positions 6 to 13, 32 to 40, 70 to 83, and 87 to 94 of SEQ ID NO: 1, and
a pharmaceutically acceptable carrier.

A fifteenth aspect of the invention relates to a pharmaceutical composition comprising a viral vector comprising the nucleic acid sequence set forth in SEQ ID NO: 43 and a pharmaceutically acceptable carrier.

TABLE 1

Table of select sequences of the invention

| SEQ ID NO: | Description | Sequence |
|---|---|---|
| 1 | 99 nucleotide long human RHO promoter fragment | AGAAGCCAATTAGGCCCTCAGTTTCTGCAGCGGGGATTAATAT GATTATGAACACCCCCAATCTCCCAGATGCTGATTCAGCCAGG AGCTTAGGAGGGG |
| 2 | 350 nucleotide long human RHO promoter fragment | AAACCAGAAAGTCTCTAGCTGTCCAGAGGACATAGCACAGAGG CCCATGGTCCCTATTTCAAACCCAGGCCACCAGACTGAGCTGG GACCTTGGGACAGACAAGTCATGCAGAAGTTAGGGGACCTTCT CCTCCCTTTTCCTGGATCCTGAGTACCTCTCCTCCCTGACCTCAG GCTTCCTCCTAGTGTCACCTTGGCCCCTCTTAGAAGCCAATTAG GCCCTCAGTTTCTGCAGCGGGGATTAATATGATTATGAACACCC CCAATCTCCCAGATGCTGATTCAGCCAGGAGCTTAGGAGGGGG AGGTCACTTTATAAGGGTCTGGGGGGTCAGAACCCAGAGTCA TC |
| 3 | Sequence of the human CNGB1 protein | MLGWVQRVLPQPPGTPRKTKMQEEEEVEPEPEMEAEVEPEPNPEE AETESESMPPEESFKEEEVAVADPSPQETKEAALTSTISLRAQGAEI SEMNSPSHRVLTWLMKGVEKVIPQPVHSITEDPAQILGHGSTGDT GCTDEPNEALEAQDTRPGLRLLLWLEQNLERVLPQPPKSSEVWRD EPAVATAPPGRPQEMGPKLQARETPSLPTPIPLQPKEEPKEAPAPEP QPGSQAQTSSLPPTRDPARLVAWVLHRLEMALPQPVLHGKIGEQE PDSPGICDVQTISILPGGQVEPDLVLEEVEPPWEDAHQDVSTSPQGT EVVPAYEEENKAVEKMPRELSRIEEEKEDEEEEEEEEEEEEEEVT EVLLDSCVVSQVGVGQSEEDGTRPQSTSDQKLWEEVGEEAKKEA EEKAKEEAEEVAEEEEAEKEPQDWAETKEEPEAEAEAASSGVPATK QHPEVQVEDTDADSCPLMAEENPPSTVLPPPSPAKSDTLIVPSSASG THRKKLPSEDDEAEELKALSPAESPVVAWSDPTTPKDTDGQDRAA STASTNSAIINDRLQELVKLFKERTEKVKEKLIDPDVTSDEESPKPS PAKKAPEPAPDTKPAEAEPVEEEHYCDMLCCKFKHRPWKKYQFP QSIDPLTNLMYVLWLFFVVMAWNWNCWLIPVRWAFPYQTPDNIH HWLLMDYLCDLIYFLDITVFQTRLQFVRGGDIITDKKDMRNNYLK SRRFKMDLLSLLPLDFLYLKVGVNPLLRLPRCLKYMAFFEFNSRLE SILSKAYVYRVIRTTAYLLYSLHLNSCLYYWASAYQGLGSTHWVY DGVGNSYIRCYYFAVKTLITIGGLPDPKTLFEIVFQLLNYFTGVFAF SVMIGQMRDVVGAATAGQTYYRSCMDSTVKYMNFYKIPKSVQN RVKTWYEYTWHSQGMLDESELMVQLPDKMRLDLAIDVNYNIVS KVALFQGCDRQMIFDMLKRLRSVVYLPNDYVCKKGEIGREMYIIQ AGQVQVLGGPDGKSVLVTLKAGSVFGEISLLAVGGGNRRTANVV AHGFTNLFILDKKDLNEILVHYPESQKLLRKKARRMLRSNNKPKE EKSVLILPPRAGTPKLFNAALAMTGKMGGKGAKGGKLAHLRARL |

TABLE 1-continued

Table of select sequences of the invention

| SEQ ID NO: | Description | Sequence |
|---|---|---|
| | | KELAALEAAAKQQELVEQAKSSQDVKGEEGSAAPDQHTHPKEAA TDPPAPRTPPEPPGSPPSSPPPASLGRPEGEEEGPAEPEEHSVRICMS PGPEPGEQILSVKMPEEREEKAE |
| 4 | SV40 polyadenyl- ation signal | GGCCGCAGACATGATAAGATACATTGATGAGTTTGGACAAACC ACAACTAGAATGCAGTGAAAAAAATGCTTTATTTGTGAAATTT GTGATGCTATTGCTTTATTTGTAACCATTATAAGCTGCAATAAA CAAGTTAACAACAACAATTGCATTCATTTTATGTTTCAGGTTCA GGGGGAGGTGTGGGAGGTTTTTTAAAGCAAGTAAAACCTCTAC AAATGTGGTA |
| 5 | Left inverted terminal repeat (L-ITR) | CTGCGCGCTCGCTCGCTCACTGAGGCCGCCCGGGCAAAGCCCG GGCGTCGGGCGACCTTTGGTCGCCCGGCCTCAGTGAGCGAGCG AGCGCGCAGAGAGGGAGTGGCCAACTCCATCACTAGGGGTTCC T |
| 6 | Right inverted terminal repeat (R-ITR) | AGGAACCCCTAGTGATGGAGTTGGCCACTCCCTCTCTGCGCGCT CGCTCGCTCACTGAGGCCGGGCGACCAAAGGTCGCCCGACGCC CGGGCTTTGCCCGGGCGGCCTCAGTGAGCGAGCGAGCGCGCAG C |
| 7 | Sequence of vector construct: pGL2.0-hRho194-hCNGB1a-SV40 | CAGCTGCGCGCTCGCTCGCTCACTGAGGCCGCCCGGGCAAAGC CCGGGCGTCGGGCGACCTTTGGTCGCCCGGCCTCAGTGAGCGA GCGAGCGCGCAGAGAGGGAGTGGCCAACTCCATCACTAGGGGT TCCTTGTAGTTAATGATTAACCCGCCATGCTACTTATCTACGTA GCCATGCTCTAGGAAGATCGGAATTCGCCCTTAAGCCTCTCCTC CCTGACCTCAGGCTTCCTCCTAGTGTCACCTTGGCCCCTCTTAG AAGCCAATTAGGCCCTCAGTTTCTGCAGCGGGGATTAATATGA TTATGAACACCCCCAATCTCCCAGATGCTGATTCAGCCAGGAG CTTAGGAGGGGAGGTCACTTTATAAGGGTCTGGGGGGGTCAG AACCCAGAGTCATCACTAGTAACGGCCGCCAGTGTGCTGGAAT TCGCCCTTCTCCACCGCCATGTTGGGCTGGGTCCAGAGGGTGCT GCCTCAGCCCCCAGGGACCCCTCGGAAGACCAAGATGCAGGAG GAAGAGGAAGTGGAACCAGAGCCAGAGATGGAGGCGGAGGTG GAACCAGAACCGAATCCTGAGGAGGCCGAGACAGAGTCCGAG TCCATGCCCCCCGAAGAGTCATTCAAGGAGGAGGAAGTGGCTG TGGCAGACCCAAGCCCTCAGGAGACCAAGGAGGCTGCCCTTAC TTCCACCATATCCCTCCGGGCCCAGGGCGCTGAGATTTCTGAAA TGAATAGTCCCAGCCACAGGGTACTGACCTGGCTCATGAAGGG TGTAGAGAAGGTGATCCCGCAGCCTGTTCACAGCATCACGGAG GACCCGGCTCAGATCCTGGGGCATGGCAGCACTGGGGACACAG GGTGCACAGATGAACCCAATGAGGCCCTTGAGGCCCAAGCAC TAGGCCTGGGCTGCGGCTGCTTCTGTGGCTGGAGCAGAATCTG GAAAGAGTGCTTCCTCAGCCCCCCAAATCCTCTGAGGTCTGGA GAGATGAGCCTGCAGTTGCTACAGCGCCTCCAGGACGCCCCCA GGAAATGGGGCCCAAGCTGCAGGCCGGGAGACCCCCTCCCTG CCCACACCCATCCCCCTGCAGCCCAAGGAGGAACCCAAGGAGG CACCAGCTCCAGAGCCCCAGCCCGGCTCCCAGGCCCAGACCTC CTCCCTGCCACCAACCAGGGACCCTGCCAGGCTGGTGGCATGG GTCCTGCACAGGCTGGAGATGGCCTTGCCGCAGCCAGTGCTAC ATGGGAAAATAGGGGAACAGGAGCCTGACTCCCCTGGGATATG TGATGTGCAGACCATCAGCATCCTTCCTGGAGGACAAGTGGAG CCTGACCTTGTCCTAGAGGAGGTTGAACCGCCCTGGGAGGATG CCCACCAGGATGTCAGTACCAGCCCACAGGGTACAGAGGTGGT TCCAGCTTATGAAGAAGAGAACAAAGCTGTGGAGAAGATGCCC AGAGAGCTGTCCCGGATTGAAGAGGAGAAAGAAGATGAGGAG GAGGAAGAGGAAGAGGAGGAGGAGGAGGAAGAGGAGGAGGT GACTGAGGTGCTGCTGGATAGCTGTGTGGTGTCGCAGGTGGGC GTGGGCCAGAGTGAAGAAGACGGGACCCGGCCCCAGAGCACT TCAGATCAGAAGCTGTGGGAGGAAGTTGGGGAGGAGGCCAAG AAGGAGGCTGAAGAGAAGGCCAAGGAGGAGGCCGAGGAGGTG GCTGAAGAGGAGGCTGAAAAGGAGCCCCAGGACTGGGCGGAG ACCAAGGAGGAGCCTGAGGCTGAGGCCGAGGCTGCCAGTTCAG GAGTGCCTGCCACGAAACAGCACCCAGAAGTGCAGGTGGAAG ATACTGATGCTGATAGCTGCCCCCTCATGGCAGAAGAGAATCC ACCCTCAACCGTGTTGCCGCCACCATCTCCTGCCAAATCAGACA CCCTTATAGTCCCAAGCTCAGCCTCGGGGACACACAGGAAGAA GCTGCCCTCTGAGGATGATGAGGCTGAAGAGCTCAAGGCGTTG TCACCAGCAGAGTCCCCAGTGGTTGCCTGGTCTGACCCCCACCAC CCCGAAGGACACTGATGGCCAGGACCGTGCGGCCTCCACGGCC AGCACAAATAGCGCCATCATCAACGACCGGCTCCAGGAGCTGG TGAAGCTCTTCAAGGAGCGGACAGAGAAAGTGAAGGAGAAAC |

TABLE 1-continued

Table of select sequences of the invention

| SEQ ID NO: | Description | Sequence |
|---|---|---|
| | | TCATTGACCCTGACGTCACCTCTGATGAGGAGAGCCCCAAGCC
CTCCCCAGCCAAGAAAGCCCCAGAGCCAGCTCCAGACACAAAG
CCCGCTGAAGCCGAGCCAGTGGAAGAGGAGCACTATTGCGACA
TGCTCTGCTGCAAGTTCAAACACCGCCCCTGGAAGAAGTACCA
GTTTCCCCAGAGCATTGACCCGCTGACCAACCTGATGTATGTCC
TATGGCTGTTCTTCGTGGTGATGGCCTGGAATTGGAACTGTTGG
CTGATTCCCGTGCGCTGGGCCTTCCCCTACCAGACCCCGGACAA
CATCCACCACTGGCTGCTGATGGATTACCTATGCGACCTCATCT
ACTTCCTGGACATCACCGTGTTCCAGACACGCCTGCAGTTTGTC
AGAGGCGGGGACATCATTACGGACAAAAAGGACATGCGAAAT
AACTACCTGAAGTCTCGCCGCTTCAAGATGGACCTGCTCAGCCT
CCTGCCCTTGGATTTTCTCTATTTGAAAGTCGGTGTGAACCCCC
TCCTCCGCCTGCCCCGCTGTTTAAAGTACATGGCCTTCTTCGAG
TTTAACAGCCGCCTGGAATCCATCCTCAGCAAAGCCTACGTGTA
CAGGGTCATCAGGACCACAGCCTACCTTCTCTACAGCCTGCATT
TGAATTCCTGTCTTTATTACTGGGCATCGGCCTATCAGGGCCTC
GGCTCCACTCACTGGGTTTACGATGGCGTGGGAAACAGTTATA
TTCGCTGTTACTACTTTGCTGTGAAGACCCTCATCACCATCGGG
GGGCTGCCTGACCCCAAGACACTCTTTGAAATTGTCTTCCAGCT
GCTGAATTATTTCACGGGCGTCTTTGCTTTCTCTGTGATGATCG
GACAGATGAGAGATGTGGTAGGGGCCGCCACCGCGGGACAGA
CCTACTACCGCAGCTGCATGGACAGCACGGTGAAGTACATGAA
TTTCTACAAGATCCCCAAGTCCGTGCAGAACCGCGTCAAGACC
TGGTACGAGTACACCTGGCACTCGCAAGGCATGCTGGATGAGT
CAGAGCTGATGGTGCAGCTTCCAGACAAGATGCGGCTGGACCT
CGCCATCGACGTGAACTACAACATCGTTAGCAAAGTCGCACTC
TTTCAGGGCTGTGACCGGCAGATGATCTTTGACATGCTGAAGA
GGCTTCGCTCTGTTGTCTACCTGCCCAACGACTATGTGTGCAAG
AAGGGGGAGATCGGCCGTGAGATGTACATCATCCAGGCAGGGC
AAGTGCAGGTCTTGGGCGGCCCTGATGGGAAATCTGTGCTGGT
GACGCTGAAAGCTGGATCTGTGTTTGGAGAAATAAGCTTGCTG
GCTGTTGGGGGCGGGAACCGGCGCACGGCCAACGTGGTGGCGC
ACGGGTTTACCAACCTCTTCATCCTGGATAAGAAGGACCTGAA
TGAGATTTTGGTGCATTATCCTGAGTCTCAGAAGTTACTCCGGA
AGAAAGCCAGGCGCATGCTGAGAAGCAACAATAAGCCCAAGG
AGGAGAAGAGCGTGCTGATCCTTCCACCCCGGGCGGGCACCCC
AAAGCTCTTCAACGCTGCCCTCGCTATGACAGGAAAGATGGGT
GGCAAGGGGCAAAAGGCGGCAAACTTGCTCACCTCCGGGCCC
GGCTCAAAGAACTGGCCGCGCTGGAGGCGGCTGCAAAGCAGC
AAGAGTTGGTGGAACAGGCCAAGAGCTCGCAAGACGTCAAGG
GAGAGGAAGGCTCCGCCGCCCCAGACCAGCACACGCACCCAA
AGGAGGCCGCCACCGACCCACCCGCGCCCCGGACGCCCCCGA
GCCCCCGGGGTCTCCACCGAGCTCTCCACCGCCTGCCTCCCTTG
GGAGGCCGGAGGGAGAGGAGGAGGGGCCGGCCGAGCCCGAAG
AGCACTCGGTGAGGATCTGCATGAGCCCGGGCCCGGAGCCGGG
AGAGCAGATCCTGTCGGTGAAGATGCCGGAGGAAAGGGAGGA
GAAGGCGGAGTAAGGTGGGGTGAGGCGGATCCATGGCCGCAG
ACATGATAAGATACATTGATGAGTTTGGACAAACCACAACTAG
AATGCAGTGAAAAAAATGCTTTATTTGTGAAATTTGTGATGCTA
TTGCTTTATTTGTAACCATTATAAGCTGCAATAAACAAGTTAAC
AACAACAATTGCATTCATTTTATGTTTCAGGTTCAGGGGGAGGT
GTGGGAGGTTTTTTAAAGCAAGTAAAACCTCTACAAATGTGGT
ACTCGAGTTAAGGGCGAATTCCCGATAAGGATCTTCCTAGAGC
ATGGCTACGTAGATAAGTAGCATGGCGGGTTAATCATTAACTA
CAAGGAACCCCTAGTGATGGAGTTGGCCACTCCCTCTCTGCGC
GCTCGCTCGCTCACTGAGGCCGGGCGACCAAAGGTCGCCCGAC
GCCCGGGCTTTGCCCGGGCGGCCTCAGTGAGCGAGCGAGCGCG
CAGCTGGGCCTCAGTGAGCGAGCGAGCGCGCAGCTGCATTAAT
GAATCGGCCAACGCGCGGGGAGAGGCGGTTTGCGTATTGGGCG
CTCTTCCGCTTCCTCGCTCACTGACTCGCTGCGCTCGGTCGTTCG
GCTGCGGCGAGCGGTATCAGCTCACTCAAAGGCGGTAATACGG
TTATCCACAGAATCAGGGGATAACGCAGGAAAGAACATGTCGC
GTTGCTGGCGTTTTTCCATAGGCTCCGCCCCCCTGACGAGCATC
ACAAAAATCGACGCTCAAGTCAGAGGTGGCGAAACCCGACAG
GACTATAAAGATACCAGGCGTTTCCCCCTGGAAGCTCCCTCGTG
CGCTCTCCTGTTCCGACCCTGCCGCTTACCGGATACCTGTCCGC
CTTTCTCCCTTCGGGAAGCGTGGCGCTTTCTCATAGCTCACGCT
GTAGGTATCTCAGTTCGGTGTAGGTCGTTCGCTCCAAGCTGGGC
TGTGTGCACGAACCCCCCGTTCAGCCCGACCGCTGCGCCTTATC
CGGTAACTATCGTCTTGAGTCCAACCCGGTAAGACACGACTTAT
CGCCACTGGCAGCAGCCACTGGTAACAGGATTAGCAGAGCGAG
GTATGTAGGCGGTGCTACAGAGTTCTTGAAGTGGTGGCCTAAC
TACGGCTACACTAGAAGAACAGTATTTGGTATCTGCGCTCTGCT
GAAGCCAGTTACCTTCGGAAAAAGAGTTGGTAGCTCTTGATCC |

TABLE 1-continued

Table of select sequences of the invention

| SEQ ID NO: | Description | Sequence |
|---|---|---|
| | | GGCAAACAAACCACCGCTGGTAGCGGTGGTTTTTTTGTTTGCAA |
| | | GCAGCAGATTACGCGCAGAAAAAAAGGATCTCAAGAAGATCCT |
| | | TTGATCTTTTCTACGGGGTCTGACGCTCAGTGGAACGAAAACTC |
| | | ACGTTAAGGGATTTTGGTCATGACTGTGGAATGTGTGTCAGTTA |
| | | GGCGACATAGGTGATCTATGTAGAAGCCTAGTGGAACAGGTTA |
| | | GTTTGAGTAGCTTTAGAATGTAAATTCTGGGATCATAGTGTAGT |
| | | AATCTCTAATTAACGGTGACGGTTTGTAAGACAGGTCTTCGCAA |
| | | AATCAAGCGGCAGGTGATTTCAACAGATTCTTGCTGATGGTTTA |
| | | GGCGTACAATGCCCTGAAGAATAAGTAAGAGAATAGCACTCCT |
| | | CGTCGCCTAGAATTACCTACCGGCGTCCACCATACCTTCGATTA |
| | | TCGCGCCCACTCTCCCATTAGTCGGCACAGGTGGATGTGTTGCG |
| | | ATAGCCCGCTAAGATATTCTAAGGCGTAACGCAGATGAATATT |
| | | CTACAGAGTTGCCATAGGCGTTGAACGCTTCACGGACGATAGG |
| | | AATGTTGCGTATAGAGCGTGAGTCATCGAAGTGGTGTATACAC |
| | | TCGTACTTAACATCTAGCCCGGCTCTATCAGTACACCAGTGCCT |
| | | TGAATGACATACTCATCATTAAACTTTCTCAACAGTCAAACGAC |
| | | CAAGTGCATTTCCAAGGAGTGCGAAGGAGATTCATTCTCTCGC |
| | | CAGCACTGTAATAGGCACTAAAAGAGTGAAGATAAGCTAGAGT |
| | | GCCGTGCTAAGACGGTGTCGGAACAAAGCGGTCTTACGGTCAG |
| | | TCGTATTTCCTGTCGAGTCCCGTCCAGTTGAGCGTATCACTCCC |
| | | AGTGTACTAGCAAGCCGAGAAGGCTGTGCTTGGAGTCAATCGG |
| | | ATGTAGGATGGTCTCCAGACACCGGGCCACCACTCTTCACGCCT |
| | | AGAAGCATAGAACGTCGAGCAGACATCAAAGTCTTAGTACCGG |
| | | ACGTGCCGTTTCACTGCGAATATTACCTGAAGCTGTACCGTTAT |
| | | TGCGGAGCAAAGTGACAGTGCTGCTCTTATCATATTTGTATTGA |
| | | CGACAGCCGCCTTCGCGGTTTCCTCAGACTCTAGATCGAATACA |
| | | GGCTTATTGTAGGCAGAGGCACGCCCTTGTTAGTGGCTGCGGC |
| | | AATATCTTCCGATCCCCTTGTCTAACCATGAATCAATTCTCTCA |
| | | TTTGAAGACCCTAATATGTCATCATTAGTGTTTCAAATGCCACC |
| | | AAATACCGCCTAGAAATGTCTATGATGTGTCCACTAGAAGTT |
| | | GATTCACAAACGACTGCTAGAATCGCGTGATAGGGCATCTTGA |
| | | AGTTTACATTGTTGTATCGCAAGGTACTCCGATCTTAATGGATG |
| | | CGAAGTGGTACGGATGCAATCAAGCGCGTGAGAGCGGTACATT |
| | | AGAGCGTTCACCTACGCTACGCTAACGGGCGATTCTGATAAGA |
| | | ATGCACATTGCGTCGATTCATAAGATGTCTCGACCGCATGCGCA |
| | | ACTTGTGAAGTGTCTACTATCCCTAAGCGCATATCTCGCACAGT |
| | | AACCGAATATGTCGGCATCTGATGTTACCGTTGAGTTAGTGTTC |
| | | AGCTCACGGAACTTATTGTATGAGTAGAGATTTGTAAGAGCTG |
| | | TTAGTTAGCTCGCTCAGCTAATAGTTGCCCACACAACGTCAAAT |
| | | TAGAGAACGGTCGTAACATTATCGGTGGTTCTCTAACTACTATC |
| | | AGTACCCACGACTCGACTCTGCCGCAGCTAGGTATCGCCTGAA |
| | | AGCCAGTCAGCGTTAAGGAGTGCTCTGACCAGGACAACAGGCG |
| | | TAGTGAGAGTTACTTGTTCGTTGCTCTTCCGACTCGGACCTGAG |
| | | TTCGCCAACGACCCACTTGAGGTCTGAGCCGGTGAAGAGAAGT |
| | | AAGCATCTCGTTCGCAGCTTGCCAGCACTTTCAGAACATGACCC |
| | | CTATTTGTTTATTTTTCTAAATACATTCAAATATGTATCCGCTCA |
| | | TGAGACAATAACCCTGATAAATGCTTCAATAATATTGAAAAAG |
| | | GAAGAGTGGCCGCCTCGGCCTAGGCTTTTGCAAAGATCGATCA |
| | | AGAGACAGGATGAGGATCGTTTCGCATGATTGAACAAGATGGA |
| | | TTGCACGCAGGTTCTCCGGCCGCTTGGGTGGAGAGGCTATTCG |
| | | GCTATGACTGGGCACAACAGACAATCGGCTGCTCTGATGCCGC |
| | | CGTGTTCCGGCTGTCAGCGCAGGGGCGCCCGGTTCTTTTTGTCA |
| | | AGACCGACCTGTCCGGTGCCCTGAATGAACTGCAAGACGAGGC |
| | | AGCGCGGCTATCGTGGCTGGCCACGACGGGCGTTCCTTGCGCA |
| | | GCTGTGCTCGACGTTGTCACTGAAGCGGGAAGGGACTGGCTGC |
| | | TATTGGGCGAAGTGCCGGGGCAGGATCTCCTGTCATCTCACCTT |
| | | GCTCCTGCCGAGAAAGTATCCATCATGGCTGATGCAATGCGGC |
| | | GGCTGCATACGCTTGATCCGGCTACCTGCCCATTCGACCACCAA |
| | | GCGAAACATCGCATCGAGCGAGCACGTACTCGGATGGAAGCCG |
| | | GTCTTGTCGATCAGGATGATCTGGACGAAGAGCATCAGGGGCT |
| | | CGCGCCAGCCGAACTGTTCGCCAGGCTCAAGGCGAGCATGCCC |
| | | GACGGCGAGGATCTCGTCGTGACCCATGGCGATGCCTGCTTGC |
| | | CGAATATCATGGTGGAAAATGGCCGCTTTTCTGGATTCATCGAC |
| | | TGTGGCCGGCTGGGTGTGGCGGACCGCTATCAGGACATAGCGT |
| | | TGGCTACCCGTGATATTGCTGAAGAGCTTGGCGGCGAATGGGC |
| | | TGACCGCTTCCTCGTGCTTTACGGTATCGCCGCTCCCGATTCGC |
| | | AGCGCATCGCCTTCTATCGCCTTCTTGACGAGTTCTTCTGAGGT |
| | | ACCATGATGCGTGCATGGTAGAATGACTCTTGATAACGGACTT |
| | | CGACTAGGCAATATCCCTTGTCAACTTGTCGAGGAGAAAAGTA |
| | | TTGACTGAAGCGCTCCCGGCACAACGGCCAAAGAAGTCTCAGC |
| | | AATGTTCTTATTTCCGAATGACATGCGTCTCCTTGCGGGTAAAT |
| | | CGCCGACCGCAAAACTTAGGAGCCAGGATACAGATAGGTCTAA |
| | | CTTAGGTTAAGGGAGTAAATCCTGGGATCGTTCAGTTGTAACC |
| | | ATATACTTACGCTGGGGCTTCTCCGGCGGATGTTACTGTCACCA |

TABLE 1-continued

Table of select sequences of the invention

| SEQ ID NO: | Description | Sequence |
|---|---|---|
| | | ACCACGAGATTTGAAGTAAACGCATGATTGAGCACATAGCCGC GCTATCCGACAATCTCCAAATTGATAACATACCGTTCCATGAAG GCCAGAATTACTTACCGGCCCTTTCCATGCGTGCGCCATACCGC ACTCTGCGCTTATCCGTCCGAGGGGAGAGTGTGCGATCCTCCGT TAAGATATTCTCACGTATGACGTAGCTATGTATTGTGCAGAGGT AGCGAAGGCGTTGAACACTTCACAGATGGTGGGGATTCGGGCA AAGGGCGTGATAACTTGGGGACTAACATAGGCGTAAACTACGA TGGCACCAACTCAATCGCAGCTCGTGCGCCCTGAATCAACGTA CTCATCTCAACTGATTCTCGGCAATCTACGGAGCGACTTGATTA TCAACACCTGTCTAGCAGTTCTAATCTTCTGCCAACATCGTACA TAGCCTCCAAGAGATTATCATACCTATCGGCACAGAAGTGACA CGACGCCGAAGGGTAGCGGACTTCTGGTCAACCACAATTCCCC AGGGGACAGGTCCTGCGGTGCGCATCACTTTGTAAGTGCAAGC AACCCAAGTGAGCCCAGCCTGGACTGAGCTGGTTCCTGTGTCA GGTCGAGGCTGGGGATGACAGCTCTTGTAAACATAGTGATCAA GCGTGGCGTCGAACGGTCGAGAAACTCATAGTACCTCGGGTAG CAACTTACTCAGGTTATTGCTTGAAGCTGTACTATTTCAGGAGC GCTGAAGGTCTCTTCTTCTGTAGACTGAACTCGCAAGGGTCGTG AAGTCGGTTCCTTCAATGCTTAACAAGAACAAAGGCTTACTGT GCAGACTGGAACGCCCATCTAGCGGCTCGCGTCTTGAATGCTC GGTCCCCTTTGTCATTGCGGATACAATCCATTTCCCTCATTCAC CAGCTTGCGAAGTCTACATTGAGTAGACGAATGCGACCTAGAA GAGGTGCGCTTCAGAACTTGTGAGGAGTGGTTGATGCTCTATA CTCCATTTGGTGTTTCGTGCATCACCGCGATAGGCTGACAAGAG GTCTTGAACATTGAATAGCAAGGCACTTCCGGTCTCATAGAAG AGAGCACGGGATAAGGTACGCGCGTGGTACGGGAGGATCAAG GGGCTACACGATAGAAAGGCTTCTCCCTCACTCGCTAGGAGGC AAATGCAGAACGCTGGTTACTACTACGATACGTGAAACTTGTC CAACGGTTGCCCAAAGTGTTAAGTGTCTATCACCCTAGTGCCGT TTCCCGGAGAAAACGCCAGGTTGAATCCGCATTTGAAGCTACG ATGGTGAAGTCTGGGTCGAGCGCGCCGCATGTTGATTGCGTGA GTAGGCTCGACCAAGAACCGCTAGTAGCGTCGCTGTAGAAATA GTTCTCGACAGACCGTCGAGTTTAGAAAATGGTAGCAGCATTG TTCGCATCTCAATCAAGTATGGATTACGGTGTTTACACTGTCCT GCGGCTACCCATCGCCTGAAATCCAGCTCGTGTCAAGCCATTGC CTCTCCGGGACGCCGCATGAAGTAACTACATATACCTTGCACG GGTTGACTGCGGTCCGTTCAGACTCGACCAAGGACACAATCCA GCGATCGGTGCGGGCCTCTTCGCTATTACGC |
| 8 | Sequence of the human CNGB1 gene | ATGTTGGGCTGGGTCCAGAGGGTGCTGCCTCAGCCCCCAGGGA CCCCTCGGAAGACCAAGATGCAGGAGGAAGAGGAAGTGGAAC CAGAGCCAGAGATGGAGGCGGAGGTGGAACCAGAACCGAATC CTGAGGAGGCCGAGACAGAGTCCGAGTCCATGCCCCCCGAAGA GTCATTCAAGGAGGAGGAAGTGGCTGTGGCAGACCCAAGCCCT CAGGAGACCAAGGAGGCTGCCCTTACTTCCACCATATCCCTCC GGGCCCAGGGCGCTGAGATTTCTGAAATGAATAGTCCCAGCCA CAGGGTACTGACCTGGCTCATGAAGGGTGTAGAGAAGGTGATC CCGCAGCCTGTTCACAGCATCACGGAGGACCCGGCTCAGATCC TGGGGCATGGCAGCACTGGGGACACAGGGTGCACAGATGAAC CCAATGAGGCCCTTGAGGCCCAAGACACTAGGCCTGGGCTGCG GCTGCTTCTGTGGCTGGAGCAGAATCTGGAAAGAGTGCTTCCTC AGCCCCCCAAATCCTCTGAGGTCTGGAGAGATGAGCCTGCAGT TGCTACAGCGCCTCCAGGACGCCCCAGGAAATGGGGCCCAAG CTGCAGGCCCGGGAGACCCCCTCCCTGCCCACACCCATCCCCCT GCAGCCCAAGGAGGAACCCAAGGAGGCACCAGCTCCAGAGCC CCAGCCCGGCTCCCAGGCCCAGACCTCCTCCCTGCCACCAACC AGGGACCCTGCCAGGCTGGTGGCATGGGTCCTGCACAGGCTGG AGATGGCCTTGCCGCAGCCAGTGCTACATGGGAAAATAGGGGA ACAGGAGCCTGACTCCCCTGGGATATGTGATGTGCAGACCATC AGCATCCTTCCTGGAGGACAAGTGGAGCCTGACCTTGTCCTAG AGGAGGTTGAACCGCCCTGGGAGGATGCCCACCAGGATGTCAG TACCAGCCCACAGGGTACAGAGGTGGTTCCAGCTTATGAAGAA GAGAACAAAGCTGTGGAGAAGATGCCCAGAGAGCTGTCCCGG ATTGAAGAGGAGAAAGAAGATGAGGAGGAGGAAGAGGAAGA GGAGGAGGAGGAGGAAGAGGAGGAGGTGACTGAGGTGCTGCT GGATAGCTGTGTGGTGTCGCAGGTGGGCGTGGGCCAGAGTGAA GAAGACGGGACCCGGCCCCAGAGCACTTCAGATCAGAAGCTGT GGGAGGAAGTTGGGGAGGAGGCCAAGAAGGAGGCTGAAGAGA AGGCCAAGGAGGAGGCCGAGGAGGTGGCTGAAGAGGAGGCTG AAAAGGAGCCCCAGGACTGGGCGGAGACCAAGGAGGAGCCTG AGGCTGAGGCCGAGGCTGCCAGTTCAGGAGTGCCTGCCACGAA ACAGCACCCAGAAGTGCAGGTGGAAGATACTGATGCTGATAGC TGCCCCCTCATGGCAGAAAGAGAATCCACCCTCAACCGTGTTGC CGCCACCATCTCCTGCCAAATCAGACACCCTTATAGTCCCAAGC |

TABLE 1-continued

Table of select sequences of the invention

| SEQ ID NO: | Description | Sequence |
|---|---|---|
| | | TCAGCCTCGGGGACACACAGGAAGAAGCTGCCCTCTGAGGATG<br>ATGAGGCTGAAGAGCTCAAGGCGTTGTCACCAGCAGAGTCCCC<br>AGTGGTTGCCTGGTCTGACCCCACCACCCCGAAGGACACTGAT<br>GGCCAGGACCGTGCGGCCTCCACGGCCAGCACAAATAGCGCCA<br>TCATCAACGACCGGCTCCAGGAGCTGGTGAAGCTCTTCAAGGA<br>GCGGACAGAGAAAGTGAAGGAGAAACTCATTGACCCTGACGTC<br>ACCTCTGATGAGGAGAGCCCCAAGCCCTCCCCAGCCAAGAAAG<br>CCCCAGAGCCAGCTCCAGACACAAAGCCCGCTGAAGCCGAGCC<br>AGTGGAAGAGGAGCACTATTGCGACATGCTCTGCTGCAAGTTC<br>AAACACCGCCCCTGGAAGAAGTACCAGTTTCCCCAGAGCATTG<br>ACCCGCTGACCAACCTGATGTATGTCCTATGGCTGTTCTTCGTG<br>GTGATGGCCTGGAATTGGAACTGTTGGCTGATTCCCGTGCGCTG<br>GGCCTTCCCCTACCAGACCCCGGACAACATCCACCACTGGCTG<br>CTGATGGATTACCTATGCGACCTCATCTACTTCCTGGACATCAC<br>CGTGTTCCAGACACGCCTGCAGTTTGTCAGAGGCGGGGACATC<br>ATTACGGACAAAAAGGACATGCGAAATAACTACCTGAAGTCTC<br>GCCGCTTCAAGATGGACCTGCTCAGCCTCCTGCCCTTGGATTTT<br>CTCTATTTGAAAGTCGGTGTGAACCCCCTCCTCCGCCTGCCCCG<br>CTGTTTAAAGTACATGGCCTTCTTCGAGTTTAACAGCCGCCTGG<br>AATCCATCCTCAGCAAAGCCTACGTGTACAGGGTCATCAGGAC<br>CACAGCCTACCTTCTCTACAGCCTGCATTTGAATTCCTGTCTTTA<br>TTACTGGGCATCGGCCTATCAGGGCCTCGGCTCCACTCACTGGG<br>TTTACGATGGCGTGGGAAACAGTTATATTCGCTGTTACTACTTT<br>GCTGTGAAGACCCTCATCACCATCGGGGGGCTGCCTGACCCCA<br>AGACACTCTTTGAAATTGTCTTCCAGCTGCTGAATTATTTCACG<br>GGCGTCTTTGCTTTCTCTGTGATGATCGGACAGATGAGAGATGT<br>GGTAGGGGCCGCCACCGCGGGACAGACCTACTACCGCAGCTGC<br>ATGGACAGCACGGTGAAGTACATGAATTTCTACAAGATCCCCA<br>AGTCCGTGCAGAACCGCGTCAAGACCTGGTACGAGTACACCTG<br>GCACTCGCAAGGCATGCTGGATGAGTCAGAGCTGATGGTGCAG<br>CTTCCAGACAAGATGCGGCTGGACCTCGCCATCGACGTGAACT<br>ACAACATCGTTAGCAAAGTCGCACTCTTTCAGGGCTGTGACCG<br>GCAGATGATCTTTGACATGCTGAAGAGGCTTCGCTCTGTTGTCT<br>ACCTGCCCAACGACTATGTGTGCAAGAAGGGGGAGATCGGCCG<br>TGAGATGTACATCATCCAGGCAGGGCAAGTGCAGGTCTTGGGC<br>GGCCCTGATGGGAAATCTGTGCTGGTGACGCTGAAAGCTGGAT<br>CTGTGTTTGGAGAAATAAGCTTGCTGGCTGTTGGGGGCGGGAA<br>CCGGCGCACGGCCAACGTGGTGGCGCACGGGTTTACCAACCTC<br>TTCATCCTGGATAAGAAGGACCTGAATGAGATTTTGGTGCATTA<br>TCCTGAGTCTCAGAAGTTACTCCGGAAGAAAGCCAGGCGCATG<br>CTGAGAAGCAACAATAAGCCCAAGGAGGAGAAGAGCGTGCTG<br>ATCCTTCCACCCCGGGCGGGCACCCCAAAGCTCTTCAACGCTGC<br>CCTCGCTATGACAGGAAAGATGGGTGGCAAGGGGGCAAAAGG<br>CGGCAAACTTGCTCACCTCCGGGCCCGGCTCAAAGAACTGGCC<br>GCGCTGGAGGCGGCTGCAAAGCAGCAAGAGTTGGTGGAACAG<br>GCCAAGAGCTCGCAAGACGTCAAGGGAGAGGAAGGCTCCGCC<br>GCCCCAGACCAGCACACGCACCCAAAGGAGGCCGCCACCGACC<br>CACCCGCGCCCCGGACGCCCCCCGAGCCCCCGGGTCTCCACC<br>GAGCTCTCCACCGCCTGCCTCCCTTGGGAGGCCGGAGGGAGAG<br>GAGGAGGGGCCGGCCGAGCCCGAAGAGCACTCGGTGAGGATC<br>TGCATGAGCCCGGGCCCGGAGCCGGGAGAGCAGATCCTGTCGG<br>TGAAGATGCCGGAGGAAAGGGAGGAGAAGGCGGAGTAA |
| 9 | 194 nucleotide long fragment of human RHO promoter | TCTCCTCCCTGACCTCAGGCTTCCTCCTAGTGTCACCTTGGCCCC<br>TCTTAGAAGCCAATTAGGCCCTCAGTTTCTGCAGCGGGGATTAA<br>TATGATTATGAACACCCCCAATCTCCCAGATGCTGATTCAGCCA<br>GGAGCTTAGGAGGGGAGGTCACTTTATAAGGGTCTGGGGGGG<br>TCAGAACCCAGAGTCATC |
| 40 | Sequence of the human CNGB1 protein translated from next generation sequencing (NGS) results | MLGWVQRVLPQPPGTPRKTKMQEEEEVEPEPEMEAEVEPEPNPEE<br>AETESESMPPEESFKEEEVAVADPSPQETKEAALTSTISLRAQGAEI<br>SEMNSPSHRVLTWLMKGVEKVIPQPVHSITEDPAQILGHGSTGDT<br>GCTDEPNEALEAQDTRPGLRLLLWLEQNLERVLPQPPKSSEVWRD<br>EPAVATGAASDPAPPGRPQEMGPKLQARETPSLPTPIPLQPKEEPK<br>EAPAPEPQPGSQAQTSSLPPTRDPARLVAWVLHRLEMALPQPVLH<br>GKIGEQEPDSPGICDVQTISILPGGQVEPDLVLEEVEPPWEDAHQD<br>VSTSPQGTEVVPAYEEENKAVEKMPRELSRIEEEKEDEEEEEEEEE<br>EEEEEEVTEVLLDSCVVSQVGVGQSEEDGTRPQSTSDQLWEEVGE<br>EAKKEAEEKAKEEAEEVAEEEAEKEPQDWAETKEEPEAEAEAASS<br>GVPATKQHPEVQVEDTDADSCPLMAEENPPSTVLPPPSPAKSDTLI<br>VPSSASGTHRKKLPSEDDEAEELKALSPAESPVVAWSDPTTPKDTD<br>GQDRAASTASTNSAIINDRLQELVKLFKERTEKVKEKLIDPDVTSD<br>EESPKPSPAKKAPEPAPDTKPAEAEPVEEEHYCDMLCCKFKHRPW |

TABLE 1-continued

Table of select sequences of the invention

| SEQ ID NO: | Description | Sequence |
|---|---|---|
| | | KKYQFPQSIDPLTNLMYVLWLFFVVMAWNWNCWLIPVRWAFPY<br>QTPDNIHHWLLMDYLCDLIYFLDITVFQTRLQFVRGGDIITDKKDM<br>RNNYLKSRRFKMDLLSLLPLDFLYLKVGVNPLLRLPRCLKYMAFF<br>EFNSRLESILSKAYVYRVIRTTAYLLYSLHLNSCLYYWASAYQGL<br>GSTHWVYDGVGNSYIRCYYFAVKTLITIGGLPDPKTLFEIVFQLLN<br>YFTGVFAFSVMIGQMRDVVGAATAGQTYYRSCMDSTVKYMNFY<br>KIPKSVQNRVKTWYEYTWHSQGMLDESELMVQLPDKMRLDLAID<br>VNYNIVSKVALFQGCDRQMIFDMLKRLRSVVYLPNDYVCKKGEI<br>GREMYIIQAGQVQVLGGPDGKSVLVTLKAGSVFGEISLLAVGGGN<br>RRTANVVAHGFTNLFILDKKDLNEILVHYPESQKLLRKKARRMLR<br>SNNKPQEEKSVLILPPRAGTPKLFNAALAMTGKMGGKGAKGGKL<br>AHLRARLKELAALEAAAKQQELVEQAKSSQDVKGEEGSAAPDQH<br>THPKEAATDPPAPRTPPEPPGSPPSSPPPASLGRPEGEEEGPAEPEEH<br>SVRICMSPGPEPGEQILSVKMPEEREEKAE |
| 41 | Sequence of the CNGB1 protein (GenBank NG_016351) | MLGWVQRVLPQPPGTPRKTKMQEEEEVEPEPEMEAEVEPEPNPEE<br>AETESESMPPEESFKEEEVAVADPSPQETKEAALTSTISLRAQGEAI<br>SEMNSPSRRVLTWLMKGVEKVIPQPVHSITEDPAQILGHGSTGDTG<br>CTDEPNEALEAQDTRPGLRLLLWLEQNLERVLPQPPKSSEVWRDE<br>PAVATGAAASDPAPPGRPQEMGPKLQARETPSLPTPIPLQPKEEPKE<br>APAPEPQPGSQAQTSSLPPTRDPARLVAWVLHRLEMALPQPVLHG<br>KIGEQEPDSPGICDVQTISILPGGQVEPDLVLEEVEPPWEDAHQDVS<br>TSPQGTEVVPAYEEENKAVEKMPRELSRIEEEKEDEEEEEEEEEEE<br>EEEEVTEVLLDSCVVSQVGVGQSEEDGTRPQSTSDQKLWEEVGEE<br>AKKEAEEKAKEEAEEVAEEEAEKEPQDWAETKEEPEAEAEAASS<br>GVPATKQHPEVQVEDTDADSCPLMAEENPPSTVLPPPSPAKSDTLI<br>VPSSASGTHRKKLPSEDDEAEELKALSPAESPVVAWSDPTTPKDTD<br>GQDRAASTASTNSAIINDRLQELVKLFKERTEKVKEKLIDPDVTSD<br>EESPKPSPAKKAPEPAPDTKPAEAEPVEEEHYCDMLCCKFKHRPW<br>KKYQFPQSIDPLTNLMYVLWLFFVVMAWNWNCWLIPVRWAFPY<br>QTPDNIHHWLLMDYLCDLIYFLDITVFQTRLQFVRGGDIITDKKDM<br>RNNYLKSRRFKMDLLSLLPLDFLYLKVGVNPLLRLPRCLKYMAFF<br>EFNSRLESILSKAYVYRVIRTTAYLLYSLHLNSCLYYWASAYQGL<br>GSTHWVYDGVGNSYIRCYYFAVKTLITIGGLPDPKTLFEIVFQLLN<br>YFTGVFAFSVMIGQMRDVVGAATAGQTYYRSCMDSTVKYMNFY<br>KIPKSVQNRVKTWYEYTWHSQGMLDESELMVQLPDKMRLDLAID<br>VNYNIVSKVALFQGCDRQMIFDMLKRLRSVVYLPNDYVCKKGEI<br>GREMYIIQAGQVQVLGGPDGKSVLVTLKAGSVFGEISLLAVGGGN<br>RRTANVVAHGFTNLFILDKKDLNEILVHYPESQKLLRKKARRMLR<br>SNNKPKEEKSVLILPPRAGTPKLFNAALAMTGKMGGKGAKGGKL<br>AHLRARLKELAALEAAAKQQELVEQAKSSQDVKGEEGSAAPDQH<br>THPKEAATDPPAPRTPPEPPGSPPSSPPPASLGRPEGEEEGPAEPEEH<br>SVRICMSPGPEPGEQILSVKMPEEREEKAE |
| 42 | Sequence of 5'ITR-hRHO promoter-CNGB1a-SV40polyA-3'ITR | CTGCGCGCTCGCTCGCTCACTGAGGCCGCCCGGGCAAAGCCCG<br>GGCGTCGGGCGACCTTTGGTCGCCCGGCCTCAGTGAGCGAGCG<br>AGCGCGCAGAGAGGGAGTGGCCAACTCCATCACTAGGGGTTCC<br>TTGTAGTTAATGATTAACCCGCCATGCTACTTATCTACGTAGCC<br>ATGCTCTAGGAAGATCGGAATTCGCCCTTAAGCCTCTCCTCCCT<br>GACCTCAGGCTTCCTCCTAGTGTCACCTTGGCCCCTCTTAGAAG<br>CCAATTAGGCCCTCAGTTTCTGCAGCGGGGATTAATATGATTAT<br>GAACACCCCCAATCTCCCAGATGCTGATTCAGCCAGGAGCTTA<br>GGAGGGGGAGGTCACTTTTATAAGGGTCTGGGGGGGTCAGAACC<br>CAGAGTCATCACTAGTAACGGCCGCCAGTGTGCTGGAATTCGC<br>CCTTCTCCACCGCCATGTTGGGCTGGGTCCAGAGGGTGCTGCCT<br>CAGCCCCCAGGGACCCCTCGGAAGACCAAGATGCAGGAGGAA<br>GAGGAAGTGGAACCAGAGCCAGAGATGGAGGCGGAGGTGGAA<br>CCAGAACCGAATCCTGAGGAGGCCGAGACAGAGTCCGAGTCCA<br>TGCCCCCCGAAGAGTCATTCAAGGAGGAGGAAGTGGCTGTGGC<br>AGACCCAAGCCCTCAGGAGACCAAGGAGGCTGCCCTTACTTCC<br>ACCATATCCCTCCGGGCCCAGGGCGCTGAGATTTCTGAAATGA<br>ATAGTCCCAGCCACAGGGTACTGACCTGGCTCATGAAGGGTGT<br>AGAGAAGGTGATCCCGCAGCCTGTTCACAGCATCACGGAGGAC<br>CCGGCTCAGATCCTGGGGCATGGCAGCACTGGGGACACAGGGT<br>GCACAGATGAACCCAATGAGGCCCTTGAGGCCCAAGACACTAG<br>GCCTGGGCTGCGGCTGCTTCTGTGGCTGGAGCAGAATCTGGAA<br>AGAGTGCTTCCTCAGCCCCCAAATCCTCTGAGGTCTGGAGAG<br>ATGAGCCTGCAGTTGCTACAGCGCCTCCAGGACGCCCCAGGA<br>AATGGGCCCAAGCTGCAGGCCCGGGAGACCCCCTCCCTGCCC<br>ACACCCATCCCCCTGCAGCCCAAGGAGGAACCCAAGGAGGCAC<br>CAGCTCCAGAGCCCCAGCCCGGCTCCCAGGCCCAGACCTCCTC<br>CCTGCCACCAACCAGGGACCCTGCCAGGCTGGTGGCATGGGTC<br>CTGCACAGGCTGGAGATGGCCTTGCCGCAGCCAGTGCTACATG<br>GGAAAATAGGGGAACAGGAGCCTGACTCCCCTGGGATATGTGA |

TABLE 1-continued

Table of select sequences of the invention

| SEQ ID NO: | Description | Sequence |
|---|---|---|
| | | TGTGCAGACCATCAGCATCCTTCCTGGAGGACAAGTGGAGCCT |
| | | GACCTTGTCCTAGAGGAGGTTGAACCGCCCTGGGAGGATGCCC |
| | | ACCAGGATGTCAGTACCAGCCCACAGGGTACAGAGGTGGTTCC |
| | | AGCTTATGAAGAAGAGAACAAAGCTGTGGAGAAGATGCCCAG |
| | | AGAGCTGTCCCGGATTGAAGAGGAGAAAGAAGATGAGGAGGA |
| | | GGAAGAGGAAGAGGAGGAGGAGGAGGAAGAGGAGGAGGTGA |
| | | CTGAGGTGCTGCTGGATAGCTGTGTGGTGTCGCAGGTGGGCGT |
| | | GGGCCAGAGTGAAGAAGACGGGACCCGGCCCCAGAGCACTTC |
| | | AGATCAGAAGCTGTGGGAGGAAGTTGGGGAGGAGGCCAAGAA |
| | | GGAGGCTGAAGAGAAGGCCAAGGAGGAGGCCGAGGAGGTGGC |
| | | TGAAGAGGAGGCTGAAAAGGAGCCCCAGGACTGGGCGGAGAC |
| | | CAAGGAGGAGCCTGAGGCTGAGGCCGAGGCTGCCAGTTCAGG |
| | | AGTGCCTGCCACGAAACAGCACCCAGAAGTGCAGGTGGAAGAT |
| | | ACTGATGCTGATAGCTGCCCCCTCATGGCAGAAGAGAATCCAC |
| | | CCTCAACCGTGTTGCCGCCACCATCTCCTGCCAAATCAGACACC |
| | | CTTATAGTCCCAAGCTCAGCCTCGGGGACACACAGGAAGAAGC |
| | | TGCCCTCTGAGGATGATGAGGCTGAAGAGCTCAAGGCGTTGTC |
| | | ACCAGCAGAGTCCCCAGTGGTTGCCTGGTCTGACCCCACCACC |
| | | CCGAAGGACACTGATGGCCAGGACCGTGCGGCCTCCACGGCCA |
| | | GCACAAATAGCGCCATCATCAACGACCGGCTCCAGGAGCTGGT |
| | | GAAGCTCTTCAAGGAGCGGACAGAGAAAGTGAAGGAGAAACT |
| | | CATTGACCCTGACGTCACCTCTGATGAGGAGAGCCCCAAGCCC |
| | | TCCCCAGCCAAGAAAGCCCCAGAGCCAGCTCCAGACACAAAGC |
| | | CCGCTGAAGCCGAGCCAGTGGAAGAGGAGCACTATTGCGACAT |
| | | GCTCTGCTGCAAGTTCAAACACCGCCCCTGGAAGAAGTACCAG |
| | | TTTCCCCAGAGCATTGACCCGCTGACCAACCTGATGTATGTCCT |
| | | ATGGCTGTTCTTCGTGGTGATGGCCTGGAATTGGAACTGTTGGC |
| | | TGATTCCCGTGCGCTGGGCCTTCCCCTACCAGACCCCGGACAAC |
| | | ATCCACCACTGGCTGCTGATGGATTACCTATGCGACCTCATCTA |
| | | CTTCCTGGACATCACCGTGTTCCAGACACGCCTGCAGTTTGTCA |
| | | GAGGCGGGGACATCATTACGGACAAAAAGGACATGCGAAATA |
| | | ACTACCTGAAGTCTCGCCGCTTCAAGATGGACCTGCTCAGCCTC |
| | | CTGCCCCTTGGATTTTCTCTATTTGAAAGTCGGTGTGAACCCCCT |
| | | CCTCCGCCTGCCCCGCTGTTTAAAGTACATGGCCTTCTTCGAGT |
| | | TTAACAGCCGCCTGGAATCCATCCTCAGCAAAGCCTACGTGTA |
| | | CAGGGTCATCAGGACCACAGCCTACCTTCTCTACAGCCTGCATT |
| | | TGAATTCCTGTCTTTATTACTGGGCATCGGCCTATCAGGGCCTC |
| | | GGCTCCACTCACTGGGTTTACGATGGCGTGGGAAACAGTTATA |
| | | TTCGCTGTTACTACTTTGCTGTGAAGACCCTCATCACCATCGGG |
| | | GGGCTGCCTGACCCCAAGACACTCTTTGAAATTGTCTTCCAGCT |
| | | GCTGAATTATTTCACGGGCGTCTTTGCTTTCTCTGTGATGATCG |
| | | GACAGATGAGAGATGTGGTAGGGGCCGCCACCGCGGGACAGA |
| | | CCTACTACCGCAGCTGCATGGACAGCACGGTGAAGTACATGAA |
| | | TTTCTACAAGATCCCCAAGTCCGTGCAGAACCGCGTCAAGACC |
| | | TGGTACGAGTACACCTGGCACTCGCAAGGCATGCTGGATGAGT |
| | | CAGAGCTGATGGTGCAGCTTCCAGACAAGATGCGGCTGGACCT |
| | | CGCCATCGACGTGAACTACAACATCGTTAGCAAAGTCGCACTC |
| | | TTTCAGGGCTGTGACCGGCAGATGATCTTTGACATGCTGAAGA |
| | | GGCTTCGCTCTGTTGTCTACCTGCCCAACGACTATGTGTGCAAG |
| | | AAGGGGGAGATCGGCCGTGAGATGTACATCATCCAGGCAGGGC |
| | | AAGTGCAGGTCTTGGCGGCCCTGATGGGAAATCTGTGCTGGT |
| | | GACGCTGAAAGCTGGATCTGTGTTTGGAGAAATAAGCTTGCTG |
| | | GCTGTTGGGGCGGGAACCGGCGCACGGCCAACGTGGTGGCGC |
| | | ACGGGTTTACCAACCTCTTCATCCTGGATAAGAAGGACCTGAA |
| | | TGAGATTTTGGTGCATTATCCTGAGTCTCAGAAGTTACTCCGGA |
| | | AGAAAGCCAGGCGCATGCTGAGAAGCAACAATAAGCCCAAGG |
| | | AGGAGAAGAGCGTGCTGATCCTTCCACCCCGGGCGGGCACCCC |
| | | AAAGCTCTTCAACGCTGCCCTCGCTATGACAGGAAAGATGGGT |
| | | GGCAAGGGGCAAAAGGCGGCAAACTTGCTCACCTCCGGGCCC |
| | | GGCTCAAAGAACTGGCCGCGCTGGAGGCGGCTGCAAAGCAGC |
| | | AAGAGTTGGTGGAACAGGCCAAGAGCTCGCAAGACGTCAAGG |
| | | GAGAGGAAGGCTCCGCCGCCCCAGACCAGCACACGCACCCAA |
| | | AGGAGGCCGCCACCGACCCACCCGCGCCCCGGACGCCCCCCGA |
| | | GCCCCCGGGGTCTCCACCGAGCTCTCCACCGCCTGCCTCCCTTG |
| | | GGAGGCCGGAGGGAGAGGAGGAGGGGCCGGCCGAGCCCGAAG |
| | | AGCACTCGGTGAGGATCTGCATGAGCCCGGGCCCGGAGCCGGG |
| | | AGAGCAGATCCTGTCGGTGAAGATGCCGGAGGAAAGGGAGGA |
| | | GAAGGCGGAGTAAGGTGGGGTGAGGCGGATCCATGGCCGCAG |
| | | ACATGATAAGATACATTGATGAGTTTGGACAAACCACAACTAG |
| | | AATGCAGTGAAAAAAATGCTTTATTTGTGAAATTTGTGATGCTA |
| | | TTGCTTTATTTGTAACCATTATAAGCTGCAATAAACAAGTTAAC |
| | | AACAACAATTGCATTCATTTTATGTTTCAGGTTCAGGGGGAGGT |
| | | GTGGGAGGTTTTTTAAAGCAAGTAAAACCTCTACAAATGTGGT |
| | | ACTCGAGTTAAGGGCGAATTCCCGATAAGGATCTTCCTAGAGC |

TABLE 1-continued

Table of select sequences of the invention

| SEQ ID NO: | Description | Sequence |
|---|---|---|
| | | ATGGCTACGTAGATAAGTAGCATGGCGGGTTAATCATTAACTA<br>CAAGGAACCCCTAGTGATGGAGTTGGCCACTCCCTCTCTGCGC<br>GCTCGCTCGCTCACTGAGGCCGGGCGACCAAAGGTCGCCCGAC<br>GCCCGGGCTTTGCCCGGGCGGCCTCAGTGAGCGAGCGAGCGCG<br>CAG |
| 43 | Sequence of 5'ITR-hRHO promoter-CNGB1a-SV40polyA-3'ITR (NGS) | CTGCGCGCTCGCTCGCTCACTGAGGCCGCCCGGGCAAAGCCCG<br>GGCGTCGGGCGACCTTTGGTCGCCCGGCCTCAGTGAGCGAGCG<br>AGCGCGCAGAGAGGGAGTGGCCAACTCCATCACTAGGGGTTCC<br>TTGTAGTTAATGATTAACCCGCCATGCTACTTATCTACGTAGCC<br>ATGCTCTAGGAAGATCGGAATTCGCCCTTAAGCCTCTCCTCCCT<br>GACCTCAGGCTTCCTCCTAGTGTCACCTTGGCCCCTCTTAGAAG<br>CCAATTAGGCCCTCAGTTTCTGCAGCGGGGATTAATATGATTAT<br>GAACACCCCCAATCTCCCAGATGCTGATTCAGCCAGGAGCTTA<br>GGAGGGGGAGGTCACTTTATAAGGGTCTGGGGGGGTCAGAACC<br>CAGAGTCATCACTAGTAACGGCCGCCAGTGTGCTGGAATTCGC<br>CCTTCTCCACCGCCATGTTGGGCTGGGTCCAGAGGGTGCTGCCT<br>CAGCCCCCAGGGACCCCTCGGAAGACCAAGATGCAGGAGGAA<br>GAGGAAGTGGAACCAGAGCCAGAGATGGAGGCGGAGGTGGAA<br>CCAGAACCGAATCCTGAGGAGGCCGAGACAGAGTCCGAGTCCA<br>TGCCCCCCGAAGAGTCATTCAAGGAGGAGGAAGTGGCTGTGGC<br>AGACCCAAGCCCTCAGGAGACCAAGGAGGCTGCCCTTACTTCC<br>ACCATATCCCTCCGGGCCCAGGGCGCTGAGATTTCTGAAATGA<br>ATAGTCCCAGCCACAGGGTACTGACCTGGCTCATGAAGGGTGT<br>AGAGAAGGTGATCCCGCAGCCTGTTCACAGCATCACGGAGGAC<br>CCGGCTCAGATCCTGGGGCATGGCAGCACTGGGGACACAGGGT<br>GCACAGATGAACCCAATGAGGCCCTTGAGGCCCAAGACACTAG<br>GCCTGGGCTGCGGCTGCTTCTGTGGCTGGAGCAGAATCTGGAA<br>AGAGTGCTTCCTCAGCCCCCCAAATCCTCTGAGGTCTGGAGAG<br>ATGAGCCTGCAGTTGCTACAGGTGCTGCCTCAGACCCAGCGCC<br>TCCAGGACGCCCCCAGGAAATGGGGCCCAAGCTGCAGGCCCGG<br>GAGACCCCCTCCCTGCCCACACCCATCCCCCTGCAGCCCAAGG<br>AGGAACCCAAGGAGGCACCAGCTCCAGAGCCCCAGCCCGGCTC<br>CCAGGCCCAGACCTCCTCCCTGCCACCAACCAGGGACCCTGCC<br>AGGCTGGTGGCATGGGTCCTGCACAGGCTGGAGATGGCCTTGC<br>CGCAGCCAGTGCTACATGGGAAAATAGGGGAACAGGAGCCTG<br>ACTCCCCTGGGATATGTGATGTGCAGACCATCAGCATCCTTCCT<br>GGAGGACAAGTGGAGCCTGACCTTGTCCTAGAGGAGGTTGAAC<br>CGCCCTGGGAGGATGCCCACCAGGATGTCAGTACCAGCCCACA<br>GGGTACAGAGGTGGTTCCAGCTTATGAAGAAGAGAACAAAGCT<br>GTGGAGAAGATGCCCAGAGAGCTGTCCCGGATTGAAGAGGAG<br>AAAGAAGATGAGGAGGAGGAAGAGGAAGAGGAGGAGGAGGA<br>GGAAGAGGAGGAGGTGACTGAGGTGCTGCTGGATAGCTGTGTG<br>GTGTCGCAGGTGGGCGTGGGCCAGAGTGAAGAAGACGGGACC<br>CGGCCCCAGAGCACTTCAGATCAGCTGTGGGAGGAAGTTGGGG<br>AGGAGGCCAAGAAGGAGGCTGAAGAGAAGGCCAAGGAGGAG<br>GCCGAGGAGGTGGCTGAAGAGGAGGCTGAAAAGGAGCCCCAG<br>GACTGGGCGGAGACCAAGGAGGAGCCTGAGGCTGAGGCCGAG<br>GCTGCCAGTTCAGGAGTGCCTGCCACGAAACAGCACCCAGAAG<br>TGCAGGTGGAAGATACTGATGCTGATAGCTGCCCCCTCATGGC<br>AGAAGAGAATCCACCCTCAACCGTGTTGCCGCCACCGTCTCCT<br>GCCAAATCAGACACCCTTATAGTCCCAAGCTCAGCCTCGGGGA<br>CACACAGGAAGAAGCTGCCCTCTGAGGATGATGAGGCTGAAGA<br>GCTCAAGGCGTTGTCACCAGCAGAGTCCCCAGTGGTTGCCTGG<br>TCTGACCCCACCACCCCGAAGGACACTGATGGCCAGGACCGTG<br>CGGCCTCCACGGCCAGCACAAATAGCGCCATCATCAACGACCG<br>GCTCCAGGAGCTGGTGAAGCTCTTCAAGGAGCGGACAGAGAAA<br>GTGAAGGAGAAACTCATTGACCCTGACGTCACCTCTGATGAGG<br>AGAGCCCCAAGCCCTCCCCAGCCAAGAAAGCCCCAGAGCCAGC<br>TCCAGACACAAAGCCCGCTGAAGCCGAGCCAGTGGAAGAGGA<br>GCACTATTGCGACATGCTCTGCTGCAAGTTCAAACACCGCCCCT<br>GGAAGAAGTACCAGTTTCCCCAGAGCATTGACCCGCTGACCAA<br>CCTGATGTATGTCCTATGGCTGTTCTTCGTGGTGATGGCCTGGA<br>ATTGGAACTGTTGGCTGATTCCCGTGCGCTGGGCCTTCCCCTAC<br>CAGACCCCGGACAACATCCACCACTGGCTGCTGATGGATTACC<br>TATGCGACCTCATCTACTTCCTGGACATCACCGTGTTCCAGACA<br>CGCCTGCAGTTTGTCAGAGGCGGGGACATCATTACGGACAAAA<br>AGGACATGCGAAATAATTACCTGAAGTCTGCCGCTTCAAGAT<br>GGACCTGCTCAGCCTCCTGCCCTTGGATTTTCTCTATTTGAAAG<br>TCGGTGTGAACCCCCTCCTCCGCCTGCCCCGCTGTTTAAAGTAC<br>ATGGCCTTCTTCGAGTTTAACAGCCGCCTGGAATCCATCCTCAG<br>CAAAGCCTACGTGTACAGGGTCATCAGGACCACAGCCTACCTT<br>CTCTACAGCCTGCATTTGAATTCCTGTCTTTATTACTGGGCATC<br>GGCCTATCAGGGCCTCGGCTCCACTCACTGGGTTTACGATGGCG |

TABLE 1-continued

Table of select sequences of the invention

| SEQ ID NO: | Description | Sequence |
|---|---|---|
| | | TGGGAAACAGTTATATTCGCTGTTACTACTTTGCTGTGAAGACC
CTCATCACCATCGGGGGGCTGCCTGACCCCAAGACACTCTTTGA
AATTGTCTTCCAGCTGCTGAATTATTTCACGGGCGTCTTTGCTTT
CTCTGTGATGATCGGACAGATGAGAGATGTGGTAGGGGCCGCC
ACCGCGGGACAGACCTACTACCGCAGCTGCATGGACAGCACGG
TGAAGTACATGAATTTCTACAAGATCCCCAAGTCCGTGCAGAA
CCGCGTCAAGACCTGGTACGAGTACACCTGGCACTCGCAAGGC
ATGCTGGATGAGTCAGAGCTGATGGTGCAGCTTCCAGACAAGA
TGCGGCTGGACCTCGCCATCGACGTGAACTACAACATCGTTAG
CAAAGTCGCACTCTTTCAGGGCTGTGACCGGCAGATGATCTTTG
ACATGCTGAAGAGGCTTCGCTCTGTTGTCTACCTGCCCAACGAC
TATGTGTGCAAGAAGGGGGAGATCGGCCGTGAGATGTACATCA
TCCAGGCAGGGCAAGTGCAGGTCTTGGGCGGCCCTGATGGGAA
ATCTGTGCTGGTGACGCTGAAAGCTGGATCTGTGTTTGGAGAA
ATAAGCTTGCTGGCTGTTGGGGGCGGGAACCGGCGCACGGCCA
ACGTGGTGGCGCACGGGTTTACCAACCTCTTCATCCTGGATAAG
AAGGACCTGAATGAGATTTTGGTGCATTATCCTGAGTCTCAGA
AGTTACTCCGGAAGAAAGCCAGGCGCATGCTGAGAAGCAACA
ATAAGCCCCAGGAGGAGAAGAGCGTGCTGATCCTTCCACCCCG
GGCGGGCACCCCAAAGCTCTTCAACGCTGCCCTCGCTATGACA
GGAAAGATGGGTGGCAAGGGGGCAAAAGGCGGCAAACTTGCT
CACCTCCGGGCCCGGCTCAAAGAACTGGCCGCGCTGGAGGCGG
CTGCAAAGCAGCAAGAGTTGGTGGAACAGGCCAAGAGCTCGC
AAGACGTCAAGGGAGAGGAAGGCTCCGCCGCCCCAGACCAGC
ACACGCACCCAAAGGAGGCCGCCACCGACCCACCCGCGCCCCG
GACGCCCCCCGAGCCCCCGGGGTCTCCACCGAGCTCTCCACCG
CCTGCCTCCCTTGGGAGGCCGGAGGGAGGAGGAGGAGGGGCCG
GCCGAGCCCGAAGAGCACTCGGTGAGGATCTGCATGAGCCCGG
GCCCGGAGCCGGGAGAGCAGATCCTGTCGGTGAAGATGCCGGA
GGAAAGGGAGGAGAAGGCGGAGTAAGGTGGGGTGAGGCGGAT
CCATGGCCGCAGACATGATAAGATACATTGATGAGTTTGGACA
AACCACAACTAGAATGCAGTGAAAAAAATGCTTTATTTGTGAA
ATTTGTGATGCTATTGCTTTATTTGTAACCATTATAAGCTGCAA
TAAACAAGTTAACAACAACAATTGCATTCATTTTATGTTTCAGG
TTCAGGGGGAGGTGTGGGAGGTTTTTTAAAGCAAGTAAAACCT
CTACAAATGTGGTCTCGAGTTAAGGGCGAATTCCCGATAAGGA
TCTTCCTAGAGCATGGCTACGTAGATAAGTAGCATGGCGGGTT
AATCATTAACTACAAGGAACCCCTAGTGATGGAGTTGGCCACT
CCCTCTCTGCGCGCTCGCTCGCTCACTGAGGCCGGGCGACCAA
AGGTCGCCCGACGCCCGGGCTTTGCCCGGGCGGCCTCAGTGAG
CGAGCGAGCGCGCAG |
| 44 | Sequence of 5'ITR-hRHO promoter-CNGB1a-SV40polyA-3'ITR (GenBank) | GGCCACTCCCTCTCTGCGCGCTCGCTCGCTCACTGAGGCCGCCC
GGGCAAAGCCCGGGCGTCGGGCGACCTTTGGTCGCCCGGCCTC
AGTGAGCGAGCGAGCGCGCAGAGAGGGAGTGGCCAACTCCAT
CACTAGGGGTTCCTCAGATCGTAGCCATGCTCTAGGAAGATCG
GAATTCGCCCTTAAGCCTCTCCTCCCTGACCTCAGGCTTCCTCC
TAGTGTCACCTTGGCCCCTCTTAGAAGCCAATTAGGCCCTCAGT
TTCTGCAGCGGGGATTAATATGATTATGAACACCCCCAATCTCC
CAGATGCTGATTCAGCCAGGAGCTTAGGAGGGGAGGTCACTT
TATAAGGGTCTGGGGGGGTCAGAACCCAGAGTCATCACTAGTA
ACGGCCGCCAGTGTGCTGGAATTCGCCCTTCTCCACCGCCATGT
TGGGCTGGGTCCAGAGGGTGCTGCCTCAGCCCCCAGGGACCCC
TCGGAAGACCAAGATGCAGGAGGAAGAGGAAGTGGAACCAGA
GCCAGAGATGGAGGCGGAGGTGGAACCAGAACCGAATCCTGA
GGAGGCCGAGACAGAGTCCGAGTCCATGCCCCCCGAAGAGTCA
TTCAAGGAGGAGGAAGTGGCTGTGGCAGACCCAAGCCCTCAGG
AGACCAAGGAGGCTGCCCTTACTTCCACCATATCCCTCCGGGCC
CAGGGCGCTGAGATTTCTGAAATGAATAGTCCCAGCCGCAGGG
TACTGACCTGGCTCATGAAGGGTGTAGAGAAGGTGATCCCGCA
GCCTGTTCACAGCATCACGGAGGACCCGGCTCAGATCCTGGGG
CATGGCAGCACTGGGGACACAGGGTGCACAGATGAACCCAATG
AGGCCCTTGAGGCCCAAGACACTAGGCCTGGGCTGCGGCTGCT
TCTGTGGCTGGAGCAGAATCTGGAAAGAGTGCTTCCTCAGCCC
CCCAAATCCTCTGAGGTCTGGAGAGATGAGCCTGCAGTTGCTA
CAGGTGCTGCCTCAGACCCAGCGCCTCCAGGACGCCCCCAGGA
AATGGGGCCCAAGCTGCAGGCCGGGAGACCCCCTCCCTGCCC
ACACCCATCCCCCTGCAGCCCAAGGAGGAACCCAAGGAGGCAC
CAGCTCCAGAGCCCCAGCCCGGCTCCCAGGCCCAGACCTCCTC
CCTGCCACCAACCAGGGACCCTGCCAGGCTGGTGGCATGGGTC
CTGCACAGGCTGGAGATGGCCTTGCCGCAGCCAGTGCTACATG
GGAAAATAGGGGAACAGGAGCCTGACTCCCCTGGGATATGTGA
TGTGCAGACCATCAGCATCCTTCCTGGAGGACAAGTGGAGCCT
GACCTTGTCCTAGAGGAGGTTGAACCGCCCTGGGAGGATGCCC |

TABLE 1-continued

Table of select sequences of the invention

| SEQ ID NO: | Description | Sequence |
|---|---|---|
| | | ACCAGGATGTCAGTACCAGCCCACAGGGTACAGAGGTGGTTCC |
| | | AGCTTATGAAGAAGAGAACAAAGCTGTGGAGAAGATGCCCAG |
| | | AGAGCTGTCCCGGATTGAAGAGGAGAAAGAAGATGAGGAGGA |
| | | GGAAGAGGAAGAGGAGGAGGAGGAGGAAGAGGAGGAGGTGA |
| | | CTGAGGTGCTGCTGGATAGCTGTGTGGTGTCGCAGGTGGGCGT |
| | | GGGCCAGAGTGAAGAAGACGGGACCCGGCCCCAGAGCACTTC |
| | | AGATCAGAAGCTGTGGGAGGAAGTTGGGGAGGAGGCCAAGAA |
| | | GGAGGCTGAAGAGAAGGCCAAGGAGGAGGCCGAGGAGGTGGC |
| | | TGAAGAGGAGGCTGAAAAGGAGCCCCAGGACTGGGCGGAGAC |
| | | CAAGGAGGAGCCTGAGGCTGAGGCCGAGGCTGCCAGTTCAGG |
| | | AGTGCCTGCCACGAAACAGCACCCAGAAGTGCAGGTGGAAGAT |
| | | ACTGATGCTGATAGCTGCCCCCTCATGGCAGAAGAGAATCCAC |
| | | CCTCAACCGTGTTGCCGCCACCGTCTCCTGCCAAATCAGACACC |
| | | CTTATAGTCCCAAGCTCAGCCTCGGGGACACACAGGAAGAAGC |
| | | TGCCCTCTGAGGATGATGAGGCTGAAGAGCTCAAGGCGTTGTC |
| | | ACCAGCAGAGTCCCCAGTGGTTGCCTGGTCTGACCCCACCACC |
| | | CCGAAGGACACTGATGGCCAGGACCGTGCGGCCTCCACGGCCA |
| | | GCACAAATAGCGCCATCATCAACGACCGGCTCCAGGAGCTGGT |
| | | GAAGCTCTTCAAGGAGCGGACAGAGAAAGTGAAGGAGAAACT |
| | | CATTGACCCTGACGTCACCTCTGATGAGGAGAGCCCCAAGCCC |
| | | TCCCCAGCCAAGAAAGCCCCAGAGCCAGCTCCAGACACAAAGC |
| | | CCGCTGAAGCCGAGCCAGTGGAAGAGGAGCACTATTGCGACAT |
| | | GCTCTGCTGCAAGTTCAAACACCGCCCCTGGAAGAAGTACCAG |
| | | TTTCCCCAGAGCATTGACCCGCTGACCAACCTGATGTATGTCCT |
| | | ATGGCTGTTCTTCGTGGTGATGGCCTGGAATTGGAACTGTTGGC |
| | | TGATTCCCGTGCGCTGGGCCTTCCCCTACCAGACCCCGGACAAC |
| | | ATCCACCACTGGCTGCTGATGGATTACCTATGCGACCTCATCTA |
| | | CTTCCTGGACATCACCGTGTTCCAGACACGCCTGCAGTTTGTCA |
| | | GAGGCGGGGACATCATTACGGACAAAAAGGACATGCGAAATA |
| | | ACTACCTGAAGTCTCGCCGCTTCAAGATGGACCTGCTCAGCCTC |
| | | CTGCCCTTGGATTTTCTCTATTTGAAAGTCGGTGTGAACCCCCT |
| | | CCTCCGCCTGCCCCGCTGTTTAAAGTACATGGCCTTCTTCGAGT |
| | | TTAACAGCCGCCTGGAATCCATCCTCAGCAAAGCCTACGTGTA |
| | | CAGGGTCATCAGGACCACAGCCTACCTTCTCTACAGCCTGCATT |
| | | TGAATTCCTGTCTTTATTACTGGGCATCGGCCTATCAGGGCCTC |
| | | GGCTCCACTCACTGGGTTTACGATGGCGTGGGAAACAGTTATA |
| | | TTCGCTGTTACTACTTTGCTGTGAAGACCCTCATCACCATCGGG |
| | | GGGCTGCCTGACCCCAAGACACTCTTTGAAATTGTCTTCCAGCT |
| | | GCTGAATTATTTCACGGGCGTCTTTGCTTTCTCTGTGATGATCG |
| | | GACAGATGAGAGATGTGGTAGGGGCCGCCACCGCGGGACAGA |
| | | CCTACTACCGCAGCTGCATGGACAGCACGGTGAAGTACATGAA |
| | | TTTCTACAAGATCCCCAAGTCCGTGCAGAACCGCGTCAAGACC |
| | | TGGTACGAGTACACCTGGCACTCGCAAGGCATGCTGGATGAGT |
| | | CAGAGCTGATGGTGCAGCTTCCAGACAAGATGCGGCTGGACCT |
| | | CGCCATCGACGTGAACTACAACATCGTTAGCAAAGTCGCACTC |
| | | TTTCAGGGCTGTGACCGGCAGATGATCTTTGACATGCTGAAGA |
| | | GGCTTCGCTCTGTTGTCTACCTGCCCAACGACTATGTGTGCAAG |
| | | AAGGGGGAGATCGGCCGTGAGATGTACATCATCCAGGCAGGGC |
| | | AAGTGCAGGTCTTGGGCGGCCCTGATGGGAAATCTGTGCTGGT |
| | | GACGCTGAAAGCTGGATCTGTGTTTGGAGAAATAAGCTTGCTG |
| | | GCTGTTGGGGGCGGGAACCGGCGCACGGCCAACGTGGTGGCGC |
| | | ACGGGTTTACCAACCTCTTCATCCTGGATAAGAAGGACCTGAA |
| | | TGAGATTTTGGTGCATTATCCTGAGTCTCAGAAGTTACTCCGGA |
| | | AGAAAGCCAGGCGCATGCTGAGAAGCAACAATAAGCCCAAGG |
| | | AGGAGAAGAGCGTGCTGATCCTTCCACCCCGGGCGGGCACCCC |
| | | AAAGCTCTTCAACGCTGCCCTCGCTATGACAGGAAAGATGGGT |
| | | GGCAAGGGGGCAAAAGGCGGCAAACTTGCTCACCTCCGGGCCC |
| | | GGCTCAAAGAACTGGCCGCGCTGGAGGCGGCTGCAAAGCAGC |
| | | AAGAGTTGGTGGAACAGGCCAAGAGCTCGCAAGACGTCAAGG |
| | | GAGAGGAAGGCTCCGCCGCCCCAGACCAGCACACGCACCCAA |
| | | AGGAGGCCGCCACCGACCCACCCGCGCCCCGGACGCCCCCCGA |
| | | GCCCCGGGGTCTCCACCGAGCTCTCCACCGCCTGCCTCCCTTG |
| | | GGAGGCCGGAGGGAGGAGGAGGGGCCGGCCGAGCCCGAAG |
| | | AGCACTCGGTGAGGATCTGCATGAGCCCGGGCCCGGAGCCGGG |
| | | AGAGCAGATCCTGTCGGTGAAGATGCCGGAGGAAAGGGAGGA |
| | | GAAGGCGGAGTAAGGTGGGGTGAGGCGGATCCATGGCCGCAG |
| | | ACATGATAAGATACATTGATGAGTTTGGACAAACCACAACTAG |
| | | AATGCAGTGAAAAAAATGCTTTATTTGTGAAATTTGTGATGCTA |
| | | TTGCTTTATTTGTAACCATTATAAGCTGCAATAAACAAGTTAAC |
| | | AACAACAATTGCATTCATTTTATGTTTCAGGTTCAGGGGGAGGT |
| | | GTGGGAGGTTTTTTAAAGCAAGTAAACCTCTACAAATGTGGT |
| | | CTCGAGTTAAGGGCGAATTCCCGATAAGGATCTTCCTAGAGCA |
| | | TGGCTACGATCTGAGGAACCCCTAGTGATGGAGTTGGCCACTC |
| | | CCTCTCTGCGCGCTCGCTCGCTCACTGAGGCCGGGCGACCAAA |

TABLE 1-continued

Table of select sequences of the invention

| SEQ ID NO: | Description | Sequence |
|---|---|---|
|  |  | GGTCGCCCGACGCCCGGGCTTTGCCCGGGCGGCCTCAGTGAGC GAGCGAGCGCGCAGAGAGGGAGTGGCCAA |
| 45 | Sequence of human RPE65 protein | MSIQVEHPAGGYKKLFETVEELSSPLTAHVTGRIPLWLTGSLLRCG PGLFEVGSEPFYHLFDGQALLHKFDFKEGHVTYHRRFIRTDAYVR AMTEKRIVITEFGTCAFPDPCKNIFSRFFSYFRGVEVTDNALVNVY PVGEDYYACTETNFITKINPETLETIKQVDLCNYVSVNGATAHPHI ENDGTVYNIGNCFGKNFSIAYNIVKIPPLQADKEDPISKSEIVVQFP CSDRFKPSYVHSFGLTPNYIVFVETPVKINLFKFLSSWSLWGANYM DCFESNETMGVWLHIADKKRKKYLNNKYRTSPFNLFHHINTYED NGFLIVDLCCWKGFEFVYNYLYLANLRENWEEVKKNARKAPQPE VRRYVLPLNIDKADTGKNLVTLPNTTATAILCSDETIWLEPEVLFS GPRQAFEFPQINYQKYCGKPYTYAYGLGLNHFVPDRLCKLNVKT KETWVWQEPDSYPSEPIFVSHPDALEEDDGVVLSVVVSPGAGQKP AYLLILNAKDLSEVARAEVEINIPVTFHGLFKKS |

EXAMPLES

Example 1: Nucleic Acid Vector

Figure 1:
FIG. 1 shows the structure of the rAAV hRHO194.hCNGB1 vector genome.

In this exemplary embodiment, the rAAV.hCNGB1 vector is a hybrid AAV-based vector carrying the cDNA of the human CNGB1 gene encoding the B subunit of the rod photoreceptor cyclic nucleotide-gated (CNG) channel. The hCNGB1 cDNA expression is under the control of the rod-specific Rhodopsin promoter (hRHO) and is enhanced using a SV40 pA sequence. The expression cassette is flanked by the AAV serotype 2 inverted terminal repeats (ITRs) and the recombinant genome is packaged in the AAV serotype 8 capsid. The expression cassette comprises the following elements:

Promoter of the human rhodopsin gene: 0.194 Kb cDNA of the human CNGB1a subunit of the rod photoreceptor cGMP phosphodiesterase: 3.74 Kb Polyadenylation signal of the Simian-Virus 40 (SV40): 0.23 Kb AAV serotype 2 inverted terminal repeats (ITRs): 0.13 Kb
The structure of the rAAV.hRHO194.hCNGB1 vector genome is depicted in FIG. 1.

Example 2: pGL2.0-hRHO194-hCNGB1a-SV40 cis Vector Plasmid

In one exemplary embodiment, the pGL2.0-hRHO194-hCNGB1a-SV40 cis vector plasmid with the nucleotide sequence depicted in SEQ ID No. 7 is used which contains an expression cassette comprising a 194 bp rod photoreceptor-specific human rhodopsin (hRHO) promoter and the full-length (3738 bp) human CNGB1 cDNA. The expression cassette also contains a 227 bp Simian-Virus 40 polyadenylation signal (SV40 pA). The 5591 bp vector backbone containing a kanamycin resistance (KanR) positioned 1943 bp from the L-ITR and 2853 bp from the R-ITR and 2024 bp from a pUC18 ori. The rAAV.hCNGB1 vector is produced using transient co-transfection of the cis vector plasmid and trans helper plasmid(s) encoding rep and cap sequences and adenoviral genes in the human embryonic kidney 293 T cells (HEK293T). The rAAV.hRHO194.hCNGB1 is harvested from the culture medium and/or the cell lysate using standard purification methods, e.g. cesium chloride gradient ultracentrifugation, ion exchange chromatography and/or tangential flow filtration. The resulting rAAV.hRHO194.hCNGB1 vector suspension is then sterile-filtered, filled and stored as drug product.

Example 3: Activity and Specificity of the hRHO194 Promoter

Figure 2:
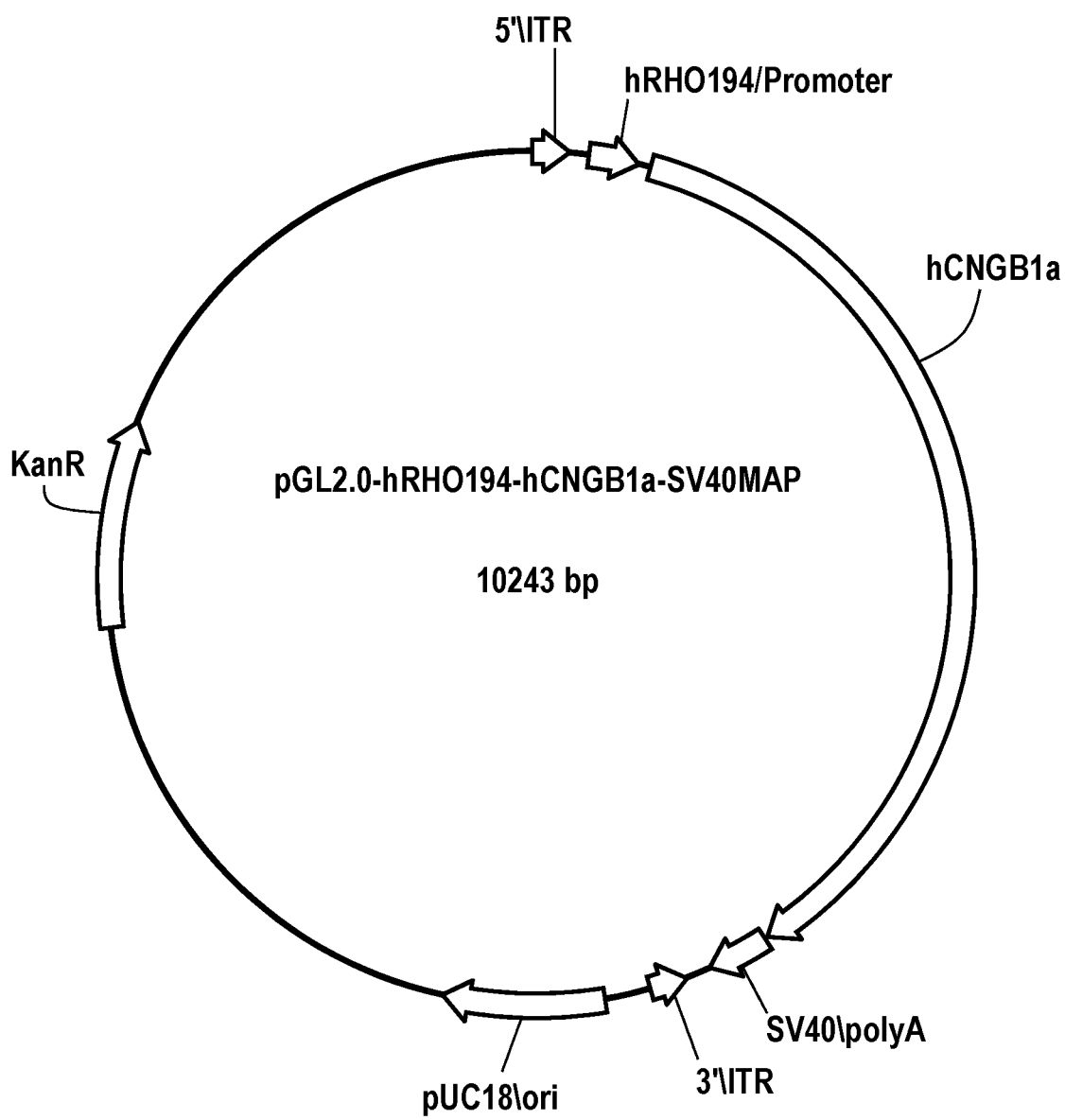
FIG. 2 shows the pGL2.0-hRHO194-hCNGB1a-SV40 cis vector plasmid map.

To verify the activity and specificity of the novel hRHO194 promoter the inventors constructed a version of the AAV cis vector which contains the eGFP cDNA instead of the hCNGB1 cDNA. The resulting pGL2.0-hRHO194-eGFP-SV40 cis vector plasmid map is shown in FIG. 2. Delivery of rAAV.hRHO194.eGFP vector into the subretinal space of 4-week-old wild type mice resulted in strong expression of eGFP protein 4 weeks after injection in rod photoreceptors only (FIG. 3A) thereby confirming the retinal cell type specificity of this promoter. For representative results see FIGS. 3A-3B. The rAAV.hRHO194.eGFP vector treatment resulted in strong eGFP protein expression in the treated eye reflected by native eGFP fluorescence in rod photoreceptors only.

Example 4: Biological Activity and Transgene Expression Conferred by the rAAV.hRHO194.hCNGB1

To verify biological activity and transgene expression the inventors delivered the AAV.hRHO194.hCNGB1 vector into the subretinal space of 4-week-old CNGB1 (−/−) mice. The delivery procedure was similar to the one described in Koch et al., Gene therapy restores vision and delays degeneration in the CNGB1(−/−) mouse model of retinitis pigmentosa. Hum Mol Genet. 2012; 21(20):4486-96. PubMed PMID: 22802073. The mice received a subretinal injection in the treated eye (TE), whereas the other, untreated eye (UE) served as control. The vector efficacy was evaluated at 4 months following the injection by means of electroretinography (ERG), an objective functional in vivo assay (FIGS. 4A and 4B). CNGB1 (−/−) mice lack normal rod photoreceptor function. Secondary to rods, non-affected cone photoreceptors also degenerate resulting in loss of cone function at later stages of the disease. Therefore, ERG protocols specifically testing for rod and cone function are suitable as an indirect measure for CNGB1 function and for the assessment of biological activity (BAA) of the rAAV hRHO194.hCNGB1 vector.

Example 5: In Vivo Optical Coherence Tomography (OTC) for the Determination of BAA In another set of experiments BAA was determined by in vivo optical coherence tomography (OCT) imaging followed by quantification of the photoreceptor layer thickness. For this, the mice received a subretinal injection in the treated eye (TE), whereas the other, untreated eye (UE) served as control. Photoreceptor layer thickness measurement was performed at 4 months following the injection by means of OCT (FIGS. 5A-5C). Rod photoreceptors of CNGB1 (−/−) mice degenerate over time resulting in thinning of the photoreceptor cell layer (FIGS. 5B and 5C). Therefore, biological activity (BAA) of the rAAV.hRHO194.hCNGB1 vector can be indirectly measured by determining the photoreceptor layer thickness in treated CNGB1 (−/−) mice using OCT. The rAAV.hRHO194.hCNGB1 vector treatment resulted in a clear therapeutic effect in the treated eye reflected by preservation of the photoreceptor layer thickness. In particular, more than 45% increase in photoreceptor layer thickness was observed (FIG. 5C).

Example 6: In Vivo CNGB1 Gene Augmentation in Cngb1$^{-/-}$ Mice

Cngb1$^{-/-}$ mice were treated with 1×10$^{10}$ viral genomes (1 e 10 vgs) of AAV8-hRHO$_{194}$-hCNGB1-SV40 or AAV5-hRHO$_{194}$-hCNGB1-SV40 subretinally at 4 weeks of age. Structural outcome measures included SD-OCT at 1 and 3 months post injection, histology, and immunohistochemistry.

General vector design is shown in FIG. 7. 1 e 10 total viral genomes in 1 ul was injected subretinally in 4 week old Cngb1$^{-/-}$ mice (postnatal week 4; PW4).

AAV8-hRHO$_{194}$-hCNGB1-SV40 gene augmentation was found to result in restoration of rod function post subretinal injection in Cngb1$^{-/-}$ mice. Efficacy was found to persist out to 8 months post-treatment. Dark adapted ERG B wave amplitudes were found to be significantly improved in the treated mice (FIGS. 8A-8B). Scotopic electroretinography (ERG) at rod-specific stimulus Cngb1$^{-/-}$ at 9 months (8 months post treatment in treated mice) is shown in FIG. 8A. ERG of wild-type and Cngb1$^{-/-}$ mice before treatment showed that ERG B wave was absent in Cngb1$^{-/-}$ mice at time of injection (FIG. 8B). CNGB1 channel expression in rod outer segments was found to be restored (FIGS. 9A-9B). A rabbit polyclonal anti-CNGB1 antibody that recognizes aa 1078-1168 of human CNGB1a (Sigma-Aldrich) was used for transgene expression assays Immunohistochemistry was performed at 9 months in Cngb1$^{-/-}$ mice treated with AAV8-hRHO$_{194}$-hCNGB/-SV40 (8 months post treatment; FIG. 9A) and in untreated Cngb1$^{-/-}$ mice (FIG. 9B), and showed restoration of CNGB1 channel expression in treated Cngb1$^{-/-}$ mice. OCT analysis revealed a significant delay in retinal degeneration (FIGS. 10A-10C). General injection schedule is shown in FIG. 10A. In vivo optical coherence tomography (OCT) images were collected at 9 months in Cngb1$^{-/-}$ mice treated with AAV8-hRHO$_{194}$-hCNGB/-SV40 (8 months post treatment; FIG. 10B) and in untreated Cngb1$^{-/-}$ mice (FIG. 10C). As shown in FIG. 10, it was found that at 9 months, treated Cngb1$^{-/-}$ mice had a thicker photoreceptor layer compared to untreated Cngb1$^{-/-}$ mice.

AAV5-hRHO$_{194}$-hCNGB/-SV40 gene augmentation was found to result in restoration of rod function by two months post subretinal injection in Cngb1$^{-/-}$ mice. Dark adapted ERG B wave amplitudes were found to be significantly improved in the treated mice (FIGS. 11A-11E). Scotopic ERG was measured in treated and untreated Cngb1$^{-/-}$ mice at 3 months of age (2 months post subretinal treatment in treated mice) and results are shown in FIG. 11A. B-wave amplitude in response to a light stimulus of −0.5 log (cd s/m$^2$) measured in treated and untreated Cngb1$^{-/-}$ mice (n=8) at 3 months of age (2 months post subretinal treatment in treated mice) is shown in FIG. 11B. OCT analysis revealed a significant delay in retinal degeneration. In vivo optical coherence tomography (OCT) images were collected at 3 months in Cngb1$^{-/-}$ mice treated with AAV5-hRHO$_{194}$-hCNGB/-SV40 (2 months post treatment; FIG. 11C) and in untreated Cngb1$^{-/-}$ mice (FIG. 11D). Measurement of the photoreceptor layer thickness showed a significant delay in retinal degeneration in treated Cngb1$^{-/-}$ mice at 3 months (2 months post treatment) compared to wild-type Cngb1$^{-/-}$ mice (n=6; FIG. 11E).

Example 7: Mutant Dog Study Design

Cngb1$^{-/-}$ dogs have a mutation in exon 26 that leads to a truncated and non-functional protein, resulting in loss of rod function and retinal degeneration. Three Cngb1$^{-/-}$ dogs were treated with AAV5-hRHO$_{194}$-hCNGB/a subretinally in both eyes at 3 months of age. For each animal, eye 1 was treated at a dose of 5 e 11 vgs (aiming for 2×100 ul blebs; "low dose") and eye 2 was treated at a dose of 1 e 12 vgs (aiming for 2×100 ul blebs; "high dose"). Structural outcome measures included SC-OCT at 1 and 3 months post injection, histology and immunohistochemistry. Functional outcome measures included vision testing and ERG at 1 and 3 months post injection.

Example 8: Results of Mutant Dog Studies

AAV5-hRHO$_{194}$-hCNGB/a-SV40 gene augmentation was found to result in restoration of rod function by one month post subretinal injection in Cngb1$^{-/-}$ dogs.

Dark adapted ERG waveforms were found to be significantly improved post treatment at both doses evaluated. Comparable injections were performed in both eyes. Obvious ERG rescue was observed in both eyes of treated dogs compared to untreated dogs, using both rod-specific stimulus (FIG. 12A) and flicker response (FIG. 12B). Larger ERG amplitudes were observed in eyes treated with the higher dose.

Vision testing showed that treated dogs had rod-mediated vision and improved performance in a four-choice vision testing device. FIGS. 13A-13B shows the results of vision testing of treated dogs at 1 month post injection and untreated dogs. A four-choice vision testing device was used. Untreated Cngb1$^{-/-}$ dogs were found to have normal cone vision at this age, but lack rod-mediated vision. Untreated Cngb1$^{-/-}$ dogs are blind at lower light levels (e.g., 5.7 e-2 cd/m$^2$) and make fewer correct exit choices and take longer to exit from the testing device. Both treatment groups (high and low dose) were found to have restored rod vision as indicated by the significantly improved performance in correct exit choice (FIG. 13A) and time to exit (FIG. 13B), at the lowest lighting level.

The mean ERG A- and B-wave amplitudes in the high dose group were found to be higher compared to the low dose group. A- and B-wave amplitudes in treated eyes were found to be about 80% of wild-type levels. FIGS. 14A-14B shows ERG amplitude measurements one month post injection in each treatment group and the untreated group. A highly significant increase in A-wave amplitude for both treatment groups was observed compared to untreated controls. Improvement in response threshold in treated eyes was found to be greater than 1.5 log units (FIG. 14A). A highly significant increase in B-wave amplitude for all stages in the high dose group and all but the second and third strongest stimuli for the low dose group was found, compared to untreated controls. Improvement in response threshold in treated eyes was found to be greater than 2 log units (FIG. 14B).

What is claimed is:

1. A vector comprising the nucleic acid sequence of SEQ ID NO: 43.

2. The vector of claim 1, wherein the vector is an AAV vector.

3. A composition comprising the vector of claim 1 and a pharmaceutically acceptable carrier.

4. A polynucleotide comprising the nucleic acid sequence of SEQ ID NO: 43.

* * * * *

SEQUENCE LISTING

<160> NUMBER OF SEQ ID NOS: 45

<210> SEQ ID NO 1
<211> LENGTH: 99
<212> TYPE: DNA
<213> ORGANISM: Homo sapiens
<220> FEATURE:
<221> NAME/KEY: misc_feature
<222> LOCATION: (1)..(99)
<223> OTHER INFORMATION: human RHO promoter fragment

<400> SEQUENCE: 1
agaagccaat taggccctca gtttctgcag cggggattaa tatgattatg aacaccccca    60
atctcccaga tgctgattca gccaggagct taggagggg                          99

<210> SEQ ID NO 2
<211> LENGTH: 350
<212> TYPE: DNA
<213> ORGANISM: Homo sapiens
<220> FEATURE:
<221> NAME/KEY: misc_feature
<222> LOCATION: (1)..(350)
<223> OTHER INFORMATION: human RHO promoter fragment

<400> SEQUENCE: 2
aaaccagaaa gtctctagct gtccagagga catagcacag aggcccatgg tccctatttc    60
aaacccaggc caccagactg agctgggacc ttgggacaga caagtcatgc agaagttagg   120
ggaccttctc ctccctttc ctggatcctg agtacctctc ctccctgacc tcaggcttcc    180
tcctagtgtc accttggccc ctcttagaag ccaattaggc cctcagtttc tgcagcgggg   240
attaatatga ttatgaacac ccccaatctc ccagatgctg attcagccag gagcttagga   300
gggggaggtc actttataag ggtctggggg ggtcagaacc cagagtcatc              350

<210> SEQ ID NO 3
<211> LENGTH: 1245
<212> TYPE: PRT
<213> ORGANISM: Homo sapiens
<220> FEATURE:
<221> NAME/KEY: MISC_FEATURE
<222> LOCATION: (1)..(1245)
<223> OTHER INFORMATION: human CNGB1 protein

<400> SEQUENCE: 3

Met Leu Gly Trp Val Gln Arg Val Leu Pro Gln Pro Gly Thr Pro
1               5                   10                  15

Arg Lys Thr Lys Met Gln Glu Glu Glu Val Glu Pro Glu Pro Glu
                20                  25                  30

Met Glu Ala Glu Val Glu Pro Pro Asn Pro Glu Glu Ala Glu Thr
                35                  40                  45

Glu Ser Glu Ser Met Pro Pro Glu Glu Ser Phe Lys Glu Glu Val
            50                  55                  60

Ala Val Ala Asp Pro Ser Pro Gln Glu Thr Lys Glu Ala Ala Leu Thr
65                  70                  75                  80

Ser Thr Ile Ser Leu Arg Ala Gln Gly Ala Glu Ile Ser Glu Met Asn
                85                  90                  95

Ser Pro Ser His Arg Val Leu Thr Trp Leu Met Lys Gly Val Glu Lys
                100                 105                 110

Val Ile Pro Gln Pro Val His Ser Ile Thr Glu Asp Pro Ala Gln Ile
                115                 120                 125

Leu Gly His Gly Ser Thr Gly Asp Thr Gly Cys Thr Asp Glu Pro Asn

```
                130             135             140
    Glu Ala Leu Glu Ala Gln Asp Thr Arg Pro Gly Leu Arg Leu Leu Leu
    145                 150                 155                 160

Trp Leu Glu Gln Asn Leu Glu Arg Val Leu Pro Gln Pro Pro Lys Ser
                    165                 170                 175

Ser Glu Val Trp Arg Asp Glu Pro Ala Val Ala Thr Ala Pro Pro Gly
                180                 185                 190

Arg Pro Gln Glu Met Gly Pro Lys Leu Gln Ala Arg Glu Thr Pro Ser
                    195                 200                 205

Leu Pro Thr Pro Ile Pro Leu Gln Pro Lys Glu Glu Pro Lys Glu Ala
                210                 215                 220

Pro Ala Pro Glu Pro Gln Pro Gly Ser Gln Ala Gln Thr Ser Ser Leu
    225                 230                 235                 240

Pro Pro Thr Arg Asp Pro Ala Arg Leu Val Ala Trp Val Leu His Arg
                    245                 250                 255

Leu Glu Met Ala Leu Pro Gln Pro Val Leu His Gly Lys Ile Gly Glu
                260                 265                 270

Gln Glu Pro Asp Ser Pro Gly Ile Cys Asp Val Gln Thr Ile Ser Ile
                    275                 280                 285

Leu Pro Gly Gly Gln Val Glu Pro Asp Leu Val Leu Glu Glu Val Glu
                290                 295                 300

Pro Pro Trp Glu Asp Ala His Gln Asp Val Ser Thr Ser Pro Gln Gly
    305                 310                 315                 320

Thr Glu Val Val Pro Ala Tyr Glu Glu Asn Lys Ala Val Glu Lys
                    325                 330                 335

Met Pro Arg Glu Leu Ser Arg Ile Glu Glu Lys Glu Asp Glu Glu
                340                 345                 350

Glu Glu Glu Glu Glu Glu Glu Glu Glu Glu Glu Glu Val Thr Glu
                355                 360                 365

Val Leu Leu Asp Ser Cys Val Val Ser Gln Val Gly Val Gly Gln Ser
    370                 375                 380

Glu Glu Asp Gly Thr Arg Pro Gln Ser Thr Ser Asp Gln Lys Leu Trp
    385                 390                 395                 400

Glu Glu Val Gly Glu Glu Ala Lys Lys Glu Ala Glu Lys Ala Lys
                    405                 410                 415

Glu Glu Ala Glu Glu Val Ala Glu Glu Ala Glu Lys Glu Pro Gln
                420                 425                 430

Asp Trp Ala Glu Thr Lys Glu Glu Pro Glu Ala Glu Ala Glu Ala Ala
                    435                 440                 445

Ser Ser Gly Val Pro Ala Thr Lys Gln His Pro Glu Val Gln Val Glu
                450                 455                 460

Asp Thr Asp Ala Asp Ser Cys Pro Leu Met Ala Glu Glu Asn Pro Pro
    465                 470                 475                 480

Ser Thr Val Leu Pro Pro Ser Pro Ala Lys Ser Asp Thr Leu Ile
                    485                 490                 495

Val Pro Ser Ser Ala Ser Gly Thr His Arg Lys Lys Leu Pro Ser Glu
                500                 505                 510

Asp Asp Glu Ala Glu Glu Leu Lys Ala Leu Ser Pro Ala Glu Ser Pro
                    515                 520                 525

Val Val Ala Trp Ser Asp Pro Thr Thr Pro Lys Asp Thr Asp Gly Gln
                530                 535                 540

Asp Arg Ala Ala Ser Thr Ala Ser Thr Asn Ser Ala Ile Ile Asn Asp
    545                 550                 555                 560
```

```
Arg Leu Gln Glu Leu Val Lys Leu Phe Lys Glu Arg Thr Glu Lys Val
                565                 570                 575

Lys Glu Lys Leu Ile Asp Pro Asp Val Thr Ser Asp Glu Glu Ser Pro
            580                 585                 590

Lys Pro Ser Pro Ala Lys Lys Ala Pro Glu Pro Ala Pro Asp Thr Lys
            595                 600                 605

Pro Ala Glu Ala Glu Pro Val Glu Glu Glu His Tyr Cys Asp Met Leu
        610                 615                 620

Cys Cys Lys Phe Lys His Arg Pro Trp Lys Lys Tyr Gln Phe Pro Gln
625             630                 635                 640

Ser Ile Asp Pro Leu Thr Asn Leu Met Tyr Val Leu Trp Leu Phe Phe
                645                 650                 655

Val Val Met Ala Trp Asn Trp Asn Cys Trp Leu Ile Pro Val Arg Trp
            660                 665                 670

Ala Phe Pro Tyr Gln Thr Pro Asp Asn Ile His His Trp Leu Leu Met
        675                 680                 685

Asp Tyr Leu Cys Asp Leu Ile Tyr Phe Leu Asp Ile Thr Val Phe Gln
690                 695                 700

Thr Arg Leu Gln Phe Val Arg Gly Gly Asp Ile Ile Thr Asp Lys Lys
705                 710                 715                 720

Asp Met Arg Asn Asn Tyr Leu Lys Ser Arg Arg Phe Lys Met Asp Leu
            725                 730                 735

Leu Ser Leu Leu Pro Leu Asp Phe Leu Tyr Leu Lys Val Gly Val Asn
            740                 745                 750

Pro Leu Leu Arg Leu Pro Arg Cys Leu Lys Tyr Met Ala Phe Phe Glu
        755                 760                 765

Phe Asn Ser Arg Leu Glu Ser Ile Leu Ser Lys Ala Tyr Val Tyr Arg
770                 775                 780

Val Ile Arg Thr Thr Ala Tyr Leu Leu Tyr Ser Leu His Leu Asn Ser
785                 790                 795                 800

Cys Leu Tyr Tyr Trp Ala Ser Ala Tyr Gln Gly Leu Gly Ser Thr His
                805                 810                 815

Trp Val Tyr Asp Gly Val Gly Asn Ser Tyr Ile Arg Cys Tyr Tyr Phe
            820                 825                 830

Ala Val Lys Thr Leu Ile Thr Ile Gly Gly Leu Pro Asp Pro Lys Thr
        835                 840                 845

Leu Phe Glu Ile Val Phe Gln Leu Leu Asn Tyr Phe Thr Gly Val Phe
850                 855                 860

Ala Phe Ser Val Met Ile Gly Gln Met Arg Asp Val Val Gly Ala Ala
865                 870                 875                 880

Thr Ala Gly Gln Thr Tyr Tyr Arg Ser Cys Met Asp Ser Thr Val Lys
            885                 890                 895

Tyr Met Asn Phe Tyr Lys Ile Pro Lys Ser Val Gln Asn Arg Val Lys
            900                 905                 910

Thr Trp Tyr Glu Tyr Thr Trp His Ser Gln Gly Met Leu Asp Glu Ser
        915                 920                 925

Glu Leu Met Val Gln Leu Pro Asp Lys Met Arg Leu Asp Leu Ala Ile
930                 935                 940

Asp Val Asn Tyr Asn Ile Val Ser Lys Val Ala Leu Phe Gln Gly Cys
945                 950                 955                 960

Asp Arg Gln Met Ile Phe Asp Met Leu Lys Arg Leu Arg Ser Val Val
            965                 970                 975
```

```
        Tyr Leu Pro Asn Asp Tyr Val Cys Lys Lys Gly Glu Ile Gly Arg Glu
                980                 985                 990

Met Tyr Ile Ile Gln Ala Gly Gln Val Gln Val Leu Gly Gly Pro Asp
                995                1000                1005

Gly Lys Ser Val Leu Val Thr Leu Lys Ala Gly Ser Val Phe Gly
            1010                1015                1020

Glu Ile Ser Leu Leu Ala Val Gly Gly Asn Arg Arg Thr Ala
            1025                1030                1035

Asn Val Ala His Gly Phe Thr Asn Leu Phe Ile Leu Asp Lys
            1040                1045                1050

Lys Asp Leu Asn Glu Ile Leu Val His Tyr Pro Glu Ser Gln Lys
            1055                1060                1065

Leu Leu Arg Lys Lys Ala Arg Arg Met Leu Arg Ser Asn Asn Lys
            1070                1075                1080

Pro Lys Glu Glu Lys Ser Val Leu Ile Leu Pro Arg Ala Gly
            1085                1090                1095

Thr Pro Lys Leu Phe Asn Ala Ala Leu Ala Met Thr Gly Lys Met
            1100                1105                1110

Gly Gly Lys Gly Ala Lys Gly Gly Lys Leu Ala His Leu Arg Ala
            1115                1120                1125

Arg Leu Lys Glu Leu Ala Ala Leu Glu Ala Ala Ala Lys Gln Gln
            1130                1135                1140

Glu Leu Val Glu Gln Ala Lys Ser Ser Gln Asp Val Lys Gly Glu
            1145                1150                1155

Glu Gly Ser Ala Ala Pro Asp Gln His Thr His Pro Lys Glu Ala
            1160                1165                1170

Ala Thr Asp Pro Pro Ala Pro Arg Thr Pro Glu Pro Pro Gly
            1175                1180                1185

Ser Pro Pro Ser Ser Pro Pro Ala Ser Leu Gly Arg Pro Glu
            1190                1195                1200

Gly Glu Glu Glu Gly Pro Ala Glu Pro Glu Glu His Ser Val Arg
            1205                1210                1215

Ile Cys Met Ser Pro Gly Pro Glu Pro Gly Glu Gln Ile Leu Ser
            1220                1225                1230

Val Lys Met Pro Glu Glu Arg Glu Glu Lys Ala Glu
            1235                1240                1245

<210> SEQ ID NO 4
<211> LENGTH: 227
<212> TYPE: DNA
<213> ORGANISM: Simian virus 40
<220> FEATURE:
<221> NAME/KEY: misc_feature
<222> LOCATION: (1)..(227)
<223> OTHER INFORMATION: SV40 polyadenylation signal

<400> SEQUENCE: 4
ggccgcagac atgataagat acattgatga gtttggacaa accacaacta gaatgcagtg     60
aaaaaaatgc tttatttgtg aaatttgtga tgctattgct ttatttgtaa ccattataag    120
ctgcaataaa caagttaaca acaacaattg cattcatttt atgtttcagg ttcaggggga    180
ggtgtgggag gttttttaaa gcaagtaaaa cctctacaaa tgtggta                   227

<210> SEQ ID NO 5
<211> LENGTH: 130
<212> TYPE: DNA
<213> ORGANISM: adeno-associated virus 2
```

```
<220> FEATURE:
<221> NAME/KEY: misc_feature
<223> OTHER INFORMATION: L-ITR

<400> SEQUENCE: 5
ctgcgcgctc gctcgctcac tgaggccgcc cgggcaaagc ccgggcgtcg ggcgaccttt    60
ggtcgcccgg cctcagtgag cgagcgagcg cgcagagagg gagtggccaa ctccatcact   120
aggggttcct                                                          130

<210> SEQ ID NO 6
<211> LENGTH: 131
<212> TYPE: DNA
<213> ORGANISM: adeno-associated virus 2
<220> FEATURE:
<221> NAME/KEY: misc_feature
<223> OTHER INFORMATION: R-ITR

<400> SEQUENCE: 6
aggaacccct agtgatggag ttggccactc cctctctgcg cgctcgctcg ctcactgagg    60
ccgggcgacc aaaggtcgcc cgacgcccgg gctttgcccg gcggcctcag tgagcgagc   120 gagcgcgcag c                                                        131

<210> SEQ ID NO 7
<211> LENGTH: 10243
<212> TYPE: DNA
<213> ORGANISM: Artificial Sequence
<220> FEATURE:
<223> OTHER INFORMATION: pGL2.0-hRHO194-hCNGB1a-SV40 vector molecule

<400> SEQUENCE: 7
cagctgcgcg ctcgctcgct cactgaggcc gcccggcaa agcccgggcg tcgggcgacc     60
tttggtcgcc cggcctcagt gagcgagcga gcgcgcagag agggagtggc caactccatc   120
actaggggtt ccttgtagtt aatgattaac ccgccatgct acttatctac gtagccatgc   180
tctaggaaga tcggaattcg cccttaagcc tctcctcccct gacctcaggc ttcctcctag   240
tgtcaccttg gcccctctta gaagccaatt aggccctcag tttctgcagc ggggattaat   300
atgattatga cacccccaa tctcccagat gctgattcag ccaggagctt aggaggggga    360
ggtcacttta agggtctgg ggggggtcag aacccagagt catcactagt aacggccgcc    420
agtgtgctgg aattcgccct tctccaccgc catgttgggc tgggtccaga gggtgctgcc   480
tcagccccca gggacccctc ggaagaccaa gatgcaggag gaagaggaag tggaaccaga   540
gccagagatg gaggcggagg tggaaccaga accgaatcct gaggaggccg agacagagtc   600
cgagtccatg ccccccgaag agtcattcaa ggaggaggaa gtggctgtgg cagacccaag   660
ccctcaggag accaaggagg ctgcccttac ttccaccata tccctccggg cccagggcgc   720
tgagatttct gaaatgaata gtcccagcca cagggtactg acctggctca tgaagggtgt   780
agagaaggtg atcccgcagc ctgttcacag catcacggag gacccggctc agatcctggg   840
gcatggcagc actggggaca cagggtgcac agatgaaccc aatgaggccc ttgaggccca   900
agacactagg cctgggctgc ggctgcttct gtgctggag cagaatctgg aaagagtgct    960
tcctcagccc cccaaatcct ctgaggtctg gagagatgag cctgcagttg ctacagcgcg  1020
tccaggacgc ccccaggaaa tggggcccaa gctgcaggcc cgggagaccc cctccctgcc  1080
cacacccatc cccctgcagc ccaaggagga acccaaggag gcaccagctc cagagcccca  1140
gcccggctcc caggcccaga cctcctcccct gccaccaacc agggaccctg ccaggctggt  1200
```

```
ggcatgggtc ctgcacaggc tggagatggc cttgccgcag ccagtgctac atgggaaaat      1260
agggaacag  gagcctgact ccctgggat  atgtgatgtg cagaccatca gcatccttcc      1320
tggaggacaa gtggagcctg accttgtcct agaggaggtt gaaccgccct gggaggatgc      1380
ccaccaggat gtcagtacca gcccacaggg tacagaggtg gttccagctt atgaagaaga      1440
gaacaaagct gtggagaaga tgcccagaga gctgtcccgg attgaagagg agaaagaaga      1500
tgaggaggag gaagaggaag aggaggagga ggaggaagag gaggaggtga ctgaggtgct      1560
gctggatagc tgtgtggtgt cgcaggtggg cgtgggccag agtgaagaag acgggacccg      1620
gccccagagc acttcagatc agaagctgtg ggaggaagtt ggggaggagg ccaagaagga      1680
ggctgaagag aaggccaagg aggaggccga ggaggtggct gaagaggagg ctgaaaagga      1740
gccccaggac tgggcggaga ccaaggagga gcctgaggct gaggccgagg ctgccagttc      1800
aggagtgcct gccacgaaac agcacccaga agtgcaggtg gaagatactg atgctgatag      1860
ctgcccctc  atggcagaag agaatccacc ctcaaccgtg ttgccgccac catctcctgc      1920
caaatcagac acccttatag tcccaagctc agcctcgggg acacacagga agaagctgcc      1980
ctctgaggat gatgaggctg aagagctcaa ggcgttgtca ccagcagagt ccccagtggt      2040
tgcctggtct gaccccacca ccccgaagga cactgatggc caggaccgtg cggcctccac      2100
ggccagcaca aatagcgcca tcatcaacga ccggctccag agctggtga  agctcttcaa      2160
ggagcggaca gagaaagtga aggagaaact cattgaccct gacgtcacct ctgatgagga      2220
gagccccaag ccctccccag ccaagaaagc cccagagcca gctccagaca caaagcccgc      2280
tgaagccgag ccagtggaag aggagcacta ttgcgacatg ctctgctgca agttcaaaca      2340
ccgcccctgg aagaagtacc agtttccca  gagcattgac ccgctgacca acctgatgta      2400
tgtcctatgg ctgttcttcg tggtgatggc ctggaattgg aactgttggc tgattcccgt      2460
gcgctgggcc ttcccctacc agaccccgga caacatccac cactggctgc tgatggatta      2520
cctatgcgac ctcatctact tcctggacat caccgtgttc cagacacgcc tgcagttgt     2580
cagaggcggg gacatcatta cggacaaaaa ggacatgcga ataactacc  tgaagtctcg      2640
ccgcttcaag atggacctgc tcagcctcct gcccttggat tttctctatt tgaaagtcgg      2700
tgtgaacccc ctcctccgcc tgccccgctg tttaaagtac atggccttct tcgagtttaa      2760
cagccgcctg gaatccatcc tcagcaaagc ctacgtgtac agggtcatca ggaccacagc      2820
ctaccttctc tacagcctgc atttgaattc ctgtctttat tactgggcat cggcctatca      2880
gggcctcggc tccactcact gggtttacga tggcgtggga aacagttata ttcgctgtta      2940
ctactttgct gtgaagaccc tcatcaccat cggggggctg cctgacccca agacactctt      3000
tgaaattgtc ttccagctgc tgaattattt cacgggcgtc tttgctttct ctgtgatgat      3060
cggacagatg agagatgtgg taggggccgc caccgcggga cagacctact accgcagctg      3120
catggacagc acggtgaagt acatgaattt ctacaagatc cccaagtccg tgcagaaccg      3180
cgtcaagacc tggtacgagt acacctggca ctcgcaaggc atgctggatg agtcagagct      3240
gatggtgcag cttccagaca agatgcggct ggacctcgcc atcgacgtga actacaacat      3300
cgttagcaaa gtcgcactct ttcagggctg tgaccggcag atgatctttg acatgctgaa      3360
gaggcttcgc tctgttgtct acctgcccaa cgactatgtg tgcaagaagg gggagatcgg      3420
ccgtgagatg tacatcatcc aggcagggca agtgcaggtc ttgggcggcc ctgatgggaa      3480
atctgtgctg gtgacgctga aagctggatc tgtgtttgga gaaataagct tgctggctgt      3540
tgggggcggg aaccggcgca cggccaacgt ggtggcgcac gggtttacca acctcttcat      3600
```

```
cctggataag aaggacctga atgagatttt ggtgcattat cctgagtctc agaagttact    3660
ccggaagaaa gccaggcgca tgctgagaag caacaataag cccaaggagg agaagagcgt    3720
gctgatcctt ccaccccggg cgggcacccc aaagctcttc aacgctgccc tcgctatgac    3780
aggaaagatg ggtggcaagg gggcaaaagg cggcaaactt gctcacctcc gggcccggct    3840
caaagaactg gccgcgctgg aggcggctgc aaagcagcaa gagttggtgg aacaggccaa    3900
gagctcgcaa gacgtcaagg gagaggaagg ctccgccgcc ccagaccagc acacgcaccc    3960
aaaggaggcc gccaccgacc cacccgcgcc ccggacgccc ccgagccccc ggggtctcc     4020 accgagctct ccaccgcctg cctcccttgg gaggccggag ggagaggagg aggggccggc    4080
cgagcccgaa gagcactcgg tgaggatctg catgagcccg ggcccggagc cgggagagca    4140
gatcctgtcg gtgaagatgc cggaggaaag ggaggagaag gcggagtaag gtggggtgag    4200
gcggatccat ggccgcagac atgataagat acattgatga gtttggacaa accacaacta    4260
gaatgcagtg aaaaaaatgc tttatttgtg aaatttgtga tgctattgct ttatttgtaa    4320
ccattataag ctgcaataaa caagttaaca acaacaattg cattcatttt atgtttcagg    4380 ttcagggga ggtgtgggag gttttttaaa gcaagtaaaa cctctacaaa tgtggtactc    4440
gagttaaggg cgaattcccg ataaggatct tcctagagca tggctacgta gataagtagc    4500
atggcgggtt aatcattaac tacaaggaac ccctagtgat ggagtggcc actccctctc    4560 tgcgcgctcg ctcgctcact gaggccgggc gaccaaaggt cgcccgacgc ccgggctttg    4620
cccgggcggc ctcagtgagc gagcgagcgc gcagctgggc ctcagtgagc gagcgagcgc    4680
gcagctgcat taatgaatcg gccaacgcgc ggggagaggc ggtttgcgta ttgggcgctc    4740
ttccgcttcc tcgctcactg actcgctgcg ctcggtcgtt cggctgcggc gagcggtatc    4800
agctcactca aaggcggtaa tacggttatc cacagaatca ggggataacg caggaaagaa    4860
catgtcgcgt tgctggcgtt tttccatagg ctccgccccc ctgacgagca tcacaaaaat    4920
cgacgctcaa gtcagaggtg gcgaaacccg acaggactat aaagatacca ggcgtttccc    4980
cctggaagct ccctcgtgcg ctctcctgtt ccgaccctgc cgcttaccgg atacctgtcc    5040
gcctttctcc cttcgggaag cgtggcgctt tctcatagct cacgctgtag gtatctcagt    5100
tcggtgtagg tcgttcgctc caagctgggc tgtgtgcacg aaccccccgt tcagcccgac    5160
cgctgcgcct tatccggtaa ctatcgtctt gagtccaacc cggtaagaca cgacttatcg    5220
ccactggcag cagccactgg taacaggatt agcagagcga ggtatgtagg cggtgctaca    5280
gagttcttga agtggtggcc taactacggc tacactagaa gaacagtatt tggtatctgc    5340
gctctgctga gccagttac cttcggaaaa agagttggta gctcttgatc cggcaaacaa    5400
accaccgctg gtagcggtgg ttttttgtt tgcaagcagc agattacgcg cagaaaaaaa    5460
ggatctcaag aagatccttt gatcttttct acggggtctg acgctcagtg gaacgaaaac    5520
tcacgttaag ggattttggt catgactgtg aatgtgtgt cagttaggcg acataggtga    5580
tctatgtaga agcctagtgg aacaggttag tttgagtagc tttagaatgt aaattctggg    5640
atcatagtgt agtaatctct aattaacggt gacggtttgt aagacaggtc ttcgcaaaat    5700
caagcggcag gtgatttcaa cagattcttg ctgatggttt aggcgtacaa tgccctgaag    5760
aataagtaag agaatagcac tcctcgtcgc ctagaattac ctaccggcgt ccaccatacc    5820
ttcgattatc gcgcccactc tcccattagt cggcacaggt ggatgtgttg cgatagcccg    5880
ctaagatatt ctaaggcgta acgcagatga atattctaca gagttgccat aggcgttgaa    5940
```

```
cgcttcacgg acgataggaa tgttgcgtat agagcgtgag tcatcgaagt ggtgtataca      6000
ctcgtactta acatctagcc cggctctatc agtacaccag tgccttgaat gacatactca      6060
tcattaaact ttctcaacag tcaaacgacc aagtgcattt ccaaggagtg cgaaggagat      6120
tcattctctc gccagcactg taataggcac taaaagagtg aagataagct agagtgccgt      6180
gctaagacgg tgtcggaaca aagcggtctt acggtcagtc gtatttcctg tcgagtcccg      6240
tccagttgag cgtatcactc ccagtgtact agcaagccga aaggctgtg cttggagtca       6300 atcggatgta ggatggtctc cagacaccgg gccaccactc ttcacgccta aagcatagaa      6360
acgtcgagca gacatcaaag tcttagtacc ggacgtgccg tttcactgcg aatattacct      6420
gaagctgtac cgttattgcg gagcaaagtg acagtgctgc tcttatcata tttgtattga      6480
cgacagccgc cttcgcggtt tcctcagact ctagatcgaa tacaggctta ttgtaggcag      6540
aggcacgccc ttgttagtgg ctgcggcaat atcttccgat cccctgtct aaccatgaat       6600 caattctctc atttgaagac cctaatatgt catcattagt gtttcaaatg ccaccaaata      6660
ccgcctagaa atgtctatga tgtgtgtcca ctagaagttg attcacaaac gactgctaga      6720
atcgcgtgat agggcatctt gaagtttaca ttgttgtatc gcaaggtact ccgatcttaa      6780
tggatgcgaa gtggtacgga tgcaatcaag cgcgtgagag cggtacatta gagcgttcac      6840
ctacgctacg ctaacgggcg attctgataa gaatgcacat tgcgtcgatt cataagatgt      6900
ctcgaccgca tgcgcaactt gtgaagtgtc tactatccct aagcgcatat ctcgcacagt      6960
aaccgaatat gtcggcatct gatgttaccg ttgagttagt gttcagctca cggaacttat      7020
tgtatgagta gagatttgta agagctgtta gttagctcgc tcagctaata gttgcccaca      7080
caacgtcaaa ttagagaacg gtcgtaacat tatcggtggt tctctaacta ctatcagtac      7140
ccacgactcg actctgccgc agctaggtat cgcctgaaag ccagtcagcg ttaaggagtg      7200
ctctgaccag gacaacaggc gtagtgagag ttacttgttc gttgctcttc cgactcggac      7260
ctgagttcgc caacgaccca cttgaggtct gagccggtga agagaagtaa gcatctcgtt      7320
cgcagcttgc cagcactttc agaacatgac ccctatttgt ttattttct aaatacattc       7380 aaatatgtat ccgctcatga gacaataacc ctgataaatg cttcaataat attgaaaaag      7440
gaagagtggc cgcctcggcc taggcttttg caaagatcga tcaagagaca ggatgaggat      7500
cgtttcgcat gattgaacaa gatggattgc acgcaggttc tccggccgct tgggtggaga      7560
ggctattcgg ctatgactgg gcacaacaga caatcggctg ctctgatgcc gccgtgttcc      7620
ggctgtcagc gcaggggcgc ccggttcttt ttgtcaagac cgacctgtcc ggtgccctga      7680
atgaactgca agacgaggca gcgcggctat cgtggctggc cacgacgggc gttccttgcg      7740
cagctgtgct cgacgttgtc actgaagcgg gaagggactg gctgctattg ggcgaagtgc      7800
cggggcagga tctcctgtca tctcaccttg ctcctgccga aaagtatcc atcatggctg       7860 atgcaatgcg gcggctgcat acgcttgatc cggctacctg cccattcgac caccaagcga      7920
aacatcgcat cgagcgagca cgtactcgga tggaagccgg tcttgtcgat caggatgatc      7980
tggacgaaga gcatcagggg ctcgcgccag ccgaactgtt cgccaggctc aaggcgagca      8040
tgcccgacgg cgaggatctc gtcgtgaccc atggcgatgc ctgcttgccg aatatcatgg      8100
tggaaaatgg ccgcttttct ggattcatcg actgtggccg gctgggtgtg gcggaccgct      8160
atcaggacat agcgttggct acccgtgata ttgctgaaga gcttggcggc gaatgggctg      8220
accgcttcct cgtgctttac ggtatcgccg ctcccgattc gcagcgcatc gccttctatc      8280
gccttcttga cgagttcttc tgaggtacca tgatgcgtgc atggtagaat gactcttgat      8340
```

| | |
|---|---|
| aacggacttc gactaggcaa tatcccttgt caacttgtcg aggagaaaag tattgactga | 8400 |
| agcgctcccg gcacaacggc caaagaagtc tcagcaatgt tcttatttcc gaatgacatg | 8460 |
| cgtctccttg cgggtaaatc gccgaccgca aacttagga gccaggatac agataggtct | 8520 |
| aacttaggtt aagggagtaa atcctgggat cgttcagttg taaccatata cttacgctgg | 8580 |
| ggcttctccg gcggatgtta ctgtcaccaa ccacgagatt tgaagtaaac gcatgattga | 8640 |
| gcacatagcc gcgctatccg acaatctcca aattgataac ataccgttcc atgaaggcca | 8700 |
| gaattactta ccggcccttt ccatgcgtgc gccataccgc actctgcgct tatccgtccg | 8760 |
| aggggagagt gtgcgatcct ccgttaagat attctcacgt atgacgtagc tatgtattgt | 8820 |
| gcagaggtag cgaaggcgtt gaacacttca cagatggtgg ggattcgggc aaagggcgtg | 8880 |
| ataacttggg gactaacata ggcgtaaact acgatgcac caactcaatc gcagctcgtg | 8940 |
| cgccctgaat caacgtactc atctcaactg attctcggca atctacggag cgacttgatt | 9000 |
| atcaacacct gtctagcagt tctaatcttc tgccaacatc gtacatagcc tccaagagat | 9060 |
| tatcatacct atcggcacag aagtgacacg acgccgaagg gtagcggact tctggtcaac | 9120 |
| cacaattccc caggggacag gtcctgcggt gcgcatcact ttgtaagtgc aagcaaccca | 9180 |
| agtgagccca gcctggactg agctggttcc tgtgtcaggt cgaggctggg gatgacagct | 9240 |
| cttgtaaaca tagtgatcaa gcgtggcgtc gaacggtcga gaaactcata gtacctcggg | 9300 |
| tagcaactta ctcaggttat tgcttgaagc tgtactattt caggagcgct gaaggtctct | 9360 |
| tcttctgtag actgaactcg caagggtcgt gaagtcggtt ccttcaatgc ttaacaagaa | 9420 |
| caaaggctta ctgtgcagac tggaacgccc atctagcggc tcgcgtcttg aatgctcggt | 9480 |
| ccccttttgtc attgcggata caatccattt ccctcattca ccagcttgcg aagtctacat | 9540 |
| tgagtagacg aatgcgacct agaagaggtg cgcttcagaa cttgtgagga gtggttgatg | 9600 |
| ctctatactc catttggtgt ttcgtgcatc accgcgatag gctgacaaga ggtcttgaac | 9660 |
| attgaatagc aaggcacttc cggtctcata gaagagagca cgggataagg tacgcgcgtg | 9720 |
| gtacgggagg atcaagggc tacacgatag aaaggcttct ccctcactcg ctaggaggca | 9780 |
| aatgcagaac gctggttact actacgatac gtgaaacttg tccaacggtt gcccaaagtg | 9840 |
| ttaagtgtct atcacccctag tgccgttttcc cggagaaaac gccaggttga atccgcattt | 9900 |
| gaagctacga tggtgaagtc tgggtcgagc gcgccgcatg ttgattgcgt gagtaggctc | 9960 |
| gaccaagaac cgctagtagc gtcgctgtag aaatagttct cgacagaccg tcgagtttag | 10020 |
| aaaatggtag cagcattgtt cgcatctcaa tcaagtatgg attacggtgt ttacactgtc | 10080 |
| ctgcggctac ccatcgcctg aaatccagct cgtgtcaagc cattgcctct ccgggacgcc | 10140 |
| gcatgaagta actacatata ccttgcacgg gttgactgcg gtccgttcag actcgaccaa | 10200 |
| ggacacaatc cagcgatcgg tgcgggcctc ttcgctatta cgc | 10243 |

<210> SEQ ID NO 8
<211> LENGTH: 3738
<212> TYPE: DNA
<213> ORGANISM: Homo sapiens
<220> FEATURE:
<221> NAME/KEY: misc_feature
<223> OTHER INFORMATION: human CNGB1 gerne

<400> SEQUENCE: 8

| | |
|---|---|
| atgttgggct gggtccagag ggtgctgcct cagcccccag ggacccctcg gaagaccaag | 60 |
| atgcaggagg aagaggaagt ggaaccagag ccagagatgg aggcggaggt ggaaccagaa | 120 |

```
ccgaatcctg aggaggccga gacagagtcc gagtccatgc cccccgaaga gtcattcaag      180
gaggaggaag tggctgtggc agacccaagc cctcaggaga ccaaggaggc tgcccttact      240
tccaccatat ccctccgggc ccagggcgct gagatttctg aaatgaatag tcccagccac      300
agggtactga cctggctcat gaagggtgta gagaaggtga tcccgcagcc tgttcacagc      360
atcacggagg acccggctca gatcctgggg catggcagca ctggggacac agggtgcaca      420
gatgaaccca tgaggccct  tgaggcccaa gacactaggc tgggctgcg  gctgcttctg      480 tggctggagc agaatctgga aagagtgctt cctcagcccc ccaaatcctc tgaggtctgg      540
agagatgagc ctgcagttgc tacagcgcct ccaggacgcc cccaggaaat ggggcccaag      600
ctgcaggccc gggagacccc ctccctgccc acacccatcc ccctgcagcc caaggaggaa      660
cccaaggagg caccagctcc agagcccag  cccggctccc aggcccagac ctcctccctg      720
ccaccaacca gggaccctgc caggctggtg gcatgggtcc tgcacaggct ggagatggcc      780
ttgccgcagc cagtgctaca tgggaaaata ggggaacagg agcctgactc ccctgggata      840
tgtgatgtgc agaccatcag catccttcct ggaggacaag tggagcctga ccttgtccta      900
gaggaggttg aaccgccctg gaggatgcc  caccaggatg tcagtaccag cccacagggt      960
acagaggtgg ttccagctta tgaagaagag aacaaagctg tggagaagat gcccagagag     1020
ctgtcccgga ttgaagagga gaagaagat gaggaggagg aagaggaaga ggaggaggag      1080
gaggaagagg aggaggtgac tgaggtgctg ctggatagct gtgtggtgtc gcaggtgggc     1140
gtgggccaga gtgaagaaga cgggacccgg cccccagagca cttcagatca gaagctgtgg     1200
gaggaagttg gggaggaggc caagaaggag gctgaagaga aggccaagga ggaggccgag     1260
gaggtggctg aagaggaggc tgaaaaggag ccccaggact gggcggagac caaggaggag     1320
cctgaggctg aggccgaggc tgccagttca ggagtgcctg ccacgaaaca gcacccagaa     1380
gtgcaggtgg aagatactga tgctgatagc tgccccctca tggcagaaga gaatccaccc     1440
tcaaccgtgt tgccgccacc atctcctgcc aaatcagaca cccttatagt cccaagctca     1500
gcctcgggga cacacaggaa gaagctgccc tctgaggatg atgaggctga agagctcaag     1560
gcgttgtcac cagcagagtc cccagtggtt gcctggtctg accccaccac cccgaaggac     1620
actgatggcc aggaccgtgc ggcctccacg gccagcacaa atagcgccat catcaacgac     1680
cggctccagg agctggtgaa gctcttcaag gagcggacag agaaagtgaa ggagaaactc     1740
attgaccctg acgtcacctc tgatgaggag agccccaagc cctccccagc caagaaagcc     1800
ccagagccag ctccagacac aaagcccgct gaagccgagc cagtggaaga ggagcactat     1860
tgcgacatgc tctgctgcaa gttcaaacac cgcccctgga gaagtacca  gtttccccag     1920 agcattgacc cgctgaccaa cctgatgtat gtcctatgcc tgttcttcgt ggtgatggcc     1980
tggaattgga actgttggct gattcccgtg cgctgggcct tccctacca  gaccccggac     2040 aacatccacc actggctgct gatggattac ctatgcgacc tcatctactt cctggacatc     2100
accgtgttcc agacacgcct gcagtttgtc agaggcgggg acatcattac ggacaaaaag     2160
gacatgcgaa ataactacct gaagtctcgc cgcttcaaga tggacctgct cagcctcctg     2220
cccttggatt ttctctattt gaaagtcggt gtgaacccc  tcctccgcct gccccgctgt     2280
ttaaagtaca tggccttctt cgagtttaac agccgcctgg aatccatcct cagcaaagcc     2340
tacgtgtaca gggtcatcag gaccacagcc taccttctct acagcctgca tttgaattcc     2400
tgtctttatt actgggcatc ggcctatcag ggcctcggct ccactcactg ggtttacgat     2460
```

```
ggcgtgggaa acagttatat tcgctgttac tactttgctg tgaagaccct catcaccatc    2520 gggggggctgc ctgaccccaa gacactcttt gaaattgtct tccagctgct gaattatttc    2580
acgggcgtct ttgctttctc tgtgatgatc ggacagatga gagatgtggt aggggccgcc    2640
accgcgggac agacctacta ccgcagctgc atggacagca cggtgaagta catgaatttc    2700
tacaagatcc ccaagtccgt gcagaaccgc gtcaagacct ggtacgagta cacctggcac    2760
tcgcaaggca tgctggatga gtcagagctg atggtgcagc ttccagacaa gatgcggctg    2820
gacctcgcca tcgacgtgaa ctacaacatc gttagcaaag tcgcactctt tcagggctgt    2880
gaccggcaga tgatctttga catgctgaag aggcttcgct ctgttgtcta cctgcccaac    2940
gactatgtgt gcaagaaggg ggagatcggc cgtgagatgt acatcatcca ggcagggcaa    3000
gtgcaggtct tgggcggccc tgatgggaaa tctgtgctgg tgacgctgaa agctggatct    3060
gtgtttggag aaataagctt gctggctgtt ggggcggga accggcgcac ggccaacgtg    3120
gtggcgcacg ggtttaccaa cctcttcatc ctggataaga aggacctgaa tgagattttg    3180
gtgcattatc ctgagtctca gaagttactc cggaagaaag ccaggcgcat gctgagaagc    3240
aacaataagc ccaaggagga gaagagcgtg ctgatccttc accccgggc gggcacccca    3300 aagctcttca acgctgccct cgctatgaca ggaaagatgg gtggcaaggg ggcaaaaggc    3360
ggcaaacttg ctcacctccg ggcccggctc aaagaactgg ccgcgctgga ggcggctgca    3420
aagcagcaag agttggtgga acaggccaag agctcgcaag acgtcaaggg agaggaaggc    3480
tccgccgccc cagaccagca cacgcaccca aggaggccg ccaccgaccc acccgcgccc    3540
cggacgcccc ccgagccccc gggtctccca ccgagctctc caccgcctgc ctcccttggg    3600
aggccggagg gagaggagga ggggccggcc gagcccgaag agcactcggt gaggatctgc    3660
atgagcccgg gccggagcc gggagagcag atcctgtcgg tgaagatgcc ggaggaaagg    3720
gaggagaagg cggagtaa                                                  3738
```

<210> SEQ ID NO 9
<211> LENGTH: 194
<212> TYPE: DNA
<213> ORGANISM: Homo sapiens
<220> FEATURE:
<221> NAME/KEY: misc_feature
<222> LOCATION: (1)..(194)
<223> OTHER INFORMATION: human RHO promoter fragment

<400> SEQUENCE: 9

```
tctcctccct gacctcaggc ttcctcctag tgtcaccttg gccctctta gaagccaatt      60 aggccctcag tttctgcagc ggggattaat atgattatga acaccccaa tctcccagat     120 gctgattcag ccaggagctt aggaggggga ggtcacttta taagggtctg gggggtcag     180 aacccagagt catc                                                      194
```

<210> SEQ ID NO 10
<211> LENGTH: 1065
<212> TYPE: PRT
<213> ORGANISM: Homo sapiens
<220> FEATURE:
<221> NAME/KEY: MISC_FEATURE
<222> LOCATION: (1)..(1065)
<223> OTHER INFORMATION: Abca4 (ATP binding cassette subfamily A member 4)

<400> SEQUENCE: 10

```
Met Asp Val Val Leu His His Val Pro Glu Ala Lys Leu Val Glu Cys
1               5                   10                  15
```

Ile Gly Gln Glu Leu Ile Phe Leu Leu Pro Asn Lys Asn Phe Lys His
                    20                  25                  30

Arg Ala Tyr Ala Ser Leu Phe Arg Glu Leu Glu Thr Leu Ala Asp
                35                  40                  45

Leu Gly Leu Ser Ser Phe Gly Ile Ser Asp Thr Pro Leu Glu Glu Ile
50                  55                  60

Phe Leu Lys Val Thr Glu Asp Ser Asp Ser Gly Pro Leu Phe Ala Gly
65                  70                  75                  80

Gly Ala Gln Gln Lys Arg Glu Asn Val Asn Pro Arg His Pro Cys Leu
                85                  90                  95

Gly Pro Arg Glu Lys Ala Gly Gln Thr Pro Gln Asp Ser Asn Val Cys
                100                 105                 110

Ser Pro Gly Ala Pro Ala Ala His Pro Glu Gly Gln Pro Pro Glu
            115                 120                 125

Pro Glu Cys Pro Gly Pro Gln Leu Asn Thr Gly Thr Gln Leu Val Leu
            130                 135                 140

Gln His Val Gln Ala Leu Leu Val Lys Arg Phe Gln His Thr Ile Arg
145                 150                 155                 160

Ser His Lys Asp Phe Leu Ala Gln Ile Val Leu Pro Ala Thr Phe Val
                165                 170                 175

Phe Leu Ala Leu Met Leu Ser Ile Val Ile Pro Pro Phe Gly Glu Tyr
            180                 185                 190

Pro Ala Leu Thr Leu His Pro Trp Ile Tyr Gly Gln Gln Tyr Thr Phe
            195                 200                 205

Phe Ser Met Asp Glu Pro Gly Ser Glu Gln Phe Thr Val Leu Ala Asp
            210                 215                 220

Val Leu Asn Lys Pro Gly Phe Gly Asn Arg Cys Leu Lys Glu Gly
225                 230                 235                 240

Trp Leu Pro Glu Tyr Pro Cys Gly Asn Ser Thr Pro Trp Lys Thr Pro
                245                 250                 255

Ser Val Ser Pro Asn Ile Thr Gln Leu Phe Gln Lys Gln Lys Trp Thr
            260                 265                 270

Gln Val Asn Pro Ser Pro Ser Cys Arg Cys Ser Thr Arg Glu Lys Leu
            275                 280                 285

Thr Met Leu Pro Glu Cys Pro Glu Gly Ala Gly Gly Leu Pro Pro Pro
290                 295                 300

Gln Arg Thr Gln Arg Ser Thr Glu Ile Leu Gln Asp Leu Thr Asp Arg
305                 310                 315                 320

Asn Ile Ser Asp Phe Leu Val Lys Thr Tyr Pro Ala Leu Ile Arg Ser
                325                 330                 335

Ser Leu Lys Ser Lys Phe Trp Val Asn Glu Gln Arg Tyr Gly Gly Ile
            340                 345                 350

Ser Ile Gly Gly Lys Leu Pro Val Pro Ile Thr Gly Glu Ala Leu
            355                 360                 365

Val Gly Phe Leu Ser Asp Leu Gly Arg Ile Met Asn Val Ser Gly Gly
            370                 375                 380

Pro Ile Thr Arg Glu Ala Ser Lys Glu Ile Pro Asp Phe Leu Lys His
385                 390                 395                 400

Leu Glu Thr Glu Asp Asn Ile Lys Val Trp Phe Asn Asn Lys Gly Trp
                405                 410                 415

His Ala Leu Val Ser Phe Leu Asn Val Ala His Asn Ala Ile Leu Arg
            420                 425                 430

```
Ala Ser Leu Pro Lys Asp Arg Ser Pro Glu Glu Tyr Gly Ile Thr Val
        435                 440                 445

Ile Ser Gln Pro Leu Asn Leu Thr Lys Glu Gln Leu Ser Glu Ile Thr
    450                 455                 460

Val Leu Thr Thr Ser Val Asp Ala Val Val Ala Ile Cys Val Ile Phe
465                 470                 475                 480

Ser Met Ser Phe Val Pro Ala Ser Phe Val Leu Tyr Leu Ile Gln Glu
                485                 490                 495

Arg Val Asn Lys Ser Lys His Leu Gln Phe Ile Ser Gly Val Ser Pro
            500                 505                 510

Thr Thr Tyr Trp Val Thr Asn Phe Leu Trp Asp Ile Met Asn Tyr Ser
        515                 520                 525

Val Ser Ala Gly Leu Val Val Gly Ile Phe Ile Gly Phe Gln Lys Lys
    530                 535                 540

Ala Tyr Thr Ser Pro Glu Asn Leu Pro Ala Leu Val Ala Leu Leu Leu
545                 550                 555                 560

Leu Tyr Gly Trp Ala Val Ile Pro Met Met Tyr Pro Ala Ser Phe Leu
                565                 570                 575

Phe Asp Val Pro Ser Thr Ala Tyr Val Ala Leu Ser Cys Ala Asn Leu
            580                 585                 590

Phe Ile Gly Ile Asn Ser Ser Ala Ile Thr Phe Ile Leu Glu Leu Phe
        595                 600                 605

Glu Asn Asn Arg Thr Leu Leu Arg Phe Asn Ala Val Leu Arg Lys Leu
    610                 615                 620

Leu Ile Val Phe Pro His Phe Cys Leu Gly Arg Gly Leu Ile Asp Leu
625                 630                 635                 640

Ala Leu Ser Gln Ala Val Thr Asp Val Tyr Ala Arg Phe Gly Glu Glu
                645                 650                 655

His Ser Ala Asn Pro Phe His Trp Asp Leu Ile Gly Lys Asn Leu Phe
            660                 665                 670

Ala Met Val Val Glu Gly Val Val Tyr Phe Leu Leu Thr Leu Leu Val
        675                 680                 685

Gln Arg His Phe Phe Leu Ser Gln Trp Ile Ala Glu Pro Thr Lys Glu
    690                 695                 700

Pro Ile Val Asp Glu Asp Asp Val Ala Glu Glu Arg Gln Arg Ile
705                 710                 715                 720

Ile Thr Gly Gly Asn Lys Thr Asp Ile Leu Arg Leu His Glu Leu Thr
                725                 730                 735

Lys Ile Tyr Pro Gly Thr Ser Ser Pro Ala Val Asp Arg Leu Cys Val
            740                 745                 750

Gly Val Arg Pro Gly Glu Cys Phe Gly Leu Leu Gly Val Ser Gly Ala
        755                 760                 765

Gly Lys Thr Thr Thr Phe Lys Met Leu Thr Gly Asp Thr Thr Val Thr
    770                 775                 780

Ser Gly Asp Ala Thr Val Ala Gly Lys Ser Ile Leu Thr Asn Ile Ser
785                 790                 795                 800

Glu Val His Gln Asn Met Gly Tyr Cys Pro Gln Phe Asp Ala Ile Asp
                805                 810                 815

Glu Leu Leu Thr Gly Arg Glu His Leu Tyr Leu Tyr Ala Arg Leu Arg
            820                 825                 830

Gly Val Pro Ala Glu Glu Ile Glu Lys Val Ala Asn Trp Ser Ile Lys
        835                 840                 845

Ser Leu Gly Leu Thr Val Tyr Ala Asp Cys Leu Ala Gly Thr Tyr Ser
```

-continued

```
              850             855             860
Gly Gly Asn Lys Arg Lys Leu Ser Thr Ala Ile Ala Leu Ile Gly Cys
865                 870                 875                 880

Pro Pro Leu Val Leu Leu Asp Glu Pro Thr Thr Gly Met Asp Pro Gln
                885                 890                 895

Ala Arg Arg Met Leu Trp Asn Val Ile Val Ser Ile Ile Arg Glu Gly
                900                 905                 910

Arg Ala Val Val Leu Thr Ser His Ser Met Glu Glu Cys Glu Ala Leu
            915                 920                 925

Cys Thr Arg Leu Ala Ile Met Val Lys Gly Ala Phe Arg Cys Met Gly
        930                 935                 940

Thr Ile Gln His Leu Lys Ser Lys Phe Gly Asp Gly Tyr Ile Val Thr
945                 950                 955                 960

Met Lys Ile Lys Ser Pro Lys Asp Asp Leu Leu Pro Asp Leu Asn Pro
                965                 970                 975

Val Glu Gln Phe Phe Gln Gly Asn Phe Pro Gly Ser Val Gln Arg Glu
                980                 985                 990

Arg His Tyr Asn Met Leu Gln Phe Gln Val Ser Ser Ser Ser Leu Ala
            995                 1000                1005

Arg Ile Phe Gln Leu Leu Leu Ser His Lys Asp Ser Leu Leu Ile
    1010                1015                1020

Glu Glu Tyr Ser Val Thr Gln Thr Thr Leu Asp Gln Val Phe Val
    1025                1030                1035

Asn Phe Ala Lys Gln Gln Thr Glu Ser His Asp Leu Pro Leu His
    1040                1045                1050

Pro Arg Ala Ala Gly Ala Ser Arg Gln Ala Gln Asp
    1055                1060                1065

<210> SEQ ID NO 11
<211> LENGTH: 384
<212> TYPE: PRT
<213> ORGANISM: Homo sapiens
<220> FEATURE:
<221> NAME/KEY: MISC_FEATURE
<222> LOCATION: (1)..(384)
<223> OTHER INFORMATION: AIPL1 (Aryl-hydrocarbon-interacting protein-
      like 1)

<400> SEQUENCE: 11

Met Asp Ala Ala Leu Leu Leu Asn Val Glu Gly Val Lys Lys Thr Ile
1               5                   10                  15

Leu His Gly Gly Thr Gly Glu Leu Pro Asn Phe Ile Thr Gly Ser Arg
            20                  25                  30

Val Ile Phe His Phe Arg Thr Met Lys Cys Asp Glu Glu Arg Thr Val
        35                  40                  45

Ile Asp Asp Ser Arg Gln Val Gly Gln Pro Met His Ile Ile Ile Gly
    50                  55                  60

Asn Met Phe Lys Leu Glu Val Trp Glu Ile Leu Leu Thr Ser Met Arg
65                  70                  75                  80

Val His Glu Val Ala Glu Phe Trp Cys Asp Thr Ile His Thr Gly Val
                85                  90                  95

Tyr Pro Ile Leu Ser Arg Ser Leu Arg Gln Met Ala Gln Gly Lys Asp
            100                 105                 110

Pro Thr Glu Trp His Val His Thr Cys Gly Leu Ala Asn Met Phe Ala
        115                 120                 125

Tyr His Thr Leu Gly Tyr Glu Asp Leu Asp Glu Leu Gln Lys Glu Pro
```

```
                130                 135                 140
Gln Pro Leu Val Phe Val Ile Glu Leu Leu Gln Val Asp Ala Pro Ser
145                 150                 155                 160

Asp Tyr Gln Arg Glu Thr Trp Asn Leu Ser Asn His Glu Lys Met Lys
                165                 170                 175

Ala Val Pro Val Leu His Gly Glu Gly Asn Arg Leu Phe Lys Leu Gly
                180                 185                 190

Arg Tyr Glu Glu Ala Ser Ser Lys Tyr Gln Glu Ala Ile Ile Cys Leu
                195                 200                 205

Arg Asn Leu Gln Thr Lys Glu Lys Pro Trp Glu Val Gln Trp Leu Lys
                210                 215                 220

Leu Glu Lys Met Ile Asn Thr Leu Ile Leu Asn Tyr Cys Gln Cys Leu
225                 230                 235                 240

Leu Lys Lys Glu Glu Tyr Tyr Glu Val Leu Glu His Thr Ser Asp Ile
                245                 250                 255

Leu Arg His His Pro Gly Ile Val Lys Ala Tyr Tyr Val Arg Ala Arg
                260                 265                 270

Ala His Ala Glu Val Trp Asn Glu Ala Glu Lys Ala Asp Leu Gln
                275                 280                 285

Lys Val Leu Glu Leu Glu Pro Ser Met Gln Lys Ala Val Arg Arg Glu
290                 295                 300

Leu Arg Leu Leu Glu Asn Arg Met Ala Glu Lys Gln Glu Glu Arg
305                 310                 315                 320

Leu Arg Cys Arg Asn Met Leu Ser Gln Gly Ala Thr Gln Pro Pro Ala
                325                 330                 335

Glu Pro Pro Thr Glu Pro Ala Gln Ser Ser Thr Glu Pro Pro Ala
                340                 345                 350

Glu Pro Pro Thr Ala Pro Ser Ala Glu Leu Ser Ala Gly Pro Pro Ala
                355                 360                 365

Glu Pro Ala Thr Glu Pro Pro Ser Pro Gly His Ser Leu Gln His
                370                 375                 380

<210> SEQ ID NO 12
<211> LENGTH: 585
<212> TYPE: PRT
<213> ORGANISM: Homo sapiens
<220> FEATURE:
<221> NAME/KEY: MISC_FEATURE
<222> LOCATION: (1)..(585)
<223> OTHER INFORMATION: BEST1 (Bestrophin-1), isoform 1

<400> SEQUENCE: 12

Met Thr Ile Thr Tyr Thr Ser Gln Val Ala Asn Ala Arg Leu Gly Ser
1               5                   10                  15

Phe Ser Arg Leu Leu Leu Cys Trp Arg Gly Ser Ile Tyr Lys Leu Leu
                20                  25                  30

Tyr Gly Glu Phe Leu Ile Phe Leu Leu Cys Tyr Tyr Ile Ile Arg Phe
                35                  40                  45

Ile Tyr Arg Leu Ala Leu Thr Glu Glu Gln Gln Leu Met Phe Glu Lys
        50                  55                  60

Leu Thr Leu Tyr Cys Asp Ser Tyr Ile Gln Leu Ile Pro Ile Ser Phe
65                  70                  75                  80

Val Leu Gly Phe Tyr Val Thr Leu Val Val Thr Arg Trp Trp Asn Gln
                85                  90                  95

Tyr Glu Asn Leu Pro Trp Pro Asp Arg Leu Met Ser Leu Val Ser Gly
                100                 105                 110
```

Phe Val Glu Gly Lys Asp Glu Gln Gly Arg Leu Leu Arg Arg Thr Leu
    115                 120                 125

Ile Arg Tyr Ala Asn Leu Gly Asn Val Leu Ile Leu Arg Ser Val Ser
    130                 135                 140

Thr Ala Val Tyr Lys Arg Phe Pro Ser Ala Gln His Leu Val Gln Ala
145                 150                 155                 160

Gly Phe Met Thr Pro Ala Glu His Lys Gln Leu Glu Lys Leu Ser Leu
                165                 170                 175

Pro His Asn Met Phe Trp Val Pro Trp Val Trp Phe Ala Asn Leu Ser
                180                 185                 190

Met Lys Ala Trp Leu Gly Gly Arg Ile Arg Asp Pro Ile Leu Leu Gln
            195                 200                 205

Ser Leu Leu Asn Glu Met Asn Thr Leu Arg Thr Gln Cys Gly His Leu
        210                 215                 220

Tyr Ala Tyr Asp Trp Ile Ser Ile Pro Leu Val Tyr Thr Gln Val Val
225                 230                 235                 240

Thr Val Ala Val Tyr Ser Phe Phe Leu Thr Cys Leu Val Gly Arg Gln
                245                 250                 255

Phe Leu Asn Pro Ala Lys Ala Tyr Pro Gly His Glu Leu Asp Leu Val
            260                 265                 270

Val Pro Val Phe Thr Phe Leu Gln Phe Phe Phe Tyr Val Gly Trp Leu
        275                 280                 285

Lys Val Ala Glu Gln Leu Ile Asn Pro Phe Gly Glu Asp Asp Asp Asp
            290                 295                 300

Phe Glu Thr Asn Trp Ile Val Asp Arg Asn Leu Gln Val Ser Leu Leu
305                 310                 315                 320

Ala Val Asp Glu Met His Gln Asp Leu Pro Arg Met Glu Pro Asp Met
                325                 330                 335

Tyr Trp Asn Lys Pro Glu Pro Gln Pro Pro Tyr Thr Ala Ala Ser Ala
            340                 345                 350

Gln Phe Arg Arg Ala Ser Phe Met Gly Ser Thr Phe Asn Ile Ser Leu
        355                 360                 365

Asn Lys Glu Glu Met Glu Phe Gln Pro Asn Gln Glu Asp Glu Glu Asp
    370                 375                 380

Ala His Ala Gly Ile Ile Gly Arg Phe Leu Gly Leu Gln Ser His Asp
385                 390                 395                 400

His His Pro Pro Arg Ala Asn Ser Arg Thr Lys Leu Leu Trp Pro Lys
                405                 410                 415

Arg Glu Ser Leu Leu His Glu Gly Leu Pro Lys Asn His Lys Ala Ala
            420                 425                 430

Lys Gln Asn Val Arg Gly Gln Glu Asp Asn Lys Ala Trp Lys Leu Lys
        435                 440                 445

Ala Val Asp Ala Phe Lys Ser Ala Pro Leu Tyr Gln Arg Pro Gly Tyr
    450                 455                 460

Tyr Ser Ala Pro Gln Thr Pro Leu Ser Pro Thr Pro Met Phe Phe Pro
465                 470                 475                 480

Leu Glu Pro Ser Ala Pro Ser Lys Leu His Ser Val Thr Gly Ile Asp
                485                 490                 495

Thr Lys Asp Lys Ser Leu Lys Thr Val Ser Ser Gly Ala Lys Lys Ser
            500                 505                 510

Phe Glu Leu Leu Ser Glu Ser Asp Gly Ala Leu Met Glu His Pro Glu
        515                 520                 525

Val Ser Gln Val Arg Arg Lys Thr Val Glu Phe Asn Leu Thr Asp Met
530                 535                 540

Pro Glu Ile Pro Glu Asn His Leu Lys Glu Pro Leu Glu Gln Ser Pro
545                 550                 555                 560

Thr Asn Ile His Thr Thr Leu Lys Asp His Met Asp Pro Tyr Trp Ala
            565                 570                 575

Leu Glu Asn Arg Asp Glu Ala His Ser
            580                 585

<210> SEQ ID NO 13
<211> LENGTH: 1977
<212> TYPE: PRT
<213> ORGANISM: Homo sapiens
<220> FEATURE:
<221> NAME/KEY: MISC_FEATURE
<222> LOCATION: (1)..(1977)
<223> OTHER INFORMATION: CACNA1F (Voltage-dependent L-type calcium
      channel subunit alpha-1F), isoform 1

<400> SEQUENCE: 13

Met Ser Glu Ser Glu Gly Gly Lys Asp Thr Thr Pro Glu Pro Ser Pro
1               5                   10                  15

Ala Asn Gly Ala Gly Pro Gly Pro Glu Trp Gly Leu Cys Pro Gly Pro
            20                  25                  30

Pro Ala Val Glu Gly Glu Ser Ser Gly Ala Ser Gly Leu Gly Thr Pro
        35                  40                  45

Lys Arg Arg Asn Gln His Ser Lys His Lys Thr Val Ala Val Ala Ser
50                  55                  60

Ala Gln Arg Ser Pro Arg Ala Leu Phe Cys Leu Thr Leu Ala Asn Pro
65                  70                  75                  80

Leu Arg Arg Ser Cys Ile Ser Ile Val Glu Trp Lys Pro Phe Asp Ile
                85                  90                  95

Leu Ile Leu Leu Thr Ile Phe Ala Asn Cys Val Ala Leu Gly Val Tyr
            100                 105                 110

Ile Pro Phe Pro Glu Asp Asp Ser Asn Thr Ala Asn His Asn Leu Glu
        115                 120                 125

Gln Val Glu Tyr Val Phe Leu Val Ile Phe Thr Val Glu Thr Val Leu
130                 135                 140

Lys Ile Val Ala Tyr Gly Leu Val Leu His Pro Ser Ala Tyr Ile Arg
145                 150                 155                 160

Asn Gly Trp Asn Leu Leu Asp Phe Ile Ile Val Val Gly Leu Phe
                165                 170                 175

Ser Val Leu Leu Glu Gln Gly Pro Gly Arg Pro Gly Asp Ala Pro His
            180                 185                 190

Thr Gly Gly Lys Pro Gly Gly Phe Asp Val Lys Ala Leu Arg Ala Phe
        195                 200                 205

Arg Val Leu Arg Pro Leu Arg Leu Val Ser Gly Val Pro Ser Leu His
210                 215                 220

Ile Val Leu Asn Ser Ile Met Lys Ala Leu Val Pro Leu Leu His Ile
225                 230                 235                 240

Ala Leu Leu Val Leu Phe Val Ile Ile Tyr Ala Ile Ile Gly Leu
                245                 250                 255

Glu Leu Phe Leu Gly Arg Met His Lys Thr Cys Tyr Phe Leu Gly Ser
            260                 265                 270

Asp Met Glu Ala Glu Glu Asp Pro Ser Pro Cys Ala Ser Ser Gly Ser
        275                 280                 285

-continued

Gly Arg Ala Cys Thr Leu Asn Gln Thr Glu Cys Arg Gly Arg Trp Pro
290                 295                 300

Gly Pro Asn Gly Gly Ile Thr Asn Phe Asp Asn Phe Phe Ala Met
305                 310                 315                 320

Leu Thr Val Phe Gln Cys Val Thr Met Glu Gly Trp Thr Asp Val Leu
                325                 330                 335

Tyr Trp Met Gln Asp Ala Met Gly Tyr Glu Leu Pro Trp Val Tyr Phe
            340                 345                 350

Val Ser Leu Val Ile Phe Gly Ser Phe Val Leu Asn Leu Val Leu
        355                 360                 365

Gly Val Leu Ser Gly Glu Phe Ser Lys Glu Arg Glu Lys Ala Lys Ala
    370                 375                 380

Arg Gly Asp Phe Gln Lys Gln Arg Glu Lys Gln Gln Met Glu Glu Asp
385                 390                 395                 400

Leu Arg Gly Tyr Leu Asp Trp Ile Thr Gln Ala Glu Glu Leu Asp Met
                405                 410                 415

Glu Asp Pro Ser Ala Asp Asp Asn Leu Gly Ser Met Ala Glu Glu Gly
            420                 425                 430

Arg Ala Gly His Arg Pro Gln Leu Ala Glu Leu Thr Asn Arg Arg Arg
        435                 440                 445

Gly Arg Leu Arg Trp Phe Ser His Ser Thr Arg Ser Thr His Ser Thr
    450                 455                 460

Ser Ser His Ala Ser Leu Pro Ala Ser Asp Thr Gly Ser Met Thr Glu
465                 470                 475                 480

Thr Gln Gly Asp Glu Asp Glu Glu Gly Ala Leu Ala Ser Cys Thr
                485                 490                 495

Arg Cys Leu Asn Lys Ile Met Lys Thr Arg Val Cys Arg Arg Leu Arg
            500                 505                 510

Arg Ala Asn Arg Val Leu Arg Ala Arg Cys Arg Arg Ala Val Lys Ser
        515                 520                 525

Asn Ala Cys Tyr Trp Ala Val Leu Leu Leu Val Phe Leu Asn Thr Leu
530                 535                 540

Thr Ile Ala Ser Glu His His Gly Gln Pro Val Trp Leu Thr Gln Ile
545                 550                 555                 560

Gln Glu Tyr Ala Asn Lys Val Leu Leu Cys Leu Phe Thr Val Glu Met
                565                 570                 575

Leu Leu Lys Leu Tyr Gly Leu Gly Pro Ser Ala Tyr Val Ser Ser Phe
            580                 585                 590

Phe Asn Arg Phe Asp Cys Phe Val Val Cys Gly Gly Ile Leu Glu Thr
        595                 600                 605

Thr Leu Val Glu Val Gly Ala Met Gln Pro Leu Gly Ile Ser Val Leu
610                 615                 620

Arg Cys Val Arg Leu Leu Arg Ile Phe Lys Val Thr Arg His Trp Ala
625                 630                 635                 640

Ser Leu Ser Asn Leu Val Ala Ser Leu Leu Asn Ser Met Lys Ser Ile
                645                 650                 655

Ala Ser Leu Leu Leu Leu Leu Phe Leu Phe Ile Ile Ile Phe Ser Leu
            660                 665                 670

Leu Gly Met Gln Leu Phe Gly Gly Lys Phe Asn Phe Asp Gln Thr His
        675                 680                 685

Thr Lys Arg Ser Thr Phe Asp Thr Phe Pro Gln Ala Leu Leu Thr Val
690                 695                 700

Phe Gln Ile Leu Thr Gly Glu Asp Trp Asn Val Val Met Tyr Asp Gly

-continued

```
            705                 710                 715                 720
        Ile Met Ala Tyr Gly Gly Pro Phe Phe Pro Gly Met Leu Val Cys Ile
                        725                 730                 735

Tyr Phe Ile Ile Leu Phe Ile Cys Gly Asn Tyr Ile Leu Leu Asn Val
                        740                 745                 750

Phe Leu Ala Ile Ala Val Asp Asn Leu Ala Ser Gly Asp Ala Gly Thr
                        755                 760                 765

Ala Lys Asp Lys Gly Gly Glu Lys Ser Asn Glu Lys Asp Leu Pro Gln
                        770                 775                 780

Glu Asn Glu Gly Leu Val Pro Gly Val Glu Lys Glu Glu Glu Glu Gly
        785                 790                 795                 800

Ala Arg Arg Glu Gly Ala Asp Met Glu Glu Glu Glu Glu Glu Glu Glu
                        805                 810                 815

Glu Glu Glu Glu Glu Glu Glu Glu Gly Ala Gly Gly Val Glu Leu
                        820                 825                 830

Leu Gln Glu Val Val Pro Lys Glu Lys Val Val Pro Ile Pro Glu Gly
                        835                 840                 845

Ser Ala Phe Phe Cys Leu Ser Gln Thr Asn Pro Leu Arg Lys Gly Cys
        850                 855                 860

His Thr Leu Ile His His His Val Phe Thr Asn Leu Ile Leu Val Phe
        865                 870                 875                 880

Ile Ile Leu Ser Ser Val Ser Leu Ala Ala Glu Asp Pro Ile Arg Ala
                        885                 890                 895

His Ser Phe Arg Asn His Ile Leu Gly Tyr Phe Asp Tyr Ala Phe Thr
                        900                 905                 910

Ser Ile Phe Thr Val Glu Ile Leu Leu Lys Met Thr Val Phe Gly Ala
                        915                 920                 925

Phe Leu His Arg Gly Ser Phe Cys Arg Ser Trp Phe Asn Met Leu Asp
                        930                 935                 940

Leu Leu Val Val Ser Val Ser Leu Ile Ser Phe Gly Ile His Ser Ser
        945                 950                 955                 960

Ala Ile Ser Val Val Lys Ile Leu Arg Val Leu Arg Val Leu Arg Pro
                        965                 970                 975

Leu Arg Ala Ile Asn Arg Ala Lys Gly Leu Lys His Val Val Gln Cys
                        980                 985                 990

Val Phe Val Ala Ile Arg Thr Ile Gly Asn Ile Met Ile Val Thr Thr
                        995                 1000                1005

Leu Leu Gln Phe Met Phe Ala Cys Ile Gly Val Gln Leu Phe Lys
                        1010                1015                1020

Gly Lys Phe Tyr Thr Cys Thr Asp Glu Ala Lys His Thr Pro Gln
                        1025                1030                1035

Glu Cys Lys Gly Ser Phe Leu Val Tyr Pro Asp Gly Asp Val Ser
                        1040                1045                1050

Arg Pro Leu Val Arg Glu Leu Trp Val Asn Ser Asp Phe Asn
                        1055                1060                1065

Phe Asp Asn Val Leu Ser Ala Met Met Ala Leu Phe Thr Val Ser
                        1070                1075                1080

Thr Phe Glu Gly Trp Pro Ala Leu Leu Tyr Lys Ala Ile Asp Ala
                        1085                1090                1095

Tyr Ala Glu Asp His Gly Pro Ile Tyr Asn Tyr Arg Val Glu Ile
                        1100                1105                1110

Ser Val Phe Phe Ile Val Tyr Ile Ile Ile Ile Ala Phe Phe Met
                        1115                1120                1125
```

```
Met Asn Ile Phe Val Gly Phe Val Ile Thr Phe Arg Ala Gln
1130                    1135                1140

Gly Glu Gln Glu Tyr Gln Asn Cys Glu Leu Asp Lys Asn Gln Arg
1145                    1150                1155

Gln Cys Val Glu Tyr Ala Leu Lys Ala Gln Pro Leu Arg Arg Tyr
1160                    1165                1170

Ile Pro Lys Asn Pro His Gln Tyr Arg Val Trp Ala Thr Val Asn
1175                    1180                1185

Ser Ala Ala Phe Glu Tyr Leu Met Phe Leu Leu Ile Leu Leu Asn
1190                    1195                1200

Thr Val Ala Leu Ala Met Gln His Tyr Glu Gln Thr Ala Pro Phe
1205                    1210                1215

Asn Tyr Ala Met Asp Ile Leu Asn Met Val Phe Thr Gly Leu Phe
1220                    1225                1230

Thr Ile Glu Met Val Leu Lys Ile Ile Ala Phe Lys Pro Lys His
1235                    1240                1245

Tyr Phe Thr Asp Ala Trp Asn Thr Phe Asp Ala Leu Ile Val Val
1250                    1255                1260

Gly Ser Ile Val Asp Ile Ala Val Thr Glu Val Asn Asn Gly Gly
1265                    1270                1275

His Leu Gly Glu Ser Ser Glu Asp Ser Ser Arg Ile Ser Ile Thr
1280                    1285                1290

Phe Phe Arg Leu Phe Arg Val Met Arg Leu Val Lys Leu Leu Ser
1295                    1300                1305

Lys Gly Glu Gly Ile Arg Thr Leu Leu Trp Thr Phe Ile Lys Ser
1310                    1315                1320

Phe Gln Ala Leu Pro Tyr Val Ala Leu Leu Ile Ala Met Ile Phe
1325                    1330                1335

Phe Ile Tyr Ala Val Ile Gly Met Gln Met Phe Gly Lys Val Ala
1340                    1345                1350

Leu Gln Asp Gly Thr Gln Ile Asn Arg Asn Asn Asn Phe Gln Thr
1355                    1360                1365

Phe Pro Gln Ala Val Leu Leu Leu Phe Arg Cys Ala Thr Gly Glu
1370                    1375                1380

Ala Trp Gln Glu Ile Met Leu Ala Ser Leu Pro Gly Asn Arg Cys
1385                    1390                1395

Asp Pro Glu Ser Asp Phe Gly Pro Gly Glu Glu Phe Thr Cys Gly
1400                    1405                1410

Ser Asn Phe Ala Ile Ala Tyr Phe Ile Ser Phe Phe Met Leu Cys
1415                    1420                1425

Ala Phe Leu Ile Ile Asn Leu Phe Val Ala Val Ile Met Asp Asn
1430                    1435                1440

Phe Asp Tyr Leu Thr Arg Asp Trp Ser Ile Leu Gly Pro His His
1445                    1450                1455

Leu Asp Glu Phe Lys Arg Ile Trp Ser Glu Tyr Asp Pro Gly Ala
1460                    1465                1470

Lys Gly Arg Ile Lys His Leu Asp Val Val Ala Leu Leu Arg Arg
1475                    1480                1485

Ile Gln Pro Pro Leu Gly Phe Gly Lys Leu Cys Pro His Arg Val
1490                    1495                1500

Ala Cys Lys Arg Leu Val Ala Met Asn Met Pro Leu Asn Ser Asp
1505                    1510                1515
```

```
Gly Thr Val Thr Phe Asn Ala Thr Leu Phe Ala Leu Val Arg Thr
    1520                1525                1530

Ser Leu Lys Ile Lys Thr Glu Gly Asn Leu Glu Gln Ala Asn Gln
    1535                1540                1545

Glu Leu Arg Ile Val Ile Lys Lys Ile Trp Lys Arg Met Lys Gln
    1550                1555                1560

Lys Leu Leu Asp Glu Val Ile Pro Pro Pro Asp Glu Glu Glu Val
    1565                1570                1575

Thr Val Gly Lys Phe Tyr Ala Thr Phe Leu Ile Gln Asp Tyr Phe
    1580                1585                1590

Arg Lys Phe Arg Arg Arg Lys Glu Lys Gly Leu Leu Gly Asn Asp
    1595                1600                1605

Ala Ala Pro Ser Thr Ser Ser Ala Leu Gln Ala Gly Leu Arg Ser
    1610                1615                1620

Leu Gln Asp Leu Gly Pro Glu Met Arg Gln Ala Leu Thr Cys Asp
    1625                1630                1635

Thr Glu Glu Glu Glu Glu Gly Gln Glu Gly Val Glu Glu Glu
    1640                1645                1650

Asp Glu Lys Asp Leu Glu Thr Asn Lys Ala Thr Met Val Ser Gln
    1655                1660                1665

Pro Ser Ala Arg Arg Gly Ser Gly Ile Ser Val Ser Leu Pro Val
    1670                1675                1680

Gly Asp Arg Leu Pro Asp Ser Leu Ser Phe Gly Pro Ser Asp Asp
    1685                1690                1695

Asp Arg Gly Thr Pro Thr Ser Ser Gln Pro Ser Val Pro Gln Ala
    1700                1705                1710

Gly Ser Asn Thr His Arg Arg Gly Ser Gly Ala Leu Ile Phe Thr
    1715                1720                1725

Ile Pro Glu Glu Gly Asn Ser Gln Pro Lys Gly Thr Lys Gly Gln
    1730                1735                1740

Asn Lys Gln Asp Glu Asp Glu Val Pro Asp Arg Leu Ser Tyr
    1745                1750                1755

Leu Asp Glu Gln Ala Gly Thr Pro Pro Cys Ser Val Leu Leu Pro
    1760                1765                1770

Pro His Arg Ala Gln Arg Tyr Met Asp Gly His Leu Val Pro Arg
    1775                1780                1785

Arg Arg Leu Leu Pro Pro Thr Pro Ala Gly Arg Lys Pro Ser Phe
    1790                1795                1800

Thr Ile Gln Cys Leu Gln Arg Gln Gly Ser Cys Glu Asp Leu Pro
    1805                1810                1815

Ile Pro Gly Thr Tyr His Arg Gly Arg Asn Ser Gly Pro Asn Arg
    1820                1825                1830

Ala Gln Gly Ser Trp Ala Thr Pro Pro Gln Arg Gly Arg Leu Leu
    1835                1840                1845

Tyr Ala Pro Leu Leu Leu Val Glu Glu Gly Ala Ala Gly Glu Gly
    1850                1855                1860

Tyr Leu Gly Arg Ser Ser Gly Pro Leu Arg Thr Phe Thr Cys Leu
    1865                1870                1875

His Val Pro Gly Thr His Ser Asp Pro Ser His Gly Lys Arg Gly
    1880                1885                1890

Ser Ala Asp Ser Leu Val Glu Ala Val Leu Ile Ser Glu Gly Leu
    1895                1900                1905

Gly Leu Phe Ala Arg Asp Pro Arg Phe Val Ala Leu Ala Lys Gln
```

```
                    1910                1915                1920

Glu Ile Ala Asp Ala Cys Arg Leu Thr Leu Asp Glu Met Asp Asn
    1925                1930                1935

Ala Ala Ser Asp Leu Leu Ala Gln Gly Thr Ser Ser Leu Tyr Ser
    1940                1945                1950

Asp Glu Glu Ser Ile Leu Ser Arg Phe Asp Glu Glu Asp Leu Gly
    1955                1960                1965

Asp Glu Met Ala Cys Val His Ala Leu
    1970                1975

<210> SEQ ID NO 14
<211> LENGTH: 438
<212> TYPE: PRT
<213> ORGANISM: Homo sapiens
<220> FEATURE:
<221> NAME/KEY: MISC_FEATURE
<222> LOCATION: (1)..(438)
<223> OTHER INFORMATION: CLN3 (Battenin), isoform 1

<400> SEQUENCE: 14

Met Gly Gly Cys Ala Gly Ser Arg Arg Phe Ser Asp Ser Glu Gly
1               5                   10                  15

Glu Glu Thr Val Pro Glu Pro Arg Leu Pro Leu Asp His Gln Gly
                20                  25                  30

Ala His Trp Lys Asn Ala Val Gly Phe Trp Leu Leu Gly Leu Cys Asn
        35                  40                  45

Asn Phe Ser Tyr Val Val Met Leu Ser Ala Ala His Asp Ile Leu Ser
    50                  55                  60

His Lys Arg Thr Ser Gly Asn Gln Ser His Val Asp Pro Gly Pro Thr
65              70                  75                  80

Pro Ile Pro His Asn Ser Ser Arg Phe Asp Cys Asn Ser Val Ser
                85                  90                  95

Thr Ala Ala Val Leu Leu Ala Asp Ile Leu Pro Thr Leu Val Ile Lys
                100                 105                 110

Leu Leu Ala Pro Leu Gly Leu His Leu Leu Pro Tyr Ser Pro Arg Val
            115                 120                 125

Leu Val Ser Gly Ile Cys Ala Ala Gly Ser Phe Val Leu Val Ala Phe
        130                 135                 140

Ser His Ser Val Gly Thr Ser Leu Cys Gly Val Val Phe Ala Ser Ile
145                 150                 155                 160

Ser Ser Gly Leu Gly Glu Val Thr Phe Leu Ser Leu Thr Ala Phe Tyr
                165                 170                 175

Pro Arg Ala Val Ile Ser Trp Trp Ser Ser Gly Thr Gly Ala Gly
            180                 185                 190

Leu Leu Gly Ala Leu Ser Tyr Leu Gly Leu Thr Gln Ala Gly Leu Ser
        195                 200                 205

Pro Gln Gln Thr Leu Leu Ser Met Leu Gly Ile Pro Ala Leu Leu Leu
    210                 215                 220

Ala Ser Tyr Phe Leu Leu Leu Thr Ser Pro Glu Ala Gln Asp Pro Gly
225                 230                 235                 240

Gly Glu Glu Glu Ala Glu Ser Ala Ala Arg Gln Pro Leu Ile Arg Thr
                245                 250                 255

Glu Ala Pro Glu Ser Lys Pro Gly Ser Ser Ser Ser Leu Ser Leu Arg
            260                 265                 270

Glu Arg Trp Thr Val Phe Lys Gly Leu Leu Trp Tyr Ile Val Pro Leu
        275                 280                 285
```

```
Val Val Val Tyr Phe Ala Glu Tyr Phe Ile Asn Gln Gly Leu Phe Glu
        290                 295                 300

Leu Leu Phe Phe Trp Asn Thr Ser Leu Ser His Ala Gln Gln Tyr Arg
305                 310                 315                 320

Trp Tyr Gln Met Leu Tyr Gln Ala Gly Val Phe Ala Ser Arg Ser Ser
                325                 330                 335

Leu Arg Cys Cys Arg Ile Arg Phe Thr Trp Ala Leu Ala Leu Leu Gln
                340                 345                 350

Cys Leu Asn Leu Val Phe Leu Leu Ala Asp Val Trp Phe Gly Phe Leu
                355                 360                 365

Pro Ser Ile Tyr Leu Val Phe Leu Ile Ile Leu Tyr Glu Gly Leu Leu
                370                 375                 380

Gly Gly Ala Ala Tyr Val Asn Thr Phe His Asn Ile Ala Leu Glu Thr
385                 390                 395                 400

Ser Asp Glu His Arg Glu Phe Ala Met Ala Thr Cys Ile Ser Asp
                405                 410                 415

Thr Leu Gly Ile Ser Leu Ser Gly Leu Leu Ala Leu Pro Leu His Asp
                420                 425                 430

Phe Leu Cys Gln Leu Ser
                435

<210> SEQ ID NO 15
<211> LENGTH: 232
<212> TYPE: PRT
<213> ORGANISM: Homo sapiens
<220> FEATURE:
<221> NAME/KEY: MISC_FEATURE
<222> LOCATION: (1)..(232)
<223> OTHER INFORMATION: CLRN1 (Clarin-1)

<400> SEQUENCE: 15

Met Pro Ser Gln Gln Lys Lys Ile Ile Phe Cys Met Ala Gly Val Phe
1               5                   10                  15

Ser Phe Ala Cys Ala Leu Gly Val Val Thr Ala Leu Gly Thr Pro Leu
                20                  25                  30

Trp Ile Lys Ala Thr Val Leu Cys Lys Thr Gly Ala Leu Leu Val Asn
                35                  40                  45

Ala Ser Gly Gln Glu Leu Asp Lys Phe Met Gly Glu Met Gln Tyr Gly
        50                  55                  60

Leu Phe His Gly Glu Gly Val Arg Gln Cys Gly Leu Gly Ala Arg Pro
65                  70                  75                  80

Phe Arg Phe Ser Phe Phe Pro Asp Leu Leu Lys Ala Ile Pro Val Ser
                85                  90                  95

Ile His Val Asn Val Ile Leu Phe Ser Ala Ile Leu Ile Val Leu Thr
                100                 105                 110

Met Val Gly Thr Ala Phe Phe Met Tyr Asn Ala Phe Gly Lys Pro Phe
                115                 120                 125

Glu Thr Leu His Gly Pro Leu Gly Leu Tyr Leu Leu Ser Phe Ile Ser
                130                 135                 140

Gly Ser Cys Gly Cys Leu Val Met Ile Leu Phe Ala Ser Glu Val Lys
145                 150                 155                 160

Ile His His Leu Ser Glu Lys Ile Ala Asn Tyr Lys Glu Gly Thr Tyr
                165                 170                 175

Val Tyr Lys Thr Gln Ser Glu Lys Tyr Thr Thr Ser Phe Trp Val Ile
                180                 185                 190
```

-continued

```
Phe Phe Cys Phe Phe Val His Phe Leu Asn Gly Leu Leu Ile Arg Leu
            195                 200                 205

Ala Gly Phe Gln Phe Pro Phe Ala Lys Ser Lys Asp Ala Glu Thr Thr
210                 215                 220

Asn Val Ala Ala Asp Leu Met Tyr
225                 230

<210> SEQ ID NO 16
<211> LENGTH: 690
<212> TYPE: PRT
<213> ORGANISM: Homo sapiens
<220> FEATURE:
<221> NAME/KEY: MISC_FEATURE
<222> LOCATION: (1)..(690)
<223> OTHER INFORMATION: CNGA1 (cGMP-gated cation channel alpha-1),
      isoform 1

<400> SEQUENCE: 16

Met Lys Leu Ser Met Lys Asn Ile Ile Asn Thr Gln Gln Ser Phe
1               5                   10                  15

Val Thr Met Pro Asn Val Ile Val Pro Asp Ile Glu Lys Glu Ile Arg
                20                  25                  30

Arg Met Glu Asn Gly Ala Cys Ser Ser Phe Ser Glu Asp Asp Asp Ser
            35                  40                  45

Ala Ser Thr Ser Glu Glu Ser Glu Asn Glu Asn Pro His Ala Arg Gly
        50                  55                  60

Ser Phe Ser Tyr Lys Ser Leu Arg Lys Gly Gly Pro Ser Gln Arg Glu
65                  70                  75                  80

Gln Tyr Leu Pro Gly Ala Ile Ala Leu Phe Asn Val Asn Asn Ser Ser
                85                  90                  95

Asn Lys Asp Gln Glu Pro Glu Glu Lys Lys Lys Lys Lys Glu Lys
            100                 105                 110

Lys Ser Lys Ser Asp Asp Lys Asn Glu Asn Lys Asn Asp Pro Glu Lys
        115                 120                 125

Lys Lys Lys Lys Lys Asp Lys Glu Lys Lys Lys Glu Glu Lys Ser
130                 135                 140

Lys Asp Lys Lys Glu Glu Glu Lys Lys Glu Val Val Ile Asp Pro
145                 150                 155                 160

Ser Gly Asn Thr Tyr Tyr Asn Trp Leu Phe Cys Ile Thr Leu Pro Val
                165                 170                 175

Met Tyr Asn Trp Thr Met Val Ile Ala Arg Ala Cys Phe Asp Glu Leu
            180                 185                 190

Gln Ser Asp Tyr Leu Glu Tyr Trp Leu Ile Leu Asp Tyr Val Ser Asp
        195                 200                 205

Ile Val Tyr Leu Ile Asp Met Phe Val Arg Thr Arg Thr Gly Tyr Leu
210                 215                 220

Glu Gln Gly Leu Leu Val Lys Glu Glu Leu Lys Leu Ile Asn Lys Tyr
225                 230                 235                 240

Lys Ser Asn Leu Gln Phe Lys Leu Asp Val Leu Ser Leu Ile Pro Thr
                245                 250                 255

Asp Leu Leu Tyr Phe Lys Leu Gly Trp Asn Tyr Pro Glu Ile Arg Leu
            260                 265                 270

Asn Arg Leu Leu Arg Phe Ser Arg Met Phe Glu Phe Phe Gln Arg Thr
        275                 280                 285

Glu Thr Arg Thr Asn Tyr Pro Asn Ile Phe Arg Ile Ser Asn Leu Val
290                 295                 300
```

```
Met Tyr Ile Val Ile Ile His Trp Asn Ala Cys Val Phe Tyr Ser
305                 310                 315                 320

Ile Ser Lys Ala Ile Gly Phe Gly Asn Asp Thr Trp Val Tyr Pro Asp
                325                 330                 335

Ile Asn Asp Pro Glu Phe Gly Arg Leu Ala Arg Lys Tyr Val Tyr Ser
            340                 345                 350

Leu Tyr Trp Ser Thr Leu Thr Leu Thr Thr Ile Gly Glu Thr Pro Pro
        355                 360                 365

Pro Val Arg Asp Ser Glu Tyr Val Phe Val Val Asp Phe Leu Ile
370                 375                 380

Gly Val Leu Ile Phe Ala Thr Ile Val Gly Asn Ile Gly Ser Met Ile
385                 390                 395                 400

Ser Asn Met Asn Ala Ala Arg Ala Glu Phe Gln Ala Arg Ile Asp Ala
                405                 410                 415

Ile Lys Gln Tyr Met His Phe Arg Asn Val Ser Lys Asp Met Glu Lys
            420                 425                 430

Arg Val Ile Lys Trp Phe Asp Tyr Leu Trp Thr Asn Lys Lys Thr Val
        435                 440                 445

Asp Glu Lys Glu Val Leu Lys Tyr Leu Pro Asp Lys Leu Arg Ala Glu
450                 455                 460

Ile Ala Ile Asn Val His Leu Asp Thr Leu Lys Lys Val Arg Ile Phe
465                 470                 475                 480

Ala Asp Cys Glu Ala Gly Leu Leu Val Glu Leu Val Leu Lys Leu Gln
                485                 490                 495

Pro Gln Val Tyr Ser Pro Gly Asp Tyr Ile Cys Lys Lys Gly Asp Ile
            500                 505                 510

Gly Arg Glu Met Tyr Ile Ile Lys Glu Gly Lys Leu Ala Val Val Ala
        515                 520                 525

Asp Asp Gly Val Thr Gln Phe Val Val Leu Ser Asp Gly Ser Tyr Phe
530                 535                 540

Gly Glu Ile Ser Ile Leu Asn Ile Lys Gly Ser Lys Ala Gly Asn Arg
545                 550                 555                 560

Arg Thr Ala Asn Ile Lys Ser Ile Gly Tyr Ser Asp Leu Phe Cys Leu
                565                 570                 575

Ser Lys Asp Asp Leu Met Glu Ala Leu Thr Glu Tyr Pro Asp Ala Lys
            580                 585                 590

Thr Met Leu Glu Glu Lys Gly Lys Gln Ile Leu Met Lys Asp Gly Leu
        595                 600                 605

Leu Asp Leu Asn Ile Ala Asn Ala Gly Ser Asp Pro Lys Asp Leu Glu
610                 615                 620

Glu Lys Val Thr Arg Met Glu Gly Ser Val Asp Leu Leu Gln Thr Arg
625                 630                 635                 640

Phe Ala Arg Ile Leu Ala Glu Tyr Glu Ser Met Gln Gln Lys Leu Lys
                645                 650                 655

Gln Arg Leu Thr Lys Val Glu Lys Phe Leu Lys Pro Leu Ile Asp Thr
            660                 665                 670

Glu Phe Ser Ser Ile Glu Gly Pro Gly Ala Glu Ser Gly Pro Ile Asp
        675                 680                 685

Ser Thr
    690

<210> SEQ ID NO 17
<211> LENGTH: 2479
<212> TYPE: PRT
```

```
<213> ORGANISM: Homo sapiens
<220> FEATURE:
<221> NAME/KEY: MISC_FEATURE
<222> LOCATION: (1)..(2479)
<223> OTHER INFORMATION: CEP290 (centrosomal protein of 290 kDa),
      isoform 1

<400> SEQUENCE: 17
```

| | | | | | | | | | | | | | | |
|---|---|---|---|---|---|---|---|---|---|---|---|---|---|---|
| Met | Pro | Pro | Asn | Ile | Asn | Trp | Lys | Glu | Ile | Met | Lys | Val | Asp | Pro | Asp |
| 1 | | | | 5 | | | | | 10 | | | | | 15 | |

| Asp | Leu | Pro | Arg | Gln | Glu | Glu | Leu | Ala | Asp | Asn | Leu | Leu | Ile | Ser | Leu |
|---|---|---|---|---|---|---|---|---|---|---|---|---|---|---|---|
| | | | 20 | | | | | 25 | | | | | 30 | | |

| Ser | Lys | Val | Glu | Val | Asn | Glu | Leu | Lys | Ser | Glu | Lys | Gln | Glu | Asn | Val |
|---|---|---|---|---|---|---|---|---|---|---|---|---|---|---|---|
| | | | 35 | | | | | 40 | | | | | 45 | | |

| Ile | His | Leu | Phe | Arg | Ile | Thr | Gln | Ser | Leu | Met | Lys | Met | Lys | Ala | Gln |
|---|---|---|---|---|---|---|---|---|---|---|---|---|---|---|---|
| | 50 | | | | | 55 | | | | | 60 | | | | |

| Glu | Val | Glu | Leu | Ala | Leu | Glu | Val | Glu | Lys | Ala | Gly | Glu | Glu | Gln |
|---|---|---|---|---|---|---|---|---|---|---|---|---|---|---|
| 65 | | | | | 70 | | | | | 75 | | | | 80 |

| Ala | Lys | Phe | Glu | Asn | Gln | Leu | Lys | Thr | Lys | Val | Met | Lys | Leu | Glu | Asn |
|---|---|---|---|---|---|---|---|---|---|---|---|---|---|---|---|
| | | | | 85 | | | | | 90 | | | | | 95 | |

| Glu | Leu | Glu | Met | Ala | Gln | Gln | Ser | Ala | Gly | Gly | Arg | Asp | Thr | Arg | Phe |
|---|---|---|---|---|---|---|---|---|---|---|---|---|---|---|---|
| | | | 100 | | | | | 105 | | | | | 110 | | |

| Leu | Arg | Asn | Glu | Ile | Cys | Gln | Leu | Glu | Lys | Gln | Leu | Glu | Gln | Lys | Asp |
|---|---|---|---|---|---|---|---|---|---|---|---|---|---|---|---|
| | | | 115 | | | | | 120 | | | | | 125 | | |

| Arg | Glu | Leu | Glu | Asp | Met | Glu | Lys | Glu | Leu | Glu | Lys | Glu | Lys | Lys | Val |
|---|---|---|---|---|---|---|---|---|---|---|---|---|---|---|---|
| | 130 | | | | | 135 | | | | | 140 | | | | |

| Asn | Glu | Gln | Leu | Ala | Leu | Arg | Asn | Glu | Glu | Ala | Glu | Asn | Glu | Asn | Ser |
|---|---|---|---|---|---|---|---|---|---|---|---|---|---|---|---|
| 145 | | | | | 150 | | | | | 155 | | | | | 160 |

| Lys | Leu | Arg | Arg | Glu | Asn | Lys | Arg | Leu | Lys | Lys | Asn | Glu | Gln | Leu |
|---|---|---|---|---|---|---|---|---|---|---|---|---|---|---|
| | | | | 165 | | | | | 170 | | | | | 175 |

| Cys | Gln | Asp | Ile | Ile | Asp | Tyr | Gln | Lys | Gln | Ile | Asp | Ser | Gln | Lys | Glu |
|---|---|---|---|---|---|---|---|---|---|---|---|---|---|---|---|
| | | | 180 | | | | | 185 | | | | | 190 | | |

| Thr | Leu | Leu | Ser | Arg | Arg | Gly | Glu | Asp | Ser | Asp | Tyr | Arg | Ser | Gln | Leu |
|---|---|---|---|---|---|---|---|---|---|---|---|---|---|---|---|
| | | | 195 | | | | | 200 | | | | | 205 | | |

| Ser | Lys | Lys | Asn | Tyr | Glu | Leu | Ile | Gln | Tyr | Leu | Asp | Glu | Ile | Gln | Thr |
|---|---|---|---|---|---|---|---|---|---|---|---|---|---|---|---|
| | 210 | | | | | 215 | | | | | 220 | | | | |

| Leu | Thr | Glu | Ala | Asn | Glu | Lys | Ile | Glu | Val | Gln | Asn | Gln | Glu | Met | Arg |
|---|---|---|---|---|---|---|---|---|---|---|---|---|---|---|---|
| 225 | | | | | 230 | | | | | 235 | | | | | 240 |

| Lys | Asn | Leu | Glu | Glu | Ser | Val | Gln | Glu | Met | Glu | Lys | Met | Thr | Asp | Glu |
|---|---|---|---|---|---|---|---|---|---|---|---|---|---|---|---|
| | | | | 245 | | | | | 250 | | | | | 255 | |

| Tyr | Asn | Arg | Met | Lys | Ala | Ile | Val | His | Gln | Thr | Asp | Asn | Val | Ile | Asp |
|---|---|---|---|---|---|---|---|---|---|---|---|---|---|---|---|
| | | | 260 | | | | | 265 | | | | | 270 | | |

| Gln | Leu | Lys | Lys | Glu | Asn | Asp | His | Tyr | Gln | Leu | Gln | Val | Gln | Glu | Leu |
|---|---|---|---|---|---|---|---|---|---|---|---|---|---|---|---|
| | | | 275 | | | | | 280 | | | | | 285 | | |

| Thr | Asp | Leu | Leu | Lys | Ser | Lys | Asn | Glu | Glu | Asp | Asp | Pro | Ile | Met | Val |
|---|---|---|---|---|---|---|---|---|---|---|---|---|---|---|---|
| | 290 | | | | | 295 | | | | | 300 | | | | |

| Ala | Val | Asn | Ala | Lys | Val | Glu | Glu | Trp | Lys | Leu | Ile | Leu | Ser | Ser | Lys |
|---|---|---|---|---|---|---|---|---|---|---|---|---|---|---|---|
| 305 | | | | | 310 | | | | | 315 | | | | | 320 |

| Asp | Asp | Glu | Ile | Ile | Glu | Tyr | Gln | Gln | Met | Leu | His | Asn | Leu | Arg | Glu |
|---|---|---|---|---|---|---|---|---|---|---|---|---|---|---|---|
| | | | | 325 | | | | | 330 | | | | | 335 | |

| Lys | Leu | Lys | Asn | Ala | Gln | Leu | Asp | Ala | Asp | Lys | Ser | Asn | Val | Met | Ala |
|---|---|---|---|---|---|---|---|---|---|---|---|---|---|---|---|
| | | | 340 | | | | | 345 | | | | | 350 | | |

| Leu | Gln | Gln | Gly | Ile | Gln | Glu | Arg | Asp | Ser | Gln | Ile | Lys | Met | Leu | Thr |
|---|---|---|---|---|---|---|---|---|---|---|---|---|---|---|---|
| | | | 355 | | | | | 360 | | | | | 365 | | |

| Glu | Gln | Val | Glu | Gln | Tyr | Thr | Lys | Glu | Met | Glu | Lys | Asn | Thr | Cys | Ile |

```
                370                 375                 380
Ile Glu Asp Leu Lys Asn Glu Leu Gln Arg Asn Lys Gly Ala Ser Thr
385                 390                 395                 400

Leu Ser Gln Gln Thr His Met Lys Ile Gln Ser Thr Leu Asp Ile Leu
            405                 410                 415

Lys Glu Lys Thr Lys Glu Ala Glu Arg Thr Ala Glu Leu Ala Glu Ala
                420                 425                 430

Asp Ala Arg Glu Lys Asp Lys Glu Leu Val Glu Ala Leu Lys Arg Leu
            435                 440                 445

Lys Asp Tyr Glu Ser Gly Val Tyr Gly Leu Glu Asp Ala Val Val Glu
        450                 455                 460

Ile Lys Asn Cys Lys Asn Gln Ile Lys Ile Arg Asp Arg Glu Ile Glu
465                 470                 475                 480

Ile Leu Thr Lys Glu Ile Asn Lys Leu Glu Leu Lys Ile Ser Asp Phe
                485                 490                 495

Leu Asp Glu Asn Glu Ala Leu Arg Glu Arg Val Gly Leu Glu Pro Lys
            500                 505                 510

Thr Met Ile Asp Leu Thr Glu Phe Arg Asn Ser Lys His Leu Lys Gln
        515                 520                 525

Gln Gln Tyr Arg Ala Glu Asn Gln Ile Leu Leu Lys Glu Ile Glu Ser
        530                 535                 540

Leu Glu Glu Glu Arg Leu Asp Leu Lys Lys Lys Ile Arg Gln Met Ala
545                 550                 555                 560

Gln Glu Arg Gly Lys Arg Ser Ala Thr Ser Gly Leu Thr Thr Glu Asp
                565                 570                 575

Leu Asn Leu Thr Glu Asn Ile Ser Gln Gly Asp Arg Ile Ser Glu Arg
            580                 585                 590

Lys Leu Asp Leu Leu Ser Leu Lys Asn Met Ser Glu Ala Gln Ser Lys
        595                 600                 605

Asn Glu Phe Leu Ser Arg Glu Leu Ile Glu Lys Glu Arg Asp Leu Glu
        610                 615                 620

Arg Ser Arg Thr Val Ile Ala Lys Phe Gln Asn Lys Leu Lys Glu Leu
625                 630                 635                 640

Val Glu Glu Asn Lys Gln Leu Glu Glu Gly Met Lys Glu Ile Leu Gln
                645                 650                 655

Ala Ile Lys Glu Met Gln Lys Asp Pro Asp Val Lys Gly Gly Glu Thr
            660                 665                 670

Ser Leu Ile Ile Pro Ser Leu Glu Arg Leu Val Asn Ala Ile Glu Ser
        675                 680                 685

Lys Asn Ala Glu Gly Ile Phe Asp Ala Ser Leu His Leu Lys Ala Gln
        690                 695                 700

Val Asp Gln Leu Thr Gly Arg Asn Glu Glu Leu Arg Gln Glu Leu Arg
705                 710                 715                 720

Glu Ser Arg Lys Glu Ala Ile Asn Tyr Ser Gln Gln Leu Ala Lys Ala
                725                 730                 735

Asn Leu Lys Ile Asp His Leu Glu Lys Glu Thr Ser Leu Leu Arg Gln
            740                 745                 750

Ser Glu Gly Ser Asn Val Val Phe Lys Gly Ile Asp Leu Pro Asp Gly
        755                 760                 765

Ile Ala Pro Ser Ser Ala Ser Ile Ile Asn Ser Gln Asn Glu Tyr Leu
        770                 775                 780

Ile His Leu Leu Gln Glu Leu Glu Asn Lys Glu Lys Lys Leu Lys Asn
785                 790                 795                 800
```

-continued

```
Leu Glu Asp Ser Leu Glu Asp Tyr Asn Arg Lys Phe Ala Val Ile Arg
                805                 810                 815

His Gln Gln Ser Leu Leu Tyr Lys Glu Tyr Leu Ser Glu Lys Glu Thr
            820                 825                 830

Trp Lys Thr Glu Ser Lys Thr Ile Lys Glu Glu Lys Arg Lys Leu Glu
        835                 840                 845

Asp Gln Val Gln Gln Asp Ala Ile Lys Val Lys Glu Tyr Asn Asn Leu
    850                 855                 860

Leu Asn Ala Leu Gln Met Asp Ser Asp Glu Met Lys Lys Ile Leu Ala
865                 870                 875                 880

Glu Asn Ser Arg Lys Ile Thr Val Leu Gln Val Asn Glu Lys Ser Leu
                885                 890                 895

Ile Arg Gln Tyr Thr Thr Leu Val Glu Leu Glu Arg Gln Leu Arg Lys
            900                 905                 910

Glu Asn Glu Lys Gln Lys Asn Glu Leu Leu Ser Met Glu Ala Glu Val
        915                 920                 925

Cys Glu Lys Ile Gly Cys Leu Gln Arg Phe Lys Glu Met Ala Ile Phe
    930                 935                 940

Lys Ile Ala Ala Leu Gln Lys Val Val Asp Asn Ser Val Ser Leu Ser
945                 950                 955                 960

Glu Leu Glu Leu Ala Asn Lys Gln Tyr Asn Glu Leu Thr Ala Lys Tyr
                965                 970                 975

Arg Asp Ile Leu Gln Lys Asp Asn Met Leu Val Gln Arg Thr Ser Asn
            980                 985                 990

Leu Glu His Leu Glu Cys Glu Asn Ile Ser Leu Lys Glu Gln Val Glu
        995                 1000                1005

Ser Ile Asn Lys Glu Leu Glu Ile Thr Lys Glu Lys Leu His Thr
    1010                1015                1020

Ile Glu Gln Ala Trp Glu Gln Glu Thr Lys Leu Gly Asn Glu Ser
    1025                1030                1035

Ser Met Asp Lys Ala Lys Lys Ser Ile Thr Asn Ser Asp Ile Val
    1040                1045                1050

Ser Ile Ser Lys Lys Ile Thr Met Leu Glu Met Lys Glu Leu Asn
    1055                1060                1065

Glu Arg Gln Arg Ala Glu His Cys Gln Lys Met Tyr Glu His Leu
    1070                1075                1080

Arg Thr Ser Leu Lys Gln Met Glu Glu Arg Asn Phe Glu Leu Glu
    1085                1090                1095

Thr Lys Phe Ala Glu Leu Thr Lys Ile Asn Leu Asp Ala Gln Lys
    1100                1105                1110

Val Glu Gln Met Leu Arg Asp Glu Leu Ala Asp Ser Val Ser Lys
    1115                1120                1125

Ala Val Ser Asp Ala Asp Arg Gln Arg Ile Leu Glu Leu Glu Lys
    1130                1135                1140

Asn Glu Met Glu Leu Lys Val Glu Val Ser Lys Leu Arg Glu Ile
    1145                1150                1155

Ser Asp Ile Ala Arg Arg Gln Val Glu Ile Leu Asn Ala Gln Gln
    1160                1165                1170

Gln Ser Arg Asp Lys Glu Val Glu Ser Leu Arg Met Gln Leu Leu
    1175                1180                1185

Asp Tyr Gln Ala Gln Ser Asp Glu Lys Ser Leu Ile Ala Lys Leu
    1190                1195                1200
```

-continued

```
His Gln His Asn Val Ser Leu Gln Leu Ser Glu Ala Thr Ala Leu
    1205                1210                1215
Gly Lys Leu Glu Ser Ile Thr Ser Lys Leu Gln Lys Met Glu Ala
    1220                1225                1230
Tyr Asn Leu Arg Leu Glu Gln Lys Leu Asp Glu Lys Glu Gln Ala
    1235                1240                1245
Leu Tyr Tyr Ala Arg Leu Glu Gly Arg Asn Arg Ala Lys His Leu
    1250                1255                1260
Arg Gln Thr Ile Gln Ser Leu Arg Arg Gln Phe Ser Gly Ala Leu
    1265                1270                1275
Pro Leu Ala Gln Gln Glu Lys Phe Ser Lys Thr Met Ile Gln Leu
    1280                1285                1290
Gln Asn Asp Lys Leu Lys Ile Met Gln Glu Met Lys Asn Ser Gln
    1295                1300                1305
Gln Glu His Arg Asn Met Glu Asn Lys Thr Leu Glu Met Glu Leu
    1310                1315                1320
Lys Leu Lys Gly Leu Glu Glu Leu Ile Ser Thr Leu Lys Asp Thr
    1325                1330                1335
Lys Gly Ala Gln Lys Val Ile Asn Trp His Met Lys Ile Glu Glu
    1340                1345                1350
Leu Arg Leu Gln Glu Leu Lys Leu Asn Arg Glu Leu Val Lys Asp
    1355                1360                1365
Lys Glu Glu Ile Lys Tyr Leu Asn Asn Ile Ile Ser Glu Tyr Glu
    1370                1375                1380
Arg Thr Ile Ser Ser Leu Glu Glu Glu Ile Val Gln Gln Asn Lys
    1385                1390                1395
Phe His Glu Glu Arg Gln Met Ala Trp Asp Gln Arg Glu Val Asp
    1400                1405                1410
Leu Glu Arg Gln Leu Asp Ile Phe Asp Arg Gln Gln Asn Glu Ile
    1415                1420                1425
Leu Asn Ala Ala Gln Lys Phe Glu Glu Ala Thr Gly Ser Ile Pro
    1430                1435                1440
Asp Pro Ser Leu Pro Leu Pro Asn Gln Leu Glu Ile Ala Leu Arg
    1445                1450                1455
Lys Ile Lys Glu Asn Ile Arg Ile Ile Leu Glu Thr Arg Ala Thr
    1460                1465                1470
Cys Lys Ser Leu Glu Glu Lys Leu Lys Glu Lys Glu Ser Ala Leu
    1475                1480                1485
Arg Leu Ala Glu Gln Asn Ile Leu Ser Arg Asp Lys Val Ile Asn
    1490                1495                1500
Glu Leu Arg Leu Arg Leu Pro Ala Thr Ala Glu Arg Glu Lys Leu
    1505                1510                1515
Ile Ala Glu Leu Gly Arg Lys Glu Met Glu Pro Lys Ser His His
    1520                1525                1530
Thr Leu Lys Ile Ala His Gln Thr Ile Ala Asn Met Gln Ala Arg
    1535                1540                1545
Leu Asn Gln Lys Glu Glu Val Leu Lys Lys Tyr Gln Arg Leu Leu
    1550                1555                1560
Glu Lys Ala Arg Glu Glu Gln Arg Glu Ile Val Lys Lys His Glu
    1565                1570                1575
Glu Asp Leu His Ile Leu His His Arg Leu Glu Leu Gln Ala Asp
    1580                1585                1590
Ser Ser Leu Asn Lys Phe Lys Gln Thr Ala Trp Asp Leu Met Lys
```

-continued

```
            1595                1600                1605

Gln Ser Pro Thr Pro Val Pro Thr Asn Lys His Phe Ile Arg Leu
    1610                1615                1620

Ala Glu Met Glu Gln Thr Val Ala Glu Gln Asp Asp Ser Leu Ser
    1625                1630                1635

Ser Leu Leu Val Lys Leu Lys Lys Val Ser Gln Asp Leu Glu Arg
    1640                1645                1650

Gln Arg Glu Ile Thr Glu Leu Lys Val Lys Glu Phe Glu Asn Ile
    1655                1660                1665

Lys Leu Gln Leu Gln Glu Asn His Glu Asp Glu Val Lys Lys Val
    1670                1675                1680

Lys Ala Glu Val Glu Asp Leu Lys Tyr Leu Leu Asp Gln Ser Gln
    1685                1690                1695

Lys Glu Ser Gln Cys Leu Lys Ser Glu Leu Gln Ala Gln Lys Glu
    1700                1705                1710

Ala Asn Ser Arg Ala Pro Thr Thr Thr Met Arg Asn Leu Val Glu
    1715                1720                1725

Arg Leu Lys Ser Gln Leu Ala Leu Lys Glu Lys Gln Gln Lys Ala
    1730                1735                1740

Leu Ser Arg Ala Leu Leu Glu Leu Arg Ala Glu Met Thr Ala Ala
    1745                1750                1755

Ala Glu Glu Arg Ile Ile Ser Ala Thr Ser Gln Lys Glu Ala His
    1760                1765                1770

Leu Asn Val Gln Gln Ile Val Asp Arg His Thr Arg Glu Leu Lys
    1775                1780                1785

Thr Gln Val Glu Asp Leu Asn Glu Asn Leu Leu Lys Leu Lys Glu
    1790                1795                1800

Ala Leu Lys Thr Ser Lys Asn Arg Glu Asn Ser Leu Thr Asp Asn
    1805                1810                1815

Leu Asn Asp Leu Asn Asn Glu Leu Gln Lys Lys Gln Lys Ala Tyr
    1820                1825                1830

Asn Lys Ile Leu Arg Glu Lys Glu Glu Ile Asp Gln Glu Asn Asp
    1835                1840                1845

Glu Leu Lys Arg Gln Ile Lys Arg Leu Thr Ser Gly Leu Gln Gly
    1850                1855                1860

Lys Pro Leu Thr Asp Asn Lys Gln Ser Leu Ile Glu Glu Leu Gln
    1865                1870                1875

Arg Lys Val Lys Lys Leu Glu Asn Gln Leu Glu Gly Lys Val Glu
    1880                1885                1890

Glu Val Asp Leu Lys Pro Met Lys Glu Lys Asn Ala Lys Glu Glu
    1895                1900                1905

Leu Ile Arg Trp Glu Glu Gly Lys Lys Trp Gln Ala Lys Ile Glu
    1910                1915                1920

Gly Ile Arg Asn Lys Leu Lys Glu Lys Glu Gly Glu Val Phe Thr
    1925                1930                1935

Leu Thr Lys Gln Leu Asn Thr Leu Lys Asp Leu Phe Ala Lys Ala
    1940                1945                1950

Asp Lys Glu Lys Leu Thr Leu Gln Arg Lys Leu Lys Thr Thr Gly
    1955                1960                1965

Met Thr Val Asp Gln Val Leu Gly Ile Arg Ala Leu Glu Ser Glu
    1970                1975                1980

Lys Glu Leu Glu Glu Leu Lys Lys Arg Asn Leu Asp Leu Glu Asn
    1985                1990                1995
```

```
Asp Ile Leu Tyr Met Arg Ala His Gln Ala Leu Pro Arg Asp Ser
    2000            2005            2010

Val Val Glu Asp Leu His Leu Gln Asn Arg Tyr Leu Gln Glu Lys
    2015            2020            2025

Leu His Ala Leu Glu Lys Gln Phe Ser Lys Asp Thr Tyr Ser Lys
    2030            2035            2040

Pro Ser Ile Ser Gly Ile Glu Ser Asp Asp His Cys Gln Arg Glu
    2045            2050            2055

Gln Glu Leu Gln Lys Glu Asn Leu Lys Leu Ser Ser Glu Asn Ile
    2060            2065            2070

Glu Leu Lys Phe Gln Leu Glu Gln Ala Asn Lys Asp Leu Pro Arg
    2075            2080            2085

Leu Lys Asn Gln Val Arg Asp Leu Lys Glu Met Cys Glu Phe Leu
    2090            2095            2100

Lys Lys Glu Lys Ala Glu Val Gln Arg Lys Leu Gly His Val Arg
    2105            2110            2115

Gly Ser Gly Arg Ser Gly Lys Thr Ile Pro Glu Leu Glu Lys Thr
    2120            2125            2130

Ile Gly Leu Met Lys Lys Val Val Glu Lys Val Gln Arg Glu Asn
    2135            2140            2145

Glu Gln Leu Lys Lys Ala Ser Gly Ile Leu Thr Ser Glu Lys Met
    2150            2155            2160

Ala Asn Ile Glu Gln Glu Asn Glu Lys Leu Lys Ala Glu Leu Glu
    2165            2170            2175

Lys Leu Lys Ala His Leu Gly His Gln Leu Ser Met His Tyr Glu
    2180            2185            2190

Ser Lys Thr Lys Gly Thr Glu Lys Ile Ile Ala Glu Asn Glu Arg
    2195            2200            2205

Leu Arg Lys Glu Leu Lys Lys Glu Thr Asp Ala Ala Glu Lys Leu
    2210            2215            2220

Arg Ile Ala Lys Asn Asn Leu Glu Ile Leu Asn Glu Lys Met Thr
    2225            2230            2235

Val Gln Leu Glu Glu Thr Gly Lys Arg Leu Gln Phe Ala Glu Ser
    2240            2245            2250

Arg Gly Pro Gln Leu Glu Gly Ala Asp Ser Lys Ser Trp Lys Ser
    2255            2260            2265

Ile Val Val Thr Arg Met Tyr Glu Thr Lys Leu Lys Glu Leu Glu
    2270            2275            2280

Thr Asp Ile Ala Lys Lys Asn Gln Ser Ile Thr Asp Leu Lys Gln
    2285            2290            2295

Leu Val Lys Glu Ala Thr Glu Arg Glu Gln Lys Val Asn Lys Tyr
    2300            2305            2310

Asn Glu Asp Leu Glu Gln Gln Ile Lys Ile Leu Lys His Val Pro
    2315            2320            2325

Glu Gly Ala Glu Thr Glu Gln Gly Leu Lys Arg Glu Leu Gln Val
    2330            2335            2340

Leu Arg Leu Ala Asn His Gln Leu Asp Lys Glu Lys Ala Glu Leu
    2345            2350            2355

Ile His Gln Ile Glu Ala Asn Lys Asp Gln Ser Gly Ala Glu Ser
    2360            2365            2370

Thr Ile Pro Asp Ala Asp Gln Leu Lys Glu Lys Ile Lys Asp Leu
    2375            2380            2385
```

```
Glu Thr Gln Leu Lys Met Ser Asp Leu Glu Lys Gln His Leu Lys
    2390                2395                2400

Glu Glu Ile Lys Lys Leu Lys Glu Leu Glu Asn Phe Asp Pro
2405                2410                2415

Ser Phe Phe Glu Glu Ile Glu Asp Leu Lys Tyr Asn Tyr Lys Glu
    2420                2425                2430

Glu Val Lys Lys Asn Ile Leu Leu Glu Glu Lys Val Lys Lys Leu
2435                2440                2445

Ser Glu Gln Leu Gly Val Glu Leu Thr Ser Pro Val Ala Ala Ser
    2450                2455                2460

Glu Glu Phe Glu Asp Glu Glu Ser Pro Val Asn Phe Pro Ile
2465                2470                2475

Tyr

<210> SEQ ID NO 18
<211> LENGTH: 1406
<212> TYPE: PRT
<213> ORGANISM: Homo sapiens
<220> FEATURE:
<221> NAME/KEY: MISC_FEATURE
<222> LOCATION: (1)..(1406)
<223> OTHER INFORMATION: CRB1 (protein crumbs homolog 1), isoform 1

<400> SEQUENCE: 18

Met Ala Leu Lys Asn Ile Asn Tyr Leu Leu Ile Phe Tyr Leu Ser Phe
1               5                   10                  15

Ser Leu Leu Ile Tyr Ile Lys Asn Ser Phe Cys Asn Lys Asn Asn Thr
            20                  25                  30

Arg Cys Leu Ser Asn Ser Cys Gln Asn Asn Ser Thr Cys Lys Asp Phe
        35                  40                  45

Ser Lys Asp Asn Asp Cys Ser Cys Ser Asp Thr Ala Asn Asn Leu Asp
50                  55                  60

Lys Asp Cys Asp Asn Met Lys Asp Pro Cys Phe Ser Asn Pro Cys Gln
65                  70                  75                  80

Gly Ser Ala Thr Cys Val Asn Thr Pro Gly Glu Arg Ser Phe Leu Cys
            85                  90                  95

Lys Cys Pro Pro Gly Tyr Ser Gly Thr Ile Cys Glu Thr Thr Ile Gly
        100                 105                 110

Ser Cys Gly Lys Asn Ser Cys Gln His Gly Gly Ile Cys His Gln Asp
        115                 120                 125

Pro Ile Tyr Pro Val Cys Ile Cys Pro Ala Gly Tyr Ala Gly Arg Phe
    130                 135                 140

Cys Glu Ile Asp His Asp Glu Cys Ala Ser Ser Pro Cys Gln Asn Gly
145                 150                 155                 160

Ala Val Cys Gln Asp Gly Ile Asp Gly Tyr Ser Cys Phe Cys Val Pro
            165                 170                 175

Gly Tyr Gln Gly Arg His Cys Asp Leu Glu Val Asp Glu Cys Ala Ser
        180                 185                 190

Asp Pro Cys Lys Asn Glu Ala Thr Cys Leu Asn Glu Ile Gly Arg Tyr
    195                 200                 205

Thr Cys Ile Cys Pro His Asn Tyr Ser Gly Val Asn Cys Glu Leu Glu
    210                 215                 220

Ile Asp Glu Cys Trp Ser Gln Pro Cys Leu Asn Gly Ala Thr Cys Gln
225                 230                 235                 240

Asp Ala Leu Gly Ala Tyr Phe Cys Asp Cys Ala Pro Gly Phe Leu Gly
            245                 250                 255
```

-continued

```
Asp His Cys Glu Leu Asn Thr Asp Glu Cys Ala Ser Gln Pro Cys Leu
            260                 265                 270

His Gly Gly Leu Cys Val Asp Gly Glu Asn Arg Tyr Ser Cys Asn Cys
            275                 280                 285

Thr Gly Ser Gly Phe Thr Gly Thr His Cys Glu Thr Leu Met Pro Leu
290                 295                 300

Cys Trp Ser Lys Pro Cys His Asn Asn Ala Thr Cys Glu Asp Ser Val
305                 310                 315                 320

Asp Asn Tyr Thr Cys His Cys Trp Pro Gly Tyr Thr Gly Ala Gln Cys
                325                 330                 335

Glu Ile Asp Leu Asn Glu Cys Asn Ser Asn Pro Cys Gln Ser Asn Gly
            340                 345                 350

Glu Cys Val Glu Leu Ser Ser Glu Lys Gln Tyr Gly Arg Ile Thr Gly
            355                 360                 365

Leu Pro Ser Ser Phe Ser Tyr His Glu Ala Ser Gly Tyr Val Cys Ile
370                 375                 380

Cys Gln Pro Gly Phe Thr Gly Ile His Cys Glu Glu Asp Val Asn Glu
385                 390                 395                 400

Cys Ser Ser Asn Pro Cys Gln Asn Gly Gly Thr Cys Glu Asn Leu Pro
                405                 410                 415

Gly Asn Tyr Thr Cys His Cys Pro Phe Asp Asn Leu Ser Arg Thr Phe
            420                 425                 430

Tyr Gly Gly Arg Asp Cys Ser Asp Ile Leu Leu Gly Cys Thr His Gln
            435                 440                 445

Gln Cys Leu Asn Asn Gly Thr Cys Ile Pro His Phe Gln Asp Gly Gln
450                 455                 460

His Gly Phe Ser Cys Leu Cys Pro Ser Gly Tyr Thr Gly Ser Leu Cys
465                 470                 475                 480

Glu Ile Ala Thr Thr Leu Ser Phe Glu Gly Asp Gly Phe Leu Trp Val
                485                 490                 495

Lys Ser Gly Ser Val Thr Thr Lys Gly Ser Val Cys Asn Ile Ala Leu
            500                 505                 510

Arg Phe Gln Thr Val Gln Pro Met Ala Leu Leu Leu Phe Arg Ser Asn
            515                 520                 525

Arg Asp Val Phe Val Lys Leu Glu Leu Leu Ser Gly Tyr Ile His Leu
530                 535                 540

Ser Ile Gln Val Asn Asn Gln Ser Lys Val Leu Leu Phe Ile Ser His
545                 550                 555                 560

Asn Thr Ser Asp Gly Glu Trp His Phe Val Glu Val Ile Phe Ala Glu
                565                 570                 575

Ala Val Thr Leu Thr Leu Ile Asp Asp Ser Cys Lys Glu Lys Cys Ile
            580                 585                 590

Ala Lys Ala Pro Thr Pro Leu Glu Ser Asp Gln Ser Ile Cys Ala Phe
            595                 600                 605

Gln Asn Ser Phe Leu Gly Gly Leu Pro Val Gly Met Thr Ser Asn Gly
            610                 615                 620

Val Ala Leu Leu Asn Phe Tyr Asn Met Pro Ser Thr Pro Ser Phe Val
625                 630                 635                 640

Gly Cys Leu Gln Asp Ile Lys Ile Asp Trp Asn His Ile Thr Leu Glu
                645                 650                 655

Asn Ile Ser Ser Gly Ser Ser Leu Asn Val Lys Ala Gly Cys Val Arg
            660                 665                 670
```

-continued

```
Lys Asp Trp Cys Glu Ser Gln Pro Cys Gln Ser Arg Gly Arg Cys Ile
            675                 680                 685
Asn Leu Trp Leu Ser Tyr Gln Cys Asp Cys His Arg Pro Tyr Glu Gly
            690                 695                 700
Pro Asn Cys Leu Arg Glu Tyr Val Ala Gly Arg Phe Gly Gln Asp Asp
705                 710                 715                 720
Ser Thr Gly Tyr Val Ile Phe Thr Leu Asp Glu Ser Tyr Gly Asp Thr
                725                 730                 735
Ile Ser Leu Ser Met Phe Val Arg Thr Leu Gln Pro Ser Gly Leu Leu
            740                 745                 750
Leu Ala Leu Glu Asn Ser Thr Tyr Gln Tyr Ile Arg Val Trp Leu Glu
            755                 760                 765
Arg Gly Arg Leu Ala Met Leu Thr Pro Asn Ser Pro Lys Leu Val Val
770                 775                 780
Lys Phe Val Leu Asn Asp Gly Asn Val His Leu Ile Ser Leu Lys Ile
785                 790                 795                 800
Lys Pro Tyr Lys Ile Glu Leu Tyr Gln Ser Ser Gln Asn Leu Gly Phe
                805                 810                 815
Ile Ser Ala Ser Thr Trp Lys Ile Glu Lys Gly Asp Val Ile Tyr Ile
            820                 825                 830
Gly Gly Leu Pro Asp Lys Gln Glu Thr Glu Leu Asn Gly Gly Phe Phe
            835                 840                 845
Lys Gly Cys Ile Gln Asp Val Arg Leu Asn Asn Gln Asn Leu Glu Phe
850                 855                 860
Phe Pro Asn Pro Thr Asn Asn Ala Ser Leu Asn Pro Val Leu Val Asn
865                 870                 875                 880
Val Thr Gln Gly Cys Ala Gly Asp Asn Ser Cys Lys Ser Asn Pro Cys
                885                 890                 895
His Asn Gly Gly Val Cys His Ser Arg Trp Asp Asp Phe Ser Cys Ser
            900                 905                 910
Cys Pro Ala Leu Thr Ser Gly Lys Ala Cys Glu Glu Val Gln Trp Cys
            915                 920                 925
Gly Phe Ser Pro Cys Pro His Gly Ala Gln Cys Gln Pro Val Leu Gln
930                 935                 940
Gly Phe Glu Cys Ile Ala Asn Ala Val Phe Asn Gly Gln Ser Gly Gln
945                 950                 955                 960
Ile Leu Phe Arg Ser Asn Gly Asn Ile Thr Arg Glu Leu Thr Asn Ile
                965                 970                 975
Thr Phe Gly Phe Arg Thr Arg Asp Ala Asn Val Ile Ile Leu His Ala
            980                 985                 990
Glu Lys Glu Pro Glu Phe Leu Asn Ile Ser Ile Gln Asp Ser Arg Leu
            995                 1000                1005
Phe Phe Gln Leu Gln Ser Gly Asn Ser Phe Tyr Met Leu Ser Leu
    1010                1015                1020
Thr Ser Leu Gln Ser Val Asn Asp Gly Thr Trp His Glu Val Thr
    1025                1030                1035
Leu Ser Met Thr Asp Pro Leu Ser Gln Thr Ser Arg Trp Gln Met
    1040                1045                1050
Glu Val Asp Asn Glu Thr Pro Phe Val Thr Ser Thr Ile Ala Thr
    1055                1060                1065
Gly Ser Leu Asn Phe Leu Lys Asp Asn Thr Asp Ile Tyr Val Gly
    1070                1075                1080
Asp Arg Ala Ile Asp Asn Ile Lys Gly Leu Gln Gly Cys Leu Ser
```

```
Thr Ile Glu Ile Gly Gly Ile Tyr Leu Ser Tyr Phe Glu Asn Val
    1100                1105                1110

His Gly Phe Ile Asn Lys Pro Gln Glu Gln Phe Leu Lys Ile
    1115                1120                1125

Ser Thr Asn Ser Val Val Thr Gly Cys Leu Gln Leu Asn Val Cys
1130                1135                1140

Asn Ser Asn Pro Cys Leu His Gly Gly Asn Cys Glu Asp Ile Tyr
    1145                1150                1155

Ser Ser Tyr His Cys Ser Cys Pro Leu Gly Trp Ser Gly Lys His
    1160                1165                1170

Cys Glu Leu Asn Ile Asp Glu Cys Phe Ser Asn Pro Cys Ile His
    1175                1180                1185

Gly Asn Cys Ser Asp Arg Val Ala Ala Tyr His Cys Thr Cys Glu
    1190                1195                1200

Pro Gly Tyr Thr Gly Val Asn Cys Glu Val Asp Ile Asp Asn Cys
    1205                1210                1215

Gln Ser His Gln Cys Ala Asn Gly Ala Thr Cys Ile Ser His Thr
    1220                1225                1230

Asn Gly Tyr Ser Cys Leu Cys Phe Gly Asn Phe Thr Gly Lys Phe
    1235                1240                1245

Cys Arg Gln Ser Arg Leu Pro Ser Thr Val Cys Gly Asn Glu Lys
    1250                1255                1260

Thr Asn Leu Thr Cys Tyr Asn Gly Gly Asn Cys Thr Glu Phe Gln
    1265                1270                1275

Thr Glu Leu Lys Cys Met Cys Arg Pro Gly Phe Thr Gly Glu Trp
    1280                1285                1290

Cys Glu Lys Asp Ile Asp Glu Cys Ala Ser Asp Pro Cys Val Asn
    1295                1300                1305

Gly Gly Leu Cys Gln Asp Leu Leu Asn Lys Phe Gln Cys Leu Cys
    1310                1315                1320

Asp Val Ala Phe Ala Gly Glu Arg Cys Glu Val Asp Leu Ala Asp
    1325                1330                1335

Asp Leu Ile Ser Asp Ile Phe Thr Thr Ile Gly Ser Val Thr Val
    1340                1345                1350

Ala Leu Leu Leu Ile Leu Leu Leu Ala Ile Val Ala Ser Val Val
    1355                1360                1365

Thr Ser Asn Lys Arg Ala Thr Gln Gly Thr Tyr Ser Pro Ser Arg
    1370                1375                1380

Gln Glu Lys Glu Gly Ser Arg Val Glu Met Trp Asn Leu Met Pro
    1385                1390                1395

Pro Pro Ala Met Glu Arg Leu Ile
    1400                1405

<210> SEQ ID NO 19
<211> LENGTH: 1285
<212> TYPE: PRT
<213> ORGANISM: Homo sapiens
<220> FEATURE:
<221> NAME/KEY: MISC_FEATURE
<222> LOCATION: (1)..(1285)
<223> OTHER INFORMATION: CRB2 (protein crumbs homolog 2)

<400> SEQUENCE: 19

Met Ala Leu Ala Arg Pro Gly Thr Pro Asp Pro Gln Ala Leu Ala Ser
1               5                   10                  15
```

```
Val Leu Leu Leu Leu Leu Trp Ala Pro Ala Leu Ser Leu Leu Ala Gly
             20                  25                  30

Thr Val Pro Ser Glu Pro Pro Ser Ala Cys Ala Ser Asp Pro Cys Ala
         35                  40                  45

Pro Gly Thr Glu Cys Gln Ala Thr Glu Ser Gly Gly Tyr Thr Cys Gly
     50                  55                  60

Pro Met Glu Pro Arg Gly Cys Ala Thr Gln Pro Cys His His Gly Ala
 65              70                  75                      80

Leu Cys Val Pro Gln Gly Pro Asp Pro Thr Gly Phe Arg Cys Tyr Cys
                 85                  90                  95

Val Pro Gly Phe Gln Gly Pro Arg Cys Glu Leu Asp Ile Asp Glu Cys
            100                 105                 110

Ala Ser Arg Pro Cys His His Gly Ala Thr Cys Arg Asn Leu Ala Asp
            115                 120                 125

Arg Tyr Glu Cys His Cys Pro Leu Gly Tyr Ala Gly Val Thr Cys Glu
        130                 135                 140

Met Glu Val Asp Glu Cys Ala Ser Ala Pro Cys Leu His Gly Gly Ser
145                 150                 155                 160

Cys Leu Asp Gly Val Gly Ser Phe Arg Cys Val Cys Ala Pro Gly Tyr
                165                 170                 175

Gly Gly Thr Arg Cys Gln Leu Asp Leu Asp Glu Cys Gln Ser Gln Pro
            180                 185                 190

Cys Ala His Gly Gly Thr Cys His Asp Leu Val Asn Gly Phe Arg Cys
            195                 200                 205

Asp Cys Ala Gly Thr Gly Tyr Glu Gly Thr His Cys Glu Arg Glu Val
        210                 215                 220

Leu Glu Cys Ala Ser Ala Pro Cys Glu His Asn Ala Ser Cys Leu Glu
225                 230                 235                 240

Gly Leu Gly Ser Phe Arg Cys Leu Cys Trp Pro Gly Tyr Ser Gly Glu
                245                 250                 255

Leu Cys Glu Val Asp Glu Asp Glu Cys Ala Ser Ser Pro Cys Gln His
            260                 265                 270

Gly Gly Arg Cys Leu Gln Arg Ser Asp Pro Ala Leu Tyr Gly Gly Val
            275                 280                 285

Gln Ala Ala Phe Pro Gly Ala Phe Ser Phe Arg His Ala Ala Gly Phe
        290                 295                 300

Leu Cys His Cys Pro Pro Gly Phe Glu Gly Ala Asp Cys Gly Val Glu
305                 310                 315                 320

Val Asp Glu Cys Ala Ser Arg Pro Cys Leu Asn Gly Gly His Cys Gln
                325                 330                 335

Asp Leu Pro Asn Gly Phe Gln Cys His Cys Pro Asp Gly Tyr Ala Gly
            340                 345                 350

Pro Thr Cys Glu Glu Asp Val Asp Glu Cys Leu Ser Asp Pro Cys Leu
        355                 360                 365

His Gly Gly Thr Cys Ser Asp Thr Val Ala Gly Tyr Ile Cys Arg Cys
        370                 375                 380

Pro Glu Thr Trp Gly Gly Arg Asp Cys Ser Val Gln Leu Thr Gly Cys
385                 390                 395                 400

Gln Gly His Thr Cys Pro Leu Ala Ala Thr Cys Ile Pro Ile Phe Glu
            405                 410                 415

Ser Gly Val His Ser Tyr Val Cys His Cys Pro Pro Gly Thr His Gly
            420                 425                 430
```

```
Pro Phe Cys Gly Gln Asn Thr Thr Phe Ser Val Met Ala Gly Ser Pro
            435                 440                 445

Ile Gln Ala Ser Val Pro Ala Gly Gly Pro Leu Gly Leu Ala Leu Arg
    450                 455                 460

Phe Arg Thr Thr Leu Pro Ala Gly Thr Leu Ala Thr Arg Asn Asp Thr
465                 470                 475                 480

Lys Glu Ser Leu Glu Leu Ala Leu Val Ala Thr Leu Gln Ala Thr
                485                 490                 495

Leu Trp Ser Tyr Ser Thr Thr Val Leu Val Leu Arg Leu Pro Asp Leu
                500                 505                 510

Ala Leu Asn Asp Gly His Trp His Gln Val Glu Val Val Leu His Leu
            515                 520                 525

Ala Thr Leu Glu Leu Arg Leu Trp His Glu Gly Cys Pro Ala Arg Leu
            530                 535                 540

Cys Val Ala Ser Gly Pro Val Ala Leu Ala Ser Thr Ala Ser Ala Thr
545                 550                 555                 560

Pro Leu Pro Ala Gly Ile Ser Ser Ala Gln Leu Gly Asp Ala Thr Phe
                565                 570                 575

Ala Gly Cys Leu Gln Asp Val Arg Val Asp Gly His Leu Leu Leu Pro
            580                 585                 590

Glu Asp Leu Gly Glu Asn Val Leu Leu Gly Cys Glu Arg Arg Glu Gln
            595                 600                 605

Cys Arg Pro Leu Pro Cys Val His Gly Gly Ser Cys Val Asp Leu Trp
            610                 615                 620

Thr His Phe Arg Cys Asp Cys Ala Arg Pro His Arg Gly Pro Thr Cys
625                 630                 635                 640

Ala Asp Glu Ile Pro Ala Ala Thr Phe Gly Leu Gly Ala Pro Ser
                645                 650                 655

Ser Ala Ser Phe Leu Leu Gln Glu Leu Pro Gly Pro Asn Leu Thr Val
                660                 665                 670

Ser Phe Leu Leu Arg Thr Arg Glu Ser Ala Gly Leu Leu Leu Gln Phe
            675                 680                 685

Ala Asn Asp Ser Ala Ala Gly Leu Thr Val Phe Leu Ser Glu Gly Arg
            690                 695                 700

Ile Arg Ala Glu Val Pro Gly Ser Pro Ala Val Val Leu Pro Gly Arg
705                 710                 715                 720

Trp Asp Asp Gly Leu Arg His Leu Val Met Leu Ser Phe Gly Pro Asp
                725                 730                 735

Gln Leu Gln Asp Leu Gly Gln His Val His Val Gly Gly Arg Leu Leu
            740                 745                 750

Ala Ala Asp Ser Gln Pro Trp Gly Gly Pro Phe Arg Gly Cys Leu Gln
            755                 760                 765

Asp Leu Arg Leu Asp Gly Cys His Leu Pro Phe Phe Pro Leu Pro Leu
            770                 775                 780

Asp Asn Ser Ser Gln Pro Ser Glu Leu Gly Gly Arg Gln Ser Trp Asn
785                 790                 795                 800

Leu Thr Ala Gly Cys Val Ser Glu Asp Met Cys Ser Pro Asp Pro Cys
                805                 810                 815

Phe Asn Gly Gly Thr Cys Leu Val Thr Trp Asn Asp Phe His Cys Thr
                820                 825                 830

Cys Pro Ala Asn Phe Thr Gly Pro Thr Cys Ala Gln Gln Leu Trp Cys
            835                 840                 845

Pro Gly Gln Pro Cys Leu Pro Pro Ala Thr Cys Glu Glu Val Pro Asp
```

```
                    850                 855                 860
Gly Phe Val Cys Val Ala Glu Ala Thr Phe Arg Glu Gly Pro Ala
865                 870                 875                 880

Ala Phe Ser Gly His Asn Ala Ser Ser Gly Arg Leu Leu Gly Leu
                    885                 890                 895

Ser Leu Ala Phe Arg Thr Arg Asp Ser Glu Ala Trp Leu Arg Ala
                900                 905                 910

Ala Ala Gly Ala Leu Glu Gly Val Trp Leu Ala Val Arg Asn Gly Ser
            915                 920                 925

Leu Ala Gly Gly Val Arg Gly Gly His Gly Leu Pro Gly Ala Val Leu
    930                 935                 940

Pro Ile Pro Gly Pro Arg Val Ala Asp Gly Ala Trp His Arg Val Arg
945                 950                 955                 960

Leu Ala Met Glu Arg Pro Ala Ala Thr Thr Ser Arg Trp Leu Leu Trp
                965                 970                 975

Leu Asp Gly Ala Ala Thr Pro Val Ala Leu Arg Gly Leu Ala Ser Asp
                980                 985                 990

Leu Gly Phe Leu Gln Gly Pro Gly Ala Val Arg Ile Leu Leu Ala Glu
        995                 1000                1005

Asn Phe Thr Gly Cys Leu Gly Arg Val Ala Leu Gly Gly Leu Pro
    1010                1015                1020

Leu Pro Leu Ala Arg Pro Arg Pro Gly Ala Ala Pro Gly Ala Arg
    1025                1030                1035

Glu His Phe Ala Ser Trp Pro Gly Thr Pro Ala Pro Ile Leu Gly
    1040                1045                1050

Cys Arg Gly Ala Pro Val Cys Ala Pro Ser Pro Cys Leu His Asp
    1055                1060                1065

Gly Ala Cys Arg Asp Leu Phe Asp Ala Phe Ala Cys Ala Cys Gly
    1070                1075                1080

Pro Gly Trp Glu Gly Pro Arg Cys Glu Ala His Val Asp Pro Cys
    1085                1090                1095

His Ser Ala Pro Cys Ala Arg Gly Arg Cys His Thr His Pro Asp
    1100                1105                1110

Gly Arg Phe Glu Cys Arg Cys Pro Pro Gly Phe Gly Gly Pro Arg
    1115                1120                1125

Cys Arg Leu Pro Val Pro Ser Lys Glu Cys Ser Leu Asn Val Thr
    1130                1135                1140

Cys Leu Asp Gly Ser Pro Cys Glu Gly Gly Ser Pro Ala Ala Asn
    1145                1150                1155

Cys Ser Cys Leu Glu Gly Leu Ala Gly Gln Arg Cys Gln Val Pro
    1160                1165                1170

Thr Leu Pro Cys Glu Ala Asn Pro Cys Leu Asn Gly Gly Thr Cys
    1175                1180                1185

Arg Ala Ala Gly Gly Val Ser Glu Cys Ile Cys Asn Ala Arg Phe
    1190                1195                1200

Ser Gly Gln Phe Cys Glu Val Ala Lys Gly Leu Pro Leu Pro Leu
    1205                1210                1215

Pro Phe Pro Leu Leu Glu Val Ala Val Pro Ala Ala Cys Ala Cys
    1220                1225                1230

Leu Leu Leu Leu Leu Leu Gly Leu Leu Ser Gly Ile Leu Ala Ala
    1235                1240                1245

Arg Lys Arg Arg Gln Ser Glu Gly Thr Tyr Ser Pro Ser Gln Gln
    1250                1255                1260
```

```
Glu Val Ala Gly Ala Arg Leu Glu Met Asp Ser Val Leu Lys Val
    1265                1270                1275

Pro Pro Glu Glu Arg Leu Ile
    1280            1285

<210> SEQ ID NO 20
<211> LENGTH: 299
<212> TYPE: PRT
<213> ORGANISM: Homo sapiens
<220> FEATURE:
<221> NAME/KEY: MISC_FEATURE
<222> LOCATION: (1)..(299)
<223> OTHER INFORMATION: CRX (cone rod honmeobox protein)

<400> SEQUENCE: 20

Met Met Ala Tyr Met Asn Pro Gly Pro His Tyr Ser Val Asn Ala Leu
1               5                   10                  15

Ala Leu Ser Gly Pro Ser Val Asp Leu Met His Gln Ala Val Pro Tyr
            20                  25                  30

Pro Ser Ala Pro Arg Lys Gln Arg Glu Arg Thr Thr Phe Thr Arg
        35                  40                  45

Ser Gln Leu Glu Glu Leu Glu Ala Leu Phe Ala Lys Thr Gln Tyr Pro
    50                  55                  60

Asp Val Tyr Ala Arg Glu Val Ala Leu Lys Ile Asn Leu Pro Glu
65                  70                  75                  80

Ser Arg Val Gln Val Trp Phe Lys Asn Arg Arg Ala Lys Cys Arg Gln
                85                  90                  95

Gln Arg Gln Gln Gln Lys Gln Gln Gln Gln Pro Pro Gly Gly Gln Ala
            100                 105                 110

Lys Ala Arg Pro Ala Lys Arg Lys Ala Gly Thr Ser Pro Arg Pro Ser
        115                 120                 125

Thr Asp Val Cys Pro Asp Pro Leu Gly Ile Ser Asp Ser Tyr Ser Pro
    130                 135                 140

Pro Leu Pro Gly Pro Ser Gly Ser Pro Thr Thr Ala Val Ala Thr Val
145                 150                 155                 160

Ser Ile Trp Ser Pro Ala Ser Glu Ser Pro Leu Pro Glu Ala Gln Arg
                165                 170                 175

Ala Gly Leu Val Ala Ser Gly Pro Ser Leu Thr Ser Ala Pro Tyr Ala
            180                 185                 190

Met Thr Tyr Ala Pro Ala Ser Ala Phe Cys Ser Ser Pro Ser Ala Tyr
        195                 200                 205

Gly Ser Pro Ser Ser Tyr Phe Ser Gly Leu Asp Pro Tyr Leu Ser Pro
    210                 215                 220

Met Val Pro Gln Leu Gly Gly Pro Ala Leu Ser Pro Leu Ser Gly Pro
225                 230                 235                 240

Ser Val Gly Pro Ser Leu Ala Gln Ser Pro Thr Ser Leu Ser Gly Gln
                245                 250                 255

Ser Tyr Gly Ala Tyr Ser Pro Val Asp Ser Leu Glu Phe Lys Asp Pro
            260                 265                 270

Thr Gly Thr Trp Lys Phe Thr Tyr Asn Pro Met Asp Pro Leu Asp Tyr
        275                 280                 285

Lys Asp Gln Ser Ala Trp Lys Phe Gln Ile Leu
    290                 295

<210> SEQ ID NO 21
<211> LENGTH: 6306
```

```
<212> TYPE: PRT
<213> ORGANISM: Homo sapiens
<220> FEATURE:
<221> NAME/KEY: MISC_FEATURE
<222> LOCATION: (1)..(6306)
<223> OTHER INFORMATION: GPR98 (G-protein coupled receptor 98)

<400> SEQUENCE: 21
```

Met Ser Val Phe Leu Gly Pro Gly Met Pro Ser Ala Ser Leu Leu Val
1               5                   10                  15

Asn Leu Leu Ser Ala Leu Leu Ile Leu Phe Val Phe Gly Glu Thr Glu
            20                  25                  30

Ile Arg Phe Thr Gly Gln Thr Glu Phe Val Val Asn Glu Thr Ser Thr
        35                  40                  45

Thr Val Ile Arg Leu Ile Ile Glu Arg Ile Gly Glu Pro Ala Asn Val
50                  55                  60

Thr Ala Ile Val Ser Leu Tyr Gly Glu Asp Ala Gly Asp Phe Phe Asp
65                  70                  75                  80

Thr Tyr Ala Ala Ala Phe Ile Pro Ala Gly Glu Thr Asn Arg Thr Val
            85                  90                  95

Tyr Ile Ala Val Cys Asp Asp Asp Leu Pro Glu Pro Asp Glu Thr Phe
            100                 105                 110

Ile Phe His Leu Thr Leu Gln Lys Pro Ser Ala Asn Val Lys Leu Gly
        115                 120                 125

Trp Pro Arg Thr Val Thr Val Thr Ile Leu Ser Asn Asp Asn Ala Phe
130                 135                 140

Gly Ile Ile Ser Phe Asn Met Leu Pro Ser Ile Ala Val Ser Glu Pro
145                 150                 155                 160

Lys Gly Arg Asn Glu Ser Met Pro Leu Thr Leu Ile Arg Glu Lys Gly
            165                 170                 175

Thr Tyr Gly Met Val Met Val Thr Phe Glu Val Glu Gly Gly Pro Asn
        180                 185                 190

Pro Pro Asp Glu Asp Leu Ser Pro Val Lys Gly Asn Ile Thr Phe Pro
    195                 200                 205

Pro Gly Arg Ala Thr Val Ile Tyr Asn Leu Thr Val Leu Asp Asp Glu
210                 215                 220

Val Pro Glu Asn Asp Glu Ile Phe Leu Ile Gln Leu Lys Ser Val Glu
225                 230                 235                 240

Gly Gly Ala Glu Ile Asn Thr Ser Arg Asn Ser Ile Glu Ile Ile Ile
            245                 250                 255

Lys Lys Asn Asp Ser Pro Val Arg Phe Leu Gln Ser Ile Tyr Leu Val
        260                 265                 270

Pro Glu Glu Asp His Ile Leu Ile Ile Pro Val Val Arg Gly Lys Asp
    275                 280                 285

Asn Asn Gly Asn Leu Ile Gly Ser Asp Glu Tyr Glu Val Ser Ile Ser
290                 295                 300

Tyr Ala Val Thr Thr Gly Asn Ser Thr Ala His Ala Gln Gln Asn Leu
305                 310                 315                 320

Asp Phe Ile Asp Leu Gln Pro Asn Thr Thr Val Val Phe Pro Pro Phe
            325                 330                 335

Ile His Glu Ser His Leu Lys Phe Gln Ile Val Asp Asp Thr Ile Pro
        340                 345                 350

Glu Ile Ala Glu Ser Phe His Ile Met Leu Leu Lys Asp Thr Leu Gln
    355                 360                 365

Gly Asp Ala Val Leu Ile Ser Pro Ser Val Val Gln Val Thr Ile Lys

```
              370                 375                 380
Pro Asn Asp Lys Pro Tyr Gly Val Leu Ser Phe Asn Ser Val Leu Phe
385                 390                 395                 400

Glu Arg Thr Val Ile Ile Asp Glu Asp Arg Ile Ser Arg Tyr Glu Glu
                    405                 410                 415

Ile Thr Val Val Arg Asn Gly Gly Thr His Gly Asn Val Ser Ala Asn
                420                 425                 430

Trp Val Leu Thr Arg Asn Ser Thr Asp Pro Ser Pro Val Thr Ala Asp
            435                 440                 445

Ile Arg Pro Ser Ser Gly Val Leu His Phe Ala Gln Gly Gln Met Leu
450                 455                 460

Ala Thr Ile Pro Leu Thr Val Val Asp Asp Leu Pro Glu Glu Ala
465                 470                 475                 480

Glu Ala Tyr Leu Leu Gln Ile Leu Pro His Thr Ile Arg Gly Gly Ala
                    485                 490                 495

Glu Val Ser Glu Pro Ala Glu Leu Leu Phe Tyr Ile Gln Asp Ser Asp
                500                 505                 510

Asp Val Tyr Gly Leu Ile Thr Phe Phe Pro Met Glu Asn Gln Lys Ile
            515                 520                 525

Glu Ser Ser Pro Gly Glu Arg Tyr Leu Ser Leu Ser Phe Thr Arg Leu
530                 535                 540

Gly Gly Thr Lys Gly Asp Val Arg Leu Leu Tyr Ser Val Leu Tyr Ile
545                 550                 555                 560

Pro Ala Gly Ala Val Asp Pro Leu Gln Ala Lys Glu Gly Ile Leu Asn
                    565                 570                 575

Ile Ser Arg Arg Asn Asp Leu Ile Phe Pro Glu Gln Lys Thr Gln Val
                580                 585                 590

Thr Thr Lys Leu Pro Ile Arg Asn Asp Ala Phe Leu Gln Asn Gly Ala
            595                 600                 605

His Phe Leu Val Gln Leu Glu Thr Val Glu Leu Leu Asn Ile Ile Pro
610                 615                 620

Leu Ile Pro Pro Ile Ser Pro Arg Phe Gly Glu Ile Cys Asn Ile Ser
625                 630                 635                 640

Leu Leu Val Thr Pro Ala Ile Ala Asn Gly Glu Ile Gly Phe Leu Ser
                    645                 650                 655

Asn Leu Pro Ile Ile Leu His Glu Pro Glu Asp Phe Ala Ala Glu Val
                660                 665                 670

Val Tyr Ile Pro Leu His Arg Asp Gly Thr Asp Gly Gln Ala Thr Val
            675                 680                 685

Tyr Trp Ser Leu Lys Pro Ser Gly Phe Asn Ser Lys Ala Val Thr Pro
690                 695                 700

Asp Asp Ile Gly Pro Phe Asn Gly Ser Val Leu Phe Leu Ser Gly Gln
705                 710                 715                 720

Ser Asp Thr Thr Ile Asn Ile Thr Ile Lys Gly Asp Asp Ile Pro Glu
                    725                 730                 735

Met Asn Glu Thr Val Thr Leu Ser Leu Asp Arg Val Asn Val Glu Asn
                740                 745                 750

Gln Val Leu Lys Ser Gly Tyr Thr Ser Arg Asp Leu Ile Ile Leu Glu
            755                 760                 765

Asn Asp Asp Pro Gly Gly Val Phe Glu Phe Ser Pro Ala Ser Arg Gly
770                 775                 780

Pro Tyr Val Ile Lys Glu Gly Glu Ser Val Glu Leu His Ile Ile Arg
785                 790                 795                 800
```

```
Ser Arg Gly Ser Leu Val Lys Gln Phe Leu His Tyr Arg Val Glu Pro
            805                 810                 815

Arg Asp Ser Asn Glu Phe Tyr Gly Asn Thr Gly Val Leu Glu Phe Lys
            820                 825                 830

Pro Gly Glu Arg Glu Ile Val Ile Thr Leu Leu Ala Arg Leu Asp Gly
            835                 840                 845

Ile Pro Glu Leu Asp Glu His Tyr Trp Val Val Leu Ser Ser His Gly
            850                 855                 860

Glu Arg Glu Ser Lys Leu Gly Ser Ala Thr Ile Val Asn Ile Thr Ile
865                 870                 875                 880

Leu Lys Asn Asp Asp Pro His Gly Ile Ile Gly Phe Val Ser Asp Gly
            885                 890                 895

Leu Ile Val Met Ile Asn Glu Ser Lys Gly Asp Ala Ile Tyr Ser Ala
            900                 905                 910

Val Tyr Asp Val Val Arg Asn Arg Gly Asn Phe Gly Asp Val Ser Val
            915                 920                 925

Ser Trp Val Val Ser Pro Asp Phe Thr Gln Asp Val Phe Pro Val Gln
            930                 935                 940

Gly Thr Val Val Phe Gly Asp Gln Glu Phe Ser Lys Asn Ile Thr Ile
945                 950                 955                 960

Tyr Ser Leu Pro Asp Glu Ile Pro Glu Glu Met Glu Glu Phe Thr Val
            965                 970                 975

Ile Leu Leu Asn Gly Thr Gly Gly Ala Lys Val Gly Asn Arg Thr Thr
            980                 985                 990

Ala Thr Leu Arg Ile Arg Arg Asn Asp Asp Pro Ile Tyr Phe Ala Glu
            995                 1000                1005

Pro Arg Val Val Arg Val Gln Glu Gly Glu Thr Ala Asn Phe Thr
        1010            1015            1020

Val Leu Arg Asn Gly Ser Val Asp Val Thr Cys Met Val Gln Tyr
        1025            1030            1035

Ala Thr Lys Asp Gly Lys Ala Thr Ala Arg Glu Arg Asp Phe Ile
        1040            1045            1050

Pro Val Glu Lys Gly Glu Thr Leu Ile Phe Glu Val Gly Ser Arg
        1055            1060            1065

Gln Gln Ser Ile Ser Ile Phe Val Asn Glu Asp Gly Ile Pro Glu
        1070            1075            1080

Thr Asp Glu Pro Phe Tyr Ile Ile Leu Leu Asn Ser Thr Gly Asp
        1085            1090            1095

Thr Val Val Tyr Gln Tyr Gly Val Ala Thr Val Ile Ile Glu Ala
        1100            1105            1110

Asn Asp Asp Pro Asn Gly Ile Phe Ser Leu Glu Pro Ile Asp Lys
        1115            1120            1125

Ala Val Glu Glu Gly Lys Thr Asn Ala Phe Trp Ile Leu Arg His
        1130            1135            1140

Arg Gly Tyr Phe Gly Ser Val Ser Val Ser Trp Gln Leu Phe Gln
        1145            1150            1155

Asn Asp Ser Ala Leu Gln Pro Gly Gln Glu Phe Tyr Glu Thr Ser
        1160            1165            1170

Gly Thr Val Asn Phe Met Asp Gly Glu Glu Ala Lys Pro Ile Ile
        1175            1180            1185

Leu His Ala Phe Pro Asp Lys Ile Pro Glu Phe Asn Glu Phe Tyr
        1190            1195            1200
```

-continued

```
Phe Leu Lys Leu Val Asn Ile Ser Gly Gly Ser Pro Gly Pro Gly
    1205                1210                1215

Gly Gln Leu Ala Glu Thr Asn Leu Gln Val Thr Val Met Val Pro
    1220                1225                1230

Phe Asn Asp Asp Pro Phe Gly Val Phe Ile Leu Asp Pro Glu Cys
    1235                1240                1245

Leu Glu Arg Glu Val Ala Glu Asp Val Leu Ser Glu Asp Asp Met
    1250                1255                1260

Ser Tyr Ile Thr Asn Phe Thr Ile Leu Arg Gln Gln Gly Val Phe
    1265                1270                1275

Gly Asp Val Gln Leu Gly Trp Glu Ile Leu Ser Ser Glu Phe Pro
    1280                1285                1290

Ala Gly Leu Pro Pro Met Ile Asp Phe Leu Leu Val Gly Ile Phe
    1295                1300                1305

Pro Thr Thr Val His Leu Gln Gln His Met Arg Arg His His Ser
    1310                1315                1320

Gly Thr Asp Ala Leu Tyr Phe Thr Gly Leu Glu Gly Ala Phe Gly
    1325                1330                1335

Thr Val Asn Pro Lys Tyr His Pro Ser Arg Asn Asn Thr Ile Ala
    1340                1345                1350

Asn Phe Thr Phe Ser Ala Trp Val Met Pro Asn Ala Asn Thr Asn
    1355                1360                1365

Gly Phe Ile Ile Ala Lys Asp Asp Gly Asn Gly Ser Ile Tyr Tyr
    1370                1375                1380

Gly Val Lys Ile Gln Thr Asn Glu Ser His Val Thr Leu Ser Leu
    1385                1390                1395

His Tyr Lys Thr Leu Gly Ser Asn Ala Thr Tyr Ile Ala Lys Thr
    1400                1405                1410

Thr Val Met Lys Tyr Leu Glu Glu Ser Val Trp Leu His Leu Leu
    1415                1420                1425

Ile Ile Leu Glu Asp Gly Ile Ile Glu Phe Tyr Leu Asp Gly Asn
    1430                1435                1440

Ala Met Pro Arg Gly Ile Lys Ser Leu Lys Gly Glu Ala Ile Thr
    1445                1450                1455

Asp Gly Pro Gly Ile Leu Arg Ile Gly Ala Gly Ile Asn Gly Asn
    1460                1465                1470

Asp Arg Phe Thr Gly Leu Met Gln Asp Val Arg Ser Tyr Glu Arg
    1475                1480                1485

Lys Leu Thr Leu Glu Glu Ile Tyr Glu Leu His Ala Met Pro Ala
    1490                1495                1500

Lys Ser Asp Leu His Pro Ile Ser Gly Tyr Leu Glu Phe Arg Gln
    1505                1510                1515

Gly Glu Thr Asn Lys Ser Phe Ile Ile Ser Ala Arg Asp Asp Asn
    1520                1525                1530

Asp Glu Glu Gly Glu Glu Leu Phe Ile Leu Lys Leu Val Ser Val
    1535                1540                1545

Tyr Gly Gly Ala Arg Ile Ser Glu Glu Asn Thr Thr Ala Arg Leu
    1550                1555                1560

Thr Ile Gln Lys Ser Asp Asn Ala Asn Gly Leu Phe Gly Phe Thr
    1565                1570                1575

Gly Ala Cys Ile Pro Glu Ile Ala Glu Glu Gly Ser Thr Ile Ser
    1580                1585                1590

Cys Val Val Glu Arg Thr Arg Gly Ala Leu Asp Tyr Val His Val
```

-continued

```
             1595                1600                1605

Phe Tyr Thr Ile Ser Gln Ile Glu Thr Asp Gly Ile Asn Tyr Leu
        1610                1615                1620

Val Asp Asp Phe Ala Asn Ala Ser Gly Thr Ile Thr Phe Leu Pro
        1625                1630                1635

Trp Gln Arg Ser Glu Val Leu Asn Ile Tyr Val Leu Asp Asp Asp
        1640                1645                1650

Ile Pro Glu Leu Asn Glu Tyr Phe Arg Val Thr Leu Val Ser Ala
        1655                1660                1665

Ile Pro Gly Asp Gly Lys Leu Gly Ser Thr Pro Thr Ser Gly Ala
        1670                1675                1680

Ser Ile Asp Pro Glu Lys Glu Thr Thr Asp Ile Thr Ile Lys Ala
        1685                1690                1695

Ser Asp His Pro Tyr Gly Leu Leu Gln Phe Ser Thr Gly Leu Pro
        1700                1705                1710

Pro Gln Pro Lys Asp Ala Met Thr Leu Pro Ala Ser Ser Val Pro
        1715                1720                1725

His Ile Thr Val Glu Glu Glu Asp Gly Glu Ile Arg Leu Leu Val
        1730                1735                1740

Ile Arg Ala Gln Gly Leu Leu Gly Arg Val Thr Ala Glu Phe Arg
        1745                1750                1755

Thr Val Ser Leu Thr Ala Phe Ser Pro Glu Asp Tyr Gln Asn Val
        1760                1765                1770

Ala Gly Thr Leu Glu Phe Gln Pro Gly Glu Arg Tyr Lys Tyr Ile
        1775                1780                1785

Phe Ile Asn Ile Thr Asp Asn Ser Ile Pro Glu Leu Glu Lys Ser
        1790                1795                1800

Phe Lys Val Glu Leu Leu Asn Leu Glu Gly Gly Val Ala Glu Leu
        1805                1810                1815

Phe Arg Val Asp Gly Ser Gly Ser Gly Asp Gly Asp Met Glu Phe
        1820                1825                1830

Phe Leu Pro Thr Ile His Lys Arg Ala Ser Leu Gly Val Ala Ser
        1835                1840                1845

Gln Ile Leu Val Thr Ile Ala Ala Ser Asp His Ala His Gly Val
        1850                1855                1860

Phe Glu Phe Ser Pro Glu Ser Leu Phe Val Ser Gly Thr Glu Pro
        1865                1870                1875

Glu Asp Gly Tyr Ser Thr Val Thr Leu Asn Val Ile Arg His His
        1880                1885                1890

Gly Thr Leu Ser Pro Val Thr Leu His Trp Asn Ile Asp Ser Asp
        1895                1900                1905

Pro Asp Gly Asp Leu Ala Phe Thr Ser Gly Asn Ile Thr Phe Glu
        1910                1915                1920

Ile Gly Gln Thr Ser Ala Asn Ile Thr Val Glu Ile Leu Pro Asp
        1925                1930                1935

Glu Asp Pro Glu Leu Asp Lys Ala Phe Ser Val Ser Val Leu Ser
        1940                1945                1950

Val Ser Ser Gly Ser Leu Gly Ala His Ile Asn Ala Thr Leu Thr
        1955                1960                1965

Val Leu Ala Ser Asp Asp Pro Tyr Gly Ile Phe Ile Phe Ser Glu
        1970                1975                1980

Lys Asn Arg Pro Val Lys Val Glu Glu Ala Thr Gln Asn Ile Thr
        1985                1990                1995
```

```
Leu Ser Ile Ile Arg Leu Lys Gly Leu Met Gly Lys Val Leu Val
    2000                2005                2010

Ser Tyr Ala Thr Leu Asp Asp Met Glu Lys Pro Pro Tyr Phe Pro
    2015                2020                2025

Pro Asn Leu Ala Arg Ala Thr Gln Gly Arg Asp Tyr Ile Pro Ala
    2030                2035                2040

Ser Gly Phe Ala Leu Phe Gly Ala Asn Gln Ser Glu Ala Thr Ile
    2045                2050                2055

Ala Ile Ser Ile Leu Asp Asp Asp Glu Pro Glu Arg Ser Glu Ser
    2060                2065                2070

Val Phe Ile Glu Leu Leu Asn Ser Thr Leu Val Ala Lys Val Gln
    2075                2080                2085

Ser Arg Ser Ile Pro Asn Ser Pro Arg Leu Gly Pro Lys Val Glu
    2090                2095                2100

Thr Ile Ala Gln Leu Ile Ile Ile Ala Asn Asp Asp Ala Phe Gly
    2105                2110                2115

Thr Leu Gln Leu Ser Ala Pro Ile Val Arg Val Ala Glu Asn His
    2120                2125                2130

Val Gly Pro Ile Ile Asn Val Thr Arg Thr Gly Gly Ala Phe Ala
    2135                2140                2145

Asp Val Ser Val Lys Phe Lys Ala Val Pro Ile Thr Ala Ile Ala
    2150                2155                2160

Gly Glu Asp Tyr Ser Ile Ala Ser Ser Asp Val Val Leu Leu Glu
    2165                2170                2175

Gly Glu Thr Ser Lys Ala Val Pro Ile Tyr Val Ile Asn Asp Ile
    2180                2185                2190

Tyr Pro Glu Leu Glu Glu Ser Phe Leu Val Gln Leu Met Asn Glu
    2195                2200                2205

Thr Thr Gly Gly Ala Arg Leu Gly Ala Leu Thr Glu Ala Val Ile
    2210                2215                2220

Ile Ile Glu Ala Ser Asp Asp Pro Tyr Gly Leu Phe Gly Phe Gln
    2225                2230                2235

Ile Thr Lys Leu Ile Val Glu Glu Pro Glu Phe Asn Ser Val Lys
    2240                2245                2250

Val Asn Leu Pro Ile Ile Arg Asn Ser Gly Thr Leu Gly Asn Val
    2255                2260                2265

Thr Val Gln Trp Val Ala Thr Ile Asn Gly Gln Leu Ala Thr Gly
    2270                2275                2280

Asp Leu Arg Val Val Ser Gly Asn Val Thr Phe Ala Pro Gly Glu
    2285                2290                2295

Thr Ile Gln Thr Leu Leu Leu Glu Val Leu Ala Asp Asp Val Pro
    2300                2305                2310

Glu Ile Glu Glu Val Ile Gln Val Gln Leu Thr Asp Ala Ser Gly
    2315                2320                2325

Gly Gly Thr Ile Gly Leu Asp Arg Ile Ala Asn Ile Ile Ile Pro
    2330                2335                2340

Ala Asn Asp Asp Pro Tyr Gly Thr Val Ala Phe Ala Gln Met Val
    2345                2350                2355

Tyr Arg Val Gln Glu Pro Leu Glu Arg Ser Ser Cys Ala Asn Ile
    2360                2365                2370

Thr Val Arg Arg Ser Gly Gly His Phe Gly Arg Leu Leu Leu Phe
    2375                2380                2385
```

-continued

Tyr Ser Thr Ser Asp Ile Asp Val Val Ala Leu Ala Met Glu Glu
     2390            2395            2400

Gly Gln Asp Leu Leu Ser Tyr Tyr Glu Ser Pro Ile Gln Gly Val
2405            2410            2415

Pro Asp Pro Leu Trp Arg Thr Trp Met Asn Val Ser Ala Val Gly
2420            2425            2430

Glu Pro Leu Tyr Thr Cys Ala Thr Leu Cys Leu Lys Glu Gln Ala
2435            2440            2445

Cys Ser Ala Phe Ser Phe Phe Ser Ala Ser Glu Gly Pro Gln Cys
2450            2455            2460

Phe Trp Met Thr Ser Trp Ile Ser Pro Ala Val Asn Asn Ser Asp
2465            2470            2475

Phe Trp Thr Tyr Arg Lys Asn Met Thr Arg Val Ala Ser Leu Phe
2480            2485            2490

Ser Gly Gln Ala Val Ala Gly Ser Asp Tyr Glu Pro Val Thr Arg
2495            2500            2505

Gln Trp Ala Ile Met Gln Glu Gly Asp Glu Phe Ala Asn Leu Thr
2510            2515            2520

Val Ser Ile Leu Pro Asp Asp Phe Pro Glu Met Asp Glu Ser Phe
2525            2530            2535

Leu Ile Ser Leu Leu Glu Val His Leu Met Asn Ile Ser Ala Ser
2540            2545            2550

Leu Lys Asn Gln Pro Thr Ile Gly Gln Pro Asn Ile Ser Thr Val
2555            2560            2565

Val Ile Ala Leu Asn Gly Asp Ala Phe Gly Val Phe Val Ile Tyr
2570            2575            2580

Asn Ile Ser Pro Asn Thr Ser Glu Asp Gly Leu Phe Val Glu Val
2585            2590            2595

Gln Glu Gln Pro Gln Thr Leu Val Glu Leu Met Ile His Arg Thr
2600            2605            2610

Gly Gly Ser Leu Gly Gln Val Ala Val Glu Trp Arg Val Val Gly
2615            2620            2625

Gly Thr Ala Thr Glu Gly Leu Asp Phe Ile Gly Ala Gly Glu Ile
2630            2635            2640

Leu Thr Phe Ala Glu Gly Glu Thr Lys Lys Thr Val Ile Leu Thr
2645            2650            2655

Ile Leu Asp Asp Ser Glu Pro Glu Asp Asp Glu Ser Ile Ile Val
2660            2665            2670

Ser Leu Val Tyr Thr Glu Gly Gly Ser Arg Ile Leu Pro Ser Ser
2675            2680            2685

Asp Thr Val Arg Val Asn Ile Leu Ala Asn Asp Asn Val Ala Gly
2690            2695            2700

Ile Val Ser Phe Gln Thr Ala Ser Arg Ser Val Ile Gly His Glu
2705            2710            2715

Gly Glu Ile Leu Gln Phe His Val Ile Arg Thr Phe Pro Gly Arg
2720            2725            2730

Gly Asn Val Thr Val Asn Trp Lys Ile Ile Gly Gln Asn Leu Glu
2735            2740            2745

Leu Asn Phe Ala Asn Phe Ser Gly Gln Leu Phe Phe Pro Glu Gly
2750            2755            2760

Ser Leu Asn Thr Thr Leu Phe Val His Leu Leu Asp Asp Asn Ile
2765            2770            2775

Pro Glu Glu Lys Glu Val Tyr Gln Val Ile Leu Tyr Asp Val Arg

-continued

```
                2780                2785                2790
Thr Gln Gly Val Pro Pro Ala Gly Ile Ala Leu Leu Asp Ala Gln
    2795                2800                2805
Gly Tyr Ala Ala Val Leu Thr Val Glu Ala Ser Asp Glu Pro His
    2810                2815                2820
Gly Val Leu Asn Phe Ala Leu Ser Ser Arg Phe Val Leu Leu Gln
    2825                2830                2835
Glu Ala Asn Ile Thr Ile Gln Leu Phe Ile Asn Arg Glu Phe Gly
    2840                2845                2850
Ser Leu Gly Ala Ile Asn Val Thr Tyr Thr Thr Val Pro Gly Met
    2855                2860                2865
Leu Ser Leu Lys Asn Gln Thr Val Gly Asn Leu Ala Glu Pro Glu
    2870                2875                2880
Val Asp Phe Val Pro Ile Ile Gly Phe Leu Ile Leu Glu Glu Gly
    2885                2890                2895
Glu Thr Ala Ala Ala Ile Asn Ile Thr Ile Leu Glu Asp Asp Val
    2900                2905                2910
Pro Glu Leu Glu Glu Tyr Phe Leu Val Asn Leu Thr Tyr Val Gly
    2915                2920                2925
Leu Thr Met Ala Ala Ser Thr Ser Phe Pro Pro Arg Leu Asp Ser
    2930                2935                2940
Glu Gly Leu Thr Ala Gln Val Ile Ile Asp Ala Asn Asp Gly Ala
    2945                2950                2955
Arg Gly Val Ile Glu Trp Gln Gln Ser Arg Phe Glu Val Asn Glu
    2960                2965                2970
Thr His Gly Ser Leu Thr Leu Val Ala Gln Arg Ser Arg Glu Pro
    2975                2980                2985
Leu Gly His Val Ser Leu Phe Val Tyr Ala Gln Asn Leu Glu Ala
    2990                2995                3000
Gln Val Gly Leu Asp Tyr Ile Phe Thr Pro Met Ile Leu His Phe
    3005                3010                3015
Ala Asp Gly Glu Arg Tyr Lys Asn Val Asn Ile Met Ile Leu Asp
    3020                3025                3030
Asp Asp Ile Pro Glu Gly Asp Glu Lys Phe Gln Leu Ile Leu Thr
    3035                3040                3045
Asn Pro Ser Pro Gly Leu Glu Leu Gly Lys Asn Thr Ile Ala Leu
    3050                3055                3060
Ile Ile Val Leu Ala Asn Asp Asp Gly Pro Gly Val Leu Ser Phe
    3065                3070                3075
Asn Asn Ser Glu His Phe Phe Leu Arg Glu Pro Thr Ala Leu Tyr
    3080                3085                3090
Val Gln Glu Ser Val Ala Val Leu Tyr Ile Val Arg Glu Pro Ala
    3095                3100                3105
Gln Gly Leu Phe Gly Thr Val Thr Val Gln Phe Ile Val Thr Glu
    3110                3115                3120
Val Asn Ser Ser Asn Glu Ser Lys Asp Leu Thr Pro Ser Lys Gly
    3125                3130                3135
Tyr Ile Val Leu Glu Glu Gly Val Arg Phe Lys Ala Leu Gln Ile
    3140                3145                3150
Ser Ala Ile Leu Asp Thr Glu Pro Glu Met Asp Glu Tyr Phe Val
    3155                3160                3165
Cys Thr Leu Phe Asn Pro Thr Gly Gly Ala Arg Leu Gly Val His
    3170                3175                3180
```

-continued

```
Val Gln Thr Leu Ile Thr Val Leu Gln Asn Gln Ala Pro Leu Gly
    3185                3190                3195

Leu Phe Ser Ile Ser Ala Val Glu Asn Arg Ala Thr Ser Ile Asp
    3200                3205                3210

Ile Glu Glu Ala Asn Arg Thr Val Tyr Leu Asn Val Ser Arg Thr
    3215                3220                3225

Asn Gly Ile Asp Leu Ala Val Ser Val Gln Trp Glu Thr Val Ser
    3230                3235                3240

Glu Thr Ala Phe Gly Met Arg Gly Met Asp Val Val Phe Ser Val
    3245                3250                3255

Phe Gln Ser Phe Leu Asp Glu Ser Ala Ser Gly Trp Cys Phe Phe
    3260                3265                3270

Thr Leu Glu Asn Leu Ile Tyr Gly Ile Met Leu Arg Lys Ser Ser
    3275                3280                3285

Val Thr Val Tyr Arg Trp Gln Gly Ile Phe Ile Pro Val Glu Asp
    3290                3295                3300

Leu Asn Ile Glu Asn Pro Lys Thr Cys Glu Ala Phe Asn Ile Gly
    3305                3310                3315

Phe Ser Pro Tyr Phe Val Ile Thr His Glu Glu Arg Asn Glu Glu
    3320                3325                3330

Lys Pro Ser Leu Asn Ser Val Phe Thr Phe Thr Ser Gly Phe Lys
    3335                3340                3345

Leu Phe Leu Val Gln Thr Ile Ile Ile Leu Glu Ser Ser Gln Val
    3350                3355                3360

Arg Tyr Phe Thr Ser Asp Ser Gln Asp Tyr Leu Ile Ile Ala Ser
    3365                3370                3375

Gln Arg Asp Asp Ser Glu Leu Thr Gln Val Phe Arg Trp Asn Gly
    3380                3385                3390

Gly Ser Phe Val Leu His Gln Lys Leu Pro Val Arg Gly Val Leu
    3395                3400                3405

Thr Val Ala Leu Phe Asn Lys Gly Gly Ser Val Phe Leu Ala Ile
    3410                3415                3420

Ser Gln Ala Asn Ala Arg Leu Asn Ser Leu Leu Phe Arg Trp Ser
    3425                3430                3435

Gly Ser Gly Phe Ile Asn Phe Gln Glu Val Pro Val Ser Gly Thr
    3440                3445                3450

Thr Glu Val Glu Ala Leu Ser Ser Ala Asn Asp Ile Tyr Leu Ile
    3455                3460                3465

Phe Ala Glu Asn Val Phe Leu Gly Asp Gln Asn Ser Ile Asp Ile
    3470                3475                3480

Phe Ile Trp Glu Met Gly Gln Ser Ser Phe Arg Tyr Phe Gln Ser
    3485                3490                3495

Val Asp Phe Ala Ala Val Asn Arg Ile His Ser Phe Thr Pro Ala
    3500                3505                3510

Ser Gly Ile Ala His Ile Leu Leu Ile Gly Gln Asp Met Ser Ala
    3515                3520                3525

Leu Tyr Cys Trp Asn Ser Glu Arg Asn Gln Phe Ser Phe Val Leu
    3530                3535                3540

Glu Val Pro Ser Ala Tyr Asp Val Ala Ser Val Thr Val Lys Ser
    3545                3550                3555

Leu Asn Ser Ser Lys Asn Leu Ile Ala Leu Val Gly Ala His Ser
    3560                3565                3570
```

```
His Ile Tyr Glu Leu Ala Tyr Ile Ser Ser His Ser Asp Phe Ile
3575                3580                3585

Pro Ser Ser Gly Glu Leu Ile Phe Glu Pro Gly Glu Arg Glu Ala
3590                3595                3600

Thr Ile Ala Val Asn Ile Leu Asp Asp Thr Val Pro Glu Lys Glu
3605                3610                3615

Glu Ser Phe Lys Val Gln Leu Lys Asn Pro Lys Gly Gly Ala Glu
3620                3625                3630

Ile Gly Ile Asn Asp Ser Val Thr Ile Thr Ile Leu Ser Asn Asp
3635                3640                3645

Asp Ala Tyr Gly Ile Val Ala Phe Ala Gln Asn Ser Leu Tyr Lys
3650                3655                3660

Gln Val Glu Glu Met Glu Gln Asp Ser Leu Val Thr Leu Asn Val
3665                3670                3675

Glu Arg Leu Lys Gly Thr Tyr Gly Arg Ile Thr Ile Ala Trp Glu
3680                3685                3690

Ala Asp Gly Ser Ile Ser Asp Ile Phe Pro Thr Ser Gly Val Ile
3695                3700                3705

Leu Phe Thr Glu Gly Gln Val Leu Ser Thr Ile Thr Leu Thr Ile
3710                3715                3720

Leu Ala Asp Asn Ile Pro Glu Leu Ser Glu Val Val Ile Val Thr
3725                3730                3735

Leu Thr Arg Ile Thr Thr Glu Gly Val Glu Asp Ser Tyr Lys Gly
3740                3745                3750

Ala Thr Ile Asp Gln Asp Arg Ser Lys Ser Val Ile Thr Thr Leu
3755                3760                3765

Pro Asn Asp Ser Pro Phe Gly Leu Val Gly Trp Arg Ala Ala Ser
3770                3775                3780

Val Phe Ile Arg Val Ala Glu Pro Lys Glu Asn Thr Thr Thr Leu
3785                3790                3795

Gln Leu Gln Ile Ala Arg Asp Lys Gly Leu Leu Gly Asp Ile Ala
3800                3805                3810

Ile His Leu Arg Ala Gln Pro Asn Phe Leu Leu His Val Asp Asn
3815                3820                3825

Gln Ala Thr Glu Asn Glu Asp Tyr Val Leu Gln Glu Thr Ile Ile
3830                3835                3840

Ile Met Lys Glu Asn Ile Lys Glu Ala His Ala Glu Val Ser Ile
3845                3850                3855

Leu Pro Asp Asp Leu Pro Glu Leu Glu Glu Gly Phe Ile Val Thr
3860                3865                3870

Ile Thr Glu Val Asn Leu Val Asn Ser Asp Phe Ser Thr Gly Gln
3875                3880                3885

Pro Ser Val Arg Arg Pro Gly Met Glu Ile Ala Glu Ile Met Ile
3890                3895                3900

Glu Glu Asn Asp Asp Pro Arg Gly Ile Phe Met Phe His Val Thr
3905                3910                3915

Arg Gly Ala Gly Glu Val Ile Thr Ala Tyr Glu Val Pro Pro Pro
3920                3925                3930

Leu Asn Val Leu Gln Val Pro Val Val Arg Leu Ala Gly Ser Phe
3935                3940                3945

Gly Ala Val Asn Val Tyr Trp Lys Ala Ser Pro Asp Ser Ala Gly
3950                3955                3960

Leu Glu Asp Phe Lys Pro Ser His Gly Ile Leu Glu Phe Ala Asp
```

-continued

```
              3965                3970                3975
Lys  Gln  Val  Thr  Ala  Met  Ile  Glu  Ile  Thr  Ile  Ile  Asp  Asp  Ala
              3980                3985                3990

Glu  Phe  Glu  Leu  Thr  Glu  Thr  Phe  Asn  Ile  Ser  Leu  Ile  Ser  Val
              3995                4000                4005

Ala  Gly  Gly  Gly  Arg  Leu  Gly  Asp  Asp  Val  Val  Val  Thr  Val  Val
              4010                4015                4020

Ile  Pro  Gln  Asn  Asp  Ser  Pro  Phe  Gly  Val  Phe  Gly  Phe  Glu  Glu
              4025                4030                4035

Lys  Thr  Val  Met  Ile  Asp  Glu  Ser  Leu  Ser  Ser  Asp  Asp  Pro  Asp
              4040                4045                4050

Ser  Tyr  Val  Thr  Leu  Thr  Val  Val  Arg  Ser  Pro  Gly  Gly  Lys  Gly
              4055                4060                4065

Thr  Val  Arg  Leu  Glu  Trp  Thr  Ile  Asp  Glu  Lys  Ala  Lys  His  Asn
              4070                4075                4080

Leu  Ser  Pro  Leu  Asn  Gly  Thr  Leu  His  Phe  Asp  Glu  Thr  Glu  Ser
              4085                4090                4095

Gln  Lys  Thr  Ile  Val  Leu  His  Thr  Leu  Gln  Asp  Thr  Val  Leu  Glu
              4100                4105                4110

Glu  Asp  Arg  Arg  Phe  Thr  Ile  Gln  Leu  Ile  Ser  Ile  Asp  Glu  Val
              4115                4120                4125

Glu  Ile  Ser  Pro  Val  Lys  Gly  Ser  Ala  Ser  Ile  Ile  Ile  Arg  Gly
              4130                4135                4140

Asp  Lys  Arg  Ala  Ser  Gly  Glu  Val  Gly  Ile  Ala  Pro  Ser  Ser  Arg
              4145                4150                4155

His  Ile  Leu  Ile  Gly  Glu  Pro  Ser  Ala  Lys  Tyr  Asn  Gly  Thr  Ala
              4160                4165                4170

Ile  Ile  Ser  Leu  Val  Arg  Gly  Pro  Gly  Ile  Leu  Gly  Glu  Val  Thr
              4175                4180                4185

Val  Phe  Trp  Arg  Ile  Phe  Pro  Pro  Ser  Val  Gly  Glu  Phe  Ala  Glu
              4190                4195                4200

Thr  Ser  Gly  Lys  Leu  Thr  Met  Arg  Asp  Glu  Gln  Ser  Ala  Val  Ile
              4205                4210                4215

Val  Val  Ile  Gln  Ala  Leu  Asn  Asp  Asp  Ile  Pro  Glu  Glu  Lys  Ser
              4220                4225                4230

Phe  Tyr  Glu  Phe  Gln  Leu  Thr  Ala  Val  Ser  Glu  Gly  Gly  Val  Leu
              4235                4240                4245

Ser  Glu  Ser  Ser  Ser  Thr  Ala  Asn  Ile  Thr  Val  Val  Ala  Ser  Asp
              4250                4255                4260

Ser  Pro  Tyr  Gly  Arg  Phe  Ala  Phe  Ser  His  Glu  Gln  Leu  Arg  Val
              4265                4270                4275

Ser  Glu  Ala  Gln  Arg  Val  Asn  Ile  Thr  Ile  Ile  Arg  Ser  Ser  Gly
              4280                4285                4290

Asp  Phe  Gly  His  Val  Arg  Leu  Trp  Tyr  Lys  Thr  Met  Ser  Gly  Thr
              4295                4300                4305

Ala  Glu  Ala  Gly  Leu  Asp  Phe  Val  Pro  Ala  Ala  Gly  Glu  Leu  Leu
              4310                4315                4320

Phe  Glu  Ala  Gly  Glu  Met  Arg  Lys  Ser  Leu  His  Val  Glu  Ile  Leu
              4325                4330                4335

Asp  Asp  Asp  Tyr  Pro  Glu  Gly  Pro  Glu  Glu  Phe  Ser  Leu  Thr  Ile
              4340                4345                4350

Thr  Lys  Val  Glu  Leu  Gln  Gly  Arg  Gly  Tyr  Asp  Phe  Thr  Ile  Gln
              4355                4360                4365
```

```
Glu Asn Gly Leu Gln Ile Asp Gln Pro Pro Glu Ile Gly Asn Ile
    4370            4375            4380

Ser Ile Val Arg Ile Ile Ile Met Lys Asn Asp Asn Ala Glu Gly
    4385            4390            4395

Ile Ile Glu Phe Asp Pro Lys Tyr Thr Ala Phe Glu Val Glu Glu
    4400            4405            4410

Asp Val Gly Leu Ile Met Ile Pro Val Val Arg Leu His Gly Thr
    4415            4420            4425

Tyr Gly Tyr Val Thr Ala Asp Phe Ile Ser Gln Ser Ser Ser Ala
    4430            4435            4440

Ser Pro Gly Gly Val Asp Tyr Ile Leu His Gly Ser Thr Val Thr
    4445            4450            4455

Phe Gln His Gly Gln Asn Leu Ser Phe Ile Asn Ile Ser Ile Ile
    4460            4465            4470

Asp Asp Asn Glu Ser Glu Phe Glu Glu Pro Ile Glu Ile Leu Leu
    4475            4480            4485

Thr Gly Ala Thr Gly Gly Ala Val Leu Gly Arg His Leu Val Ser
    4490            4495            4500

Arg Ile Ile Ile Ala Lys Ser Asp Ser Pro Phe Gly Val Ile Arg
    4505            4510            4515

Phe Leu Asn Gln Ser Lys Ile Ser Ile Ala Asn Pro Asn Ser Thr
    4520            4525            4530

Met Ile Leu Ser Leu Val Leu Glu Arg Thr Gly Gly Leu Leu Gly
    4535            4540            4545

Glu Ile Gln Val Asn Trp Glu Thr Val Gly Pro Asn Ser Gln Glu
    4550            4555            4560

Ala Leu Leu Pro Gln Asn Arg Asp Ile Ala Asp Pro Val Ser Gly
    4565            4570            4575

Leu Phe Tyr Phe Gly Glu Gly Glu Gly Gly Val Arg Thr Ile Ile
    4580            4585            4590

Leu Thr Ile Tyr Pro His Glu Glu Ile Glu Val Glu Glu Thr Phe
    4595            4600            4605

Ile Ile Lys Leu His Leu Val Lys Gly Glu Ala Lys Leu Asp Ser
    4610            4615            4620

Arg Ala Lys Asp Val Thr Leu Thr Ile Gln Glu Phe Gly Asp Pro
    4625            4630            4635

Asn Gly Val Val Gln Phe Ala Pro Glu Thr Leu Ser Lys Lys Thr
    4640            4645            4650

Tyr Ser Glu Pro Leu Ala Leu Glu Gly Pro Leu Leu Ile Thr Phe
    4655            4660            4665

Phe Val Arg Arg Val Lys Gly Thr Phe Gly Glu Ile Met Val Tyr
    4670            4675            4680

Trp Glu Leu Ser Ser Glu Phe Asp Ile Thr Glu Asp Phe Leu Ser
    4685            4690            4695

Thr Ser Gly Phe Phe Thr Ile Ala Asp Gly Glu Ser Glu Ala Ser
    4700            4705            4710

Phe Asp Val His Leu Leu Pro Asp Glu Val Pro Glu Ile Glu Glu
    4715            4720            4725

Asp Tyr Val Ile Gln Leu Val Ser Val Glu Gly Gly Ala Glu Leu
    4730            4735            4740

Asp Leu Glu Lys Ser Ile Thr Trp Phe Ser Val Tyr Ala Asn Asp
    4745            4750            4755
```

```
Asp Pro His Gly Val Phe Ala Leu Tyr Ser Asp Arg   Gln Ser Ile
4760                4765                4770

Leu Ile Gly Gln Asn Leu Ile Arg Ser Ile Gln Ile   Asn Ile Thr
4775                4780                4785

Arg Leu Ala Gly Thr Phe Gly Asp Val Ala Val Gly   Leu Arg Ile
4790                4795                4800

Ser Ser Asp His Lys Glu Gln Pro Ile Val Thr Glu   Asn Ala Glu
4805                4810                4815

Arg Gln Leu Val Val Lys Asp Gly Ala Thr Tyr Lys   Val Asp Val
4820                4825                4830

Val Pro Ile Lys Asn Gln Val Phe Leu Ser Leu Gly   Ser Asn Phe
4835                4840                4845

Thr Leu Gln Leu Val Thr Val Met Leu Val Gly Gly   Arg Phe Tyr
4850                4855                4860

Gly Met Pro Thr Ile Leu Gln Glu Ala Lys Ser Ala   Val Leu Pro
4865                4870                4875

Val Ser Glu Lys Ala Ala Asn Ser Gln Val Gly Phe   Glu Ser Thr
4880                4885                4890

Ala Phe Gln Leu Met Asn Ile Thr Ala Gly Thr Ser   His Val Met
4895                4900                4905

Ile Ser Arg Arg Gly Thr Tyr Gly Ala Leu Ser Val   Ala Trp Thr
4910                4915                4920

Thr Gly Tyr Ala Pro Gly Leu Glu Ile Pro Glu Phe   Ile Val Val
4925                4930                4935

Gly Asn Met Thr Pro Thr Leu Gly Ser Leu Ser Phe   Ser His Gly
4940                4945                4950

Glu Gln Arg Lys Gly Val Phe Leu Trp Thr Phe Pro   Ser Pro Gly
4955                4960                4965

Trp Pro Glu Ala Phe Val Leu His Leu Ser Gly Val   Gln Ser Ser
4970                4975                4980

Ala Pro Gly Gly Ala Gln Leu Arg Ser Gly Phe Ile   Val Ala Glu
4985                4990                4995

Ile Glu Pro Met Gly Val Phe Gln Phe Ser Thr Ser   Ser Arg Asn
5000                5005                5010

Ile Ile Val Ser Glu Asp Thr Gln Met Ile Arg Leu   His Val Gln
5015                5020                5025

Arg Leu Phe Gly Phe His Ser Asp Leu Ile Lys Val   Ser Tyr Gln
5030                5035                5040

Thr Thr Ala Gly Ser Ala Lys Pro Leu Glu Asp Phe   Glu Pro Val
5045                5050                5055

Gln Asn Gly Glu Leu Phe Gln Lys Phe Gln Thr       Glu Val Asp
5060                5065                5070

Phe Glu Ile Thr Ile Ile Asn Asp Gln Leu Ser Glu   Ile Glu Glu
5075                5080                5085

Phe Phe Tyr Ile Asn Leu Thr Ser Val Glu Ile Arg   Gly Leu Gln
5090                5095                5100

Lys Phe Asp Val Asn Trp Ser Pro Arg Leu Asn Leu   Asp Phe Ser
5105                5110                5115

Val Ala Val Ile Thr Ile Leu Asp Asn Asp Asp Leu   Ala Gly Met
5120                5125                5130

Asp Ile Ser Phe Pro Glu Thr Thr Val Ala Val Ala   Val Asp Thr
5135                5140                5145

Thr Leu Ile Pro Val Glu Thr Glu Ser Thr Thr Tyr   Leu Ser Thr
```

```
                5150                5155                5160

Ser Lys Thr Thr Thr Ile Leu Gln Pro Thr Asn Val Val Ala Ile
    5165                5170                5175

Val Thr Glu Ala Thr Gly Val Ser Ala Ile Pro Glu Lys Leu Val
    5180                5185                5190

Thr Leu His Gly Thr Pro Ala Val Ser Glu Lys Pro Asp Val Ala
    5195                5200                5205

Thr Val Thr Ala Asn Val Ser Ile His Gly Thr Phe Ser Leu Gly
    5210                5215                5220

Pro Ser Ile Val Tyr Ile Glu Glu Met Lys Asn Gly Thr Phe
    5225                5230                5235

Asn Thr Ala Glu Val Leu Ile Arg Arg Thr Gly Gly Phe Thr Gly
    5240                5245                5250

Asn Val Ser Ile Thr Val Lys Thr Phe Gly Glu Arg Cys Ala Gln
    5255                5260                5265

Met Glu Pro Asn Ala Leu Pro Phe Arg Gly Ile Tyr Gly Ile Ser
    5270                5275                5280

Asn Leu Thr Trp Ala Val Glu Glu Asp Phe Glu Glu Gln Thr
    5285                5290                5295

Leu Thr Leu Ile Phe Leu Asp Gly Glu Arg Glu Arg Lys Val Ser
    5300                5305                5310

Val Gln Ile Leu Asp Asp Glu Pro Glu Gly Gln Glu Phe Phe
    5315                5320                5325

Tyr Val Phe Leu Thr Asn Pro Gln Gly Gly Ala Gln Ile Val Glu
    5330                5335                5340

Glu Lys Asp Asp Thr Gly Phe Ala Ala Phe Ala Met Val Ile Ile
    5345                5350                5355

Thr Gly Ser Asp Leu His Asn Gly Ile Ile Gly Phe Ser Glu Glu
    5360                5365                5370

Ser Gln Ser Gly Leu Glu Leu Arg Glu Gly Ala Val Met Arg Arg
    5375                5380                5385

Leu His Leu Ile Val Thr Arg Gln Pro Asn Arg Ala Phe Glu Asp
    5390                5395                5400

Val Lys Val Phe Trp Arg Val Thr Leu Asn Lys Thr Val Val Val
    5405                5410                5415

Leu Gln Lys Asp Gly Val Asn Leu Val Glu Glu Leu Gln Ser Val
    5420                5425                5430

Ser Gly Thr Thr Thr Cys Thr Met Gly Gln Thr Lys Cys Phe Ile
    5435                5440                5445

Ser Ile Glu Leu Lys Pro Glu Lys Val Pro Gln Val Glu Val Tyr
    5450                5455                5460

Phe Phe Val Glu Leu Tyr Glu Ala Thr Ala Gly Ala Ala Ile Asn
    5465                5470                5475

Asn Ser Ala Arg Phe Ala Gln Ile Lys Ile Leu Glu Ser Asp Glu
    5480                5485                5490

Ser Gln Ser Leu Val Tyr Phe Ser Val Gly Ser Arg Leu Ala Val
    5495                5500                5505

Ala His Lys Lys Ala Thr Leu Ile Ser Leu Gln Val Ala Arg Asp
    5510                5515                5520

Ser Gly Thr Gly Leu Met Met Ser Val Asn Phe Ser Thr Gln Glu
    5525                5530                5535

Leu Arg Ser Ala Glu Thr Ile Gly Arg Thr Ile Ile Ser Pro Ala
    5540                5545                5550
```

```
Ile Ser Gly Lys Asp Phe Val Ile Thr Glu Gly Thr Leu Val Phe
5555                5560                5565

Glu Pro Gly Gln Arg Ser Thr Val Leu Asp Val Ile Leu Thr Pro
5570                5575                5580

Glu Thr Gly Ser Leu Asn Ser Phe Pro Lys Arg Phe Gln Ile Val
5585                5590                5595

Leu Phe Asp Pro Lys Gly Gly Ala Arg Ile Asp Lys Val Tyr Gly
5600                5605                5610

Thr Ala Asn Ile Thr Leu Val Ser Asp Ala Asp Ser Gln Ala Ile
5615                5620                5625

Trp Gly Leu Ala Asp Gln Leu His Gln Pro Val Asn Asp Asp Ile
5630                5635                5640

Leu Asn Arg Val Leu His Thr Ile Ser Met Lys Val Ala Thr Glu
5645                5650                5655

Asn Thr Asp Glu Gln Leu Ser Ala Met Met His Leu Ile Glu Lys
5660                5665                5670

Ile Thr Thr Glu Gly Lys Ile Gln Ala Phe Ser Val Ala Ser Arg
5675                5680                5685

Thr Leu Phe Tyr Glu Ile Leu Cys Ser Leu Ile Asn Pro Lys Arg
5690                5695                5700

Lys Asp Thr Arg Gly Phe Ser His Phe Ala Glu Val Thr Glu Asn
5705                5710                5715

Phe Ala Phe Ser Leu Leu Thr Asn Val Thr Cys Gly Ser Pro Gly
5720                5725                5730

Glu Lys Ser Lys Thr Ile Leu Asp Ser Cys Pro Tyr Leu Ser Ile
5735                5740                5745

Leu Ala Leu His Trp Tyr Pro Gln Gln Ile Asn Gly His Lys Phe
5750                5755                5760

Glu Gly Lys Glu Gly Asp Tyr Ile Arg Ile Pro Glu Arg Leu Leu
5765                5770                5775

Asp Val Gln Asp Ala Glu Ile Met Ala Gly Lys Ser Thr Cys Lys
5780                5785                5790

Leu Val Gln Phe Thr Glu Tyr Ser Ser Gln Gln Trp Phe Ile Ser
5795                5800                5805

Gly Asn Asn Leu Pro Thr Leu Lys Asn Lys Val Leu Ser Leu Ser
5810                5815                5820

Val Lys Gly Gln Ser Ser Gln Leu Leu Thr Asn Asp Asn Glu Val
5825                5830                5835

Leu Tyr Arg Ile Tyr Ala Ala Glu Pro Arg Ile Ile Pro Gln Thr
5840                5845                5850

Ser Leu Cys Leu Leu Trp Asn Gln Ala Ala Ser Trp Leu Ser
5855                5860                5865

Asp Ser Gln Phe Cys Lys Val Val Glu Glu Thr Ala Asp Tyr Val
5870                5875                5880

Glu Cys Ala Cys Ser His Met Ser Val Tyr Ala Val Tyr Ala Arg
5885                5890                5895

Thr Asp Asn Leu Ser Ser Tyr Asn Glu Ala Phe Phe Thr Ser Gly
5900                5905                5910

Phe Ile Cys Ile Ser Gly Leu Cys Leu Ala Val Leu Ser His Ile
5915                5920                5925

Phe Cys Ala Arg Tyr Ser Met Phe Ala Ala Lys Leu Leu Thr His
5930                5935                5940
```

Met Met Ala Ala Ser Leu Gly Thr Gln Ile Leu Phe Leu Ala Ser
5945                5950                5955

Ala Tyr Ala Ser Pro Gln Leu Ala Glu Glu Ser Cys Ser Ala Met
5960                5965                5970

Ala Ala Val Thr His Tyr Leu Tyr Leu Cys Gln Phe Ser Trp Met
5975                5980                5985

Leu Ile Gln Ser Val Asn Phe Trp Tyr Val Leu Val Met Asn Asp
5990                5995                6000

Glu His Thr Glu Arg Arg Tyr Leu Leu Phe Phe Leu Leu Ser Trp
6005                6010                6015

Gly Leu Pro Ala Phe Val Val Ile Leu Leu Ile Val Ile Leu Lys
6020                6025                6030

Gly Ile Tyr His Gln Ser Met Ser Gln Ile Tyr Gly Leu Ile His
6035                6040                6045

Gly Asp Leu Cys Phe Ile Pro Asn Val Tyr Ala Ala Leu Phe Thr
6050                6055                6060

Ala Ala Leu Val Pro Leu Thr Cys Leu Val Val Phe Val Val
6065                6070                6075

Phe Ile His Ala Tyr Gln Val Lys Pro Gln Trp Lys Ala Tyr Asp
6080                6085                6090

Asp Val Phe Arg Gly Arg Thr Asn Ala Ala Glu Ile Pro Leu Ile
6095                6100                6105

Leu Tyr Leu Phe Ala Leu Ile Ser Val Thr Trp Leu Trp Gly Gly
6110                6115                6120

Leu His Met Ala Tyr Arg His Phe Trp Met Leu Val Leu Phe Val
6125                6130                6135

Ile Phe Asn Ser Leu Gln Gly Leu Tyr Val Phe Met Val Tyr Phe
6140                6145                6150

Ile Leu His Asn Gln Met Cys Cys Pro Met Lys Ala Ser Tyr Thr
6155                6160                6165

Val Glu Met Asn Gly His Pro Gly Pro Ser Thr Ala Phe Phe Thr
6170                6175                6180

Pro Gly Ser Gly Met Pro Pro Ala Gly Gly Glu Ile Ser Lys Ser
6185                6190                6195

Thr Gln Asn Leu Ile Gly Ala Met Glu Glu Val Pro Pro Asp Trp
6200                6205                6210

Glu Arg Ala Ser Phe Gln Gln Gly Ser Gln Ala Ser Pro Asp Leu
6215                6220                6225

Lys Pro Ser Pro Gln Asn Gly Ala Thr Phe Pro Ser Ser Gly Gly
6230                6235                6240

Tyr Gly Gln Gly Ser Leu Ile Ala Asp Glu Glu Ser Gln Glu Phe
6245                6250                6255

Asp Asp Leu Ile Phe Ala Leu Lys Thr Gly Ala Gly Leu Ser Val
6260                6265                6270

Ser Asp Asn Glu Ser Gly Gln Gly Ser Gln Glu Gly Gly Thr Leu
6275                6280                6285

Thr Asp Ser Gln Ile Val Glu Leu Arg Arg Ile Pro Ile Ala Asp
6290                6295                6300

Thr His Leu
6305

<210> SEQ ID NO 22
<211> LENGTH: 201
<212> TYPE: PRT

```
<213> ORGANISM: Homo sapiens
<220> FEATURE:
<221> NAME/KEY: MISC_FEATURE
<222> LOCATION: (1)..(201)
<223> OTHER INFORMATION: GUCA1A (guanylyl cyclase-activating protein 1)

<400> SEQUENCE: 22

Met Gly Asn Val Met Glu Gly Lys Ser Val Glu Glu Leu Ser Ser Thr
1               5                   10                  15

Glu Cys His Gln Trp Tyr Lys Lys Phe Met Thr Glu Cys Pro Ser Gly
            20                  25                  30

Gln Leu Thr Leu Tyr Glu Phe Arg Gln Phe Phe Gly Leu Lys Asn Leu
        35                  40                  45

Ser Pro Ser Ala Ser Gln Tyr Val Glu Gln Met Phe Glu Thr Phe Asp
    50                  55                  60

Phe Asn Lys Asp Gly Tyr Ile Asp Phe Met Glu Tyr Val Ala Ala Leu
65                  70                  75                  80

Ser Leu Val Leu Lys Gly Lys Val Glu Gln Lys Leu Arg Trp Tyr Phe
                85                  90                  95

Lys Leu Tyr Asp Val Asp Gly Asn Gly Cys Ile Asp Arg Asp Glu Leu
            100                 105                 110

Leu Thr Ile Ile Gln Ala Ile Arg Ala Ile Asn Pro Cys Ser Asp Thr
        115                 120                 125

Thr Met Thr Ala Glu Glu Phe Thr Asp Thr Val Phe Ser Lys Ile Asp
    130                 135                 140

Val Asn Gly Asp Gly Glu Leu Ser Leu Glu Glu Phe Ile Glu Gly Val
145                 150                 155                 160

Gln Lys Asp Gln Met Leu Leu Asp Thr Leu Thr Arg Ser Leu Asp Leu
                165                 170                 175

Thr Arg Ile Val Arg Arg Leu Gln Asn Gly Glu Gln Asp Glu Glu Gly
            180                 185                 190

Ala Asp Glu Ala Ala Glu Ala Ala Gly
        195                 200

<210> SEQ ID NO 23
<211> LENGTH: 200
<212> TYPE: PRT
<213> ORGANISM: Homo sapiens
<220> FEATURE:
<221> NAME/KEY: MISC_FEATURE
<222> LOCATION: (1)..(200)
<223> OTHER INFORMATION: GUCA1B (guanylyl cyclase-activating protein 2)

<400> SEQUENCE: 23

Met Gly Gln Glu Phe Ser Trp Glu Glu Ala Glu Ala Gly Glu Ile
1               5                   10                  15

Asp Val Ala Glu Leu Gln Glu Trp Tyr Lys Lys Phe Val Met Glu Cys
            20                  25                  30

Pro Ser Gly Thr Leu Phe Met His Glu Phe Lys Arg Phe Phe Lys Val
        35                  40                  45

Thr Asp Asp Glu Glu Ala Ser Gln Tyr Val Glu Gly Met Phe Arg Ala
    50                  55                  60

Phe Asp Lys Asn Gly Asp Asn Thr Ile Asp Phe Leu Glu Tyr Val Ala
65                  70                  75                  80

Ala Leu Asn Leu Val Leu Arg Gly Thr Leu Glu His Lys Leu Lys Trp
                85                  90                  95

Thr Phe Lys Ile Tyr Asp Lys Asp Gly Asn Gly Cys Ile Asp Arg Leu
            100                 105                 110
```

-continued

```
Glu Leu Leu Asn Ile Val Glu Gly Ile Tyr Gln Leu Lys Lys Ala Cys
            115                 120                 125

Arg Arg Glu Leu Gln Thr Glu Gln Gly Gln Leu Leu Thr Pro Glu Glu
        130                 135                 140

Val Val Asp Arg Ile Phe Leu Leu Val Asp Glu Asn Gly Asp Gly Gln
145                 150                 155                 160

Leu Ser Leu Asn Glu Phe Val Glu Gly Ala Arg Arg Asp Lys Trp Val
                165                 170                 175

Met Lys Met Leu Gln Met Asp Met Asn Pro Ser Ser Trp Leu Ala Gln
            180                 185                 190

Gln Arg Arg Lys Ser Ala Met Phe
        195                 200
```

<210> SEQ ID NO 24
<211> LENGTH: 2213
<212> TYPE: PRT
<213> ORGANISM: Homo sapiens
<220> FEATURE:
<221> NAME/KEY: MISC_FEATURE
<222> LOCATION: (1)..(2213)
<223> OTHER INFORMATION: MYO7A (unconventional myosin-VIIa), isoform 1

<400> SEQUENCE: 24

```
Met Val Ile Leu Gln Gln Gly Asp His Val Trp Met Asp Leu Arg Leu
1               5                   10                  15

Gly Gln Glu Phe Asp Val Pro Ile Gly Ala Val Val Lys Leu Cys Asp
            20                  25                  30

Ser Gly Gln Val Gln Val Val Asp Asp Glu Asp Asn Glu His Trp Ile
        35                  40                  45

Ser Pro Gln Asn Ala Thr His Ile Lys Pro Met His Pro Thr Ser Val
    50                  55                  60

His Gly Val Glu Asp Met Ile Arg Leu Gly Asp Leu Asn Glu Ala Gly
65                  70                  75                  80

Ile Leu Arg Asn Leu Leu Ile Arg Tyr Arg Asp His Leu Ile Tyr Thr
                85                  90                  95

Tyr Thr Gly Ser Ile Leu Val Ala Val Asn Pro Tyr Gln Leu Leu Ser
            100                 105                 110

Ile Tyr Ser Pro Glu His Ile Arg Gln Tyr Thr Asn Lys Lys Ile Gly
        115                 120                 125

Glu Met Pro Pro His Ile Phe Ala Ile Ala Asp Asn Cys Tyr Phe Asn
    130                 135                 140

Met Lys Arg Asn Ser Arg Asp Gln Cys Cys Ile Ile Ser Gly Glu Ser
145                 150                 155                 160

Gly Ala Gly Lys Thr Glu Ser Thr Lys Leu Ile Leu Gln Phe Leu Ala
                165                 170                 175

Ala Ile Ser Gly Gln His Ser Trp Ile Glu Gln Gln Val Leu Glu Ala
            180                 185                 190

Thr Pro Ile Leu Glu Ala Phe Gly Asn Ala Lys Thr Ile Arg Asn Asp
        195                 200                 205

Asn Ser Ser Arg Phe Gly Lys Tyr Ile Asp Ile His Phe Asn Lys Arg
    210                 215                 220

Gly Ala Ile Glu Gly Ala Lys Ile Glu Gln Tyr Leu Leu Glu Lys Ser
225                 230                 235                 240

Arg Val Cys Arg Gln Ala Leu Asp Glu Arg Asn Tyr His Val Phe Tyr
                245                 250                 255
```

```
Cys Met Leu Glu Gly Met Ser Glu Asp Gln Lys Lys Leu Gly Leu
                260                 265                 270

Gly Gln Ala Ser Asp Tyr Asn Tyr Leu Ala Met Gly Asn Cys Ile Thr
            275                 280                 285

Cys Glu Gly Arg Val Asp Ser Gln Glu Tyr Ala Asn Ile Arg Ser Ala
        290                 295                 300

Met Lys Val Leu Met Phe Thr Asp Thr Glu Asn Trp Glu Ile Ser Lys
305                 310                 315                 320

Leu Leu Ala Ala Ile Leu His Leu Gly Asn Leu Gln Tyr Glu Ala Arg
                325                 330                 335

Thr Phe Glu Asn Leu Asp Ala Cys Glu Val Leu Phe Ser Pro Ser Leu
            340                 345                 350

Ala Thr Ala Ala Ser Leu Leu Glu Val Asn Pro Pro Asp Leu Met Ser
        355                 360                 365

Cys Leu Thr Ser Arg Thr Leu Ile Thr Arg Gly Glu Thr Val Ser Thr
370                 375                 380

Pro Leu Ser Arg Glu Gln Ala Leu Asp Val Arg Asp Ala Phe Val Lys
385                 390                 395                 400

Gly Ile Tyr Gly Arg Leu Phe Val Trp Ile Val Asp Lys Ile Asn Ala
                405                 410                 415

Ala Ile Tyr Lys Pro Pro Ser Gln Asp Val Lys Asn Ser Arg Arg Ser
            420                 425                 430

Ile Gly Leu Leu Asp Ile Phe Gly Phe Glu Asn Phe Ala Val Asn Ser
        435                 440                 445

Phe Glu Gln Leu Cys Ile Asn Phe Ala Asn Glu His Leu Gln Gln Phe
450                 455                 460

Phe Val Arg His Val Phe Lys Leu Glu Gln Glu Glu Tyr Asp Leu Glu
465                 470                 475                 480

Ser Ile Asp Trp Leu His Ile Glu Phe Thr Asp Asn Gln Asp Ala Leu
                485                 490                 495

Asp Met Ile Ala Asn Lys Pro Met Asn Ile Ile Ser Leu Ile Asp Glu
            500                 505                 510

Glu Ser Lys Phe Pro Lys Gly Thr Asp Thr Thr Met Leu His Lys Leu
        515                 520                 525

Asn Ser Gln His Lys Leu Asn Ala Asn Tyr Ile Pro Pro Lys Asn Asn
530                 535                 540

His Glu Thr Gln Phe Gly Ile Asn His Phe Ala Gly Ile Val Tyr Tyr
545                 550                 555                 560

Glu Thr Gln Gly Phe Leu Glu Lys Asn Arg Asp Thr Leu His Gly Asp
                565                 570                 575

Ile Ile Gln Leu Val His Ser Ser Arg Asn Lys Phe Ile Lys Gln Ile
            580                 585                 590

Phe Gln Ala Asp Val Ala Met Gly Ala Glu Thr Arg Lys Arg Ser Pro
        595                 600                 605

Thr Leu Ser Ser Gln Phe Lys Arg Ser Leu Glu Leu Leu Met Arg Thr
610                 615                 620

Leu Gly Ala Cys Gln Pro Phe Phe Val Arg Cys Ile Lys Pro Asn Glu
625                 630                 635                 640

Phe Lys Lys Pro Met Leu Phe Asp Arg His Leu Cys Val Arg Gln Leu
                645                 650                 655

Arg Tyr Ser Gly Met Met Glu Thr Ile Arg Ile Arg Arg Ala Gly Tyr
            660                 665                 670

Pro Ile Arg Tyr Ser Phe Val Glu Phe Val Glu Arg Tyr Arg Val Leu
```

```
                    675                 680                 685
Leu Pro Gly Val Lys Pro Ala Tyr Lys Gln Gly Asp Leu Arg Gly Thr
690                 695                 700

Cys Gln Arg Met Ala Glu Ala Val Leu Gly Thr His Asp Asp Trp Gln
705                 710                 715                 720

Ile Gly Lys Thr Lys Ile Phe Leu Lys Asp His His Asp Met Leu Leu
                    725                 730                 735

Glu Val Glu Arg Asp Lys Ala Ile Thr Asp Arg Val Ile Leu Leu Gln
                740                 745                 750

Lys Val Ile Arg Gly Phe Lys Asp Arg Ser Asn Phe Leu Lys Leu Lys
            755                 760                 765

Asn Ala Ala Thr Leu Ile Gln Arg His Trp Arg Gly His Asn Cys Arg
770                 775                 780

Lys Asn Tyr Gly Leu Met Arg Leu Gly Phe Leu Arg Leu Gln Ala Leu
785                 790                 795                 800

His Arg Ser Arg Lys Leu His Gln Gln Tyr Arg Leu Ala Arg Gln Arg
                805                 810                 815

Ile Ile Gln Phe Gln Ala Arg Cys Arg Ala Tyr Leu Val Arg Lys Ala
                820                 825                 830

Phe Arg His Arg Leu Trp Ala Val Leu Thr Val Gln Ala Tyr Ala Arg
                835                 840                 845

Gly Met Ile Ala Arg Arg Leu His Gln Arg Leu Arg Ala Glu Tyr Leu
850                 855                 860

Trp Arg Leu Glu Ala Glu Lys Met Arg Leu Ala Glu Glu Lys Leu
865                 870                 875                 880

Arg Lys Glu Met Ser Ala Lys Lys Ala Lys Glu Ala Glu Arg Lys
                885                 890                 895

His Gln Glu Arg Leu Ala Gln Leu Ala Arg Glu Asp Ala Glu Arg Glu
                900                 905                 910

Leu Lys Glu Lys Glu Ala Ala Arg Arg Lys Glu Leu Leu Glu Gln
                915                 920                 925

Met Glu Arg Ala Arg His Glu Pro Val Asn His Ser Asp Met Val Asp
930                 935                 940

Lys Met Phe Gly Phe Leu Gly Thr Ser Gly Gly Leu Pro Gly Gln Glu
945                 950                 955                 960

Gly Gln Ala Pro Ser Gly Phe Glu Asp Leu Glu Arg Gly Arg Arg Glu
                965                 970                 975

Met Val Glu Glu Asp Leu Asp Ala Ala Leu Pro Leu Pro Asp Glu Asp
                980                 985                 990

Glu Glu Asp Leu Ser Glu Tyr Lys Phe Ala Lys Phe Ala Ala Thr Tyr
                995                 1000                1005

Phe Gln Gly Thr Thr Thr His Ser Tyr Thr Arg Arg Pro Leu Lys
    1010                1015                1020

Gln Pro Leu Leu Tyr His Asp Asp Glu Gly Asp Gln Leu Ala Ala
    1025                1030                1035

Leu Ala Val Trp Ile Thr Ile Leu Arg Phe Met Gly Asp Leu Pro
    1040                1045                1050

Glu Pro Lys Tyr His Thr Ala Met Ser Asp Gly Ser Glu Lys Ile
    1055                1060                1065

Pro Val Met Thr Lys Ile Tyr Glu Thr Leu Gly Lys Lys Thr Tyr
    1070                1075                1080

Lys Arg Glu Leu Gln Ala Leu Gln Gly Glu Gly Glu Ala Gln Leu
    1085                1090                1095
```

-continued

Pro Glu Gly Gln Lys Lys Ser  Ser Val Arg His Lys  Leu Val His
    1100              1105               1110

Leu Thr Leu Lys Lys Lys Ser  Lys Leu Thr Glu Glu  Val Thr Lys
    1115              1120               1125

Arg Leu His Asp Gly Glu Ser  Thr Val Gln Gly Asn  Ser Met Leu
    1130              1135               1140

Glu Asp Arg Pro Thr Ser Asn  Leu Glu Lys Leu His  Phe Ile Ile
    1145              1150               1155

Gly Asn Gly Ile Leu Arg Pro  Ala Leu Arg Asp Glu  Ile Tyr Cys
    1160              1165               1170

Gln Ile Ser Lys Gln Leu Thr  His Asn Pro Ser Lys  Ser Ser Tyr
    1175              1180               1185

Ala Arg Gly Trp Ile Leu Val  Ser Leu Cys Val Gly  Cys Phe Ala
    1190              1195               1200

Pro Ser Glu Lys Phe Val Lys  Tyr Leu Arg Asn Phe  Ile His Gly
    1205              1210               1215

Gly Pro Pro Gly Tyr Ala Pro  Tyr Cys Glu Glu Arg  Leu Arg Arg
    1220              1225               1230

Thr Phe Val Asn Gly Thr Arg  Thr Gln Pro Pro Ser  Trp Leu Glu
    1235              1240               1245

Leu Gln Ala Thr Lys Ser Lys  Lys Pro Ile Met Leu  Pro Val Thr
    1250              1255               1260

Phe Met Asp Gly Thr Thr Lys  Thr Leu Leu Thr Asp  Ser Ala Thr
    1265              1270               1275

Thr Ala Lys Glu Leu Cys Asn  Ala Leu Ala Asp Lys  Ile Ser Leu
    1280              1285               1290

Lys Asp Arg Phe Gly Phe Ser  Leu Tyr Ile Ala Leu  Phe Asp Lys
    1295              1300               1305

Val Ser Ser Leu Gly Ser Gly  Ser Asp His Val Met  Asp Ala Ile
    1310              1315               1320

Ser Gln Cys Glu Gln Tyr Ala  Lys Glu Gln Gly Ala  Gln Glu Arg
    1325              1330               1335

Asn Ala Pro Trp Arg Leu Phe  Phe Arg Lys Glu Val  Phe Thr Pro
    1340              1345               1350

Trp His Ser Pro Ser Glu Asp  Asn Val Ala Thr Asn  Leu Ile Tyr
    1355              1360               1365

Gln Gln Val Val Arg Gly Val  Lys Phe Gly Glu Tyr  Arg Cys Glu
    1370              1375               1380

Lys Glu Asp Asp Leu Ala Glu  Leu Ala Ser Gln Gln  Tyr Phe Val
    1385              1390               1395

Asp Tyr Gly Ser Glu Met Ile  Leu Glu Arg Leu Leu  Asn Leu Val
    1400              1405               1410

Pro Thr Tyr Ile Pro Asp Arg  Glu Ile Thr Pro Leu  Lys Thr Leu
    1415              1420               1425

Glu Lys Trp Ala Gln Leu Ala  Ile Ala Ala His Lys  Lys Gly Ile
    1430              1435               1440

Tyr Ala Gln Arg Arg Thr Asp  Ala Gln Lys Val Lys  Glu Asp Val
    1445              1450               1455

Val Ser Tyr Ala Arg Phe Lys  Trp Pro Leu Leu Phe  Ser Arg Phe
    1460              1465               1470

Tyr Glu Ala Tyr Lys Phe Ser  Gly Pro Ser Leu Pro  Lys Asn Asp
    1475              1480               1485

Val Ile Val Ala Val Asn Trp Thr Gly Val Tyr Phe Val Asp Glu
    1490            1495            1500

Gln Glu Gln Val Leu Leu Glu Leu Ser Phe Pro Glu Ile Met Ala
1505            1510            1515

Val Ser Ser Ser Arg Glu Cys Arg Val Trp Leu Ser Leu Gly Cys
1520            1525            1530

Ser Asp Leu Gly Cys Ala Ala Pro His Ser Gly Trp Ala Gly Leu
1535            1540            1545

Thr Pro Ala Gly Pro Cys Ser Pro Cys Trp Ser Cys Arg Gly Ala
1550            1555            1560

Lys Thr Thr Ala Pro Ser Phe Thr Leu Ala Thr Ile Lys Gly Asp
1565            1570            1575

Glu Tyr Thr Phe Thr Ser Ser Asn Ala Glu Asp Ile Arg Asp Leu
1580            1585            1590

Val Val Thr Phe Leu Glu Gly Leu Arg Lys Arg Ser Lys Tyr Val
1595            1600            1605

Val Ala Leu Gln Asp Asn Pro Asn Pro Ala Gly Glu Glu Ser Gly
1610            1615            1620

Phe Leu Ser Phe Ala Lys Gly Asp Leu Ile Ile Leu Asp His Asp
1625            1630            1635

Thr Gly Glu Gln Val Met Asn Ser Gly Trp Ala Asn Gly Ile Asn
1640            1645            1650

Glu Arg Thr Lys Gln Arg Gly Asp Phe Pro Thr Asp Ser Val Tyr
1655            1660            1665

Val Met Pro Thr Val Thr Met Pro Pro Arg Glu Ile Val Ala Leu
1670            1675            1680

Val Thr Met Thr Pro Asp Gln Arg Gln Asp Val Val Arg Leu Leu
1685            1690            1695

Gln Leu Arg Thr Ala Glu Pro Glu Val Arg Ala Lys Pro Tyr Thr
1700            1705            1710

Leu Glu Glu Phe Ser Tyr Asp Tyr Phe Arg Pro Pro Pro Lys His
1715            1720            1725

Thr Leu Ser Arg Val Met Val Ser Lys Ala Arg Gly Lys Asp Arg
1730            1735            1740

Leu Trp Ser His Thr Arg Glu Pro Leu Lys Gln Ala Leu Leu Lys
1745            1750            1755

Lys Leu Leu Gly Ser Glu Glu Leu Ser Gln Glu Ala Cys Leu Ala
1760            1765            1770

Phe Ile Ala Val Leu Lys Tyr Met Gly Asp Tyr Pro Ser Lys Arg
1775            1780            1785

Thr Arg Ser Val Asn Glu Leu Thr Asp Gln Ile Phe Glu Gly Pro
1790            1795            1800

Leu Lys Ala Glu Pro Leu Lys Asp Glu Ala Tyr Val Gln Ile Leu
1805            1810            1815

Lys Gln Leu Thr Asp Asn His Ile Arg Tyr Ser Glu Glu Arg Gly
1820            1825            1830

Trp Glu Leu Leu Trp Leu Cys Thr Gly Leu Phe Pro Pro Ser Asn
1835            1840            1845

Ile Leu Leu Pro His Val Gln Arg Phe Leu Gln Ser Arg Lys His
1850            1855            1860

Cys Pro Leu Ala Ile Asp Cys Leu Gln Arg Leu Gln Lys Ala Leu
1865            1870            1875

Arg Asn Gly Ser Arg Lys Tyr Pro Pro His Leu Val Glu Val Glu 1880                1885                1890

Ala Ile Gln His Lys Thr Thr Gln Ile Phe His Lys Val Tyr Phe
        1895                1900                1905

Pro Asp Asp Thr Asp Glu Ala Phe Glu Val Glu Ser Ser Thr Lys
        1910                1915                1920

Ala Lys Asp Phe Cys Gln Asn Ile Ala Thr Arg Leu Leu Leu Lys
        1925                1930                1935

Ser Ser Glu Gly Phe Ser Leu Phe Val Lys Ile Ala Asp Lys Val
        1940                1945                1950

Leu Ser Val Pro Glu Asn Asp Phe Phe Asp Phe Val Arg His
        1955                1960                1965

Leu Thr Asp Trp Ile Lys Lys Ala Arg Pro Ile Lys Asp Gly Ile
        1970                1975                1980

Val Pro Ser Leu Thr Tyr Gln Val Phe Phe Met Lys Lys Leu Trp
        1985                1990                1995

Thr Thr Thr Val Pro Gly Lys Asp Pro Met Ala Asp Ser Ile Phe
        2000                2005                2010

His Tyr Tyr Gln Glu Leu Pro Lys Tyr Leu Arg Gly Tyr His Lys
        2015                2020                2025

Cys Thr Arg Glu Glu Val Leu Gln Leu Gly Ala Leu Ile Tyr Arg
        2030                2035                2040

Val Lys Phe Glu Glu Asp Lys Ser Tyr Phe Pro Ser Ile Pro Lys
        2045                2050                2055

Leu Leu Arg Glu Leu Val Pro Gln Asp Leu Ile Arg Gln Val Ser
        2060                2065                2070

Pro Asp Asp Trp Lys Arg Ser Ile Val Ala Tyr Phe Asn Lys His
        2075                2080                2085

Ala Gly Lys Ser Lys Glu Glu Ala Lys Leu Ala Phe Leu Lys Leu
        2090                2095                2100

Ile Phe Lys Trp Pro Thr Phe Gly Ser Ala Phe Phe Glu Val Lys
        2105                2110                2115

Gln Thr Thr Glu Pro Asn Phe Pro Glu Ile Leu Leu Ile Ala Ile
        2120                2125                2130

Asn Lys Tyr Gly Val Ser Leu Ile Asp Pro Lys Thr Lys Asp Ile
        2135                2140                2145

Leu Thr Thr His Pro Phe Thr Lys Ile Ser Asn Trp Ser Ser Gly
        2150                2155                2160

Asn Thr Tyr Phe His Ile Thr Ile Gly Asn Leu Val Arg Gly Ser
        2165                2170                2175

Lys Leu Leu Cys Glu Thr Ser Leu Gly Tyr Lys Met Asp Asp Leu
        2180                2185                2190

Leu Thr Ser Tyr Ile Ser Gln Met Leu Thr Ala Met Ser Lys Gln
        2195                2200                2205

Arg Gly Ser Arg Ser
        2210

<210> SEQ ID NO 25
<211> LENGTH: 236
<212> TYPE: PRT
<213> ORGANISM: Homo sapiens
<220> FEATURE:
<221> NAME/KEY: MISC_FEATURE
<222> LOCATION: (1)..(237)
<223> OTHER INFORMATION: NRL (neural retina-specific leucine zipper
      protein), isoform 1

-continued

```
<400> SEQUENCE: 25

Ala Leu Pro Pro Ser Pro Leu Ala Met Glu Tyr Val Asn Asp Phe Asp
1               5                   10                  15

Leu Met Lys Phe Glu Val Lys Arg Glu Pro Ser Glu Gly Arg Pro Gly
            20                  25                  30

Pro Pro Thr Ala Ser Leu Gly Ser Thr Pro Tyr Ser Ser Val Pro Pro
        35                  40                  45

Ser Pro Thr Phe Ser Glu Pro Gly Met Val Gly Ala Thr Glu Gly Thr
    50                  55                  60

Arg Pro Gly Leu Glu Glu Leu Tyr Trp Leu Ala Thr Leu Gln Gln Gln
65                  70                  75                  80

Leu Gly Ala Gly Glu Ala Leu Gly Leu Ser Pro Glu Ala Met Glu
                85                  90                  95

Leu Leu Gln Gly Gln Gly Pro Val Pro Val Asp Gly Pro His Gly Tyr
                100                 105                 110

Tyr Pro Gly Ser Pro Glu Glu Thr Gly Ala Gln His Val Gln Leu Ala
            115                 120                 125

Glu Arg Phe Ser Asp Ala Ala Leu Val Ser Met Ser Val Arg Glu Leu
130                 135                 140

Asn Arg Gln Leu Arg Gly Cys Gly Arg Asp Glu Ala Leu Arg Leu Lys
145                 150                 155                 160

Gln Arg Arg Arg Thr Leu Lys Asn Arg Gly Tyr Ala Gln Ala Cys Arg
                165                 170                 175

Ser Lys Arg Leu Gln Gln Arg Arg Gly Leu Glu Ala Glu Arg Ala Arg
            180                 185                 190

Leu Ala Ala Gln Leu Asp Ala Leu Arg Ala Glu Val Ala Arg Leu Ala
        195                 200                 205

Arg Glu Arg Asp Leu Tyr Lys Ala Arg Cys Asp Arg Leu Thr Ser Ser
    210                 215                 220

Gly Pro Gly Ser Gly Asp Pro Ser His Leu Phe Leu
225                 230                 235

<210> SEQ ID NO 26
<211> LENGTH: 860
<212> TYPE: PRT
<213> ORGANISM: Homo sapiens
<220> FEATURE:
<221> NAME/KEY: MISC_FEATURE
<222> LOCATION: (1)..(860)
<223> OTHER INFORMATION: PDE6A (rod cGMP-specific 3',5'-cyclic
      phosphodiesterase subunit alpha)

<400> SEQUENCE: 26

Met Gly Glu Val Thr Ala Glu Glu Val Glu Lys Phe Leu Asp Ser Asn
1               5                   10                  15

Ile Gly Phe Ala Lys Gln Tyr Tyr Asn Leu His Tyr Arg Ala Lys Leu
            20                  25                  30

Ile Ser Asp Leu Leu Gly Ala Lys Glu Ala Ala Val Asp Phe Ser Asn
        35                  40                  45

Tyr His Ser Pro Ser Ser Met Glu Glu Ser Glu Ile Ile Phe Asp Leu
    50                  55                  60

Leu Arg Asp Phe Gln Glu Asn Leu Gln Thr Glu Lys Cys Ile Phe Asn
65                  70                  75                  80

Val Met Lys Lys Leu Cys Phe Leu Leu Gln Ala Asp Arg Met Ser Leu
                85                  90                  95

Phe Met Tyr Arg Thr Arg Asn Gly Ile Ala Glu Leu Ala Thr Arg Leu
```

```
                 100              105              110
Phe Asn Val His Lys Asp Ala Val Leu Glu Asp Cys Leu Val Met Pro
            115              120              125
Asp Gln Glu Ile Val Phe Pro Leu Asp Met Gly Ile Val Gly His Val
            130              135              140
Ala His Ser Lys Lys Ile Ala Asn Val Pro Asn Thr Glu Glu Asp Glu
145              150              155              160
His Phe Cys Asp Phe Val Asp Ile Leu Thr Glu Tyr Lys Thr Lys Asn
                 165              170              175
Ile Leu Ala Ser Pro Ile Met Asn Gly Lys Asp Val Ala Ile Ile
                 180              185              190
Met Ala Val Asn Lys Val Asp Gly Ser His Phe Thr Lys Arg Asp Glu
            195              200              205
Glu Ile Leu Leu Lys Tyr Leu Asn Phe Ala Asn Leu Ile Met Lys Val
            210              215              220
Tyr His Leu Ser Tyr Leu His Asn Cys Glu Thr Arg Arg Gly Gln Ile
225              230              235              240
Leu Leu Trp Ser Gly Ser Lys Val Phe Glu Glu Leu Thr Asp Ile Glu
                 245              250              255
Arg Gln Phe His Lys Ala Leu Tyr Thr Val Arg Ala Phe Leu Asn Cys
                 260              265              270
Asp Arg Tyr Ser Val Gly Leu Leu Asp Met Thr Lys Gln Lys Glu Phe
                 275              280              285
Phe Asp Val Trp Pro Val Leu Met Gly Glu Val Pro Pro Tyr Ser Gly
            290              295              300
Pro Arg Thr Pro Asp Gly Arg Glu Ile Asn Phe Tyr Lys Val Ile Asp
305              310              315              320
Tyr Ile Leu His Gly Lys Glu Asp Ile Lys Val Ile Pro Asn Pro Pro
                 325              330              335
Pro Asp His Trp Ala Leu Val Ser Gly Leu Pro Ala Tyr Val Ala Gln
                 340              345              350
Asn Gly Leu Ile Cys Asn Ile Met Asn Ala Pro Ala Glu Asp Phe Phe
                 355              360              365
Ala Phe Gln Lys Glu Pro Leu Asp Glu Ser Gly Trp Met Ile Lys Asn
            370              375              380
Val Leu Ser Met Pro Ile Val Asn Lys Lys Glu Glu Ile Val Gly Val
385              390              395              400
Ala Thr Phe Tyr Asn Arg Lys Asp Gly Lys Pro Phe Asp Glu Met Asp
                 405              410              415
Glu Thr Leu Met Glu Ser Leu Thr Gln Phe Leu Gly Trp Ser Val Leu
            420              425              430
Asn Pro Asp Thr Tyr Glu Ser Met Asn Lys Leu Glu Asn Arg Lys Asp
            435              440              445
Ile Phe Gln Asp Ile Val Lys Tyr His Val Lys Cys Asp Asn Glu Glu
            450              455              460
Ile Gln Lys Ile Leu Lys Thr Arg Glu Val Tyr Gly Lys Glu Pro Trp
465              470              475              480
Glu Cys Glu Glu Glu Leu Ala Glu Ile Leu Gln Ala Glu Leu Pro
                 485              490              495
Asp Ala Asp Lys Tyr Glu Ile Asn Lys Phe His Phe Ser Asp Leu Pro
                 500              505              510
Leu Thr Glu Leu Glu Leu Val Lys Cys Gly Ile Gln Met Tyr Tyr Glu
            515              520              525
```

Leu Lys Val Val Asp Lys Phe His Ile Pro Gln Glu Ala Leu Val Arg
            530                 535                 540

Phe Met Tyr Ser Leu Ser Lys Gly Tyr Arg Lys Ile Thr Tyr His Asn
545                 550                 555                 560

Trp Arg His Gly Phe Asn Val Gly Gln Thr Met Phe Ser Leu Val
                565                 570                 575

Thr Gly Lys Leu Lys Arg Tyr Phe Thr Asp Leu Glu Ala Leu Ala Met
            580                 585                 590

Val Thr Ala Ala Phe Cys His Asp Ile Asp His Arg Gly Thr Asn Asn
            595                 600                 605

Leu Tyr Gln Met Lys Ser Gln Asn Pro Leu Ala Lys Leu His Gly Ser
            610                 615                 620

Ser Ile Leu Glu Arg His His Leu Glu Phe Gly Lys Thr Leu Leu Arg
625                 630                 635                 640

Asp Glu Ser Leu Asn Ile Phe Gln Asn Leu Asn Arg Arg Gln His Glu
                645                 650                 655

His Ala Ile His Met Met Asp Ile Ala Ile Ala Thr Asp Leu Ala
            660                 665                 670

Leu Tyr Phe Lys Lys Arg Thr Met Phe Gln Lys Ile Val Asp Gln Ser
            675                 680                 685

Lys Thr Tyr Glu Ser Glu Gln Glu Trp Thr Gln Tyr Met Met Leu Glu
690                 695                 700

Gln Thr Arg Lys Glu Ile Val Met Ala Met Met Thr Ala Cys Asp
705                 710                 715                 720

Leu Ser Ala Ile Thr Lys Pro Trp Glu Val Gln Ser Gln Val Ala Leu
                725                 730                 735

Leu Val Ala Ala Glu Phe Trp Glu Gln Gly Asp Leu Glu Arg Thr Val
            740                 745                 750

Leu Gln Gln Asn Pro Ile Pro Met Met Asp Arg Asn Lys Ala Asp Glu
            755                 760                 765

Leu Pro Lys Leu Gln Val Gly Phe Ile Asp Phe Val Cys Thr Phe Val
            770                 775                 780

Tyr Lys Glu Phe Ser Arg Phe His Glu Glu Ile Thr Pro Met Leu Asp
785                 790                 795                 800

Gly Ile Thr Asn Asn Arg Lys Glu Trp Lys Ala Leu Ala Asp Glu Tyr
                805                 810                 815

Asp Ala Lys Met Lys Val Gln Glu Glu Lys Lys Gln Lys Gln Gln Ser
            820                 825                 830

Ala Lys Ser Ala Ala Ala Gly Asn Gln Pro Gly Gly Asn Pro Ser Pro
            835                 840                 845

Gly Gly Ala Thr Thr Ser Lys Ser Cys Cys Ile Gln
            850                 855                 860

<210> SEQ ID NO 27
<211> LENGTH: 854
<212> TYPE: PRT
<213> ORGANISM: Homo sapiens
<220> FEATURE:
<221> NAME/KEY: MISC_FEATURE
<222> LOCATION: (1)..(854)
<223> OTHER INFORMATION: PDE6B (rod cGMP-specific 3',5'-cyclic
      phosphodiesterase subunit beta), isoform 1

<400> SEQUENCE: 27

Met Ser Leu Ser Glu Glu Gln Ala Arg Ser Phe Leu Asp Gln Asn Pro
1               5                   10                  15

-continued

```
Asp Phe Ala Arg Gln Tyr Phe Gly Lys Lys Leu Ser Pro Glu Asn Val
             20                  25                  30

Ala Ala Ala Cys Glu Asp Gly Cys Pro Pro Asp Cys Asp Ser Leu Arg
             35                  40                  45

Asp Leu Cys Gln Val Glu Ser Thr Ala Leu Leu Glu Leu Val Gln
 50                  55                  60

Asp Met Gln Glu Ser Ile Asn Met Glu Arg Val Val Phe Lys Val Leu
65                   70                  75                  80

Arg Arg Leu Cys Thr Leu Leu Gln Ala Asp Arg Cys Ser Leu Phe Met
                 85                  90                  95

Tyr Arg Gln Arg Asn Gly Val Ala Glu Leu Ala Thr Arg Leu Phe Ser
                100                 105                 110

Val Gln Pro Asp Ser Val Leu Glu Asp Cys Leu Val Pro Pro Asp Ser
             115                 120                 125

Glu Ile Val Phe Pro Leu Asp Ile Gly Val Val Gly His Val Ala Gln
130                 135                 140

Thr Lys Lys Met Val Asn Val Glu Asp Val Ala Glu Cys Pro His Phe
145                 150                 155                 160

Ser Ser Phe Ala Asp Glu Leu Thr Asp Tyr Lys Thr Lys Asn Met Leu
                165                 170                 175

Ala Thr Pro Ile Met Asn Gly Lys Asp Val Val Ala Val Ile Met Ala
                180                 185                 190

Val Asn Lys Leu Asn Gly Pro Phe Phe Thr Ser Glu Asp Glu Asp Val
            195                 200                 205

Phe Leu Lys Tyr Leu Asn Phe Ala Thr Leu Tyr Leu Lys Ile Tyr His
            210                 215                 220

Leu Ser Tyr Leu His Asn Cys Glu Thr Arg Arg Gly Gln Val Leu Leu
225                 230                 235                 240

Trp Ser Ala Asn Lys Val Phe Glu Glu Leu Thr Asp Ile Glu Arg Gln
                245                 250                 255

Phe His Lys Ala Phe Tyr Thr Val Arg Ala Tyr Leu Asn Cys Glu Arg
                260                 265                 270

Tyr Ser Val Gly Leu Leu Asp Met Thr Lys Glu Lys Glu Phe Phe Asp
            275                 280                 285

Val Trp Ser Val Leu Met Gly Glu Ser Gln Pro Tyr Ser Gly Pro Arg
            290                 295                 300

Thr Pro Asp Gly Arg Glu Ile Val Phe Tyr Lys Val Ile Asp Tyr Val
305                 310                 315                 320

Leu His Gly Lys Glu Glu Ile Lys Val Ile Pro Thr Pro Ser Ala Asp
                325                 330                 335

His Trp Ala Leu Ala Ser Gly Leu Pro Ser Tyr Val Ala Glu Ser Gly
            340                 345                 350

Phe Ile Cys Asn Ile Met Asn Ala Ser Ala Asp Glu Met Phe Lys Phe
            355                 360                 365

Gln Glu Gly Ala Leu Asp Asp Ser Gly Trp Leu Ile Lys Asn Val Leu
            370                 375                 380

Ser Met Pro Ile Val Asn Lys Lys Glu Glu Ile Val Gly Val Ala Thr
385                 390                 395                 400

Phe Tyr Asn Arg Lys Asp Gly Lys Pro Phe Asp Glu Gln Asp Glu Val
                405                 410                 415

Leu Met Glu Ser Leu Thr Gln Phe Leu Gly Trp Ser Val Met Asn Thr
            420                 425                 430
```

-continued

```
Asp Thr Tyr Asp Lys Met Asn Lys Leu Glu Asn Arg Lys Asp Ile Ala
            435                 440                 445

Gln Asp Met Val Leu Tyr His Val Lys Cys Asp Arg Asp Glu Ile Gln
            450                 455                 460

Leu Ile Leu Pro Thr Arg Ala Arg Leu Gly Lys Glu Pro Ala Asp Cys
465                 470                 475                 480

Asp Glu Asp Glu Leu Gly Glu Ile Leu Lys Glu Leu Pro Gly Pro
                485                 490                 495

Thr Thr Phe Asp Ile Tyr Glu Phe His Phe Ser Asp Leu Glu Cys Thr
                500                 505                 510

Glu Leu Asp Leu Val Lys Cys Gly Ile Gln Met Tyr Tyr Glu Leu Gly
            515                 520                 525

Val Val Arg Lys Phe Gln Ile Pro Gln Glu Val Leu Val Arg Phe Leu
            530                 535                 540

Phe Ser Ile Ser Lys Gly Tyr Arg Arg Ile Thr Tyr His Asn Trp Arg
545                 550                 555                 560

His Gly Phe Asn Val Ala Gln Thr Met Phe Thr Leu Leu Met Thr Gly
                565                 570                 575

Lys Leu Lys Ser Tyr Tyr Thr Asp Leu Glu Ala Phe Ala Met Val Thr
                580                 585                 590

Ala Gly Leu Cys His Asp Ile Asp His Arg Gly Thr Asn Asn Leu Tyr
            595                 600                 605

Gln Met Lys Ser Gln Asn Pro Leu Ala Lys Leu His Gly Ser Ser Ile
            610                 615                 620

Leu Glu Arg His His Leu Glu Phe Gly Lys Phe Leu Leu Ser Glu Glu
625                 630                 635                 640

Thr Leu Asn Ile Tyr Gln Asn Leu Asn Arg Arg Gln His Glu His Val
                645                 650                 655

Ile His Leu Met Asp Ile Ala Ile Ile Ala Thr Asp Leu Ala Leu Tyr
                660                 665                 670

Phe Lys Lys Arg Ala Met Phe Gln Lys Ile Val Asp Glu Ser Lys Asn
            675                 680                 685

Tyr Gln Asp Lys Lys Ser Trp Val Glu Tyr Leu Ser Leu Glu Thr Thr
690                 695                 700

Arg Lys Glu Ile Val Met Ala Met Met Met Thr Ala Cys Asp Leu Ser
705                 710                 715                 720

Ala Ile Thr Lys Pro Trp Glu Val Gln Ser Lys Val Ala Leu Leu Val
                725                 730                 735

Ala Ala Glu Phe Trp Glu Gln Gly Asp Leu Glu Arg Thr Val Leu Asp
                740                 745                 750

Gln Gln Pro Ile Pro Met Met Asp Arg Asn Lys Ala Ala Glu Leu Pro
            755                 760                 765

Lys Leu Gln Val Gly Phe Ile Asp Phe Val Cys Thr Phe Val Tyr Lys
770                 775                 780

Glu Phe Ser Arg Phe His Glu Glu Ile Leu Pro Met Phe Asp Arg Leu
785                 790                 795                 800

Gln Asn Asn Arg Lys Glu Trp Lys Ala Leu Ala Asp Glu Tyr Glu Ala
                805                 810                 815

Lys Val Lys Ala Leu Glu Glu Lys Glu Glu Glu Arg Val Ala Ala
                820                 825                 830

Lys Lys Val Gly Thr Glu Ile Cys Asn Gly Gly Pro Ala Pro Lys Ser
            835                 840                 845

Ser Thr Cys Cys Ile Leu
```

```
<210> SEQ ID NO 28
<211> LENGTH: 346
<212> TYPE: PRT
<213> ORGANISM: Homo sapiens
<220> FEATURE:
<221> NAME/KEY: MISC_FEATURE
<222> LOCATION: (1)..(346)
<223> OTHER INFORMATION: PRPH2 (peripherin-2)

<400> SEQUENCE: 28
```

| | | | | | | | | | | | | | | |
|---|---|---|---|---|---|---|---|---|---|---|---|---|---|---|
| Met | Ala | Leu | Leu | Lys | Val | Lys | Phe | Asp | Gln | Lys | Lys | Arg | Val | Lys | Leu |
| 1 | | | | 5 | | | | | 10 | | | | | 15 | |
| Ala | Gln | Gly | Leu | Trp | Leu | Met | Asn | Trp | Phe | Ser | Val | Leu | Ala | Gly | Ile |
| | | | 20 | | | | | 25 | | | | | 30 | | |
| Ile | Ile | Phe | Ser | Leu | Gly | Leu | Phe | Leu | Lys | Ile | Glu | Leu | Arg | Lys | Arg |
| | | | 35 | | | | | 40 | | | | | 45 | | |
| Ser | Asp | Val | Met | Asn | Asn | Ser | Glu | Ser | His | Phe | Val | Pro | Asn | Ser | Leu |
| | 50 | | | | | 55 | | | | | 60 | | | | |
| Ile | Gly | Met | Gly | Val | Leu | Ser | Cys | Val | Phe | Asn | Ser | Leu | Ala | Gly | Lys |
| 65 | | | | | 70 | | | | | 75 | | | | | 80 |
| Ile | Cys | Tyr | Asp | Ala | Leu | Asp | Pro | Ala | Lys | Tyr | Ala | Arg | Trp | Lys | Pro |
| | | | | 85 | | | | | 90 | | | | | 95 | |
| Trp | Leu | Lys | Pro | Tyr | Leu | Ala | Ile | Cys | Val | Leu | Phe | Asn | Ile | Ile | Leu |
| | | | 100 | | | | | 105 | | | | | 110 | | |
| Phe | Leu | Val | Ala | Leu | Cys | Cys | Phe | Leu | Leu | Arg | Gly | Ser | Leu | Glu | Asn |
| | | | 115 | | | | | 120 | | | | | 125 | | |
| Thr | Leu | Gly | Gln | Gly | Leu | Lys | Asn | Gly | Met | Lys | Tyr | Tyr | Arg | Asp | Thr |
| | 130 | | | | | 135 | | | | | 140 | | | | |
| Asp | Thr | Pro | Gly | Arg | Cys | Phe | Met | Lys | Lys | Thr | Ile | Asp | Met | Leu | Gln |
| 145 | | | | | 150 | | | | | 155 | | | | | 160 |
| Ile | Glu | Phe | Lys | Cys | Cys | Gly | Asn | Asn | Gly | Phe | Arg | Asp | Trp | Phe | Glu |
| | | | | 165 | | | | | 170 | | | | | 175 | |
| Ile | Gln | Trp | Ile | Ser | Asn | Arg | Tyr | Leu | Asp | Phe | Ser | Ser | Lys | Glu | Val |
| | | | 180 | | | | | 185 | | | | | 190 | | |
| Lys | Asp | Arg | Ile | Lys | Ser | Asn | Val | Asp | Gly | Arg | Tyr | Leu | Val | Asp | Gly |
| | | | 195 | | | | | 200 | | | | | 205 | | |
| Val | Pro | Phe | Ser | Cys | Cys | Asn | Pro | Ser | Ser | Pro | Arg | Pro | Cys | Ile | Gln |
| | 210 | | | | | 215 | | | | | 220 | | | | |
| Tyr | Gln | Ile | Thr | Asn | Asn | Ser | Ala | His | Tyr | Ser | Tyr | Asp | His | Gln | Thr |
| 225 | | | | | 230 | | | | | 235 | | | | | 240 |
| Glu | Glu | Leu | Asn | Leu | Trp | Val | Arg | Gly | Cys | Arg | Ala | Ala | Leu | Leu | Ser |
| | | | | 245 | | | | | 250 | | | | | 255 | |
| Tyr | Tyr | Ser | Ser | Leu | Met | Asn | Ser | Met | Gly | Val | Val | Thr | Leu | Leu | Ile |
| | | | 260 | | | | | 265 | | | | | 270 | | |
| Trp | Leu | Phe | Glu | Val | Thr | Ile | Thr | Ile | Gly | Leu | Arg | Tyr | Leu | Gln | Thr |
| | | | 275 | | | | | 280 | | | | | 285 | | |
| Ser | Leu | Asp | Gly | Val | Ser | Asn | Pro | Glu | Glu | Ser | Glu | Ser | Glu | Ser | Glu |
| | 290 | | | | | 295 | | | | | 300 | | | | |
| Gly | Trp | Leu | Leu | Glu | Lys | Ser | Val | Pro | Glu | Thr | Trp | Lys | Ala | Phe | Leu |
| 305 | | | | | 310 | | | | | 315 | | | | | 320 |
| Glu | Ser | Val | Lys | Lys | Leu | Gly | Lys | Gly | Asn | Gln | Val | Glu | Ala | Glu | Gly |
| | | | | 325 | | | | | 330 | | | | | 335 | |
| Ala | Gly | Ala | Gly | Gln | Ala | Pro | Glu | Ala | Gly | | | | | | |
| | | | 340 | | | | | 345 | | | | | | | |

-continued

```
<210> SEQ ID NO 29
<211> LENGTH: 865
<212> TYPE: PRT
<213> ORGANISM: Homo sapiens
<220> FEATURE:
<221> NAME/KEY: MISC_FEATURE
<222> LOCATION: (1)..(865)
<223> OTHER INFORMATION: PROM1 (prominin-1), isoform 1

<400> SEQUENCE: 29
```

Met Ala Leu Val Leu Gly Ser Leu Leu Leu Gly Leu Cys Gly Asn
1               5                   10                  15

Ser Phe Ser Gly Gly Gln Pro Ser Ser Thr Asp Ala Pro Lys Ala Trp
            20                  25                  30

Asn Tyr Glu Leu Pro Ala Thr Asn Tyr Glu Thr Gln Asp Ser His Lys
        35                  40                  45

Ala Gly Pro Ile Gly Ile Leu Phe Glu Leu Val His Ile Phe Leu Tyr
    50                  55                  60

Val Val Gln Pro Arg Asp Phe Pro Glu Asp Thr Leu Arg Lys Phe Leu
65                  70                  75                  80

Gln Lys Ala Tyr Glu Ser Lys Ile Asp Tyr Asp Lys Pro Glu Thr Val
                85                  90                  95

Ile Leu Gly Leu Lys Ile Val Tyr Tyr Glu Ala Gly Ile Ile Leu Cys
            100                 105                 110

Cys Val Leu Gly Leu Leu Phe Ile Ile Leu Met Pro Leu Val Gly Tyr
        115                 120                 125

Phe Phe Cys Met Cys Arg Cys Cys Asn Lys Cys Gly Gly Glu Met His
    130                 135                 140

Gln Arg Gln Lys Glu Asn Gly Pro Phe Leu Arg Lys Cys Phe Ala Ile
145                 150                 155                 160

Ser Leu Leu Val Ile Cys Ile Ile Ser Ile Gly Ile Phe Tyr Gly
                165                 170                 175

Phe Val Ala Asn His Gln Val Arg Thr Arg Ile Lys Arg Ser Arg Lys
    180                 185                 190

Leu Ala Asp Ser Asn Phe Lys Asp Leu Arg Thr Leu Leu Asn Glu Thr
            195                 200                 205

Pro Glu Gln Ile Lys Tyr Ile Leu Ala Gln Tyr Asn Thr Thr Lys Asp
    210                 215                 220

Lys Ala Phe Thr Asp Leu Asn Ser Ile Asn Ser Val Leu Gly Gly Gly
225                 230                 235                 240

Ile Leu Asp Arg Leu Arg Pro Asn Ile Ile Pro Val Leu Asp Glu Ile
                245                 250                 255

Lys Ser Met Ala Thr Ala Ile Lys Glu Thr Lys Glu Ala Leu Glu Asn
            260                 265                 270

Met Asn Ser Thr Leu Lys Ser Leu His Gln Gln Ser Thr Gln Leu Ser
        275                 280                 285

Ser Ser Leu Thr Ser Val Lys Thr Ser Leu Arg Ser Ser Leu Asn Asp
    290                 295                 300

Pro Leu Cys Leu Val His Pro Ser Ser Glu Thr Cys Asn Ser Ile Arg
305                 310                 315                 320

Leu Ser Leu Ser Gln Leu Asn Ser Asn Pro Glu Leu Arg Gln Leu Pro
                325                 330                 335

Pro Val Asp Ala Glu Leu Asp Asn Val Asn Asn Val Leu Arg Thr Asp
            340                 345                 350

```
Leu Asp Gly Leu Val Gln Gly Tyr Gln Ser Leu Asn Asp Ile Pro
            355                 360                 365

Asp Arg Val Gln Arg Gln Thr Thr Val Val Ala Gly Ile Lys Arg
370                 375                 380

Val Leu Asn Ser Ile Gly Ser Asp Ile Asp Asn Val Thr Gln Arg Leu
385                 390                 395                 400

Pro Ile Gln Asp Ile Leu Ser Ala Phe Ser Val Tyr Val Asn Asn Thr
                405                 410                 415

Glu Ser Tyr Ile His Arg Asn Leu Pro Thr Leu Glu Glu Tyr Asp Ser
                420                 425                 430

Tyr Trp Trp Leu Gly Gly Leu Val Ile Cys Ser Leu Leu Thr Leu Ile
            435                 440                 445

Val Ile Phe Tyr Tyr Leu Gly Leu Leu Cys Gly Val Cys Gly Tyr Asp
        450                 455                 460

Arg His Ala Thr Pro Thr Thr Arg Gly Cys Val Ser Asn Thr Gly Gly
465                 470                 475                 480

Val Phe Leu Met Val Gly Val Gly Leu Ser Phe Leu Phe Cys Trp Ile
                485                 490                 495

Leu Met Ile Ile Val Val Leu Thr Phe Val Phe Gly Ala Asn Val Glu
                500                 505                 510

Lys Leu Ile Cys Glu Pro Tyr Thr Ser Lys Glu Leu Phe Arg Val Leu
            515                 520                 525

Asp Thr Pro Tyr Leu Leu Asn Glu Asp Trp Glu Tyr Tyr Leu Ser Gly
            530                 535                 540

Lys Leu Phe Asn Lys Ser Lys Met Lys Leu Thr Phe Glu Gln Val Tyr
545                 550                 555                 560

Ser Asp Cys Lys Lys Asn Arg Gly Thr Tyr Gly Thr Leu His Leu Gln
                565                 570                 575

Asn Ser Phe Asn Ile Ser Glu His Leu Asn Ile Asn Glu His Thr Gly
                580                 585                 590

Ser Ile Ser Ser Glu Leu Glu Ser Leu Lys Val Asn Leu Asn Ile Phe
            595                 600                 605

Leu Leu Gly Ala Ala Gly Arg Lys Asn Leu Gln Asp Phe Ala Ala Cys
610                 615                 620

Gly Ile Asp Arg Met Asn Tyr Asp Ser Tyr Leu Ala Gln Thr Gly Lys
625                 630                 635                 640

Ser Pro Ala Gly Val Asn Leu Leu Ser Phe Ala Tyr Asp Leu Glu Ala
                645                 650                 655

Lys Ala Asn Ser Leu Pro Pro Gly Asn Leu Arg Asn Ser Leu Lys Arg
                660                 665                 670

Asp Ala Gln Thr Ile Lys Thr Ile His Gln Gln Arg Val Leu Pro Ile
                675                 680                 685

Glu Gln Ser Leu Ser Thr Leu Tyr Gln Ser Val Lys Ile Leu Gln Arg
    690                 695                 700

Thr Gly Asn Gly Leu Leu Glu Arg Val Thr Arg Ile Leu Ala Ser Leu
705                 710                 715                 720

Asp Phe Ala Gln Asn Phe Ile Thr Asn Thr Ser Ser Val Ile Ile
                725                 730                 735

Glu Glu Thr Lys Lys Tyr Gly Arg Thr Ile Ile Gly Tyr Phe Glu His
                740                 745                 750

Tyr Leu Gln Trp Ile Glu Phe Ser Ile Ser Glu Lys Val Ala Ser Cys
            755                 760                 765

Lys Pro Val Ala Thr Ala Leu Asp Thr Ala Val Asp Val Phe Leu Cys
```

```
                  770             775             780
Ser Tyr Ile Ile Asp Pro Leu Asn Leu Phe Trp Phe Gly Ile Gly Lys
785                 790             795                 800

Ala Thr Val Phe Leu Leu Pro Ala Leu Ile Phe Ala Val Lys Leu Ala
                805             810                 815

Lys Tyr Tyr Arg Arg Met Asp Ser Glu Asp Val Tyr Asp Asp Val Glu
                820             825                 830

Thr Ile Pro Met Lys Asn Met Glu Asn Gly Asn Asn Gly Tyr His Lys
                835             840                 845

Asp His Val Tyr Gly Ile His Asn Pro Val Met Thr Ser Pro Ser Gln
            850             855                 860

His
865

<210> SEQ ID NO 30
<211> LENGTH: 348
<212> TYPE: PRT
<213> ORGANISM: Homo sapiens
<220> FEATURE:
<221> NAME/KEY: MISC_FEATURE
<222> LOCATION: (1)..(348)
<223> OTHER INFORMATION: RHO

<400> SEQUENCE: 30

Met Asn Gly Thr Glu Gly Pro Asn Phe Tyr Val Pro Phe Ser Asn Ala
1               5                   10                  15

Thr Gly Val Val Arg Ser Pro Phe Glu Tyr Pro Gln Tyr Tyr Leu Ala
                20                  25                  30

Glu Pro Trp Gln Phe Ser Met Leu Ala Ala Tyr Met Phe Leu Leu Ile
            35                  40                  45

Val Leu Gly Phe Pro Ile Asn Phe Leu Thr Leu Tyr Val Thr Val Gln
        50                  55                  60

His Lys Lys Leu Arg Thr Pro Leu Asn Tyr Ile Leu Leu Asn Leu Ala
65                  70                  75                  80

Val Ala Asp Leu Phe Met Val Leu Gly Gly Phe Thr Ser Thr Leu Tyr
                85                  90                  95

Thr Ser Leu His Gly Tyr Phe Val Phe Gly Pro Thr Gly Cys Asn Leu
            100                 105                 110

Glu Gly Phe Phe Ala Thr Leu Gly Gly Glu Ile Ala Leu Trp Ser Leu
        115                 120                 125

Val Val Leu Ala Ile Glu Arg Tyr Val Val Val Cys Lys Pro Met Ser
    130                 135                 140

Asn Phe Arg Phe Gly Glu Asn His Ala Ile Met Gly Val Ala Phe Thr
145                 150                 155                 160

Trp Val Met Ala Leu Ala Cys Ala Ala Pro Pro Leu Ala Gly Trp Ser
                165                 170                 175

Arg Tyr Ile Pro Glu Gly Leu Gln Cys Ser Cys Gly Ile Asp Tyr Tyr
            180                 185                 190

Thr Leu Lys Pro Glu Val Asn Asn Glu Ser Phe Val Ile Tyr Met Phe
        195                 200                 205

Val Val His Phe Thr Ile Pro Met Ile Ile Ile Phe Phe Cys Tyr Gly
    210                 215                 220

Gln Leu Val Phe Thr Val Lys Glu Ala Ala Ala Gln Gln Gln Glu Ser
225                 230                 235                 240

Ala Thr Thr Gln Lys Ala Glu Lys Glu Val Thr Arg Met Val Ile Ile
                245                 250                 255
```

```
Met Val Ile Ala Phe Leu Ile Cys Trp Val Pro Tyr Ala Ser Val Ala
            260                 265                 270

Phe Tyr Ile Phe Thr His Gln Gly Ser Asn Phe Gly Pro Ile Phe Met
            275                 280                 285

Thr Ile Pro Ala Phe Phe Ala Lys Ser Ala Ala Ile Tyr Asn Pro Val
290                 295                 300

Ile Tyr Ile Met Met Asn Lys Gln Phe Arg Asn Cys Met Leu Thr Thr
305                 310                 315                 320

Ile Cys Cys Gly Lys Asn Pro Leu Gly Asp Asp Glu Ala Ser Ala Thr
                325                 330                 335

Val Ser Lys Thr Glu Thr Ser Gln Val Ala Pro Ala
            340                 345

<210> SEQ ID NO 31
<211> LENGTH: 351
<212> TYPE: PRT
<213> ORGANISM: Homo sapiens
<220> FEATURE:
<221> NAME/KEY: MISC_FEATURE
<222> LOCATION: (1)..(351)
<223> OTHER INFORMATION: ROM1 (rod outer segment membrane protein 1)

<400> SEQUENCE: 31

Met Ala Pro Val Leu Pro Leu Val Leu Pro Leu Gln Pro Arg Ile Arg
1               5                   10                  15

Leu Ala Gln Gly Leu Trp Leu Leu Ser Trp Leu Leu Ala Leu Ala Gly
            20                  25                  30

Gly Val Ile Leu Leu Cys Ser Gly His Leu Leu Val Gln Leu Arg His
            35                  40                  45

Leu Gly Thr Phe Leu Ala Pro Ser Cys Gln Phe Pro Val Leu Pro Gln
50                  55                  60

Ala Ala Leu Ala Ala Gly Ala Val Ala Leu Gly Thr Gly Leu Val Gly
65                  70                  75                  80

Val Gly Ala Ser Arg Ala Ser Leu Asn Ala Ala Leu Tyr Pro Pro Trp
                85                  90                  95

Arg Gly Val Leu Gly Pro Leu Leu Val Ala Gly Thr Ala Gly Gly Gly
            100                 105                 110

Gly Leu Leu Val Val Gly Leu Gly Leu Ala Leu Ala Leu Pro Gly Ser
            115                 120                 125

Leu Asp Glu Ala Leu Glu Glu Gly Leu Val Thr Ala Leu Ala His Tyr
130                 135                 140

Lys Asp Thr Glu Val Pro Gly His Cys Gln Ala Lys Arg Leu Val Asp
145                 150                 155                 160

Glu Leu Gln Leu Arg Tyr His Cys Cys Gly Arg His Gly Tyr Lys Asp
                165                 170                 175

Trp Phe Gly Val Gln Trp Val Ser Ser Arg Tyr Leu Asp Pro Gly Asp
            180                 185                 190

Arg Asp Val Ala Asp Arg Ile Gln Ser Asn Val Glu Gly Leu Tyr Leu
            195                 200                 205

Thr Asp Gly Val Pro Phe Ser Cys Cys Asn Pro His Ser Pro Arg Pro
210                 215                 220

Cys Leu Gln Asn Arg Leu Ser Asp Ser Tyr Ala His Pro Leu Phe Asp
225                 230                 235                 240

Pro Arg Gln Pro Asn Gln Asn Leu Trp Ala Gln Gly Cys His Glu Val
                245                 250                 255
```

Leu Leu Glu His Leu Gln Asp Leu Ala Gly Thr Leu Gly Ser Met Leu
            260                 265                 270

Ala Val Thr Phe Leu Leu Gln Ala Leu Val Leu Leu Gly Leu Arg Tyr
        275                 280                 285

Leu Gln Thr Ala Leu Glu Gly Leu Gly Gly Val Ile Asp Ala Gly Gly
    290                 295                 300

Glu Thr Gln Gly Tyr Leu Phe Pro Ser Gly Leu Lys Asp Met Leu Lys
305                 310                 315                 320

Thr Ala Trp Leu Gln Gly Gly Val Ala Cys Arg Pro Ala Pro Glu Glu
                325                 330                 335

Ala Pro Pro Gly Glu Ala Pro Pro Lys Glu Asp Leu Ser Glu Ala
            340                 345                 350

<210> SEQ ID NO 32
<211> LENGTH: 2156
<212> TYPE: PRT
<213> ORGANISM: Homo sapiens
<220> FEATURE:
<221> NAME/KEY: MISC_FEATURE
<222> LOCATION: (1)..(2156)
<223> OTHER INFORMATION: RP1 (oxygen-regulated protein 1)

<400> SEQUENCE: 32

Met Ser Asp Thr Pro Ser Thr Gly Phe Ser Ile Ile His Pro Thr Ser
1               5                   10                  15

Ser Glu Gly Gln Val Pro Pro Arg His Leu Ser Leu Thr His Pro
            20                  25                  30

Val Val Ala Lys Arg Ile Ser Phe Tyr Lys Ser Gly Asp Pro Gln Phe
        35                  40                  45

Gly Gly Val Arg Val Val Val Asn Pro Arg Ser Phe Lys Ser Phe Asp
    50                  55                  60

Ala Leu Leu Asp Asn Leu Ser Arg Lys Val Pro Leu Pro Phe Gly Val
65                  70                  75                  80

Arg Asn Ile Ser Thr Pro Arg Gly Arg His Ser Ile Thr Arg Leu Glu
                85                  90                  95

Glu Leu Glu Asp Gly Glu Ser Tyr Leu Cys Ser His Gly Arg Lys Val
            100                 105                 110

Gln Pro Val Asp Leu Asp Lys Ala Arg Arg Pro Arg Pro Trp Leu
        115                 120                 125

Ser Ser Arg Ala Ile Ser Ala His Ser Pro Pro His Pro Val Ala Val
    130                 135                 140

Ala Ala Pro Gly Met Pro Arg Pro Pro Arg Ser Leu Val Val Phe Arg
145                 150                 155                 160

Asn Gly Asp Pro Lys Thr Arg Arg Ala Val Leu Leu Ser Arg Arg Val
                165                 170                 175

Thr Gln Ser Phe Glu Ala Phe Leu Gln His Leu Thr Glu Val Met Gln
            180                 185                 190

Arg Pro Val Val Lys Leu Tyr Ala Thr Asp Gly Arg Arg Val Pro Ser
        195                 200                 205

Leu Gln Ala Val Ile Leu Ser Ser Gly Ala Val Val Ala Ala Gly Arg
    210                 215                 220

Glu Pro Phe Lys Pro Gly Asn Tyr Asp Ile Gln Lys Tyr Leu Leu Pro
225                 230                 235                 240

Ala Arg Leu Pro Gly Ile Ser Gln Arg Val Tyr Pro Lys Gly Asn Ala
                245                 250                 255

Lys Ser Glu Ser Arg Lys Ile Ser Thr His Met Ser Ser Ser Ser Arg

```
                260                 265                 270
Ser Gln Ile Tyr Ser Val Ser Ser Glu Lys Thr His Asn Asn Asp Cys
            275                 280                 285

Tyr Leu Asp Tyr Ser Phe Val Pro Glu Lys Tyr Leu Ala Leu Glu Lys
            290                 295                 300

Asn Asp Ser Gln Asn Leu Pro Ile Tyr Pro Ser Glu Asp Ile Glu
305                 310                 315                 320

Lys Ser Ile Ile Phe Asn Gln Asp Gly Thr Met Thr Val Glu Met Lys
                325                 330                 335

Val Arg Phe Arg Ile Lys Glu Glu Thr Ile Lys Trp Thr Thr Thr
                340                 345                 350

Val Ser Lys Thr Gly Pro Ser Asn Asn Asp Glu Lys Ser Glu Met Ser
            355                 360                 365

Phe Pro Gly Arg Thr Glu Ser Arg Ser Ser Gly Leu Lys Leu Ala Ala
            370                 375                 380

Cys Ser Phe Ser Ala Asp Val Ser Pro Met Glu Arg Ser Ser Asn Gln
385                 390                 395                 400

Glu Gly Ser Leu Ala Glu Glu Ile Asn Ile Gln Met Thr Asp Gln Val
                405                 410                 415

Ala Glu Thr Cys Ser Ser Ala Ser Trp Glu Asn Ala Thr Val Asp Thr
            420                 425                 430

Asp Ile Ile Gln Gly Thr Gln Asp Gln Ala Lys His Arg Phe Tyr Arg
            435                 440                 445

Pro Pro Thr Pro Gly Leu Arg Arg Val Arg Gln Lys Lys Ser Val Ile
            450                 455                 460

Gly Ser Val Thr Leu Val Ser Glu Thr Glu Val Gln Glu Lys Met Ile
465                 470                 475                 480

Gly Gln Phe Ser Tyr Ser Glu Glu Arg Glu Ser Gly Glu Asn Lys Ser
                485                 490                 495

Glu Tyr His Met Phe Thr His Ser Cys Ser Lys Met Ser Ser Val Ser
                500                 505                 510

Asn Lys Pro Val Leu Val Gln Ile Asn Asn Asn Asp Gln Met Glu Glu
            515                 520                 525

Ser Ser Leu Glu Arg Lys Lys Glu Asn Ser Leu Leu Lys Ser Ser Ala
            530                 535                 540

Ile Ser Ala Gly Val Ile Glu Ile Thr Ser Gln Lys Met Leu Glu Met
545                 550                 555                 560

Ser His Asn Asn Gly Leu Pro Ser Thr Ile Ser Asn Asn Ser Ile Val
                565                 570                 575

Glu Glu Asp Val Val Asp Cys Val Val Leu Asp Asn Lys Thr Gly Ile
            580                 585                 590

Lys Asn Phe Lys Thr Tyr Gly Asn Thr Asn Asp Arg Phe Ser Pro Ile
            595                 600                 605

Ser Ala Asp Ala Thr His Phe Ser Ser Asn Asn Ser Gly Thr Asp Lys
            610                 615                 620

Asn Ile Ser Glu Ala Pro Ala Ser Glu Ala Ser Ser Thr Val Thr Ala
625                 630                 635                 640

Arg Ile Asp Arg Leu Ile Asn Glu Phe Ala Gln Cys Gly Leu Thr Lys
                645                 650                 655

Leu Pro Lys Asn Glu Lys Lys Ile Leu Ser Ser Val Ala Ser Lys Lys
                660                 665                 670

Lys Lys Lys Ser Arg Gln Gln Ala Ile Asn Ser Arg Tyr Gln Asp Gly
            675                 680                 685
```

Gln Leu Ala Thr Lys Gly Ile Leu Asn Lys Asn Glu Arg Ile Asn Thr
690                 695                 700

Lys Gly Arg Ile Thr Lys Glu Met Ile Val Gln Asp Ser Asp Ser Pro
705                 710                 715                 720

Leu Lys Gly Gly Ile Leu Cys Glu Glu Asp Leu Gln Lys Ser Asp Thr
                725                 730                 735

Val Ile Glu Ser Asn Thr Phe Cys Ser Lys Ser Asn Leu Asn Ser Thr
            740                 745                 750

Ile Ser Lys Asn Phe His Arg Asn Lys Leu Asn Thr Thr Gln Asn Ser
        755                 760                 765

Lys Val Gln Gly Leu Leu Thr Lys Arg Lys Ser Arg Ser Leu Asn Lys
770                 775                 780

Ile Ser Leu Gly Ala Pro Lys Lys Arg Glu Ile Gly Gln Arg Asp Lys
785                 790                 795                 800

Val Phe Pro His Asn Glu Ser Lys Tyr Cys Lys Ser Thr Phe Glu Asn
                805                 810                 815

Lys Ser Leu Phe His Val Phe Asn Ile Leu Glu Gln Lys Pro Lys Asp
            820                 825                 830

Phe Tyr Ala Pro Gln Ser Gln Ala Glu Val Ala Ser Gly Tyr Leu Arg
        835                 840                 845

Gly Met Ala Lys Lys Ser Leu Val Ser Lys Val Thr Asp Ser His Ile
850                 855                 860

Thr Leu Lys Ser Gln Lys Lys Arg Lys Gly Asp Lys Val Lys Ala Ser
865                 870                 875                 880

Ala Ile Leu Ser Lys Gln His Ala Thr Thr Arg Ala Asn Ser Leu Ala
                885                 890                 895

Ser Leu Lys Lys Pro Asp Phe Pro Glu Ala Ile Ala His His Ser Ile
            900                 905                 910

Gln Asn Tyr Ile Gln Ser Trp Leu Gln Asn Ile Asn Pro Tyr Pro Thr
        915                 920                 925

Leu Lys Pro Ile Lys Ser Ala Pro Val Cys Arg Asn Glu Thr Ser Val
930                 935                 940

Val Asn Cys Ser Asn Asn Ser Phe Ser Gly Asn Asp Pro His Thr Asn
945                 950                 955                 960

Ser Gly Lys Ile Ser Asn Phe Val Met Glu Ser Asn Lys His Ile Thr
                965                 970                 975

Lys Ile Ala Gly Leu Thr Gly Asp Asn Leu Cys Lys Glu Gly Asp Lys
            980                 985                 990

Ser Phe Ile Ala Asn Asp Thr Gly Glu Glu Asp Leu His Glu Thr Gln
        995                 1000                1005

Val Gly Ser Leu Asn Asp Ala Tyr Leu Val Pro Leu His Glu His
    1010                1015                1020

Cys Thr Leu Ser Gln Ser Ala Ile Asn Asp His Asn Thr Lys Ser
    1025                1030                1035

His Ile Ala Ala Glu Lys Ser Gly Pro Glu Lys Lys Leu Val Tyr
    1040                1045                1050

Gln Glu Ile Asn Leu Ala Arg Lys Arg Gln Ser Val Glu Ala Ala
    1055                1060                1065

Ile Gln Val Asp Pro Ile Glu Glu Thr Pro Lys Asp Leu Leu
    1070                1075                1080

Pro Val Leu Met Leu His Gln Leu Gln Ala Ser Val Pro Gly Ile
    1085                1090                1095

```
His Lys Thr Gln Asn Gly Val Val Gln Met Pro Gly Ser Leu Ala
    1100                1105            1110

Gly Val Pro Phe His Ser Ala Ile Cys Asn Ser Ser Thr Asn Leu
    1115                1120            1125

Leu Leu Ala Trp Leu Leu Val Leu Asn Leu Lys Gly Ser Met Asn
    1130                1135            1140

Ser Phe Cys Gln Val Asp Ala His Lys Ala Thr Asn Lys Ser Ser
    1145                1150            1155

Glu Thr Leu Ala Leu Leu Glu Ile Leu Lys His Ile Ala Ile Thr
    1160                1165            1170

Glu Glu Ala Asp Asp Leu Lys Ala Ala Val Ala Asn Leu Val Glu
    1175                1180            1185

Ser Thr Thr Ser His Phe Gly Leu Ser Glu Lys Glu Gln Asp Met
    1190                1195            1200

Val Pro Ile Asp Leu Ser Ala Asn Cys Ser Thr Val Asn Ile Gln
    1205                1210            1215

Ser Val Pro Lys Cys Ser Glu Asn Glu Arg Thr Gln Gly Ile Ser
    1220                1225            1230

Ser Leu Asp Gly Gly Cys Ser Ala Ser Glu Ala Cys Ala Pro Glu
    1235                1240            1245

Val Cys Val Leu Glu Val Thr Cys Ser Pro Cys Glu Met Cys Thr
    1250                1255            1260

Val Asn Lys Ala Tyr Ser Pro Lys Glu Thr Cys Asn Pro Ser Asp
    1265                1270            1275

Thr Phe Phe Pro Ser Asp Gly Tyr Gly Val Asp Gln Thr Ser Met
    1280                1285            1290

Asn Lys Ala Cys Phe Leu Gly Glu Val Cys Ser Leu Thr Asp Thr
    1295                1300            1305

Val Phe Ser Asp Lys Ala Cys Ala Gln Lys Glu Asn His Thr Tyr
    1310                1315            1320

Glu Gly Ala Cys Pro Ile Asp Glu Thr Tyr Val Pro Val Asn Val
    1325                1330            1335

Cys Asn Thr Ile Asp Phe Leu Asn Ser Lys Glu Asn Thr Tyr Thr
    1340                1345            1350

Asp Asn Leu Asp Ser Thr Glu Glu Leu Glu Arg Gly Asp Asp Ile
    1355                1360            1365

Gln Lys Asp Leu Asn Ile Leu Thr Asp Pro Glu Tyr Lys Asn Gly
    1370                1375            1380

Phe Asn Thr Leu Val Ser His Gln Asn Val Ser Asn Leu Ser Ser
    1385                1390            1395

Cys Gly Leu Cys Leu Ser Glu Lys Glu Ala Glu Leu Asp Lys Lys
    1400                1405            1410

His Ser Ser Leu Asp Asp Phe Glu Asn Cys Ser Leu Arg Lys Phe
    1415                1420            1425

Gln Asp Glu Asn Ala Tyr Thr Ser Phe Asp Met Glu Glu Pro Arg
    1430                1435            1440

Thr Ser Glu Glu Pro Gly Ser Ile Thr Asn Ser Met Thr Ser Ser
    1445                1450            1455

Glu Arg Asn Ile Ser Glu Leu Glu Ser Phe Glu Glu Leu Glu Asn
    1460                1465            1470

His Asp Thr Asp Ile Phe Asn Thr Val Val Asn Gly Gly Glu Gln
    1475                1480            1485

Ala Thr Glu Glu Leu Ile Gln Glu Glu Val Glu Ala Ser Lys Thr
```

-continued

```
                   1490                1495                1500

Leu Glu Leu Ile Asp Ile Ser Ser Lys Asn Ile Met Glu Glu Lys
    1505                1510                1515

Arg Met Asn Gly Ile Ile Tyr Glu Ile Ile Ser Lys Arg Leu Ala
    1520                1525                1530

Thr Pro Pro Ser Leu Asp Phe Cys Tyr Asp Ser Lys Gln Asn Ser
    1535                1540                1545

Glu Lys Glu Thr Asn Glu Gly Glu Thr Lys Met Val Lys Met Met
    1550                1555                1560

Val Lys Thr Met Glu Thr Gly Ser Tyr Ser Glu Ser Ser Pro Asp
    1565                1570                1575

Leu Lys Lys Cys Ile Lys Ser Pro Val Thr Ser Asp Trp Ser Asp
    1580                1585                1590

Tyr Arg Pro Asp Ser Asp Ser Glu Gln Pro Tyr Lys Thr Ser Ser
    1595                1600                1605

Asp Asp Pro Asn Asp Ser Gly Glu Leu Thr Gln Glu Lys Glu Tyr
    1610                1615                1620

Asn Ile Gly Phe Val Lys Arg Ala Ile Glu Lys Leu Tyr Gly Lys
    1625                1630                1635

Ala Asp Ile Ile Lys Pro Ser Phe Phe Pro Gly Ser Thr Arg Lys
    1640                1645                1650

Ser Gln Val Cys Pro Tyr Asn Ser Val Glu Phe Gln Cys Ser Arg
    1655                1660                1665

Lys Ala Ser Leu Tyr Asp Ser Glu Gly Gln Ser Phe Gly Ser Ser
    1670                1675                1680

Glu Gln Val Ser Ser Ser Ser Met Leu Gln Glu Phe Gln Glu
    1685                1690                1695

Glu Arg Gln Asp Lys Cys Asp Val Ser Ala Val Arg Asp Asn Tyr
    1700                1705                1710

Cys Arg Gly Asp Ile Val Glu Pro Gly Thr Lys Gln Asn Asp Asp
    1715                1720                1725

Ser Arg Ile Leu Thr Asp Ile Glu Glu Gly Val Leu Ile Asp Lys
    1730                1735                1740

Gly Lys Trp Leu Leu Lys Glu Asn His Leu Leu Arg Met Ser Ser
    1745                1750                1755

Glu Asn Pro Gly Met Cys Gly Asn Ala Asp Thr Thr Ser Val Asp
    1760                1765                1770

Thr Leu Leu Asp Asn Asn Ser Ser Glu Val Pro Tyr Ser His Phe
    1775                1780                1785

Gly Asn Leu Ala Pro Gly Pro Thr Met Asp Glu Leu Ser Ser Ser
    1790                1795                1800

Glu Leu Glu Glu Leu Thr Gln Pro Leu Glu Leu Lys Cys Asn Tyr
    1805                1810                1815

Phe Asn Met Pro His Gly Ser Asp Ser Glu Pro Phe His Glu Asp
    1820                1825                1830

Leu Leu Asp Val Arg Asn Glu Thr Cys Ala Lys Glu Arg Ile Ala
    1835                1840                1845

Asn His His Thr Glu Glu Lys Gly Ser His Ser Glu Arg Val
    1850                1855                1860

Cys Thr Ser Val Thr His Ser Phe Ile Ser Ala Gly Asn Lys Val
    1865                1870                1875

Tyr Pro Val Ser Asp Asp Ala Ile Lys Asn Gln Pro Leu Pro Gly
    1880                1885                1890
```

Ser Asn Met Ile His Gly Thr Leu Gln Glu Ala Asp Ser Leu Asp
    1895                1900                1905

Lys Leu Tyr Ala Leu Cys Gly Gln His Cys Pro Ile Leu Thr Val
    1910                1915                1920

Ile Ile Gln Pro Met Asn Glu Glu Asp Arg Gly Phe Ala Tyr Arg
    1925                1930                1935

Lys Glu Ser Asp Ile Glu Asn Phe Leu Gly Phe Tyr Leu Trp Met
    1940                1945                1950

Lys Ile His Pro Tyr Leu Leu Gln Thr Asp Lys Asn Val Phe Arg
    1955                1960                1965

Glu Glu Asn Asn Lys Ala Ser Met Arg Gln Asn Leu Ile Asp Asn
    1970                1975                1980

Ala Ile Gly Asp Ile Phe Asp Gln Phe Tyr Phe Ser Asn Thr Phe
    1985                1990                1995

Asp Leu Met Gly Lys Arg Arg Lys Gln Lys Arg Ile Asn Phe Leu
    2000                2005                2010

Gly Leu Glu Glu Glu Gly Asn Leu Lys Lys Phe Gln Pro Asp Leu
    2015                2020                2025

Lys Glu Arg Phe Cys Met Asn Phe Leu His Thr Ser Leu Leu Val
    2030                2035                2040

Val Gly Asn Val Asp Ser Asn Thr Gln Asp Leu Ser Gly Gln Thr
    2045                2050                2055

Asn Glu Ile Phe Lys Ala Val Asp Glu Asn Asn Asn Leu Leu Asn
    2060                2065                2070

Asn Arg Phe Gln Gly Ser Arg Thr Asn Leu Asn Gln Val Val Arg
    2075                2080                2085

Glu Asn Ile Asn Cys His Tyr Phe Phe Glu Met Leu Gly Gln Ala
    2090                2095                2100

Cys Leu Leu Asp Ile Cys Gln Val Glu Thr Ser Leu Asn Ile Ser
    2105                2110                2115

Asn Arg Asn Ile Leu Glu Leu Cys Met Phe Glu Gly Glu Asn Leu
    2120                2125                2130

Phe Ile Trp Glu Glu Glu Asp Ile Leu Asn Leu Thr Asp Leu Glu
    2135                2140                2145

Ser Ser Arg Glu Gln Glu Asp Leu
    2150                2155

<210> SEQ ID NO 33
<211> LENGTH: 350
<212> TYPE: PRT
<213> ORGANISM: Homo sapiens
<220> FEATURE:
<221> NAME/KEY: MISC_FEATURE
<222> LOCATION: (1)..(350)
<223> OTHER INFORMATION: RP2 (protein XRP2)

<400> SEQUENCE: 33

Met Gly Cys Phe Phe Ser Lys Arg Arg Lys Ala Asp Lys Glu Ser Arg
1               5                   10                  15

Pro Glu Asn Glu Glu Glu Arg Pro Lys Gln Tyr Ser Trp Asp Gln Arg
            20                  25                  30

Glu Lys Val Asp Pro Lys Asp Tyr Met Phe Ser Gly Leu Lys Asp Glu
        35                  40                  45

Thr Val Gly Arg Leu Pro Gly Thr Val Ala Gly Gln Gln Phe Leu Ile
    50                  55                  60

Gln Asp Cys Glu Asn Cys Asn Ile Tyr Ile Phe Asp His Ser Ala Thr
 65                  70                  75                  80

Val Thr Ile Asp Asp Cys Thr Asn Cys Ile Ile Phe Leu Gly Pro Val
                 85                  90                  95

Lys Gly Ser Val Phe Phe Arg Asn Cys Arg Asp Cys Lys Cys Thr Leu
            100                 105                 110

Ala Cys Gln Gln Phe Arg Val Arg Asp Cys Arg Lys Leu Glu Val Phe
        115                 120                 125

Leu Cys Cys Ala Thr Gln Pro Ile Ile Glu Ser Ser Asn Ile Lys
130                 135                 140

Phe Gly Cys Phe Gln Trp Tyr Tyr Pro Glu Leu Ala Phe Gln Phe Lys
145                 150                 155                 160

Asp Ala Gly Leu Ser Ile Phe Asn Asn Thr Trp Ser Asn Ile His Asp
                165                 170                 175

Phe Thr Pro Val Ser Gly Glu Leu Asn Trp Ser Leu Leu Pro Glu Asp
            180                 185                 190

Ala Val Val Gln Asp Tyr Val Pro Ile Pro Thr Thr Glu Glu Leu Lys
        195                 200                 205

Ala Val Arg Val Ser Thr Glu Ala Asn Arg Ser Ile Val Pro Ile Ser
210                 215                 220

Arg Gly Gln Arg Gln Lys Ser Ser Asp Glu Ser Cys Leu Val Val Leu
225                 230                 235                 240

Phe Ala Gly Asp Tyr Thr Ile Ala Asn Ala Arg Lys Leu Ile Asp Glu
                245                 250                 255

Met Val Gly Lys Gly Phe Phe Leu Val Gln Thr Lys Val Ser Met
            260                 265                 270

Lys Ala Glu Asp Ala Gln Arg Val Phe Arg Glu Lys Ala Pro Asp Phe
        275                 280                 285

Leu Pro Leu Leu Asn Lys Gly Pro Val Ile Ala Leu Glu Phe Asn Gly
290                 295                 300

Asp Gly Ala Val Glu Val Cys Gln Leu Ile Val Asn Glu Ile Phe Asn
305                 310                 315                 320

Gly Thr Lys Met Phe Val Ser Glu Ser Lys Glu Thr Ala Ser Gly Asp
                325                 330                 335

Val Asp Ser Phe Tyr Asn Phe Ala Asp Ile Gln Met Gly Ile
            340                 345                 350

<210> SEQ ID NO 34
<211> LENGTH: 1020
<212> TYPE: PRT
<213> ORGANISM: Homo sapiens
<220> FEATURE:
<221> NAME/KEY: MISC_FEATURE
<222> LOCATION: (1)..(1020)
<223> OTHER INFORMATION: RPGR (X-linked retinitis pigmentosa GTPase
      regulator), isoform 1

<400> SEQUENCE: 34

Met Arg Glu Pro Glu Glu Leu Met Pro Asp Ser Gly Ala Val Phe Thr
1               5                   10                  15

Phe Gly Lys Ser Lys Phe Ala Glu Asn Asn Pro Gly Lys Phe Trp Phe
            20                  25                  30

Lys Asn Asp Val Pro Val His Leu Ser Cys Gly Asp Glu His Ser Ala
        35                  40                  45

Val Val Thr Gly Asn Asn Lys Leu Tyr Met Phe Gly Ser Asn Asn Trp
    50                  55                  60

```
Gly Gln Leu Gly Leu Gly Ser Lys Ser Ala Ile Ser Lys Pro Thr Cys
 65                  70                  75                  80

Val Lys Ala Leu Lys Pro Glu Lys Val Lys Leu Ala Ala Cys Gly Arg
                 85                  90                  95

Asn His Thr Leu Val Ser Thr Glu Gly Gly Asn Val Tyr Ala Thr Gly
            100                 105                 110

Gly Asn Asn Glu Gly Gln Leu Gly Leu Gly Asp Thr Glu Arg Asn
            115                 120                 125

Thr Phe His Val Ile Ser Phe Phe Thr Ser Glu His Lys Ile Lys Gln
            130                 135                 140

Leu Ser Ala Gly Ser Asn Thr Ser Ala Ala Leu Thr Glu Asp Gly Arg
145                 150                 155                 160

Leu Phe Met Trp Gly Asp Asn Ser Glu Gly Gln Ile Gly Leu Lys Asn
                165                 170                 175

Val Ser Asn Val Cys Val Pro Gln Gln Val Thr Ile Gly Lys Pro Val
            180                 185                 190

Ser Trp Ile Ser Cys Gly Tyr Tyr His Ser Ala Phe Val Thr Thr Asp
            195                 200                 205

Gly Glu Leu Tyr Val Phe Gly Glu Pro Glu Asn Gly Lys Leu Gly Leu
            210                 215                 220

Pro Asn Gln Leu Leu Gly Asn His Arg Thr Pro Gln Leu Val Ser Glu
225                 230                 235                 240

Ile Pro Glu Lys Val Ile Gln Val Ala Cys Gly Gly Glu His Thr Val
                245                 250                 255

Val Leu Thr Glu Asn Ala Val Tyr Thr Phe Gly Leu Gly Gln Phe Gly
            260                 265                 270

Gln Leu Gly Leu Gly Thr Phe Leu Phe Glu Thr Ser Glu Pro Lys Val
            275                 280                 285

Ile Glu Asn Ile Arg Asp Gln Thr Ile Ser Tyr Ile Ser Cys Gly Glu
            290                 295                 300

Asn His Thr Ala Leu Ile Thr Asp Ile Gly Leu Met Tyr Thr Phe Gly
305                 310                 315                 320

Asp Gly Arg His Gly Lys Leu Gly Leu Gly Leu Glu Asn Phe Thr Asn
                325                 330                 335

His Phe Ile Pro Thr Leu Cys Ser Asn Phe Leu Arg Phe Ile Val Lys
            340                 345                 350

Leu Val Ala Cys Gly Gly Cys His Met Val Val Phe Ala Ala Pro His
            355                 360                 365

Arg Gly Val Ala Lys Glu Ile Glu Phe Asp Glu Ile Asn Asp Thr Cys
            370                 375                 380

Leu Ser Val Ala Thr Phe Leu Pro Tyr Ser Ser Leu Thr Ser Gly Asn
385                 390                 395                 400

Val Leu Gln Arg Thr Leu Ser Ala Arg Met Arg Arg Glu Arg Glu
                405                 410                 415

Arg Ser Pro Asp Ser Phe Ser Met Arg Arg Thr Leu Pro Pro Ile Glu
            420                 425                 430

Gly Thr Leu Gly Leu Ser Ala Cys Phe Leu Pro Asn Ser Val Phe Pro
            435                 440                 445

Arg Cys Ser Glu Arg Asn Leu Gln Glu Ser Val Leu Ser Glu Gln Asp
            450                 455                 460

Leu Met Gln Pro Glu Glu Pro Asp Tyr Leu Leu Asp Glu Met Thr Lys
465                 470                 475                 480

Glu Ala Glu Ile Asp Asn Ser Ser Thr Val Glu Ser Leu Gly Glu Thr
```

-continued

```
                   485                 490                 495
Thr Asp Ile Leu Asn Met Thr His Ile Met Ser Leu Asn Ser Asn Glu
                500                 505                 510

Lys Ser Leu Lys Leu Ser Pro Val Gln Lys Gln Lys Gln Gln Thr
            515                 520                 525

Ile Gly Glu Leu Thr Gln Asp Thr Ala Leu Thr Glu Asn Asp Asp Ser
        530                 535                 540

Asp Glu Tyr Glu Glu Met Ser Glu Met Lys Glu Gly Lys Ala Cys Lys
545                 550                 555                 560

Gln His Val Ser Gln Gly Ile Phe Met Thr Gln Pro Ala Thr Thr Ile
                565                 570                 575

Glu Ala Phe Ser Asp Glu Glu Val Gly Asn Asp Thr Gly Gln Val Gly
            580                 585                 590

Pro Gln Ala Asp Thr Asp Gly Glu Gly Leu Gln Lys Glu Val Tyr Arg
        595                 600                 605

His Glu Asn Asn Asn Gly Val Asp Gln Leu Asp Ala Lys Glu Ile Glu
    610                 615                 620

Lys Glu Ser Asp Gly Gly His Ser Gln Lys Glu Ser Glu Ala Glu Glu
625                 630                 635                 640

Ile Asp Ser Glu Lys Glu Thr Lys Leu Ala Glu Ile Ala Gly Met Lys
                645                 650                 655

Asp Leu Arg Glu Arg Glu Lys Ser Thr Lys Lys Met Ser Pro Phe Phe
            660                 665                 670

Gly Asn Leu Pro Asp Arg Gly Met Asn Thr Glu Ser Glu Glu Asn Lys
        675                 680                 685

Asp Phe Val Lys Lys Arg Glu Ser Cys Lys Gln Asp Val Ile Phe Asp
    690                 695                 700

Ser Glu Arg Glu Ser Val Glu Lys Pro Asp Ser Tyr Met Glu Gly Ala
705                 710                 715                 720

Ser Glu Ser Gln Gln Gly Ile Ala Asp Gly Phe Gln Gln Pro Glu Ala
                725                 730                 735

Ile Glu Phe Ser Ser Gly Glu Lys Glu Asp Asp Glu Val Glu Thr Asp
            740                 745                 750

Gln Asn Ile Arg Tyr Gly Arg Lys Leu Ile Glu Gln Gly Asn Glu Lys
        755                 760                 765

Glu Thr Lys Pro Ile Ile Ser Lys Ser Met Ala Lys Tyr Asp Phe Lys
    770                 775                 780

Cys Asp Arg Leu Ser Glu Ile Pro Glu Glu Lys Glu Gly Ala Glu Asp
785                 790                 795                 800

Ser Lys Gly Asn Gly Ile Glu Glu Gln Glu Val Glu Ala Asn Glu Glu
                805                 810                 815

Asn Val Lys Val His Gly Gly Arg Lys Glu Lys Thr Glu Ile Leu Ser
            820                 825                 830

Asp Asp Leu Thr Asp Lys Ala Glu Asp His Glu Phe Ser Lys Thr Glu
        835                 840                 845

Glu Leu Lys Leu Glu Asp Val Asp Glu Glu Ile Asn Ala Glu Asn Val
    850                 855                 860

Glu Ser Lys Lys Lys Thr Val Gly Asp Asp Glu Ser Val Pro Thr Gly
865                 870                 875                 880

Tyr His Ser Lys Thr Glu Gly Ala Glu Arg Thr Asn Asp Asp Ser Ser
                885                 890                 895

Ala Glu Thr Ile Glu Lys Lys Glu Lys Ala Asn Leu Glu Glu Arg Ala
            900                 905                 910
```

```
Ile Cys Glu Tyr Asn Glu Asn Pro Lys Gly Tyr Met Leu Asp Asp Ala
        915                 920                 925

Asp Ser Ser Leu Glu Ile Leu Glu Asn Ser Glu Thr Thr Pro Ser
    930                 935                 940

Lys Asp Met Lys Thr Lys Lys Ile Phe Leu Phe Lys Arg Val Pro
945                 950                 955                 960

Ser Ile Asn Gln Lys Ile Val Lys Asn Asn Glu Pro Leu Pro Glu
                965                 970                 975

Ile Lys Ser Ile Gly Asp Gln Ile Ile Leu Lys Ser Asp Asn Lys Asp
            980                 985                 990

Ala Asp Gln Asn His Met Ser Gln Asn His Gln Asn Ile Pro Pro Thr
    995                 1000                1005

Asn Thr Glu Arg Arg Ser Lys Ser Cys Thr Ile Leu
    1010                1015                1020
```

<210> SEQ ID NO 35
<211> LENGTH: 405
<212> TYPE: PRT
<213> ORGANISM: Homo sapiens
<220> FEATURE:
<221> NAME/KEY: MISC_FEATURE
<222> LOCATION: (1)..(405)
<223> OTHER INFORMATION: SAG (S-arrestin)

<400> SEQUENCE: 35

```
Met Ala Ala Ser Gly Lys Thr Ser Lys Ser Glu Pro Asn His Val Ile
1               5                   10                  15

Phe Lys Lys Ile Ser Arg Asp Lys Ser Val Thr Ile Tyr Leu Gly Asn
            20                  25                  30

Arg Asp Tyr Ile Asp His Val Ser Gln Val Gln Pro Val Asp Gly Val
        35                  40                  45

Val Leu Val Asp Pro Asp Leu Val Lys Gly Lys Val Tyr Val Thr
    50                  55                  60

Leu Thr Cys Ala Phe Arg Tyr Gly Gln Glu Asp Ile Asp Val Ile Gly
65                  70                  75                  80

Leu Thr Phe Arg Arg Asp Leu Tyr Phe Ser Arg Val Gln Val Tyr Pro
                85                  90                  95

Pro Val Gly Ala Ala Ser Thr Pro Thr Lys Leu Gln Glu Ser Leu Leu
            100                 105                 110

Lys Lys Leu Gly Ser Asn Thr Tyr Pro Phe Leu Leu Thr Phe Pro Asp
        115                 120                 125

Tyr Leu Pro Cys Ser Val Met Leu Gln Pro Ala Pro Gln Asp Ser Gly
    130                 135                 140

Lys Ser Cys Gly Val Asp Phe Glu Val Lys Ala Phe Ala Thr Asp Ser
145                 150                 155                 160

Thr Asp Ala Glu Glu Asp Lys Ile Pro Lys Lys Ser Ser Val Arg Leu
                165                 170                 175

Leu Ile Arg Lys Val Gln His Ala Pro Leu Glu Met Gly Pro Gln Pro
            180                 185                 190

Arg Ala Glu Ala Ala Trp Gln Phe Phe Met Ser Asp Lys Pro Leu His
        195                 200                 205

Leu Ala Val Ser Leu Asn Lys Glu Ile Tyr Phe His Gly Glu Pro Ile
    210                 215                 220

Pro Val Thr Val Thr Val Thr Asn Asn Thr Glu Lys Thr Val Lys Lys
225                 230                 235                 240
```

```
Ile Lys Ala Phe Val Glu Gln Val Ala Asn Val Val Leu Tyr Ser Ser
                245                 250                 255

Asp Tyr Tyr Val Lys Pro Val Ala Met Glu Glu Ala Gln Glu Lys Val
            260                 265                 270

Pro Pro Asn Ser Thr Leu Thr Lys Thr Leu Thr Leu Leu Pro Leu Leu
        275                 280                 285

Ala Asn Asn Arg Glu Arg Arg Gly Ile Ala Leu Asp Gly Lys Ile Lys
290                 295                 300

His Glu Asp Thr Asn Leu Ala Ser Ser Thr Ile Ile Lys Glu Gly Ile
305                 310                 315                 320

Asp Arg Thr Val Leu Gly Ile Leu Val Ser Tyr Gln Ile Lys Val Lys
                325                 330                 335

Leu Thr Val Ser Gly Phe Leu Gly Glu Leu Thr Ser Ser Glu Val Ala
            340                 345                 350

Thr Glu Val Pro Phe Arg Leu Met His Pro Gln Pro Glu Asp Pro Ala
        355                 360                 365

Lys Glu Ser Tyr Gln Asp Ala Asn Leu Val Phe Glu Glu Phe Ala Arg
    370                 375                 380

His Asn Leu Lys Asp Ala Gly Glu Ala Glu Glu Gly Lys Arg Asp Lys
385                 390                 395                 400

Asn Asp Val Asp Glu
                405

<210> SEQ ID NO 36
<211> LENGTH: 552
<212> TYPE: PRT
<213> ORGANISM: Homo sapiens
<220> FEATURE:
<221> NAME/KEY: MISC_FEATURE
<222> LOCATION: (1)..(552)
<223> OTHER INFORMATION: USH1C (Usher syndrome type-1 C protein),
      isoform 1

<400> SEQUENCE: 36

Met Asp Arg Lys Val Ala Arg Glu Phe Arg His Lys Val Asp Phe Leu
1               5                   10                  15

Ile Glu Asn Asp Ala Glu Lys Asp Tyr Leu Tyr Asp Val Leu Arg Met
                20                  25                  30

Tyr His Gln Thr Met Asp Val Ala Val Leu Val Gly Asp Leu Lys Leu
            35                  40                  45

Val Ile Asn Glu Pro Ser Arg Leu Pro Leu Phe Asp Ala Ile Arg Pro
        50                  55                  60

Leu Ile Pro Leu Lys His Gln Val Glu Tyr Asp Gln Leu Thr Pro Arg
65                  70                  75                  80

Arg Ser Arg Lys Leu Lys Glu Val Arg Leu Asp Arg Leu His Pro Glu
                85                  90                  95

Gly Leu Gly Leu Ser Val Arg Gly Gly Leu Glu Phe Gly Cys Gly Leu
            100                 105                 110

Phe Ile Ser His Leu Ile Lys Gly Gly Gln Ala Asp Ser Val Gly Leu
        115                 120                 125

Gln Val Gly Asp Glu Ile Val Arg Ile Asn Gly Tyr Ser Ile Ser Ser
    130                 135                 140

Cys Thr His Glu Glu Val Ile Asn Leu Ile Arg Thr Lys Lys Thr Val
145                 150                 155                 160

Ser Ile Lys Val Arg His Ile Gly Leu Ile Pro Val Lys Ser Ser Pro
                165                 170                 175
```

```
Asp Glu Pro Leu Thr Trp Gln Tyr Val Asp Gln Phe Val Ser Glu Ser
                180                 185                 190

Gly Gly Val Arg Gly Ser Leu Gly Ser Pro Gly Asn Arg Glu Asn Lys
            195                 200                 205

Glu Lys Lys Val Phe Ile Ser Leu Val Gly Ser Arg Gly Leu Gly Cys
210                 215                 220

Ser Ile Ser Ser Gly Pro Ile Gln Lys Pro Gly Ile Phe Ile Ser His
225                 230                 235                 240

Val Lys Pro Gly Ser Leu Ser Ala Glu Val Gly Leu Glu Ile Gly Asp
            245                 250                 255

Gln Ile Val Glu Val Asn Gly Val Asp Phe Ser Asn Leu Asp His Lys
        260                 265                 270

Glu Ala Val Asn Val Leu Lys Ser Ser Arg Ser Leu Thr Ile Ser Ile
    275                 280                 285

Val Ala Ala Gly Arg Glu Leu Phe Met Thr Asp Arg Glu Arg Leu
290                 295                 300

Ala Glu Ala Arg Gln Arg Glu Leu Gln Arg Gln Glu Leu Leu Met Gln
305                 310                 315                 320

Lys Arg Leu Ala Met Glu Ser Asn Lys Ile Leu Gln Glu Gln Gln Glu
            325                 330                 335

Met Glu Arg Gln Arg Arg Lys Glu Ile Ala Gln Lys Ala Ala Glu Glu
        340                 345                 350

Asn Glu Arg Tyr Arg Lys Glu Met Glu Gln Ile Val Glu Glu Glu
    355                 360                 365

Lys Phe Lys Lys Gln Trp Glu Glu Asp Trp Gly Ser Lys Glu Gln Leu
370                 375                 380

Leu Leu Pro Lys Thr Ile Thr Ala Glu Val His Pro Val Pro Leu Arg
385                 390                 395                 400

Lys Pro Lys Tyr Asp Gln Gly Val Glu Pro Glu Leu Glu Pro Ala Asp
            405                 410                 415

Asp Leu Asp Gly Gly Thr Glu Glu Gln Gly Glu Gln Asp Phe Arg Lys
        420                 425                 430

Tyr Glu Glu Gly Phe Asp Pro Tyr Ser Met Phe Thr Pro Glu Gln Ile
    435                 440                 445

Met Gly Lys Asp Val Arg Leu Leu Arg Ile Lys Lys Glu Gly Ser Leu
450                 455                 460

Asp Leu Ala Leu Glu Gly Gly Val Asp Ser Pro Ile Gly Lys Val Val
465                 470                 475                 480

Val Ser Ala Val Tyr Glu Arg Gly Ala Ala Glu Arg His Gly Gly Ile
            485                 490                 495

Val Lys Gly Asp Glu Ile Met Ala Ile Asn Gly Lys Ile Val Thr Asp
        500                 505                 510

Tyr Thr Leu Ala Glu Ala Glu Ala Ala Leu Gln Lys Ala Trp Asn Gln
    515                 520                 525

Gly Gly Asp Trp Ile Asp Leu Val Val Ala Val Cys Pro Pro Lys Glu
530                 535                 540

Tyr Asp Asp Glu Leu Thr Phe Phe
545                 550

<210> SEQ ID NO 37
<211> LENGTH: 461
<212> TYPE: PRT
<213> ORGANISM: Homo sapiens
<220> FEATURE:
<221> NAME/KEY: MISC_FEATURE
```

<222> LOCATION: (1)..(461)
<223> OTHER INFORMATION: USH1G (Usher syndrome type-1G protein)

<400> SEQUENCE: 37

```
Met Asn Asp Gln Tyr His Arg Ala Ala Arg Asp Gly Tyr Leu Glu Leu
1               5                   10                  15

Leu Lys Glu Ala Thr Arg Lys Glu Leu Asn Ala Pro Asp Glu Asp Gly
                20                  25                  30

Met Thr Pro Thr Leu Trp Ala Ala Tyr His Gly Asn Leu Glu Ser Leu
            35                  40                  45

Arg Leu Ile Val Ser Arg Gly Gly Asp Pro Asp Lys Cys Asp Ile Trp
        50                  55                  60

Gly Asn Thr Pro Leu His Leu Ala Ala Ser Asn Gly His Leu His Cys
65                  70                  75                  80

Leu Ser Phe Leu Val Ser Phe Gly Ala Asn Ile Trp Cys Leu Asp Asn
                85                  90                  95

Asp Tyr His Thr Pro Leu Asp Met Ala Ala Met Lys Gly His Met Glu
            100                 105                 110

Cys Val Arg Tyr Leu Asp Ser Ile Ala Ala Lys Gln Ser Ser Leu Asn
        115                 120                 125

Pro Lys Leu Val Gly Lys Leu Lys Asp Lys Ala Phe Arg Glu Ala Glu
130                 135                 140

Arg Arg Ile Arg Glu Cys Ala Lys Leu Gln Arg Arg His His Glu Arg
145                 150                 155                 160

Met Glu Arg Arg Tyr Arg Arg Glu Leu Ala Glu Arg Ser Asp Thr Leu
                165                 170                 175

Ser Phe Ser Ser Leu Thr Ser Ser Thr Leu Ser Arg Arg Leu Gln His
            180                 185                 190

Leu Ala Leu Gly Ser His Leu Pro Tyr Ser Gln Ala Thr Leu His Gly
        195                 200                 205

Thr Ala Arg Gly Lys Thr Lys Met Gln Lys Lys Leu Glu Arg Arg Lys
210                 215                 220

Gln Gly Gly Glu Gly Thr Phe Lys Val Ser Glu Asp Gly Arg Lys Ser
225                 230                 235                 240

Ala Arg Ser Leu Ser Gly Leu Gln Leu Gly Ser Asp Val Met Phe Val
                245                 250                 255

Arg Gln Gly Thr Tyr Ala Asn Pro Lys Glu Trp Gly Arg Ala Pro Leu
            260                 265                 270

Arg Asp Met Phe Leu Ser Asp Glu Asp Ser Val Ser Arg Ala Thr Leu
        275                 280                 285

Ala Ala Glu Pro Ala His Ser Glu Val Ser Thr Asp Ser Gly His Asp
290                 295                 300

Ser Leu Phe Thr Arg Pro Gly Leu Gly Thr Met Val Phe Arg Arg Asn
305                 310                 315                 320

Tyr Leu Ser Ser Gly Leu His Gly Leu Gly Arg Glu Asp Gly Gly Leu
                325                 330                 335

Asp Gly Val Gly Ala Pro Arg Gly Arg Leu Gln Ser Ser Pro Ser Leu
            340                 345                 350

Asp Asp Asp Ser Leu Gly Ser Ala Asn Ser Leu Gln Arg Ser Cys
        355                 360                 365

Gly Glu Glu Leu Pro Trp Asp Glu Leu Asp Leu Gly Leu Asp Glu Asp
370                 375                 380

Leu Glu Pro Glu Thr Ser Pro Leu Glu Thr Phe Leu Ala Ser Leu His
385                 390                 395                 400
```

```
Met Glu Asp Phe Ala Ala Leu Leu Arg Gln Glu Lys Ile Asp Leu Glu
                405                 410                 415

Ala Leu Met Leu Cys Ser Asp Leu Asp Leu Arg Ser Ile Ser Val Pro
            420                 425                 430

Leu Gly Pro Arg Lys Lys Ile Leu Gly Ala Val Arg Arg Arg Arg Gln
        435                 440                 445

Ala Met Glu Arg Pro Pro Ala Leu Glu Asp Thr Glu Leu
    450                 455                 460

<210> SEQ ID NO 38
<211> LENGTH: 5202
<212> TYPE: PRT
<213> ORGANISM: Homo sapiens
<220> FEATURE:
<221> NAME/KEY: MISC_FEATURE
<222> LOCATION: (1)..(5202)
<223> OTHER INFORMATION: USH2A (Usherin), isoform 1

<400> SEQUENCE: 38

Met Asn Cys Pro Val Leu Ser Leu Gly Ser Gly Phe Leu Phe Gln Val
1               5                   10                  15

Ile Glu Met Leu Ile Phe Ala Tyr Phe Ala Ser Ile Ser Leu Thr Glu
            20                  25                  30

Ser Arg Gly Leu Phe Pro Arg Leu Glu Asn Val Gly Ala Phe Lys Lys
        35                  40                  45

Val Ser Ile Val Pro Thr Gln Ala Val Cys Gly Leu Pro Asp Arg Ser
    50                  55                  60

Thr Phe Cys His Ser Ala Ala Ala Glu Ser Ile Gln Phe Cys Thr
65                  70                  75                  80

Gln Arg Phe Cys Ile Gln Asp Cys Pro Tyr Arg Ser Ser His Pro Thr
                85                  90                  95

Tyr Thr Ala Leu Phe Ser Ala Gly Leu Ser Ser Cys Ile Thr Pro Asp
            100                 105                 110

Lys Asn Asp Leu His Pro Asn Ala His Ser Asn Ser Ala Ser Phe Ile
        115                 120                 125

Phe Gly Asn His Lys Ser Cys Phe Ser Ser Pro Ser Pro Lys Leu
    130                 135                 140

Met Ala Ser Phe Thr Leu Ala Val Trp Leu Lys Pro Glu Gln Gln Gly
145                 150                 155                 160

Val Met Cys Val Ile Glu Lys Thr Val Asp Gly Gln Ile Val Phe Lys
                165                 170                 175

Leu Thr Ile Ser Glu Lys Glu Thr Met Phe Tyr Tyr Arg Thr Val Asn
            180                 185                 190

Gly Leu Gln Pro Pro Ile Lys Val Met Thr Leu Gly Arg Ile Leu Val
        195                 200                 205

Lys Lys Trp Ile His Leu Ser Val Gln Val His Gln Thr Lys Ile Ser
    210                 215                 220

Phe Phe Ile Asn Gly Val Glu Lys Asp His Thr Pro Phe Asn Ala Arg
225                 230                 235                 240

Thr Leu Ser Gly Ser Ile Thr Asp Phe Ala Ser Gly Thr Val Gln Ile
                245                 250                 255

Gly Gln Ser Leu Asn Gly Leu Glu Gln Phe Val Gly Arg Met Gln Asp
            260                 265                 270

Phe Arg Leu Tyr Gln Val Ala Leu Thr Asn Arg Glu Ile Leu Glu Val
        275                 280                 285
```

```
Phe Ser Gly Asp Leu Leu Arg Leu His Ala Gln Ser His Cys Arg Cys
    290                 295                 300
Pro Gly Ser His Pro Arg Val His Pro Leu Ala Gln Arg Tyr Cys Ile
305                 310                 315                 320
Pro Asn Asp Ala Gly Asp Thr Ala Asp Asn Arg Val Ser Arg Leu Asn
                325                 330                 335
Pro Glu Ala His Pro Leu Ser Phe Val Asn Asp Asn Asp Val Gly Thr
            340                 345                 350
Ser Trp Val Ser Asn Val Phe Thr Asn Ile Thr Gln Leu Asn Gln Gly
        355                 360                 365
Val Thr Ile Ser Val Asp Leu Glu Asn Gly Gln Tyr Gln Val Phe Tyr
370                 375                 380
Ile Ile Ile Gln Phe Phe Ser Pro Gln Pro Thr Glu Ile Arg Ile Gln
385                 390                 395                 400
Arg Lys Lys Glu Asn Ser Leu Asp Trp Glu Asp Trp Gln Tyr Phe Ala
                405                 410                 415
Arg Asn Cys Gly Ala Phe Gly Met Lys Asn Asn Gly Asp Leu Glu Lys
                420                 425                 430
Pro Asp Ser Val Asn Cys Leu Gln Leu Ser Asn Phe Thr Pro Tyr Ser
            435                 440                 445
Arg Gly Asn Val Thr Phe Ser Ile Leu Thr Pro Gly Pro Asn Tyr Arg
        450                 455                 460
Pro Gly Tyr Asn Asn Phe Tyr Asn Thr Pro Ser Leu Gln Glu Phe Val
465                 470                 475                 480
Lys Ala Thr Gln Ile Arg Phe His Phe His Gly Gln Tyr Tyr Thr Thr
                485                 490                 495
Glu Thr Ala Val Asn Leu Arg His Arg Tyr Tyr Ala Val Asp Glu Ile
            500                 505                 510
Thr Ile Ser Gly Arg Cys Gln Cys His Gly His Ala Asp Asn Cys Asp
        515                 520                 525
Thr Thr Ser Gln Pro Tyr Arg Cys Leu Cys Ser Gln Glu Ser Phe Thr
530                 535                 540
Glu Gly Leu His Cys Asp Arg Cys Leu Pro Leu Tyr Asn Asp Lys Pro
545                 550                 555                 560
Phe Arg Gln Gly Asp Gln Val Tyr Ala Phe Asn Cys Lys Pro Cys Gln
                565                 570                 575
Cys Asn Ser His Ser Lys Ser Cys His Tyr Asn Ile Ser Val Asp Pro
                580                 585                 590
Phe Pro Phe Glu His Phe Arg Gly Gly Gly Val Cys Asp Asp Cys
            595                 600                 605
Glu His Asn Thr Thr Gly Arg Asn Cys Glu Leu Cys Lys Asp Tyr Phe
610                 615                 620
Phe Arg Gln Val Gly Ala Asp Pro Ser Ala Ile Asp Val Cys Lys Pro
625                 630                 635                 640
Cys Asp Cys Asp Thr Val Gly Thr Arg Asn Gly Ser Ile Leu Cys Asp
                645                 650                 655
Gln Ile Gly Gly Gln Cys Asn Cys Lys Arg His Val Ser Gly Arg Gln
            660                 665                 670
Cys Asn Gln Cys Gln Asn Gly Phe Tyr Asn Leu Gln Glu Leu Asp Pro
        675                 680                 685
Asp Gly Cys Ser Pro Cys Asn Cys Asn Thr Ser Gly Thr Val Asp Gly
        690                 695                 700
Asp Ile Thr Cys His Gln Asn Ser Gly Gln Cys Lys Cys Lys Ala Asn
```

-continued

```
          705                 710                 715                 720
      Val Ile Gly Leu Arg Cys Asp His Cys Asn Phe Gly Phe Lys Phe Leu
                      725                 730                 735
      Arg Ser Phe Asn Asp Val Gly Cys Glu Pro Cys Gln Cys Asn Leu His
                      740                 745                 750
      Gly Ser Val Asn Lys Phe Cys Asn Pro His Ser Gly Gln Cys Glu Cys
                      755                 760                 765
      Lys Lys Glu Ala Lys Gly Leu Gln Cys Asp Thr Cys Arg Glu Asn Phe
                      770                 775                 780
      Tyr Gly Leu Asp Val Thr Asn Cys Lys Ala Cys Asp Cys Asp Thr Ala
      785                 790                 795                 800
      Gly Ser Leu Pro Gly Thr Val Cys Asn Ala Lys Thr Gly Gln Cys Ile
                              805                 810                 815
      Cys Lys Pro Asn Val Glu Gly Arg Gln Cys Asn Lys Cys Leu Glu Gly
                      820                 825                 830
      Asn Phe Tyr Leu Arg Gln Asn Ser Phe Leu Cys Leu Pro Cys Asn
                      835                 840                 845
      Cys Asp Lys Thr Gly Thr Ile Asn Gly Ser Leu Leu Cys Asn Lys Ser
              850                 855                 860
      Thr Gly Gln Cys Pro Cys Lys Leu Gly Val Thr Gly Leu Arg Cys Asn
      865                 870                 875                 880
      Gln Cys Glu Pro His Arg Tyr Asn Leu Thr Ile Asp Asn Phe Gln His
                              885                 890                 895
      Cys Gln Met Cys Glu Cys Asp Ser Leu Gly Thr Leu Pro Gly Thr Ile
                      900                 905                 910
      Cys Asp Pro Ile Ser Gly Gln Cys Leu Cys Val Pro Asn Arg Gln Gly
                      915                 920                 925
      Arg Arg Cys Asn Gln Cys Gln Pro Gly Phe Tyr Ile Ser Pro Gly Asn
                      930                 935                 940
      Ala Thr Gly Cys Leu Pro Cys Ser Cys His Thr Thr Gly Ala Val Asn
      945                 950                 955                 960
      His Ile Cys Asn Ser Leu Thr Gly Gln Cys Val Cys Gln Asp Ala Ser
                              965                 970                 975
      Ile Ala Gly Gln Arg Cys Asp Gln Cys Lys Asp His Tyr Phe Gly Phe
                      980                 985                 990
      Asp Pro Gln Thr Gly Arg Cys Gln  Pro Cys Asn Cys His  Leu Ser Gly
                      995                 1000                1005
      Ala Leu  Asn Glu Thr Cys His  Leu Val Thr Gly Gln  Cys Phe Cys
              1010                1015                1020
      Lys Gln  Phe Val Thr Gly Ser  Lys Cys Asp Ala Cys  Val Pro Ser
              1025                1030                1035
      Ala Ser  His Leu Asp Val Asn  Asn Leu Leu Gly Cys  Ser Lys Thr
              1040                1045                1050
      Pro Phe  Gln Gln Pro Pro Pro  Arg Gly Gln Val Gln  Ser Ser Ser
              1055                1060                1065
      Ala Ile  Asn Leu Ser Trp Ser  Pro Pro Asp Ser Pro  Asn Ala His
              1070                1075                1080
      Trp Leu  Thr Tyr Ser Leu Leu  Arg Asp Gly Phe Glu  Ile Tyr Thr
              1085                1090                1095
      Thr Glu  Asp Gln Tyr Pro Tyr  Ser Ile Gln Tyr Phe  Leu Asp Thr
              1100                1105                1110
      Asp Leu  Leu Pro Tyr Thr Lys  Tyr Ser Tyr Tyr Ile  Glu Thr Thr
              1115                1120                1125
```

-continued

```
Asn Val His Gly Ser Thr Arg Ser Val Ala Val Thr Tyr Lys Thr
    1130            1135                 1140

Lys Pro Gly Val Pro Glu Gly Asn Leu Thr Leu Ser Tyr Ile Ile
    1145            1150                 1155

Pro Ile Gly Ser Asp Ser Val Thr Leu Thr Trp Thr Thr Leu Ser
    1160            1165                 1170

Asn Gln Ser Gly Pro Ile Glu Lys Tyr Ile Leu Ser Cys Ala Pro
    1175            1180                 1185

Leu Ala Gly Gly Gln Pro Cys Val Ser Tyr Glu Gly His Glu Thr
    1190            1195                 1200

Ser Ala Thr Ile Trp Asn Leu Val Pro Phe Ala Lys Tyr Asp Phe
    1205            1210                 1215

Ser Val Gln Ala Cys Thr Ser Gly Gly Cys Leu His Ser Leu Pro
    1220            1225                 1230

Ile Thr Val Thr Thr Ala Gln Ala Pro Pro Gln Arg Leu Ser Pro
    1235            1240                 1245

Pro Lys Met Gln Lys Ile Ser Ser Thr Glu Leu His Val Glu Trp
    1250            1255                 1260

Ser Pro Pro Ala Glu Leu Asn Gly Ile Ile Ile Arg Tyr Glu Leu
    1265            1270                 1275

Tyr Met Arg Arg Leu Arg Ser Thr Lys Glu Thr Thr Ser Glu Glu
    1280            1285                 1290

Ser Arg Val Phe Gln Ser Ser Gly Trp Leu Ser Pro His Ser Phe
    1295            1300                 1305

Val Glu Ser Ala Asn Glu Asn Ala Leu Lys Pro Pro Gln Thr Met
    1310            1315                 1320

Thr Thr Ile Thr Gly Leu Glu Pro Tyr Thr Lys Tyr Glu Phe Arg
    1325            1330                 1335

Val Leu Ala Val Asn Met Ala Gly Ser Val Ser Ser Ala Trp Val
    1340            1345                 1350

Ser Glu Arg Thr Gly Glu Ser Ala Pro Val Phe Met Ile Pro Pro
    1355            1360                 1365

Ser Val Phe Pro Leu Ser Ser Tyr Ser Leu Asn Ile Ser Trp Glu
    1370            1375                 1380

Lys Pro Ala Asp Asn Val Thr Arg Gly Lys Val Val Gly Tyr Asp
    1385            1390                 1395

Ile Asn Met Leu Ser Glu Gln Ser Pro Gln Ser Ile Pro Met
    1400            1405                 1410

Ala Phe Ser Gln Leu Leu His Thr Ala Lys Ser Gln Glu Leu Ser
    1415            1420                 1425

Tyr Thr Val Glu Gly Leu Lys Pro Tyr Arg Ile Tyr Glu Phe Thr
    1430            1435                 1440

Ile Thr Leu Cys Asn Ser Val Gly Cys Val Thr Ser Ala Ser Gly
    1445            1450                 1455

Ala Gly Gln Thr Leu Ala Ala Ala Pro Ala Gln Leu Arg Pro Pro
    1460            1465                 1470

Leu Val Lys Gly Ile Asn Ser Thr Thr Ile His Leu Arg Trp Phe
    1475            1480                 1485

Pro Pro Glu Glu Leu Asn Gly Pro Ser Pro Ile Tyr Gln Leu Glu
    1490            1495                 1500

Arg Arg Glu Ser Ser Leu Pro Ala Leu Met Thr Thr Met Met Lys
    1505            1510                 1515
```

```
Gly Ile Arg Phe Ile Gly Asn Gly Tyr Cys Lys Phe Pro Ser Ser
1520                1525                1530

Thr His Pro Val Asn Thr Asp Phe Thr Gly Ile Lys Ala Ser Phe
1535                1540                1545

Arg Thr Lys Val Pro Glu Gly Leu Ile Val Phe Ala Ala Ser Pro
1550                1555                1560

Gly Asn Gln Glu Glu Tyr Phe Ala Leu Gln Leu Lys Lys Gly Arg
1565                1570                1575

Leu Tyr Phe Leu Phe Asp Pro Gln Gly Ser Pro Val Glu Val Thr
1580                1585                1590

Thr Thr Asn Asp His Gly Lys Gln Tyr Ser Asp Gly Lys Trp His
1595                1600                1605

Glu Ile Ile Ala Ile Arg His Gln Ala Phe Gly Gln Ile Thr Leu
1610                1615                1620

Asp Gly Ile Tyr Thr Gly Ser Ser Ala Ile Leu Asn Gly Ser Thr
1625                1630                1635

Val Ile Gly Asp Asn Thr Gly Val Phe Leu Gly Gly Leu Pro Arg
1640                1645                1650

Ser Tyr Thr Ile Leu Arg Lys Asp Pro Glu Ile Ile Gln Lys Gly
1655                1660                1665

Phe Val Gly Cys Leu Lys Asp Val His Phe Met Lys Asn Tyr Asn
1670                1675                1680

Pro Ser Ala Ile Trp Glu Pro Leu Asp Trp Gln Ser Ser Glu Glu
1685                1690                1695

Gln Ile Asn Val Tyr Asn Ser Trp Glu Gly Cys Pro Ala Ser Leu
1700                1705                1710

Asn Glu Gly Ala Gln Phe Leu Gly Ala Gly Phe Leu Glu Leu His
1715                1720                1725

Pro Tyr Met Phe His Gly Gly Met Asn Phe Glu Ile Ser Phe Lys
1730                1735                1740

Phe Arg Thr Asp Gln Leu Asn Gly Leu Leu Leu Phe Val Tyr Asn
1745                1750                1755

Lys Asp Gly Pro Asp Phe Leu Ala Met Glu Leu Lys Ser Gly Ile
1760                1765                1770

Leu Thr Phe Arg Leu Asn Thr Ser Leu Ala Phe Thr Gln Val Asp
1775                1780                1785

Leu Leu Leu Gly Leu Ser Tyr Cys Asn Gly Lys Trp Asn Lys Val
1790                1795                1800

Ile Ile Lys Lys Glu Gly Ser Phe Ile Ser Ala Ser Val Asn Gly
1805                1810                1815

Leu Met Lys His Ala Ser Glu Ser Gly Asp Gln Pro Leu Val Val
1820                1825                1830

Asn Ser Pro Val Tyr Val Gly Gly Ile Pro Gln Glu Leu Leu Asn
1835                1840                1845

Ser Tyr Gln His Leu Cys Leu Glu Gln Gly Phe Gly Gly Cys Met
1850                1855                1860

Lys Asp Val Lys Phe Thr Arg Gly Ala Val Val Asn Leu Ala Ser
1865                1870                1875

Val Ser Ser Gly Ala Val Arg Val Asn Leu Asp Gly Cys Leu Ser
1880                1885                1890

Thr Asp Ser Ala Val Asn Cys Arg Gly Asn Asp Ser Ile Leu Val
1895                1900                1905

Tyr Gln Gly Lys Glu Gln Ser Val Tyr Glu Gly Gly Leu Gln Pro
```

-continued

```
                1910                1915                1920
Phe Thr Glu Tyr Leu Tyr Arg Val Ile Ala Ser His Glu Gly Gly
    1925                1930                1935
Ser Val Tyr Ser Asp Trp Ser Arg Gly Arg Thr Thr Gly Ala Ala
    1940                1945                1950
Pro Gln Ser Val Pro Thr Pro Ser Arg Val Arg Ser Leu Asn Gly
    1955                1960                1965
Tyr Ser Ile Glu Val Thr Trp Asp Glu Pro Val Val Arg Gly Val
    1970                1975                1980
Ile Glu Lys Tyr Ile Leu Lys Ala Tyr Ser Glu Asp Ser Thr Arg
    1985                1990                1995
Pro Pro Arg Met Pro Ser Ala Ser Ala Glu Phe Val Asn Thr Ser
    2000                2005                2010
Asn Leu Thr Gly Ile Leu Thr Gly Leu Leu Pro Phe Lys Asn Tyr
    2015                2020                2025
Ala Val Thr Leu Thr Ala Cys Thr Leu Ala Gly Cys Thr Glu Ser
    2030                2035                2040
Ser His Ala Leu Asn Ile Ser Thr Pro Gln Glu Ala Pro Gln Glu
    2045                2050                2055
Val Gln Pro Pro Val Ala Lys Ser Leu Pro Ser Ser Leu Leu Leu
    2060                2065                2070
Ser Trp Asn Pro Pro Lys Lys Ala Asn Gly Ile Ile Thr Gln Tyr
    2075                2080                2085
Cys Leu Tyr Met Asp Gly Arg Leu Ile Tyr Ser Gly Ser Glu Glu
    2090                2095                2100
Asn Tyr Ile Val Thr Asp Leu Ala Val Phe Thr Pro His Gln Phe
    2105                2110                2115
Leu Leu Ser Ala Cys Thr His Val Gly Cys Thr Asn Ser Ser Trp
    2120                2125                2130
Val Leu Leu Tyr Thr Ala Gln Leu Pro Pro Glu His Val Asp Ser
    2135                2140                2145
Pro Val Leu Thr Val Leu Asp Ser Arg Thr Ile His Ile Gln Trp
    2150                2155                2160
Lys Gln Pro Arg Lys Ile Ser Gly Ile Leu Glu Arg Tyr Val Leu
    2165                2170                2175
Tyr Met Ser Asn His Thr His Asp Phe Thr Ile Trp Ser Val Ile
    2180                2185                2190
Tyr Asn Ser Thr Glu Leu Phe Gln Asp His Met Leu Gln Tyr Val
    2195                2200                2205
Leu Pro Gly Asn Lys Tyr Leu Ile Lys Leu Gly Ala Cys Thr Gly
    2210                2215                2220
Gly Gly Cys Thr Val Ser Glu Ala Ser Glu Ala Leu Thr Asp Glu
    2225                2230                2235
Asp Ile Pro Glu Gly Val Pro Ala Pro Lys Ala His Ser Tyr Ser
    2240                2245                2250
Pro Asp Ser Phe Asn Val Ser Trp Thr Glu Pro Glu Tyr Pro Asn
    2255                2260                2265
Gly Val Ile Thr Ser Tyr Gly Leu Tyr Leu Asp Gly Ile Leu Ile
    2270                2275                2280
His Asn Ser Ser Glu Leu Ser Tyr Arg Ala Tyr Gly Phe Ala Pro
    2285                2290                2295
Trp Ser Leu His Ser Phe Arg Val Gln Ala Cys Thr Ala Lys Gly
    2300                2305                2310
```

```
Cys Ala Leu Gly Pro Leu Val Glu Asn Arg Thr Leu Glu Ala Pro
    2315                2320                2325
Pro Glu Gly Thr Val Asn Val Phe Val Lys Thr Gln Gly Ser Arg
    2330                2335                2340
Lys Ala His Val Arg Trp Glu Ala Pro Phe Arg Pro Asn Gly Leu
    2345                2350                2355
Leu Thr His Ser Val Leu Phe Thr Gly Ile Phe Tyr Val Asp Pro
    2360                2365                2370
Val Gly Asn Asn Tyr Thr Leu Leu Asn Val Thr Lys Val Met Tyr
    2375                2380                2385
Ser Gly Glu Glu Thr Asn Leu Trp Val Leu Ile Asp Gly Leu Val
    2390                2395                2400
Pro Phe Thr Asn Tyr Thr Val Gln Val Asn Ile Ser Asn Ser Gln
    2405                2410                2415
Gly Ser Leu Ile Thr Asp Pro Ile Thr Ile Ala Met Pro Pro Gly
    2420                2425                2430
Ala Pro Asp Gly Val Leu Pro Pro Arg Leu Ser Ser Ala Thr Pro
    2435                2440                2445
Thr Ser Leu Gln Val Val Trp Ser Thr Pro Ala Arg Asn Asn Ala
    2450                2455                2460
Pro Gly Ser Pro Arg Tyr Gln Leu Gln Met Arg Ser Gly Asp Ser
    2465                2470                2475
Thr His Gly Phe Leu Glu Leu Phe Ser Asn Pro Ser Ala Ser Leu
    2480                2485                2490
Ser Tyr Glu Val Ser Asp Leu Gln Pro Tyr Thr Glu Tyr Met Phe
    2495                2500                2505
Arg Leu Val Ala Ser Asn Gly Phe Gly Ser Ala His Ser Ser Trp
    2510                2515                2520
Ile Pro Phe Met Thr Ala Glu Asp Lys Pro Gly Pro Val Val Pro
    2525                2530                2535
Pro Ile Leu Leu Asp Val Lys Ser Arg Met Met Leu Val Thr Trp
    2540                2545                2550
Gln His Pro Arg Lys Ser Asn Gly Val Ile Thr His Tyr Asn Ile
    2555                2560                2565
Tyr Leu His Gly Arg Leu Tyr Leu Arg Thr Pro Gly Asn Val Thr
    2570                2575                2580
Asn Cys Thr Val Met His Leu His Pro Tyr Thr Ala Tyr Lys Phe
    2585                2590                2595
Gln Val Glu Ala Cys Thr Ser Lys Gly Cys Ser Leu Ser Pro Glu
    2600                2605                2610
Ser Gln Thr Val Trp Thr Leu Pro Gly Ala Pro Glu Gly Ile Pro
    2615                2620                2625
Ser Pro Glu Leu Phe Ser Asp Thr Pro Thr Ser Val Ile Ile Ser
    2630                2635                2640
Trp Gln Pro Pro Thr His Pro Asn Gly Leu Val Glu Asn Phe Thr
    2645                2650                2655
Ile Glu Arg Arg Val Lys Gly Lys Glu Glu Val Thr Thr Leu Val
    2660                2665                2670
Thr Leu Pro Arg Ser His Ser Met Arg Phe Ile Asp Lys Thr Ser
    2675                2680                2685
Ala Leu Ser Pro Trp Thr Lys Tyr Glu Tyr Arg Val Leu Met Ser
    2690                2695                2700
```

```
Thr Leu His Gly Gly Thr Asn Ser Ser Ala Trp Val Glu Val Thr
2705                2710                2715

Thr Arg Pro Ser Arg Pro Ala Gly Val Gln Pro Val Val Thr
2720                2725                2730

Val Leu Glu Pro Asp Ala Val Gln Val Thr Trp Lys Pro Pro Leu
2735                2740                2745

Ile Gln Asn Gly Asp Ile Leu Ser Tyr Glu Ile His Met Pro Asp
2750                2755                2760

Pro His Ile Thr Leu Thr Asn Val Thr Ser Ala Val Leu Ser Gln
2765                2770                2775

Lys Val Thr His Leu Ile Pro Phe Thr Asn Tyr Ser Val Thr Ile
2780                2785                2790

Val Ala Cys Ser Gly Gly Asn Gly Tyr Leu Gly Gly Cys Thr Glu
2795                2800                2805

Ser Leu Pro Thr Tyr Val Thr Thr His Pro Thr Val Pro Gln Asn
2810                2815                2820

Val Gly Pro Leu Ser Val Ile Pro Leu Ser Glu Ser Tyr Val Val
2825                2830                2835

Ile Ser Trp Gln Pro Pro Ser Lys Pro Asn Gly Pro Asn Leu Arg
2840                2845                2850

Tyr Glu Leu Leu Arg Arg Lys Ile Gln Gln Pro Leu Ala Ser Asn
2855                2860                2865

Pro Pro Glu Asp Leu Asn Arg Trp His Asn Ile Tyr Ser Gly Thr
2870                2875                2880

Gln Trp Leu Tyr Glu Asp Lys Gly Leu Ser Arg Phe Thr Thr Tyr
2885                2890                2895

Glu Tyr Met Leu Phe Val His Asn Ser Val Gly Phe Thr Pro Ser
2900                2905                2910

Arg Glu Val Thr Val Thr Thr Leu Ala Gly Leu Pro Glu Arg Gly
2915                2920                2925

Ala Asn Leu Thr Ala Ser Val Leu Asn His Thr Ala Ile Asp Val
2930                2935                2940

Arg Trp Ala Lys Pro Thr Val Gln Asp Leu Gln Gly Glu Val Glu
2945                2950                2955

Tyr Tyr Thr Leu Phe Trp Ser Ser Ala Thr Ser Asn Asp Ser Leu
2960                2965                2970

Lys Ile Leu Pro Asp Val Asn Ser His Val Ile Gly His Leu Lys
2975                2980                2985

Pro Asn Thr Glu Tyr Trp Ile Phe Ile Ser Val Phe Asn Gly Val
2990                2995                3000

His Ser Ile Asn Ser Ala Gly Leu His Ala Thr Thr Cys Asp Gly
3005                3010                3015

Glu Pro Gln Gly Met Leu Pro Pro Glu Val Val Ile Ile Asn Ser
3020                3025                3030

Thr Ala Val Arg Val Ile Trp Thr Ser Pro Ser Asn Pro Asn Gly
3035                3040                3045

Val Val Thr Glu Tyr Ser Ile Tyr Val Asn Asn Lys Leu Tyr Lys
3050                3055                3060

Thr Gly Met Asn Val Pro Gly Ser Phe Ile Leu Arg Asp Leu Ser
3065                3070                3075

Pro Phe Thr Ile Tyr Asp Ile Gln Val Glu Val Cys Thr Ile Tyr
3080                3085                3090

Ala Cys Val Lys Ser Asn Gly Thr Gln Ile Thr Thr Val Glu Asp
```

```
                    3095              3100              3105
Thr Pro Ser Asp Ile Pro Thr Pro Thr Ile Arg Gly Ile Thr Ser
        3110              3115              3120

Arg Ser Leu Gln Ile Asp Trp Val Ser Pro Arg Lys Pro Asn Gly
        3125              3130              3135

Ile Ile Leu Gly Tyr Asp Leu Leu Trp Lys Thr Trp Tyr Pro Cys
        3140              3145              3150

Ala Lys Thr Gln Lys Leu Val Gln Asp Gln Ser Asp Glu Leu Cys
        3155              3160              3165

Lys Ala Val Arg Cys Gln Lys Pro Glu Ser Ile Cys Gly His Ile
        3170              3175              3180

Cys Tyr Ser Ser Glu Ala Lys Val Cys Cys Asn Gly Val Leu Tyr
        3185              3190              3195

Asn Pro Lys Pro Gly His Arg Cys Cys Glu Glu Lys Tyr Ile Pro
        3200              3205              3210

Phe Val Leu Asn Ser Thr Gly Val Cys Cys Gly Arg Ile Gln
        3215              3220              3225

Glu Ala Gln Pro Asn His Gln Cys Cys Ser Gly Tyr Tyr Ala Arg
        3230              3235              3240

Ile Leu Pro Gly Glu Val Cys Cys Pro Asp Glu Gln His Asn Arg
        3245              3250              3255

Val Ser Val Gly Ile Gly Asp Ser Cys Cys Gly Arg Met Pro Tyr
        3260              3265              3270

Ser Thr Ser Gly Asn Gln Ile Cys Cys Ala Gly Arg Leu His Asp
        3275              3280              3285

Gly His Gly Gln Lys Cys Cys Gly Arg Gln Ile Val Ser Asn Asp
        3290              3295              3300

Leu Glu Cys Cys Gly Gly Glu Gly Val Val Tyr Asn Arg Leu
        3305              3310              3315

Pro Gly Met Phe Cys Cys Gln Asp Tyr Val Asn Met Ser Asp
        3320              3325              3330

Thr Ile Cys Cys Ser Ala Ser Gly Glu Ser Lys Ala His Ile
        3335              3340              3345

Lys Lys Asn Asp Pro Val Pro Val Lys Cys Cys Glu Thr Glu Leu
        3350              3355              3360

Ile Pro Lys Ser Gln Lys Cys Cys Asn Gly Val Gly Tyr Asn Pro
        3365              3370              3375

Leu Lys Tyr Val Cys Ser Asp Lys Ile Ser Thr Gly Met Met Met
        3380              3385              3390

Lys Glu Thr Lys Glu Cys Arg Ile Leu Cys Pro Ala Ser Met Glu
        3395              3400              3405

Ala Thr Glu His Cys Gly Arg Cys Asp Phe Asn Phe Thr Ser His
        3410              3415              3420

Ile Cys Thr Val Ile Arg Gly Ser His Asn Ser Thr Gly Lys Ala
        3425              3430              3435

Ser Ile Glu Glu Met Cys Ser Ser Ala Glu Glu Thr Ile His Thr
        3440              3445              3450

Gly Ser Val Asn Thr Tyr Ser Tyr Thr Asp Val Asn Leu Lys Pro
        3455              3460              3465

Tyr Met Thr Tyr Glu Tyr Arg Ile Ser Ala Trp Asn Ser Tyr Gly
        3470              3475              3480

Arg Gly Leu Ser Lys Ala Val Arg Ala Arg Thr Lys Glu Asp Val
        3485              3490              3495
```

```
Pro Gln Gly Val Ser Pro Pro Thr Trp Thr Lys Ile Asp Asn Leu
    3500            3505                3510

Glu Asp Thr Ile Val Leu Asn Trp Arg Lys Pro Ile Gln Ser Asn
    3515            3520                3525

Gly Pro Ile Ile Tyr Tyr Ile Leu Leu Arg Asn Gly Ile Glu Arg
    3530            3535                3540

Phe Arg Gly Thr Ser Leu Ser Phe Ser Asp Lys Glu Gly Ile Gln
    3545            3550                3555

Pro Phe Gln Glu Tyr Ser Tyr Gln Leu Lys Ala Cys Thr Val Ala
    3560            3565                3570

Gly Cys Ala Thr Ser Ser Lys Val Val Ala Ala Thr Thr Gln Gly
    3575            3580                3585

Val Pro Glu Ser Ile Leu Pro Pro Ser Ile Thr Ala Leu Ser Ala
    3590            3595                3600

Val Ala Leu His Leu Ser Trp Ser Val Pro Glu Lys Ser Asn Gly
    3605            3610                3615

Val Ile Lys Glu Tyr Gln Ile Arg Gln Val Gly Lys Gly Leu Ile
    3620            3625                3630

His Thr Asp Thr Thr Asp Arg Arg Gln His Thr Val Thr Gly Leu
    3635            3640                3645

Gln Pro Tyr Thr Asn Tyr Ser Phe Thr Leu Thr Ala Cys Thr Ser
    3650            3655                3660

Ala Gly Cys Thr Ser Ser Glu Pro Phe Leu Gly Gln Thr Leu Gln
    3665            3670                3675

Ala Ala Pro Glu Gly Val Trp Val Thr Pro Arg His Ile Ile Ile
    3680            3685                3690

Asn Ser Thr Thr Val Glu Leu Tyr Trp Ser Leu Pro Glu Lys Pro
    3695            3700                3705

Asn Gly Leu Val Ser Gln Tyr Gln Leu Ser Arg Asn Gly Asn Leu
    3710            3715                3720

Leu Phe Leu Gly Gly Ser Glu Glu Gln Asn Phe Thr Asp Lys Asn
    3725            3730                3735

Leu Glu Pro Asn Ser Arg Tyr Thr Tyr Lys Leu Glu Val Lys Thr
    3740            3745                3750

Gly Gly Gly Ser Ser Ala Ser Asp Asp Tyr Ile Val Gln Thr Pro
    3755            3760                3765

Met Ser Thr Pro Glu Glu Ile Tyr Pro Pro Tyr Asn Ile Thr Val
    3770            3775                3780

Ile Gly Pro Tyr Ser Ile Phe Val Ala Trp Ile Pro Pro Gly Ile
    3785            3790                3795

Leu Ile Pro Glu Ile Pro Val Glu Tyr Asn Val Leu Leu Asn Asp
    3800            3805                3810

Gly Ser Val Thr Pro Leu Ala Phe Ser Val Gly His His Gln Ser
    3815            3820                3825

Thr Leu Leu Glu Asn Leu Thr Pro Phe Thr Gln Tyr Glu Ile Arg
    3830            3835                3840

Ile Gln Ala Cys Gln Asn Gly Ser Cys Gly Val Ser Ser Arg Met
    3845            3850                3855

Phe Val Lys Thr Pro Glu Ala Ala Pro Met Asp Leu Asn Ser Pro
    3860            3865                3870

Val Leu Lys Ala Leu Gly Ser Ala Cys Ile Glu Ile Lys Trp Met
    3875            3880                3885
```

```
Pro Pro Glu Lys Pro Asn Gly Ile Ile Ile Asn Tyr Phe Ile Tyr
3890            3895                3900

Arg Arg Pro Ala Gly Ile Glu Glu Glu Ser Val Leu Phe Val Trp
3905            3910                3915

Ser Glu Gly Ala Leu Glu Phe Met Asp Glu Gly Asp Thr Leu Arg
3920            3925                3930

Pro Phe Thr Leu Tyr Glu Tyr Arg Val Arg Ala Cys Asn Ser Lys
3935            3940                3945

Gly Ser Val Glu Ser Leu Trp Ser Leu Thr Gln Thr Leu Glu Ala
3950            3955                3960

Pro Pro Gln Asp Phe Pro Ala Pro Trp Ala Gln Ala Thr Ser Ala
3965            3970                3975

His Ser Val Leu Leu Asn Trp Thr Lys Pro Glu Ser Pro Asn Gly
3980            3985                3990

Ile Ile Ser His Tyr Arg Val Val Tyr Gln Glu Arg Pro Asp Asp
3995            4000                4005

Pro Thr Phe Asn Ser Pro Thr Val His Ala Phe Thr Val Lys Gly
4010            4015                4020

Thr Ser His Gln Ala His Leu Tyr Gly Leu Glu Pro Phe Thr Thr
4025            4030                4035

Tyr Arg Ile Gly Val Val Ala Ala Asn His Ala Gly Glu Ile Leu
4040            4045                4050

Ser Pro Trp Thr Leu Ile Gln Thr Leu Glu Ser Ser Pro Ser Gly
4055            4060                4065

Leu Arg Asn Phe Ile Val Glu Gln Lys Glu Asn Gly Arg Ala Leu
4070            4075                4080

Leu Leu Gln Trp Ser Glu Pro Met Arg Thr Asn Gly Val Ile Lys
4085            4090                4095

Thr Tyr Asn Ile Phe Ser Asp Gly Phe Leu Glu Tyr Ser Gly Leu
4100            4105                4110

Asn Arg Gln Phe Leu Phe Arg Arg Leu Asp Pro Phe Thr Leu Tyr
4115            4120                4125

Thr Leu Thr Leu Glu Ala Cys Thr Arg Ala Gly Cys Ala His Ser
4130            4135                4140

Ala Pro Gln Pro Leu Trp Thr Asp Glu Ala Pro Pro Asp Ser Gln
4145            4150                4155

Leu Ala Pro Thr Val His Ser Val Lys Ser Thr Ser Val Glu Leu
4160            4165                4170

Ser Trp Ser Glu Pro Val Asn Pro Asn Gly Lys Ile Ile Arg Tyr
4175            4180                4185

Glu Val Ile Arg Arg Cys Phe Glu Gly Lys Ala Trp Gly Asn Gln
4190            4195                4200

Thr Ile Gln Ala Asp Glu Lys Ile Val Phe Thr Glu Tyr Asn Thr
4205            4210                4215

Glu Arg Asn Thr Phe Met Tyr Asn Asp Thr Gly Leu Gln Pro Trp
4220            4225                4230

Thr Gln Cys Glu Tyr Lys Ile Tyr Thr Trp Asn Ser Ala Gly His
4235            4240                4245

Thr Cys Ser Ser Trp Asn Val Val Arg Thr Leu Gln Ala Pro Pro
4250            4255                4260

Glu Gly Leu Ser Pro Pro Val Ile Ser Tyr Val Ser Met Asn Pro
4265            4270                4275

Gln Lys Leu Leu Ile Ser Trp Ile Pro Pro Glu Gln Ser Asn Gly
```

```
                4280                4285                4290

Ile  Ile  Gln  Ser  Tyr  Arg  Leu  Gln  Arg  Asn  Glu  Met  Leu  Tyr  Pro
          4295                4300                4305

Phe  Ser  Phe  Asp  Pro  Val  Thr  Phe  Asn  Tyr  Thr  Asp  Glu  Glu  Leu
          4310                4315                4320

Leu  Pro  Phe  Ser  Thr  Tyr  Ser  Tyr  Ala  Leu  Gln  Ala  Cys  Thr  Ser
          4325                4330                4335

Gly  Gly  Cys  Ser  Thr  Ser  Lys  Pro  Thr  Ser  Ile  Thr  Thr  Leu  Glu
          4340                4345                4350

Ala  Ala  Pro  Ser  Glu  Val  Ser  Pro  Pro  Asp  Leu  Trp  Ala  Val  Ser
          4355                4360                4365

Ala  Thr  Gln  Met  Asn  Val  Cys  Trp  Ser  Pro  Pro  Thr  Val  Gln  Asn
          4370                4375                4380

Gly  Lys  Ile  Thr  Lys  Tyr  Leu  Val  Arg  Tyr  Asp  Asn  Lys  Glu  Ser
          4385                4390                4395

Leu  Ala  Gly  Gln  Gly  Leu  Cys  Leu  Leu  Val  Ser  His  Leu  Gln  Pro
          4400                4405                4410

Tyr  Ser  Gln  Tyr  Asn  Phe  Ser  Leu  Val  Ala  Cys  Thr  Asn  Gly  Gly
          4415                4420                4425

Cys  Thr  Ala  Ser  Val  Ser  Lys  Ser  Ala  Trp  Thr  Met  Glu  Ala  Leu
          4430                4435                4440

Pro  Glu  Asn  Met  Asp  Ser  Pro  Thr  Leu  Gln  Val  Thr  Gly  Ser  Glu
          4445                4450                4455

Ser  Ile  Glu  Ile  Thr  Trp  Lys  Pro  Pro  Arg  Asn  Pro  Asn  Gly  Gln
          4460                4465                4470

Ile  Arg  Ser  Tyr  Glu  Leu  Arg  Arg  Asp  Gly  Thr  Ile  Val  Tyr  Thr
          4475                4480                4485

Gly  Leu  Glu  Thr  Arg  Tyr  Arg  Asp  Phe  Thr  Leu  Thr  Pro  Gly  Val
          4490                4495                4500

Glu  Tyr  Ser  Tyr  Thr  Val  Thr  Ala  Ser  Asn  Ser  Gln  Gly  Gly  Ile
          4505                4510                4515

Leu  Ser  Pro  Leu  Val  Lys  Asp  Arg  Thr  Ser  Pro  Ser  Ala  Pro  Ser
          4520                4525                4530

Gly  Met  Glu  Pro  Pro  Lys  Leu  Gln  Ala  Arg  Gly  Pro  Gln  Glu  Ile
          4535                4540                4545

Leu  Val  Asn  Trp  Asp  Pro  Pro  Val  Arg  Thr  Asn  Gly  Asp  Ile  Ile
          4550                4555                4560

Asn  Tyr  Thr  Leu  Phe  Ile  Arg  Glu  Leu  Phe  Glu  Arg  Glu  Thr  Lys
          4565                4570                4575

Ile  Ile  His  Ile  Asn  Thr  Thr  His  Asn  Ser  Phe  Gly  Met  Gln  Ser
          4580                4585                4590

Tyr  Ile  Val  Asn  Gln  Leu  Lys  Pro  Phe  His  Arg  Tyr  Glu  Ile  Arg
          4595                4600                4605

Ile  Gln  Ala  Cys  Thr  Thr  Leu  Gly  Cys  Ala  Ser  Ser  Asp  Trp  Thr
          4610                4615                4620

Phe  Ile  Gln  Thr  Pro  Glu  Ile  Ala  Pro  Leu  Met  Gln  Pro  Pro  Pro
          4625                4630                4635

His  Leu  Glu  Val  Gln  Met  Ala  Pro  Gly  Gly  Phe  Gln  Pro  Thr  Val
          4640                4645                4650

Ser  Leu  Leu  Trp  Thr  Gly  Pro  Leu  Gln  Pro  Asn  Gly  Lys  Val  Leu
          4655                4660                4665

Tyr  Tyr  Glu  Leu  Tyr  Arg  Arg  Gln  Ile  Ala  Thr  Gln  Pro  Arg  Lys
          4670                4675                4680
```

-continued

```
Ser Asn Pro Val Leu Ile Tyr Asn Gly Ser Ser Thr Ser Phe Ile
    4685                4690                4695

Asp Ser Glu Leu Leu Pro Phe Thr Glu Tyr Glu Tyr Gln Val Trp
    4700                4705                4710

Ala Val Asn Ser Ala Gly Lys Ala Pro Ser Ser Trp Thr Trp Cys
    4715                4720                4725

Arg Thr Gly Pro Ala Pro Pro Glu Gly Leu Arg Ala Pro Thr Phe
    4730                4735                4740

His Val Ile Ser Ser Thr Gln Ala Val Val Asn Ile Ser Ala Pro
    4745                4750                4755

Gly Lys Pro Asn Gly Ile Val Ser Leu Tyr Arg Leu Phe Ser Ser
    4760                4765                4770

Ser Ala His Gly Ala Glu Thr Val Leu Ser Glu Gly Met Ala Thr
    4775                4780                4785

Gln Gln Thr Leu His Gly Leu Gln Ala Phe Thr Asn Tyr Ser Ile
    4790                4795                4800

Gly Val Glu Ala Cys Thr Cys Phe Asn Cys Cys Ser Lys Gly Pro
    4805                4810                4815

Thr Ala Glu Leu Arg Thr His Pro Ala Pro Pro Ser Gly Leu Ser
    4820                4825                4830

Ser Pro Gln Ile Gly Thr Leu Ala Ser Arg Thr Ala Ser Phe Arg
    4835                4840                4845

Trp Ser Pro Pro Met Phe Pro Asn Gly Val Ile His Ser Tyr Glu
    4850                4855                4860

Leu Gln Phe His Val Ala Cys Pro Pro Asp Ser Ala Leu Pro Cys
    4865                4870                4875

Thr Pro Ser Gln Ile Glu Thr Lys Tyr Thr Gly Leu Gly Gln Lys
    4880                4885                4890

Ala Ser Leu Gly Gly Leu Gln Pro Tyr Thr Thr Tyr Lys Leu Arg
    4895                4900                4905

Val Val Ala His Asn Glu Val Gly Ser Thr Ala Ser Glu Trp Ile
    4910                4915                4920

Ser Phe Thr Thr Gln Lys Glu Leu Pro Gly Tyr Arg Ala Pro Phe
    4925                4930                4935

Ser Val Asp Ser Asn Leu Ser Val Val Cys Val Asn Trp Ser Asp
    4940                4945                4950

Thr Phe Leu Leu Asn Gly Gln Leu Lys Glu Tyr Val Leu Thr Asp
    4955                4960                4965

Gly Gly Arg Arg Val Tyr Ser Gly Leu Asp Thr Thr Leu Tyr Ile
    4970                4975                4980

Pro Arg Thr Ala Asp Lys Thr Phe Phe Phe Gln Val Ile Cys Thr
    4985                4990                4995

Thr Asp Glu Gly Ser Val Lys Thr Pro Leu Ile Gln Tyr Asp Thr
    5000                5005                5010

Ser Thr Gly Leu Gly Leu Val Leu Thr Thr Pro Gly Lys Lys Lys
    5015                5020                5025

Gly Ser Arg Ser Lys Ser Thr Glu Phe Tyr Ser Glu Leu Trp Phe
    5030                5035                5040

Ile Val Leu Met Ala Met Leu Gly Leu Ile Leu Leu Ala Ile Phe
    5045                5050                5055

Leu Ser Leu Ile Leu Gln Arg Lys Ile His Lys Glu Pro Tyr Ile
    5060                5065                5070
```

-continued

```
Arg Glu Arg Pro Pro Leu Val Pro Leu Gln Lys Arg Met Ser Pro
    5075            5080                5085

Leu Asn Val Tyr Pro Pro Gly Glu Asn His Met Gly Leu Ala Asp
    5090            5095                5100

Thr Lys Ile Pro Arg Ser Gly Thr Pro Val Ser Ile Arg Ser Asn
    5105            5110                5115

Arg Ser Ala Cys Val Leu Arg Ile Pro Ser Gln Asn Gln Thr Ser
    5120            5125                5130

Leu Thr Tyr Ser Gln Gly Ser Leu His Arg Ser Val Ser Gln Leu
    5135            5140                5145

Met Asp Ile Gln Asp Lys Lys Val Leu Met Asp Asn Ser Leu Trp
    5150            5155                5160

Glu Ala Ile Met Gly His Asn Ser Gly Leu Tyr Val Asp Glu Glu
    5165            5170                5175

Asp Leu Met Asn Ala Ile Lys Asp Phe Ser Ser Val Thr Lys Glu
    5180            5185                5190

Arg Thr Thr Phe Thr Asp Thr His Leu
    5195            5200
```

<210> SEQ ID NO 39
<211> LENGTH: 410
<212> TYPE: PRT
<213> ORGANISM: Homo sapiens
<220> FEATURE:
<221> NAME/KEY: MISC_FEATURE
<222> LOCATION: (1)..(410)
<223> OTHER INFORMATION: NR2E3 (photoreceptor-specific nuclear receptor), isoform long

<400> SEQUENCE: 39

```
Met Glu Thr Arg Pro Thr Ala Leu Met Ser Ser Thr Val Ala Ala
1               5                   10                  15

Ala Pro Ala Ala Gly Ala Ala Ser Arg Lys Glu Ser Pro Gly Arg Trp
            20                  25                  30

Gly Leu Gly Glu Asp Pro Thr Gly Val Ser Pro Ser Leu Gln Cys Arg
            35                  40                  45

Val Cys Gly Asp Ser Ser Gly Lys His Tyr Gly Ile Tyr Ala Cys
    50                  55                  60

Asn Gly Cys Ser Gly Phe Phe Lys Arg Ser Val Arg Arg Arg Leu Ile
65                  70                  75                  80

Tyr Arg Cys Gln Val Gly Ala Gly Met Cys Pro Val Asp Lys Ala His
                85                  90                  95

Arg Asn Gln Cys Gln Ala Cys Arg Leu Lys Lys Cys Leu Gln Ala Gly
            100                 105                 110

Met Asn Gln Asp Ala Val Gln Asn Glu Arg Gln Pro Arg Ser Thr Ala
            115                 120                 125

Gln Val His Leu Asp Ser Met Glu Ser Asn Thr Glu Ser Arg Pro Glu
    130                 135                 140

Ser Leu Val Ala Pro Ala Pro Ala Gly Arg Ser Pro Arg Gly Pro
145             150                 155                 160

Thr Pro Met Ser Ala Ala Arg Ala Leu Gly His His Phe Met Ala Ser
                165                 170                 175

Leu Ile Thr Ala Glu Thr Cys Ala Lys Leu Glu Pro Glu Asp Ala Asp
            180                 185                 190

Glu Asn Ile Asp Val Thr Ser Asn Asp Pro Gly Phe Pro Ser Ser Pro
            195                 200                 205
```

```
Tyr Ser Ser Ser Ser Pro Cys Gly Leu Asp Ser Ile His Glu Thr Ser
    210                 215                 220

Ala Arg Leu Leu Phe Met Ala Val Lys Trp Ala Lys Asn Leu Pro Val
225                 230                 235                 240

Phe Ser Ser Leu Pro Phe Arg Asp Gln Val Ile Leu Leu Glu Glu Ala
                245                 250                 255

Trp Ser Glu Leu Phe Leu Leu Gly Ala Ile Gln Trp Ser Leu Pro Leu
                260                 265                 270

Asp Ser Cys Pro Leu Leu Ala Pro Pro Glu Ala Ser Ala Ala Gly Gly
            275                 280                 285

Ala Gln Gly Arg Leu Thr Leu Ala Ser Met Glu Thr Arg Val Leu Gln
290                 295                 300

Glu Thr Ile Ser Arg Phe Arg Ala Leu Ala Val Asp Pro Thr Glu Phe
305                 310                 315                 320

Ala Cys Met Lys Ala Leu Val Leu Phe Lys Pro Glu Thr Arg Gly Leu
                325                 330                 335

Lys Asp Pro Glu His Val Glu Ala Leu Gln Asp Gln Ser Gln Val Met
                340                 345                 350

Leu Ser Gln His Ser Lys Ala His His Pro Ser Gln Pro Val Arg Phe
                355                 360                 365

Gly Lys Leu Leu Leu Leu Pro Ser Leu Arg Phe Ile Thr Ala Glu
370                 375                 380

Arg Ile Glu Leu Leu Phe Phe Arg Lys Thr Ile Gly Asn Thr Pro Met
385                 390                 395                 400

Glu Lys Leu Leu Cys Asp Met Phe Lys Asn
                405                 410

<210> SEQ ID NO 40
<211> LENGTH: 1250
<212> TYPE: PRT
<213> ORGANISM: Homo sapiens
<220> FEATURE:
<221> NAME/KEY: MISC_FEATURE
<222> LOCATION: (1)..(1250)
<223> OTHER INFORMATION: human CNGB1 protein (NGS)

<400> SEQUENCE: 40

Met Leu Gly Trp Val Gln Arg Val Leu Pro Gln Pro Pro Gly Thr Pro
1               5                   10                  15

Arg Lys Thr Lys Met Gln Glu Glu Glu Val Glu Pro Glu Pro Glu
                20                  25                  30

Met Glu Ala Glu Val Glu Pro Glu Pro Asn Pro Glu Glu Ala Glu Thr
                35                  40                  45

Glu Ser Glu Ser Met Pro Pro Glu Glu Ser Phe Lys Glu Glu Glu Val
50                  55                  60

Ala Val Ala Asp Pro Ser Pro Gln Glu Thr Lys Glu Ala Ala Leu Thr
65                  70                  75                  80

Ser Thr Ile Ser Leu Arg Ala Gln Gly Ala Glu Ile Ser Glu Met Asn
                85                  90                  95

Ser Pro Ser His Arg Val Leu Thr Trp Leu Met Lys Gly Val Glu Lys
                100                 105                 110

Val Ile Pro Gln Pro Val His Ser Ile Thr Glu Asp Pro Ala Gln Ile
                115                 120                 125

Leu Gly His Gly Ser Thr Gly Asp Thr Gly Cys Thr Asp Glu Pro Asn
                130                 135                 140

Glu Ala Leu Glu Ala Gln Asp Thr Arg Pro Gly Leu Arg Leu Leu Leu
```

```
                145                 150                 155                 160
Trp Leu Glu Gln Asn Leu Glu Arg Val Leu Pro Gln Pro Pro Lys Ser
                165                 170                 175

Ser Glu Val Trp Arg Asp Glu Pro Ala Val Ala Thr Gly Ala Ala Ser
                180                 185                 190

Asp Pro Ala Pro Pro Gly Arg Pro Gln Glu Met Gly Pro Lys Leu Gln
                195                 200                 205

Ala Arg Glu Thr Pro Ser Leu Pro Thr Pro Ile Pro Leu Gln Pro Lys
                210                 215                 220

Glu Glu Pro Lys Glu Ala Pro Ala Pro Glu Pro Gln Pro Gly Ser Gln
225                 230                 235                 240

Ala Gln Thr Ser Ser Leu Pro Pro Thr Arg Asp Pro Ala Arg Leu Val
                245                 250                 255

Ala Trp Val Leu His Arg Leu Glu Met Ala Leu Pro Gln Pro Val Leu
                260                 265                 270

His Gly Lys Ile Gly Glu Gln Glu Pro Asp Ser Pro Gly Ile Cys Asp
                275                 280                 285

Val Gln Thr Ile Ser Ile Leu Pro Gly Gly Gln Val Glu Pro Asp Leu
                290                 295                 300

Val Leu Glu Glu Val Glu Pro Pro Trp Glu Asp Ala His Gln Asp Val
305                 310                 315                 320

Ser Thr Ser Pro Gln Gly Thr Glu Val Val Pro Ala Tyr Glu Glu Glu
                325                 330                 335

Asn Lys Ala Val Glu Lys Met Pro Arg Glu Leu Ser Arg Ile Glu Glu
                340                 345                 350

Glu Lys Glu Asp Glu Glu Glu Glu Glu Glu Glu Glu Glu Glu Glu Glu
                355                 360                 365

Glu Glu Glu Val Thr Glu Val Leu Leu Asp Ser Cys Val Val Ser Gln
                370                 375                 380

Val Gly Val Gly Gln Ser Glu Glu Asp Gly Thr Arg Pro Gln Ser Thr
385                 390                 395                 400

Ser Asp Gln Leu Trp Glu Glu Val Gly Glu Glu Ala Lys Lys Glu Ala
                405                 410                 415

Glu Glu Lys Ala Lys Glu Ala Glu Glu Val Ala Glu Glu Glu Ala
                420                 425                 430

Glu Lys Glu Pro Gln Asp Trp Ala Glu Thr Lys Glu Glu Pro Glu Ala
                435                 440                 445

Glu Ala Glu Ala Ala Ser Ser Gly Val Pro Ala Thr Lys Gln His Pro
450                 455                 460

Glu Val Gln Val Glu Asp Thr Asp Ala Asp Ser Cys Pro Leu Met Ala
465                 470                 475                 480

Glu Glu Asn Pro Pro Ser Thr Val Leu Pro Pro Ser Pro Ala Lys
                485                 490                 495

Ser Asp Thr Leu Ile Val Pro Ser Ser Ala Ser Gly Thr His Arg Lys
                500                 505                 510

Lys Leu Pro Ser Glu Asp Asp Glu Ala Glu Glu Leu Lys Ala Leu Ser
                515                 520                 525

Pro Ala Glu Ser Pro Val Val Ala Trp Ser Asp Pro Thr Thr Pro Lys
                530                 535                 540

Asp Thr Asp Gly Gln Asp Arg Ala Ala Ser Thr Ala Ser Thr Asn Ser
545                 550                 555                 560

Ala Ile Ile Asn Asp Arg Leu Gln Glu Leu Val Lys Leu Phe Lys Glu
                565                 570                 575
```

```
Arg Thr Glu Lys Val Lys Glu Lys Leu Ile Asp Pro Asp Val Thr Ser
            580                 585                 590

Asp Glu Glu Ser Pro Lys Pro Ser Pro Ala Lys Lys Ala Pro Glu Pro
        595                 600                 605

Ala Pro Asp Thr Lys Pro Ala Glu Ala Glu Pro Val Glu Glu Glu His
    610                 615                 620

Tyr Cys Asp Met Leu Cys Cys Lys Phe Lys His Arg Pro Trp Lys Lys
625                 630                 635                 640

Tyr Gln Phe Pro Gln Ser Ile Asp Pro Leu Thr Asn Leu Met Tyr Val
                645                 650                 655

Leu Trp Leu Phe Phe Val Val Met Ala Trp Asn Trp Asn Cys Trp Leu
            660                 665                 670

Ile Pro Val Arg Trp Ala Phe Pro Tyr Gln Thr Pro Asp Asn Ile His
        675                 680                 685

His Trp Leu Leu Met Asp Tyr Leu Cys Asp Leu Ile Tyr Phe Leu Asp
    690                 695                 700

Ile Thr Val Phe Gln Thr Arg Leu Gln Phe Val Arg Gly Gly Asp Ile
705                 710                 715                 720

Ile Thr Asp Lys Lys Asp Met Arg Asn Asn Tyr Leu Lys Ser Arg Arg
                725                 730                 735

Phe Lys Met Asp Leu Leu Ser Leu Leu Pro Leu Asp Phe Leu Tyr Leu
            740                 745                 750

Lys Val Gly Val Asn Pro Leu Leu Arg Leu Pro Arg Cys Leu Lys Tyr
        755                 760                 765

Met Ala Phe Phe Glu Phe Asn Ser Arg Leu Glu Ser Ile Leu Ser Lys
    770                 775                 780

Ala Tyr Val Tyr Arg Val Ile Arg Thr Thr Ala Tyr Leu Leu Tyr Ser
785                 790                 795                 800

Leu His Leu Asn Ser Cys Leu Tyr Tyr Trp Ala Ser Ala Tyr Gln Gly
                805                 810                 815

Leu Gly Ser Thr His Trp Val Tyr Asp Gly Val Gly Asn Ser Tyr Ile
            820                 825                 830

Arg Cys Tyr Tyr Phe Ala Val Lys Thr Leu Ile Thr Ile Gly Gly Leu
        835                 840                 845

Pro Asp Pro Lys Thr Leu Phe Glu Ile Val Phe Gln Leu Leu Asn Tyr
    850                 855                 860

Phe Thr Gly Val Phe Ala Phe Ser Val Met Ile Gly Gln Met Arg Asp
865                 870                 875                 880

Val Val Gly Ala Ala Thr Ala Gly Gln Thr Tyr Tyr Arg Ser Cys Met
                885                 890                 895

Asp Ser Thr Val Lys Tyr Met Asn Phe Tyr Lys Ile Pro Lys Ser Val
            900                 905                 910

Gln Asn Arg Val Lys Thr Trp Tyr Glu Tyr Thr Trp His Ser Gln Gly
        915                 920                 925

Met Leu Asp Glu Ser Glu Leu Met Val Gln Leu Pro Asp Lys Met Arg
    930                 935                 940

Leu Asp Leu Ala Ile Asp Val Asn Tyr Asn Ile Val Ser Lys Val Ala
945                 950                 955                 960

Leu Phe Gln Gly Cys Asp Arg Gln Met Ile Phe Asp Met Leu Lys Arg
                965                 970                 975

Leu Arg Ser Val Val Tyr Leu Pro Asn Asp Tyr Val Cys Lys Lys Gly
            980                 985                 990
```

```
Glu Ile Gly Arg Glu Met Tyr Ile Ile Gln Ala Gly Gln Val Gln Val
            995                 1000                1005

Leu Gly Gly Pro Asp Gly Lys Ser Val Leu Val Thr Leu Lys Ala
        1010                1015                1020

Gly Ser Val Phe Gly Glu Ile Ser Leu Leu Ala Val Gly Gly Gly
        1025                1030                1035

Asn Arg Arg Thr Ala Asn Val Val Ala His Gly Phe Thr Asn Leu
        1040                1045                1050

Phe Ile Leu Asp Lys Lys Asp Leu Asn Glu Ile Leu Val His Tyr
        1055                1060                1065

Pro Glu Ser Gln Lys Leu Leu Arg Lys Lys Ala Arg Arg Met Leu
        1070                1075                1080

Arg Ser Asn Asn Lys Pro Gln Glu Glu Lys Ser Val Leu Ile Leu
        1085                1090                1095

Pro Pro Arg Ala Gly Thr Pro Lys Leu Phe Asn Ala Ala Leu Ala
        1100                1105                1110

Met Thr Gly Lys Met Gly Gly Lys Gly Ala Lys Gly Gly Lys Leu
        1115                1120                1125

Ala His Leu Arg Ala Arg Leu Lys Glu Leu Ala Ala Leu Glu Ala
        1130                1135                1140

Ala Ala Lys Gln Gln Glu Leu Val Glu Gln Ala Lys Ser Ser Gln
        1145                1150                1155

Asp Val Lys Gly Glu Glu Gly Ser Ala Ala Pro Asp Gln His Thr
        1160                1165                1170

His Pro Lys Glu Ala Ala Thr Asp Pro Pro Ala Pro Arg Thr Pro
        1175                1180                1185

Pro Glu Pro Pro Gly Ser Pro Pro Ser Ser Pro Pro Ala Ser
        1190                1195                1200

Leu Gly Arg Pro Glu Gly Glu Glu Gly Pro Ala Glu Pro Glu
        1205                1210                1215

Glu His Ser Val Arg Ile Cys Met Ser Pro Gly Pro Glu Pro Gly
        1220                1225                1230

Glu Gln Ile Leu Ser Val Lys Met Pro Glu Glu Arg Glu Glu Lys
        1235                1240                1245

Ala Glu
1250

<210> SEQ ID NO 41
<211> LENGTH: 1251
<212> TYPE: PRT
<213> ORGANISM: Homo sapiens
<220> FEATURE:
<221> NAME/KEY: MISC_FEATURE
<222> LOCATION: (1)..(1251)
<223> OTHER INFORMATION: human CNGB1 protein (GenBank)

<400> SEQUENCE: 41

Met Leu Gly Trp Val Gln Arg Val Leu Pro Gln Pro Pro Gly Thr Pro
1               5                   10                  15

Arg Lys Thr Lys Met Gln Glu Glu Glu Val Glu Pro Glu Pro Glu
            20                  25                  30

Met Glu Ala Glu Val Glu Pro Pro Asn Pro Glu Ala Glu Thr
        35                  40                  45

Glu Ser Glu Ser Met Pro Pro Glu Glu Ser Phe Lys Glu Glu Val
        50                  55                  60

Ala Val Ala Asp Pro Ser Pro Gln Glu Thr Lys Glu Ala Ala Leu Thr
```

-continued

```
            65                  70                  75                  80
Ser Thr Ile Ser Leu Arg Ala Gln Gly Ala Glu Ile Ser Glu Met Asn
                    85                  90                  95

Ser Pro Ser Arg Arg Val Leu Thr Trp Leu Met Lys Gly Val Glu Lys
                100                 105                 110

Val Ile Pro Gln Pro Val His Ser Ile Thr Glu Asp Pro Ala Gln Ile
                115                 120                 125

Leu Gly His Gly Ser Thr Gly Asp Thr Gly Cys Thr Asp Glu Pro Asn
            130                 135                 140

Glu Ala Leu Glu Ala Gln Asp Thr Arg Pro Gly Leu Arg Leu Leu Leu
145                 150                 155                 160

Trp Leu Glu Gln Asn Leu Glu Arg Val Leu Pro Gln Pro Pro Lys Ser
                165                 170                 175

Ser Glu Val Trp Arg Asp Glu Pro Ala Val Ala Thr Gly Ala Ala Ser
                180                 185                 190

Asp Pro Ala Pro Pro Gly Arg Pro Gln Glu Met Gly Pro Lys Leu Gln
            195                 200                 205

Ala Arg Glu Thr Pro Ser Leu Pro Thr Pro Ile Pro Leu Gln Pro Lys
            210                 215                 220

Glu Glu Pro Lys Glu Ala Pro Ala Pro Glu Pro Gln Pro Gly Ser Gln
225                 230                 235                 240

Ala Gln Thr Ser Ser Leu Pro Pro Thr Arg Asp Pro Ala Arg Leu Val
                245                 250                 255

Ala Trp Val Leu His Arg Leu Glu Met Ala Leu Pro Gln Pro Val Leu
                260                 265                 270

His Gly Lys Ile Gly Glu Gln Glu Pro Asp Ser Pro Gly Ile Cys Asp
            275                 280                 285

Val Gln Thr Ile Ser Ile Leu Pro Gly Gly Gln Val Glu Pro Asp Leu
            290                 295                 300

Val Leu Glu Glu Val Glu Pro Pro Trp Glu Asp Ala His Gln Asp Val
305                 310                 315                 320

Ser Thr Ser Pro Gln Gly Thr Glu Val Val Pro Ala Tyr Glu Glu Glu
                325                 330                 335

Asn Lys Ala Val Glu Lys Met Pro Arg Glu Leu Ser Arg Ile Glu Glu
            340                 345                 350

Glu Lys Glu Asp Glu Glu Glu Glu Glu Glu Glu Glu Glu Glu Glu Glu
            355                 360                 365

Glu Glu Glu Val Thr Glu Val Leu Leu Asp Ser Cys Val Val Ser Gln
        370                 375                 380

Val Gly Val Gly Gln Ser Glu Asp Gly Thr Arg Pro Gln Ser Thr
385                 390                 395                 400

Ser Asp Gln Lys Leu Trp Glu Val Gly Glu Glu Ala Lys Lys Glu
            405                 410                 415

Ala Glu Glu Lys Ala Lys Glu Glu Ala Glu Val Ala Glu Glu Glu
            420                 425                 430

Ala Glu Lys Glu Pro Gln Asp Trp Ala Glu Thr Lys Glu Glu Pro Glu
            435                 440                 445

Ala Glu Ala Glu Ala Ala Ser Ser Gly Val Pro Ala Thr Lys Gln His
            450                 455                 460

Pro Glu Val Gln Val Glu Asp Thr Asp Ala Asp Ser Cys Pro Leu Met
465                 470                 475                 480

Ala Glu Glu Asn Pro Pro Ser Thr Val Leu Pro Pro Ser Pro Ala
                485                 490                 495
```

```
Lys Ser Asp Thr Leu Ile Val Pro Ser Ser Ala Ser Gly Thr His Arg
            500                 505                 510

Lys Lys Leu Pro Ser Glu Asp Glu Ala Glu Leu Lys Ala Leu
            515                 520                 525

Ser Pro Ala Glu Ser Pro Val Val Ala Trp Ser Asp Pro Thr Thr Pro
            530                 535                 540

Lys Asp Thr Asp Gly Gln Asp Arg Ala Ala Ser Thr Ala Ser Thr Asn
545                 550                 555                 560

Ser Ala Ile Ile Asn Asp Arg Leu Gln Glu Leu Val Lys Leu Phe Lys
                565                 570                 575

Glu Arg Thr Glu Lys Val Lys Glu Lys Leu Ile Asp Pro Asp Val Thr
            580                 585                 590

Ser Asp Glu Glu Ser Pro Lys Pro Ser Pro Ala Lys Lys Ala Pro Glu
            595                 600                 605

Pro Ala Pro Asp Thr Lys Pro Ala Glu Ala Glu Pro Val Glu Glu Glu
            610                 615                 620

His Tyr Cys Asp Met Leu Cys Cys Lys Phe Lys His Arg Pro Trp Lys
625                 630                 635                 640

Lys Tyr Gln Phe Pro Gln Ser Ile Asp Pro Leu Thr Asn Leu Met Tyr
                645                 650                 655

Val Leu Trp Leu Phe Phe Val Val Met Ala Trp Asn Trp Asn Cys Trp
            660                 665                 670

Leu Ile Pro Val Arg Trp Ala Phe Pro Tyr Gln Thr Pro Asp Asn Ile
            675                 680                 685

His His Trp Leu Leu Met Asp Tyr Leu Cys Asp Leu Ile Tyr Phe Leu
            690                 695                 700

Asp Ile Thr Val Phe Gln Thr Arg Leu Gln Phe Val Arg Gly Gly Asp
705                 710                 715                 720

Ile Ile Thr Asp Lys Lys Asp Met Arg Asn Asn Tyr Leu Lys Ser Arg
                725                 730                 735

Arg Phe Lys Met Asp Leu Leu Ser Leu Leu Pro Leu Asp Phe Leu Tyr
            740                 745                 750

Leu Lys Val Gly Val Asn Pro Leu Leu Arg Leu Pro Arg Cys Leu Lys
            755                 760                 765

Tyr Met Ala Phe Phe Glu Phe Asn Ser Arg Leu Glu Ser Ile Leu Ser
            770                 775                 780

Lys Ala Tyr Val Tyr Arg Val Ile Arg Thr Thr Ala Tyr Leu Leu Tyr
785                 790                 795                 800

Ser Leu His Leu Asn Ser Cys Leu Tyr Tyr Trp Ala Ser Ala Tyr Gln
                805                 810                 815

Gly Leu Gly Ser Thr His Trp Val Tyr Asp Gly Val Gly Asn Ser Tyr
            820                 825                 830

Ile Arg Cys Tyr Tyr Phe Ala Val Lys Thr Leu Ile Thr Ile Gly Gly
            835                 840                 845

Leu Pro Asp Pro Lys Thr Leu Phe Glu Ile Val Phe Gln Leu Leu Asn
            850                 855                 860

Tyr Phe Thr Gly Val Phe Ala Phe Ser Val Met Ile Gly Gln Met Arg
865                 870                 875                 880

Asp Val Val Gly Ala Ala Thr Ala Gly Gln Thr Tyr Tyr Arg Ser Cys
                885                 890                 895

Met Asp Ser Thr Val Lys Tyr Met Asn Phe Tyr Lys Ile Pro Lys Ser
            900                 905                 910
```

| | | | | | | | | | | | |
|---|---|---|---|---|---|---|---|---|---|---|---|
|Val|Gln|Asn|Arg|Val|Lys|Thr|Trp|Tyr|Glu|Tyr|Thr|Trp|His|Ser|Gln|
| | |915| | | |920| | | |925| |

```
Val Gln Asn Arg Val Lys Thr Trp Tyr Glu Tyr Thr Trp His Ser Gln
            915                 920                 925

Gly Met Leu Asp Glu Ser Glu Leu Met Val Gln Leu Pro Asp Lys Met
    930                 935                 940

Arg Leu Asp Leu Ala Ile Asp Val Asn Tyr Asn Ile Val Ser Lys Val
945                 950                 955                 960

Ala Leu Phe Gln Gly Cys Asp Arg Gln Met Ile Phe Asp Met Leu Lys
            965                 970                 975

Arg Leu Arg Ser Val Val Tyr Leu Pro Asn Asp Tyr Val Cys Lys Lys
            980                 985                 990

Gly Glu Ile Gly Arg Glu Met Tyr Ile Ile Gln Ala Gly Gln Val Gln
            995                 1000                1005

Val Leu Gly Gly Pro Asp Gly Lys Ser Val Leu Val Thr Leu Lys
    1010                1015                1020

Ala Gly Ser Val Phe Gly Glu Ile Ser Leu Leu Ala Val Gly Gly
    1025                1030                1035

Gly Asn Arg Arg Thr Ala Asn Val Val Ala His Gly Phe Thr Asn
    1040                1045                1050

Leu Phe Ile Leu Asp Lys Lys Asp Leu Asn Glu Ile Leu Val His
    1055                1060                1065

Tyr Pro Glu Ser Gln Lys Leu Leu Arg Lys Lys Ala Arg Arg Met
    1070                1075                1080

Leu Arg Ser Asn Asn Lys Pro Lys Glu Glu Lys Ser Val Leu Ile
    1085                1090                1095

Leu Pro Pro Arg Ala Gly Thr Pro Lys Leu Phe Asn Ala Ala Leu
    1100                1105                1110

Ala Met Thr Gly Lys Met Gly Gly Lys Gly Ala Lys Gly Gly Lys
    1115                1120                1125

Leu Ala His Leu Arg Ala Arg Leu Lys Glu Leu Ala Ala Leu Glu
    1130                1135                1140

Ala Ala Ala Lys Gln Gln Glu Leu Val Glu Gln Ala Lys Ser Ser
    1145                1150                1155

Gln Asp Val Lys Gly Glu Glu Gly Ser Ala Ala Pro Asp Gln His
    1160                1165                1170

Thr His Pro Lys Glu Ala Ala Thr Asp Pro Pro Ala Pro Arg Thr
    1175                1180                1185

Pro Pro Glu Pro Pro Gly Ser Pro Pro Ser Ser Pro Pro Pro Ala
    1190                1195                1200

Ser Leu Gly Arg Pro Glu Gly Glu Glu Glu Gly Pro Ala Glu Pro
    1205                1210                1215

Glu Glu His Ser Val Arg Ile Cys Met Ser Pro Gly Pro Glu Pro
    1220                1225                1230

Gly Glu Gln Ile Leu Ser Val Lys Met Pro Glu Glu Arg Glu Glu
    1235                1240                1245

Lys Ala Glu
    1250
```

<210> SEQ ID NO 42
<211> LENGTH: 4651
<212> TYPE: DNA
<213> ORGANISM: Artificial Sequence
<220> FEATURE:
<223> OTHER INFORMATION: 5'ITR-hRHO promoter-CNGB1a-SV40polyA-3'ITR

<400> SEQUENCE: 42

```
ctgcgcgctc gctcgctcac tgaggccgcc cgggcaaagc ccgggcgtcg ggcgaccttt      60
ggtcgcccgg cctcagtgag cgagcgagcg cgcagagagg gagtggccaa ctccatcact     120
aggggttcct tgtagttaat gattaacccg ccatgctact tatctacgta gccatgctct     180
aggaagatcg gaattcgccc ttaagcctct cctcccctgac ctcaggcttc ctcctagtgt    240
caccttggcc cctcttagaa gccaattagg ccctcagttt ctgcagcggg gattaatatg     300
attatgaaca cccccaatct cccagatgct gattcagcca ggagcttagg aggggaggt      360
cactttataa gggtctgggg gggtcagaac ccagagtcat cactagtaac ggccgccagt     420
gtgctggaat tcgcccttct ccaccgccat gttgggctgg gtccagaggg tgctgcctca     480
gcccccaggg acccctcgga agaccaagat gcaggaggaa gaggaagtgg aaccagagcc     540
agagatggag gcgaggtgg aaccagaacc gaatcctgag gaggccgaga cagagtccga      600
gtccatgccc cccgaagagt cattcaagga ggaggaagtg gctgtggcag acccaagccc     660
tcaggagacc aaggaggctg cccttacttc caccatatcc ctccgggccc agggcgctga    720
gatttctgaa atgaatagtc ccagccacag ggtactgacc tggctcatga agggtgtaga    780
gaaggtgatc ccgcagcctg ttcacagcat cacggaggac ccggctcaga tcctggggca    840
tggcagcact ggggacacag ggtgcacaga tgaacccaat gaggcccttg aggcccaaga    900
cactaggcct gggctgcggc tgcttctgtg gctggagcag aatctggaaa gagtgcttcc    960
tcagcccccc aaatcctctg aggtctggag agatgagcct gcagttgcta cagcgcctcc   1020
aggacgcccc caggaaatgg ggcccaagct gcaggcccgg gagaccccct ccctgcccac   1080
acccatcccc ctgcagccca aggaggaacc caaggaggca ccagtccag agccccagcc    1140
cggctcccag gcccagacct cctccctgcc accaaccagg gaccctgcca ggctggtggc   1200
atgggtcctg cacaggctgg agatggcctt gccgcagcca gtgctacatg ggaaaatagg   1260
ggaacaggag cctgactccc ctgggatatg tgatgtgcag accatcagca tccttcctgg   1320
aggacaagtg gagcctgacc ttgtcctaga ggaggttgaa ccgccctggg aggatgccca   1380
ccaggatgtc agtaccagcc cacagggtac agaggtggtt ccagcttatg aagaagagaa   1440
caaagctgtg gagaagatgc ccagagagct gtcccggatt gaagaggaga aagaagatga   1500
ggaggaggaa gaggaagagg aggaggagga ggaagaggag gaggtgactg aggtgctgct   1560
ggatagctgt gtggtgtcgc aggtgggcgt gggccagagt gaagaagacg ggacccggcc   1620
ccagagcact tcagatcaga agctgtggga ggaagttggg gaggaggcca agaaggaggc   1680
tgaagagaag gccaaggagg aggccgagga ggtggctgaa gaggaggctg aaaaggagcc   1740
ccaggactgg gcggagacca aggaggagcc tgaggctgag gccgaggctg ccagttcagg   1800
agtgcctgcc acgaaacagc acccagaagt gcaggtggaa gatactgatg ctgatagctg   1860
cccctcatg gcagaagaga atccaccctc aaccgtgttg ccgccaccat ctcctgccaa    1920
atcagacacc cttatagtcc caagctcagc ctcggggaca cacaggaaga agctgccctc   1980
tgaggatgat gaggctgaag agctcaaggc gttgtcacca gcagagtccc cagtggttgc   2040
ctggtctgac cccaccaccc cgaaggacac tgatggccag gaccgtgcgg cctccacggc   2100
cagcacaaat agcgccatca tcaacgaccg gctccaggag ctggtgaagc tcttcaagga   2160
gcggacagag aaagtgaagg agaaactcat tgaccctgac gtcacctctg atgaggagag   2220
ccccaagccc tccccagcca agaaagcccc agagccagct ccagacacaa agcccgctga   2280
agccgagcca gtgaagagg agcactattg cgacatgctc tgctgcaagt tcaaacaccg    2340
ccctggaag aagtaccagt ttcccccagag cattgacccg ctgaccaacc tgatgtatgt   2400
```

```
cctatggctg ttcttcgtgg tgatggcctg gaattggaac tgttggctga ttcccgtgcg    2460
ctgggccttc ccctaccaga ccccggacaa catccaccac tggctgctga tggattacct    2520
atgcgacctc atctacttcc tggacatcac cgtgttccag acacgcctgc agtttgtcag    2580
aggcggggac atcattacgg acaaaaagga catgcgaaat aactacctga agtctcgccg    2640
cttcaagatg gacctgctca gcctcctgcc cttggatttt ctctatttga agtcggtgt    2700 gaaccccctc ctccgcctgc cccgctgttt aaagtacatg gccttcttcg agtttaacag    2760
ccgcctggaa tccatcctca gcaaagccta cgtgtacagg gtcatcagga ccacagccta    2820
ccttctctac agcctgcatt tgaattcctg tctttattac tgggcatcgg cctatcaggg    2880
cctcggctcc actcactggg tttacgatgg cgtgggaaac agttatattc gctgttacta    2940
ctttgctgtg aagaccctca tcaccatcgg ggggctgcct gaccccaaga cactctttga    3000
aattgtcttc cagctgctga attatttcac gggcgtcttt gctttctctg tgatgatcgg    3060
acagatgaga gatgtggtag gggccgccac cgcgggacag acctactacc gcagctgcat    3120
ggacagcacg gtgaagtaca tgaatttcta caagatcccc aagtccgtgc agaaccgcgt    3180
caagacctgg tacgagtaca cctggcactc gcaaggcatg ctggatgagt cagagctgat    3240
ggtgcagctt ccagacaaga tgcggctgga cctcgccatc gacgtgaact acaacatcgt    3300
tagcaaagtc gcactctttc agggctgtga ccggcagatg atctttgaca tgctgaagag    3360
gcttcgctct gttgtctacc tgcccaacga ctatgtgtgc aagaaggggg agatcggccg    3420
tgagatgtac atcatccagg cagggcaagt gcaggtcttg gcggcccctg atgggaaatc    3480
tgtgctggtg acgctgaaag ctggatctgt gtttggagaa ataagcttgc tggctgttgg    3540
gggcgggaac cggcgcacgg ccaacgtggt ggcgcacggg tttaccaacc tcttcatcct    3600
ggataagaag gacctgaatg agattttggt gcattatcct gagtctcaga agttactccg    3660
gaagaaagcc aggcgcatgc tgagaagcaa caataagccc aaggaggaga gagcgtgct    3720 gatccttcca ccccgggcgg gcaccccaaa gctcttcaac gctgccctcg ctatgacagg    3780
aaagatgggt ggcaaggggg caaaaggcgg caaacttgct cacctccggg cccggctcaa    3840
agaactggcc gcgctggagg cggctgcaaa gcagcaagag ttggtggaac aggccaagag    3900
ctcgcaagac gtcaagggag aggaaggctc cgccgcccca gaccagcaca cgcacccaaa    3960
ggaggccgcc accgacccac ccgcgccccg gacgcccccc gagcccccgg ggtctccacc    4020
gagctctcca ccgcctgcct cccttgggag gccggaggga gaggaggagg ggccggccga    4080 gccccgaagag cactcggtga ggatctgcat gagcccgggc ccggagccgg gagagcagat    4140
cctgtcggtg aagatgccgg aggaaaggga ggagaaggcg gagtaaggtg gggtgaggcg    4200
gatccatggc cgcagacatg ataagataca ttgatgagtt tggacaaacc acaactagaa    4260
tgcagtgaaa aaaatgcttt atttgtgaaa tttgtgatgc tattgcttta tttgtaacca    4320
ttataagctg caataaacaa gttaacaaca caattgcat tcattttatg tttcaggttc    4380
agggggaggt gtgggaggtt ttttaaagca agtaaaacct ctacaaatgt ggtactcgag    4440
ttaagggcga attcccgata aggatcttcc tagagcatgg ctacgtagat aagtagcatg    4500
gcgggttaat cattaactac aaggaacccc tagtgatgga gttggccact ccctctctgc    4560
gcgctcgctc gctcactgag gccgggcgac caaaggtcgc ccgacgcccg ggctttgccc    4620
gggcggcctc agtgagcgag cgagcgcgca g                                   4651
```

<210> SEQ ID NO 43

<211> LENGTH: 4665
<212> TYPE: DNA
<213> ORGANISM: Artificial Sequence
<220> FEATURE:
<223> OTHER INFORMATION: 5'ITR-hRHO promoter-CNGB1a-SV40polyA-3'ITR (NGS)

<400> SEQUENCE: 43

```
ctgcgcgctc gctcgctcac tgaggccgcc cgggcaaagc ccgggcgtcg ggcgaccttt      60
ggtcgcccgg cctcagtgag cgagcgagcg cgcagagagg gagtggccaa ctccatcact     120
aggggttcct tgtagttaat gattaacccg ccatgctact tatctacgta gccatgctct     180
aggaagatcg gaattcgccc ttaagcctct cctccctgac ctcaggcttc ctcctagtgt     240
caccttggcc cctcttagaa gccaattagg ccctcagttt ctgcagcggg gattaatatg     300
attatgaaca cccccaatct cccagatgct gattcagcca ggagcttagg aggggaggt      360
cactttataa gggtctgggg gggtcagaac ccagagtcat cactagtaac ggccgccagt     420
gtgctggaat tcgcccttct ccaccgccat gttgggctgg gtccagaggg tgctgcctca     480
gccccagggg acccctcgga agaccaagat gcaggaggaa gaggaagtgg aaccagagcc     540
agagatggag gcggaggtgg aaccagaacc gaatcctgag gaggccgaga cagagtccga     600
gtccatgccc cccgaagagt cattcaagga ggaggaagtg gctgtggcag acccaagccc     660
tcaggagacc aaggaggctg cccttacttc caccatatcc ctccgggccc agggcgctga     720
gatttctgaa atgaatagtc ccagccacag ggtactgacc tggctcatga agggtgtaga     780
gaaggtgatc ccgcagcctg ttcacagcat cacggaggac ccggctcaga tcctggggca     840
tggcagcact ggggacacag ggtgcacaga tgaacccaat gaggcccttg aggcccaaga     900
cactaggcct gggctgcggc tgcttctgtg gctggagcag aatctggaaa gagtgcttcc     960
tcagccccc aaatcctctg aggtctggag agatgagcct gcagttgcta caggtgctgc    1020
ctcagaccca gcgcctccag gacgccccca ggaaatgggg cccaagctgc aggcccggga    1080
gaccccctcc ctgcccacac ccatccccct gcagcccaag gaggaaccca aggaggcacc    1140
agctccagag ccccagcccg gctcccaggc ccagacctcc tccctgccac caaccaggga    1200
ccctgccagg ctggtggcat gggtcctgca caggctggag atggcttgc gcagccagt     1260
gctacatggg aaaatagggg aacaggagcc tgactcccct gggatatgtg atgtgcagac    1320
catcagcatc cttcctggag acaagtggac gcctgacctt gtcctagagg aggttgaacc    1380
gccctgggag gatgcccacc aggatgtcag taccagccca cagggtacag aggtggttcc    1440
agcttatgaa gaagagaaca agctgtggga gaagatgccc agagagctgt cccggattga    1500
agaggagaaa gaagatgagg aggaggaaga ggaagaggag gaggaggagg aagaggagga    1560
ggtgactgag gtgctgctgg atagctgtgt ggtgtcgcag gtgggcgtgg gccagagtga    1620
agaagacggg acccggcccc agagcacttc agatcagctg tgggaggaag ttggggagga    1680
ggccaagaag gaggctgaag agaaggccaa ggaggaggcc gaggaggtgg ctgaagagga    1740
ggctgaaaag gagccccagg actgggcgga gaccaaggag gagcctgagg ctgaggccga    1800
ggctgccagt tcaggagtgc ctgccacgaa acagcaccca gaagtgcagg tggaagatac    1860
tgatgctgat agctgccccc tcatggcaga agagaatcca ccctcaaccg tgttgcgcc    1920
accgtctcct gccaaatcag acacccttat agtcccaagc tcagcctcgg gacacacag    1980
gaagaagctg ccctctgagg atgatgaggc tgaagagctc aaggcgttgt caccagcaga    2040
gtccccagtg gttgcctggt ctgaccccac cacccccgaag gacactgatg ccaggaccg    2100
```

```
tgcggcctcc acggccagca caaatagcgc catcatcaac gaccggctcc aggagctggt    2160
gaagctcttc aaggagcgga cagagaaagt gaaggagaaa ctcattgacc ctgacgtcac    2220
ctctgatgag gagagcccca agccctcccc agccaagaaa gccccagagc cagctccaga    2280
cacaaagccc gctgaagccg agccagtgga agaggagcac tattgcgaca tgctctgctg    2340
caagttcaaa caccgcccct ggaagaagta ccagtttccc cagagcattg acccgctgac    2400
caacctgatg tatgtcctat ggctgttctt cgtggtgatg gcctggaatt ggaactgttg    2460
gctgattccc gtgcgctggg ccttcccta ccagaccccg acaacatcc accactggct    2520 gctgatggat tacctatgcg acctcatcta cttcctggac atcaccgtgt ccagacacg    2580 cctgcagttt gtcagaggcg gggacatcat tacggacaaa aaggacatgc gaaataatta    2640
cctgaagtct cgccgcttca agatggacct gctcagcctc ctgcccttgg attttctcta    2700
tttgaaagtc ggtgtgaacc ccctcctccg cctgccccgc tgtttaaagt acatggcctt    2760
cttcgagttt aacagccgcc tggaatccat cctcagcaaa gcctacgtgt acagggtcat    2820
caggaccaca gcctaccttc tctacagcct gcatttgaat tcctgtcttt attactgggc    2880
atcggcctat cagggcctcg gctccactca ctgggtttac gatggcgtgg gaaacagtta    2940
tattcgctgt tactactttg ctgtgaagac cctcatcacc atcggggggc tgcctgaccc    3000
caagacactc tttgaaattg tcttccagct gctgaattat ttcacgggcg tctttgcttt    3060
ctctgtgatg atcggacaga tgagagatgt ggtaggggcc gccaccgcgg acagaccta    3120 ctaccgcagc tgcatggaca gcacggtgaa gtacatgaat ttctacaaga tccccaagtc    3180
cgtgcagaac cgcgtcaaga cctggtacga gtacacctgg cactcgcaag gcatgctgga    3240
tgagtcagag ctgatggtgc agcttccaga caagatgcgg ctggacctcg ccatcgacgt    3300
gaactacaac atcgttagca agtcgcact cttcagggc tgtgaccggc agatgatctt    3360
tgacatgctg aagaggcttc gctctgttgt ctacctgccc aacgactatg tgtgcaagaa    3420
gggggagatc ggccgtgaga tgtacatcat ccaggcaggg caagtgcagg tcttgggcgg    3480
ccctgatggg aaatctgtgc tggtgacgct gaaagctgga tctgtgtttg gagaaataag    3540
cttgctggct gttgggggcg ggaaccggcg cacggccaac gtggtggcgc acgggtttac    3600
caacctcttc atcctggata gaaggacct gaatgagatt ttggtgcatt atcctgagtc    3660
tcagaagtta ctccggaaga aagccaggcg catgctgaga agcaacaata gccccagga    3720 ggagaagagc gtgctgatcc ttccaccccg ggcgggcacc ccaaagctct tcaacgctgc    3780
cctcgctatg acaggaaaga tgggtggcaa ggggcaaaa ggcggcaaac ttgctcacct    3840
ccgggcccgg ctcaaagaac tggccgcgct ggaggcggct gcaaagcagc aagagttggt    3900
ggaacaggcc aagagctcgc aagacgtcaa gggagaggaa ggctccgccg ccccagacca    3960
gcacacgcac ccaaaggagg ccgccaccga cccacccgcg ccccggacgc cccccgagcc    4020 cccgggggtct ccaccgagct ctccaccgcc tgcctccctt gggaggccgg agggagagga    4080
ggaggggccg gccgagcccg aagagcactc ggtgaggate tgcatgagcc cgggcccgga    4140
gccgggagag cagatcctgt cggtgaagat gccggaggaa agggaggaga aggcggagta    4200 aggtgggtg aggcggatcc atggccgcag acatgataag atacattgat gagtttggac    4260
aaaccacaac tagaatgcag tgaaaaaaat gctttattg tgaaatttgt gatgctattg    4320
ctttatttgt aaccattata agctgcaata aacaagttaa caacaacaat tgcattcatt    4380
ttatgtttca ggttcagggg gaggtgtggg aggttttta aagcaagtaa aacctctaca    4440
aatgtggtct cgagttaagg gcgaattccc gataaggatc ttcctagagc atggctacgt    4500
```

```
agataagtag catggcgggt taatcattaa ctacaaggaa cccctagtga tggagttggc   4560
cactccctct ctgcgcgctc gctcgctcac tgaggccggg cgaccaaagg tcgcccgacg   4620
cccgggcttt gcccgggcgg cctcagtgag cgagcgagcg cgcag                  4665
```

<210> SEQ ID NO 44
<211> LENGTH: 4634
<212> TYPE: DNA
<213> ORGANISM: Artificial Sequence
<220> FEATURE:
<223> OTHER INFORMATION: 5'ITR-hRHO promoter-CNGB1a-SV40polyA-3'ITR (GenBank)

<400> SEQUENCE: 44

```
ggccactccc tctctgcgcg ctcgctcgct cactgaggcc gcccgggcaa agcccgggcg     60
tcgggcgacc tttggtcgcc cggcctcagt gagcgagcga gcgcgcagag agggagtggc    120
caactccatc actaggggtt cctcagatcg tagccatgct ctaggaagat cggaattcgc    180
ccttaagcct ctcctccctg acctcaggct tcctcctagt gtcaccttgg cccctcttag    240
aagccaatta ggccctcagt ttctgcagcg gggattaata tgattatgaa caccccaat     300 ctcccagatg ctgattcagc caggagctta ggaggggag gtcactttat aagggtctgg    360
gggggtcaga acccagagtc atcactagta acggccgcca gtgtgctgga attcgccctt    420
ctccaccgcc atgttgggct gggtccgag ggtgctgcct cagcccccag ggaccctcg      480 gaagaccaag atgcaggagg aagaggaagt ggaaccagag ccagagatgg aggcggaggt    540
ggaaccagaa ccgaatcctg aggaggccga acagagtcc gagtccatgc cccccgaaga    600
gtcattcaag gaggaggaag tggctgtggc agacccaagc cctcaggaga ccaaggaggc    660
tgcccttact tccaccatat ccctccgggc ccagggcgct gagatttctg aaatgaatag    720
tcccagccgc agggtactga cctggctcat gaagggtgta gagaaggtga tcccgcagcc    780
tgttcacagc atcacggagg accccggctca gatcctgggg catggcagca ctggggacac    840
agggtgcaca gatgaaccca tgaggccct tgaggcccaa gacactaggc ctgggctgcg    900
gctgcttctg tggctggagc agaatctgga aagagtgctt cctcagcccc caaatcctc    960 tgaggtctgg agagatgagc ctgcagttgc tacaggtgct gcctcagacc cagcgcctcc   1020
aggacgcccc caggaaatgg ggcccaagct gcaggcccgg gagacccct ccctgccac     1080 acccatcccc ctgcagccca aggaggaacc caaggaggca ccagctccag agcccccagcc   1140 cggctcccag gccagacct cctccctgcc accaaccagg gaccctgcca ggctggtggc    1200
atgggtcctg cacaggctgg agatggcctt gccgcagcca gtgctacatg ggaaaatagg    1260
ggaacaggag cctgactccc ctgggatatg tgatgtgcag accatcagca tccttcctgg   1320
aggacaagtg gagcctgacc ttgtcctaga ggaggttgaa ccgccctggg aggatgccca    1380
ccaggatgtc agtaccagcc cacagggtac agaggtggtt ccagcttatg aagaagagaa    1440
caaagctgtg gagaagatgc ccagagagct gtcccggatt gaagaggaga agaagatga    1500 ggaggaggaa gaggaagagg aggaggagga ggaagaggag gaggtgactg aggtgctgct    1560
ggatagctgt gtggtgtcgc aagtgggcgt gggccagtg aagaagacg ggacccggcc      1620 ccagagcact tcagatcaga agctgtggga ggaagttggg gaggaggcca agaaggaggc    1680
tgaagagaag gccaaggagg aggccggagga ggtggctgaa gaggaggctg aaaaggagcc   1740
ccaggactgg gcgagaacca aggaggagcc tgaggctgag gccgaggctg ccagttcagg    1800
agtgcctgcc acgaaacagc acccagaagt gcaggtggaa gatactgatg ctgatagctg    1860
```

```
cccccctcatg gcagaagaga atccaccctc aaccgtgttg ccgccaccgt ctcctgccaa    1920
atcagacacc cttatagtcc caagctcagc ctcggggaca cacaggaaga agctgccctc    1980
tgaggatgat gaggctgaag agctcaaggc gttgtcacca gcagagtccc cagtggttgc    2040
ctggtctgac cccaccaccc cgaaggacac tgatggccag gaccgtgcgg cctccacggc    2100
cagcacaaat agcgccatca tcaacgaccg gctccaggag ctggtgaagc tcttcaagga    2160
gcggacagag aaagtgaagg agaaactcat tgaccctgac gtcacctctg atgaggagag    2220
ccccaagccc tccccagcca agaaagcccc agagccagct ccagacacaa gcccgctga    2280 agccgagcca gtggaagagg agcactattg cgacatgctc tgctgcaagt tcaaacaccg    2340
cccctggaag aagtaccagt ttccccagag cattgacccg ctgaccaacc tgatgtatgt    2400
cctatgcctg ttcttcgtgg tgatggcctg aattggaac tgttggctga ttcccgtgcg    2460
ctgggccttc ccctaccaga ccccggacaa catccaccac tggctgctga tggattacct    2520
atgcgacctc atctacttcc tggacatcac cgtgttccag acacgcctgc agtttgtcag    2580
aggcggggac atcattacgg acaaaaagga catgcgaaat aactacctga agtctcgccg    2640
cttcaagatg gacctgctca gcctcctgcc cttggatttt ctctatttga aagtcggtgt    2700
gaaccccctc ctccgcctgc cccgctgttt aaagtacatg gccttcttcg agtttaacag    2760
ccgcctggaa tccatcctca gcaaagccta cgtgtacagg gtcatcagga ccacagccta    2820
ccttctctac agcctgcatt tgaattcctg tctttattac tgggcatcgg cctatcaggg    2880
cctcggctcc actcactggg tttacgatgg cgtgggaaac agttatattc gctgttacta    2940 cttttgctgtg aagaccctca tcaccatcgg ggggctgcct gaccccaaga cactctttga    3000
aattgtcttc cagctgctga attatttcac gggcgtcttt gctttctctg tgatgatcgg    3060
acagatgaga gatgtggtag gggccgccac cgcgggacag acctactacc gcagctgcat    3120
ggacagcacg gtgaagtaca tgaatttcta caagatcccc aagtccgtgc agaaccgcgt    3180
caagacctgg tacgagtaca cctggcactc gcaaggcatg ctggatgagt cagagctgat    3240
ggtgcagctt ccagacaaga tgcggctgga cctcgccatc gacgtgaact acaacatcgt    3300
tagcaaagtc gcactctttc agggctgtga ccggcagatg atctttgaca tgctgaagag    3360
gcttcgctct gttgtctacc tgcccaacga ctatgtgtgc aagaagggggg agatcggccg    3420 tgagatgtac atcatccagg cagggcaagt gcaggtcttg ggcggccctg atgggaaatc    3480
tgtgctggtg acgctgaaag ctggatctgt gtttggagaa ataagcttgc tggctgttgg    3540
gggcgggaac cggcgcacgg ccaacgtggt ggcgcacggg tttaccaacc tcttcatcct    3600
ggataagaag gacctgaatg agattttggt gcattatcct gagtctcaga agttactccg    3660
gaagaaagcc aggcgcatgc tgagaagcaa caataagccc aaggaggaga agagcgtgct    3720
gatccttcca ccccggggcgg gcaccccaaa gctcttcaac gctgccctcg ctatgacagg    3780
aaagatgggt ggcaagggggg caaaggcggg caaacttgct cacctccggg cccggctcaa    3840
agaactggcc gcgctggagg cggctgcaaa gcagcaagag ttggtggaac aggccaagag    3900
ctcgcaagac gtcaagggag aggaaggctc cgccgcccca gaccagcaca cgcacccaaa    3960
ggaggccgcc accgacccac ccgcgccccg gacgcccccc gagccccgg gtctccacc    4020 gagctctcca ccgcctgcct cccttgggag gccggaggga gaggaggag ggccggccga    4080 gcccgaagag cactcggtga ggatctgcat gagcccggg ccggagccgg gagagcagat    4140
cctgtcggtg aagatgccgg aggaaagggga ggagaaggcg gagtaaggtg gggtgaggcg    4200
```

-continued

```
gatccatggc cgcagacatg ataagataca ttgatgagtt tggacaaacc acaactagaa      4260
tgcagtgaaa aaaatgcttt atttgtgaaa tttgtgatgc tattgcttta tttgtaacca      4320
ttataagctg caataaacaa gttaacaaca acaattgcat tcattttatg tttcaggttc      4380 aggggggaggt gtgggaggtt ttttaaagca agtaaaacct ctacaaatgt ggtctcgagt      4440
taagggcgaa ttcccgataa ggatcttcct agagcatggc tacgatctga ggaacccta       4500 gtgatggagt tggccactcc ctctctgcgc gctcgctcgc tcactgaggc cgggcgacca      4560
aaggtcgccc gacgcccggg ctttgcccgg gcggcctcag tgagcgagcg agcgcgcaga      4620
gagggagtgg ccaa                                                        4634
```

<210> SEQ ID NO 45
<211> LENGTH: 533
<212> TYPE: PRT
<213> ORGANISM: Homo sapiens
<220> FEATURE:
<221> NAME/KEY: MISC_FEATURE
<222> LOCATION: (1)..(533)
<223> OTHER INFORMATION: human RPE65 protein

<400> SEQUENCE: 45

```
Met Ser Ile Gln Val Glu His Pro Ala Gly Gly Tyr Lys Lys Leu Phe
1               5                   10                  15

Glu Thr Val Glu Glu Leu Ser Ser Pro Leu Thr Ala His Val Thr Gly
            20                  25                  30

Arg Ile Pro Leu Trp Leu Thr Gly Ser Leu Leu Arg Cys Gly Pro Gly
        35                  40                  45

Leu Phe Glu Val Gly Ser Glu Pro Phe Tyr His Leu Phe Asp Gly Gln
    50                  55                  60

Ala Leu Leu His Lys Phe Asp Phe Lys Glu Gly His Val Thr Tyr His
65                  70                  75                  80

Arg Arg Phe Ile Arg Thr Asp Ala Tyr Val Arg Ala Met Thr Glu Lys
                85                  90                  95

Arg Ile Val Ile Thr Glu Phe Gly Thr Cys Ala Phe Pro Asp Pro Cys
            100                 105                 110

Lys Asn Ile Phe Ser Arg Phe Phe Ser Tyr Phe Arg Gly Val Glu Val
        115                 120                 125

Thr Asp Asn Ala Leu Val Asn Val Tyr Pro Val Gly Glu Asp Tyr Tyr
    130                 135                 140

Ala Cys Thr Glu Thr Asn Phe Ile Thr Lys Ile Asn Pro Glu Thr Leu
145                 150                 155                 160

Glu Thr Ile Lys Gln Val Asp Leu Cys Asn Tyr Val Ser Val Asn Gly
                165                 170                 175

Ala Thr Ala His Pro His Ile Glu Asn Asp Gly Thr Val Tyr Asn Ile
            180                 185                 190

Gly Asn Cys Phe Gly Lys Asn Phe Ser Ile Ala Tyr Asn Ile Val Lys
        195                 200                 205

Ile Pro Pro Leu Gln Ala Asp Lys Glu Asp Pro Ile Ser Lys Ser Glu
    210                 215                 220

Ile Val Val Gln Phe Pro Cys Ser Asp Arg Phe Lys Pro Ser Tyr Val
225                 230                 235                 240

His Ser Phe Gly Leu Thr Pro Asn Tyr Ile Val Phe Val Glu Thr Pro
                245                 250                 255

Val Lys Ile Asn Leu Phe Lys Phe Leu Ser Ser Trp Ser Leu Trp Gly
            260                 265                 270
```

-continued

```
Ala Asn Tyr Met Asp Cys Phe Glu Ser Asn Glu Thr Met Gly Val Trp
            275                 280                 285

Leu His Ile Ala Asp Lys Lys Arg Lys Lys Tyr Leu Asn Asn Lys Tyr
    290                 295                 300

Arg Thr Ser Pro Phe Asn Leu Phe His His Ile Asn Thr Tyr Glu Asp
305                 310                 315                 320

Asn Gly Phe Leu Ile Val Asp Leu Cys Cys Trp Lys Gly Phe Glu Phe
                325                 330                 335

Val Tyr Asn Tyr Leu Tyr Leu Ala Asn Leu Arg Glu Asn Trp Glu Glu
            340                 345                 350

Val Lys Lys Asn Ala Arg Lys Ala Pro Gln Pro Glu Val Arg Arg Tyr
            355                 360                 365

Val Leu Pro Leu Asn Ile Asp Lys Ala Asp Thr Gly Lys Asn Leu Val
            370                 375                 380

Thr Leu Pro Asn Thr Thr Ala Thr Ala Ile Leu Cys Ser Asp Glu Thr
385                 390                 395                 400

Ile Trp Leu Glu Pro Glu Val Leu Phe Ser Gly Pro Arg Gln Ala Phe
                405                 410                 415

Glu Phe Pro Gln Ile Asn Tyr Gln Lys Tyr Cys Gly Lys Pro Tyr Thr
                420                 425                 430

Tyr Ala Tyr Gly Leu Gly Leu Asn His Phe Val Pro Asp Arg Leu Cys
            435                 440                 445

Lys Leu Asn Val Lys Thr Lys Glu Thr Trp Val Trp Gln Glu Pro Asp
            450                 455                 460

Ser Tyr Pro Ser Glu Pro Ile Phe Val Ser His Pro Asp Ala Leu Glu
465                 470                 475                 480

Glu Asp Asp Gly Val Val Leu Ser Val Val Ser Pro Gly Ala Gly
                485                 490                 495

Gln Lys Pro Ala Tyr Leu Leu Ile Leu Asn Ala Lys Asp Leu Ser Glu
                500                 505                 510

Val Ala Arg Ala Glu Val Glu Ile Asn Ile Pro Val Thr Phe His Gly
            515                 520                 525

Leu Phe Lys Lys Ser
    530
```